(12) United States Patent
Collette et al.

(10) Patent No.: US 8,288,347 B2
(45) Date of Patent: *Oct. 16, 2012

(54) DERMAL FILLERS COMPRISING SILK FIBROIN HYDROGELS AND USES THEREOF

(75) Inventors: Adam L. Collette, Westminister, MA (US); Rebecca L. Horan, Arlington, MA (US); Jingsong Chen, Virginia Beach, VA (US); Gregory H. Altman, Arlington, MA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/906,777

(22) Filed: Oct. 18, 2010

(65) Prior Publication Data

US 2011/0129531 A1 Jun. 2, 2011

Related U.S. Application Data

(63) Continuation-in-part of application No. 12/883,139, filed on Sep. 15, 2010, which is a continuation-in-part of application No. 12/764,039, filed on Apr. 20, 2010.

(60) Provisional application No. 61/170,895, filed on Apr. 20, 2009.

(51) Int. Cl.
*A61K 38/00* (2006.01)
*A61K 9/14* (2006.01)
*A61K 9/50* (2006.01)

(52) U.S. Cl. ...... 514/18.6; 514/18.8; 424/484; 424/489; 424/497

(58) Field of Classification Search .............. 424/93.7, 424/484, 489, 497; 514/18.6, 18.8
See application file for complete search history.

(56) References Cited

U.S. PATENT DOCUMENTS

| | | | |
|---|---|---|---|
| 5,120,829 A | 6/1992 | Pierschbacher et al. | |
| 5,587,456 A | 12/1996 | Pierschbacher et al. | |
| 5,591,822 A | 1/1997 | Pierschbacher et al. | |
| 5,760,176 A | 6/1998 | Pierschbacher et al. | |
| 6,287,340 B1 | 9/2001 | Altman et al. | |
| 6,902,932 B2 | 6/2005 | Altman et al. | |
| 7,635,755 B2 | 12/2009 | Kaplan et al. | |
| 7,674,882 B2 | 3/2010 | Kaplan et al. | |
| 2002/0025340 A1 | 2/2002 | Dyer | |
| 2002/0156437 A1 | 10/2002 | McDevitt et al. | |
| 2003/0087433 A1 | 5/2003 | Tsubouchi et al. | |
| 2003/0099630 A1 | 5/2003 | DiBenedetto et al. | |
| 2003/0165548 A1 | 9/2003 | Tsubouchi et al. | |
| 2003/0183978 A1 | 10/2003 | Asakura | |
| 2004/0005363 A1 | 1/2004 | Tsukada et al. | |
| 2004/0170827 A1 | 9/2004 | Crighton | |
| 2004/0219630 A1 | 11/2004 | Tsubouchi | |
| 2004/0224406 A1 | 11/2004 | Altman et al. | |
| 2004/0266992 A1 | 12/2004 | Miliaresi et al. | |
| 2005/0089552 A1 | 4/2005 | Altman et al. | |
| 2005/0260706 A1 | 11/2005 | Kaplan et al. | |
| 2006/0205927 A1 | 9/2006 | Jin et al. | |
| 2007/0187862 A1 | 8/2007 | Kaplan et al. | |
| 2008/0038236 A1 | 2/2008 | Gimble et al. | |
| 2008/0075749 A1 | 3/2008 | Dyer | |
| 2008/0085272 A1* | 4/2008 | Kaplan et al. ............ 424/130.1 |
| 2008/0131509 A1 | 6/2008 | Hossainy et al. | |
| 2008/0176960 A1 | 7/2008 | Tsukada et al. | |
| 2008/0300683 A1 | 12/2008 | Altman et al. | |
| 2009/0024162 A1 | 1/2009 | Shalaby et al. | |
| 2009/0030454 A1 | 1/2009 | Knight et al. | |
| 2009/0214649 A1 | 8/2009 | Gazit et al. | |
| 2010/0209405 A1 | 8/2010 | Altman et al. | |
| 2010/0249924 A1 | 9/2010 | Powell et al. | |
| 2010/0256756 A1 | 10/2010 | Altman et al. | |
| 2011/0008406 A1 | 1/2011 | Altman et al. | |
| 2011/0008436 A1 | 1/2011 | Altman et al. | |
| 2011/0008437 A1 | 1/2011 | Altman et al. | |
| 2011/0009960 A1 | 1/2011 | Altman et al. | |
| 2011/0014263 A1 | 1/2011 | Altman et al. | |
| 2011/0014287 A1 | 1/2011 | Altman et al. | |
| 2011/0020409 A1 | 1/2011 | Altman et al. | |
| 2011/0052695 A1 | 3/2011 | Jiang et al. | |
| 2011/0111031 A1 | 5/2011 | Jiang et al. | |
| 2011/0129531 A1 | 6/2011 | Collette et al. | |
| 2011/0167602 A1 | 7/2011 | Altman et al. | |
| 2011/0171453 A1 | 7/2011 | Altman et al. | |
| 2011/0184227 A1 | 7/2011 | Altman et al. | |
| 2011/0189292 A1 | 8/2011 | Lebreton et al. | |
| 2011/0189773 A1 | 8/2011 | Altman et al. | |
| 2011/0224703 A1 | 9/2011 | Mortarino et al. | |
| 2011/0257665 A1 | 10/2011 | Mortarino et al. | |
| 2011/0257761 A1 | 10/2011 | Mortarino et al. | |

FOREIGN PATENT DOCUMENTS

| | | |
|---|---|---|
| JP | 02-245189 | 9/1990 |
| WO | WO 03-022909 | 3/2003 |
| WO | WO 2005/123114 | 12/2005 |
| WO | WO 2010/141133 | 12/2010 |

OTHER PUBLICATIONS

Belousove, Natalya; et al.: "Modulation of Adenovirus Vector Tropism Via Incorporation of Plypeptide Ligands Into the Fiber Protein" Journal of Virology, vol. 76, No. 17, Sep. 2002, pp. 8621-8631.

Etienne, Olivier; et al.: "Soft Tissue Augmentation Using Silk Gels: and in Vitro and in Vivo Study." Journal of Periodontology, vol. 80, No. 11, Nov. 2009, pp. 1852-1858.

Gil, E.; et al.: "Effect of β-Sheet Crystals on the Thermal and Rheological Behavior of Protein-Based Hydrogels Derived from Gelatin and Silk Fibroin" Macromolecular Bioscience 20050812 vol. 5, No. 8, Aug. 12, 2005, pp. 702-709.

Gil, E.; et al.: "Swelling Behavior and Morphological Evolution of Mixed Gelatin/Silk Fibroin Hydrogels" Biomacromolecules Nov./Dec. 2005 American Chemical Society US, vol. 6, No. 6, Nov. 2005, pp. 3079-3087.

Hersel, U.; et al.: "RGD Modified Polymers: Biomaterials for Stimulated Cell Adhesion and Beyond" Biomaterials, Elsevier Science Publishers, vol. 24, No. 24, Nov. 1, 2003, pp. 4385-4415.

Sofia, S.; et al.: "Functionalized Silk-Based Biomaterials for Bone Formation" Journal of Biomedical Materials Research, vol. 54, No. 1, Jan. 1, 2001, pp. 139-148.

(Continued)

*Primary Examiner* — Maryam Monshipouri
(74) *Attorney, Agent, or Firm* — Stephen Donovan; Debra Condino

(57) ABSTRACT

The present specification provides compositions useful as dermal fillers and methods using such compositions to treat a condition of skin.

13 Claims, 24 Drawing Sheets

OTHER PUBLICATIONS

Ajisawa, Akiyoshi, Dissolution of silk fibroin with calcium chloride/ethanol aqueous solution, Nippon Sanshigaku Zasshi (1998), 67(2): 91-94.

Asakura, et al., NMR imaging of diffusion of small organic molecules in silk fibroin gel. *Macromolecules* (1991), 24(2): 620-622.

Ayub, et al., Effect of pH on silk fibroin gelation, *Sen'i Gakkaishi* (1992), 48(3): 141-144.

Ayub et al., Mechanism of the gelation of fibroin solution, *Bioscience, Biotechnology, and Biochemistry* (1993), 57(11): 1910-1912.

Ayub et al., Quantitative structural analysis and physical properties of silk fibroin hydrogels, *Polymer* (1994), 35(10): 2197-2200.

Cappello et al., In-situ self-assembling protein polymer gel systems for administration, delivery, and release of drugs, *Journal of controlled release* (1998), 53(1-3): 105-117.

Collette et al., Comparative in vivo evaluation of a novel silk hydrogel injectable for drug delivery, Society for Biomaterials, 2007 Annual Meeting, Chicago, IL., (2007), Abstract No. 719.

Fang, Characterization and Evaluation of Silk Protein Hydrogels for Drug Delivery, *Chem Pharm Bulletin* (2006), 54(2): 156-162.

Freddi, Swelling and Dissolution of Silk Fibroin (Bombyx Mori) in N-methyl morpholine N-oxide, *International Journal of Biological Macromolecules* (1999), 24: 251-263.

Gil, Swelling Behavior and Morphological Evolution of Mixed Gelatin/Silk Fibroin Hydrogels, *Biomacromolecules* (2005), 6(6): 3079-3087.

Ha, Structural Studies of bombyx Mori Silk Fibroin During Regeneration from Solutions and Wet Fiber Spinning, *Biomacromolecules* (2005), 6(3): 1772-1731.

Hanawa, New Oral Dosage Form for Elderly Patients: Preparation and Characterization of Silk Fibroin Gel, *Chem Pharm Bulletin* (1995), 43(2): 284-288.

Hofmann, Silk as a Biomaterial for Controlled Drug Delivery, *European Cells and Materials* (2005), 10(1): 11.

Hofmann, Silk Fibroin as an Organic Polymer for Controlled Drug Delivery, *Journal of Controlled Release* (2006), 111: 219-227.

Horan et al., In vitro degradation of silk fibroin, *USA Biomaterials* (2005), 26(17): 3385-3393.

Hossain, Dilute-Solution Properties of Regenerated Silk Fibroin, *Journal of Physical Chemistry* (2003), 107(32): 8066-8073.

Hu et al., Studies on the stability of gel and gelation of silk protein fibroin, *Journal of Zhejiang Institute of Science and Technology* (1999), 16(3): 172-176.

Jin, Biomaterial Films of Bombyx Mori Silk Fibroin with Poly(ethylene oxide), *Biomacromolecules* (2004), 5(3): 711-717.

Kim, et al., Solution behavior of silk fibroin, *Polymeric Materials Science and Engineering* (2003), 89: 490-491.

Kim, et al. Structure and Properties of Silk Hydrogels. *Biomacromolecules* (2004), 5(3): 786-792.

Kim et al., Dissolvable films of silk fibroin for ultrathin, conformal bio-integrated electronics. *Nature Materials* (2010), 9(6): 511-517.

M.M. Tanaka et al., Rheological behavior of silk fibroin aqueous solution: Gel-sol transition and fiber formation, *Abstracts of Papers*, 222nd ACS National Meeting, Chicago, IL, Aug. 26-30, 2001, POLY-113.

Kobayashi, et al., Study of gel-sol transition of silk fibroin, *National Institute of Agrobiological Resources*, Abstracts of Papers, 221st ACS National Meeting, San Diego, CA, Apr. 1-5, 2001, PMSE-340.

Kobayashi, et al., Study of the gel-sol transition of silk fibroin, *Polymeric Materials Science and Engineering* (2001), 84: 620.

Kratky, et al., Molecular morphology of silk fibroin, *Chemie* (1956), 87: 269-280.

Lee K Y, Hydrogels for tissue engineering, *Chemical reviews* (2001), 101(7): 1869-1879.

Magoshi, et al., Gelation and subsequent molecular orientation of silk fibroin, (1992), pp. 231-248 in *ACS Symposium Series Viscoelasticity of Biomaterials* (eds. Glasser, et al.).

Matsumoto et al., Silk Fibroin Solution Properties Related to Assembly and Structure, *Macromolecular Bioscience* (2008) 8: 1006-1018.

Migliaresi, et al., Physical and biological evaluation of silk fibroin gels, *Abstracts of Papers*, 228th ACS National Meeting, Philadelphia, PA, Aug. 22-26, 2004, POLY-395.

Phillips, Dissolution and Regeneration of Bombyx Mori Silk Fibroin Using Ionic Liquids, *Journal of the American Chemical Society* (2004), 126: 14350-14351.

Servoli, Surface Properties of Silk Fibroin Films and Their Interaction with Fibroblasts, *Macromolecular Bioscience* (2005), 5: 1175-1183.

Sohn, Phase Behavior and Hydration of Silk Fibroin, *Biomacromolecules* (2004), 5(3): 751-757.

Sun, et al., A Study of preparation, structure and properties of pure silk fibroin gel. (2003), 24(2): 12-14.

Tamada, Y., Symposium Preprints, *The Society of Fiber Science and Technology* (1998) p. S-51.

Tsukada, Preparation and application of porous silk fibroin materials, *Journal of Applied Polymer Science* (1994), 54: 507-514.

Zhu et al., Gelation of silk sericin and physical properties of the gel, *Journal of Sericultural Science of Japan* (1995), 64(5): 415-419.

* cited by examiner

DERMAL FILLERS COMPRISING SILK FIBROIN HYDROGELS AND USES THEREOF

CROSS REFERENCE

This patent application is a continuation-in-part that claims priority under 35 U.S.C. §120 to U.S. Non-Provisional patent application Ser. No. 12/883,139, filed Sep. 15, 2010, pending, which is a continuation-in-part that claims priority under 35 U.S.C. §120 to U.S. Non-Provisional patent application Ser. No. 12/764,039, filed Apr. 20, 2010, pending, both of which patent applications claim priority pursuant to 35 U.S.C. §119(e) to U.S. Provisional Patent Application Ser. No. 61/170,895 filed Apr. 20, 2009, all of which is hereby incorporated by reference in its entirety.

FIELD OF THE INVENTION

The present specification discloses purified silk fibroin and method for purifying silk fibroins, hydrogels comprising silk fibroin with or without an amphiphilic peptide and methods for making hydrogels comprising silk fibroin and the use of silk fibroin hydrogels in a variety of medical uses, including, without limitation fillers for tissue space, templates for tissue reconstruction or regeneration, scaffolds for cells in tissue engineering applications and for disease models, a surface coating to improve medical device function, or as a platform for drug delivery.

BACKGROUND

Silk refers to a filamentous product secreted by an organism such as a spider or silkworm. Fibroin is the primary structural component of silk. It is composed of monomeric units comprising an about 350 kDa heavy chain (see, e.g., SEQ ID NO: 92) and an about 25 kDa light chain (see, e.g., SEQ ID NO: 93), and interspersed within the fibroin monomers is another about 25 kDa protein (see, e.g., SEQ ID NO: 94) derived from the P25 gene. The ratio of heavy chain:light chain:P25 protein is about 6:6:1. Fibroin is secreted by the silk glands of the organism as a pair of complementary fibrils called "brins". As fibroin brins leave the glands, they are coated with sericin, a glue-like substance which binds the brins together. Sericin is often antigenic and may be associated with an adverse tissue reaction when sericin-containing silk is implanted in vivo.

Silkworm silk fibers traditionally available in the commercial market are often termed "degummed", which refers to the loosening and removal of a portion of the sericin coat surrounding the two fibroin brins through washing or extraction in hot soapy water. This degummed silk often contains or is recoated with sericin and other impurities in order to bind the plied multifilament together into a single fiber. Therefore, degummed silk, unless explicitly stated to the contrary, typically contains twenty percent to twenty-eight percent (by weight) sericin and can not be assumed to be sericin-free.

Silk fibers have historically been valued in surgery for their mechanical properties, particularly in the form of braided filaments used as a suture material. Residual sericin that may be contained in these materials stands as a potential obstacle to its use as a biomaterial as it does present the possibility for a heightened immune response. This sericin contamination may be substantially removed though, resulting in a virtually sericin-free fibroin which may be used either as fibers or dissolved and reconstituted in a number of forms. For example, natural silk from the silkworm *Bombyx mori* may be subjected to sericin extraction, spun into yarns then used to create a matrix with high tensile strength suitable for applications such as bioengineered ligaments and tendons. Use of regenerated silk materials has also been proposed for a number of medical purposes including wound protection, cell culture substrate, enzyme immobilization, soft contact lenses, and drug-release agents.

Silk fibroin devices whether native, dissolved, or reconstituted, do not typically contain cell-binding domains such as those found in collagen, fibronectin, and many other extracellular matrix (ECM) molecules. Fibroin is also strongly hydrophobic due to the β-sheet-rich crystalline network of the core fibroin protein. These two factors couple to severely limit the capacity of native host cells to bind to and interact with implanted silk devices, as neither inflammatory cells like macrophages or reparative cells like fibroblasts are able to attach strongly, infiltrate and bioresorb the silk fibroin devices. In the case of virgin silk and black braided (wax or silicone coated) silk sutures, this is typically manifested in a harsh foreign-body response featuring peripheral encapsulation. Substantially sericin-free silk experiences a similar, though substantially less vigorous response when implanted. In essence, the host cells identify silk as a foreign body and opt to wall it off rather than interact with it. This severely limits the subsequent long-term potential of the device particularly relating to tissue in-growth and remodeling and potentially, the overall utility of the device. If it is possible to provide a more effective biomaterial formulation for mediating host-device interactions whereby cells are provided with a recognizable, acceptable and hence biocompatible surface, the biological, medicinal and surgical utility of silk is dramatically improved.

One possible means of introducing this improved cell-material interaction is to alter the silk fibroin material format into a more biocompatible matrix. Manipulating the silk fibroin to make it into a silk hydrogel formulation is one particularly intriguing option because it consists of a silk protein network which is fully saturated with water, coupling the molecular resiliency of silk with the biocompatibility of a "wet" material. Generation of a silk hydrogel may be accomplished in short by breaking apart native silk fibroin polymers into its individual monomeric components using a solvent species, replacing the solvent with water, then inducing a combination of inter- and intra-molecular aggregation. It has been shown that the sol-gel transition can be selectively initiated by changing the concentration of the protein, temperature, pH and additive (e.g., ions and hygroscopic polymers such as poly(ethylene oxide) (PEO), poloxamer, and glycerol). Increasing the silk concentration and temperature may alter the time taken for silk gelation by increasing the frequency of molecular interactions, increasing the chances of polymer nucleation. Another means of accelerating silk gelation is through use of calcium ions which may interact with the hydrophilic blocks at the ends of silk molecules in solution prior to gelation. Decreasing pH and the addition of a hydrophilic polymer have been shown to enhance gelation, possibly by decreasing repulsion between individual silk molecules in solution and subsequently competing with silk fibroin molecules in solution for bound water, causing fibroin precipitation and aggregation.

Other silk fibroin gels have been produced by, for example, mixing an aqueous silk fibroin solution with protein derived biomaterials such as gelatin or chitosan. Recombinant proteins materials based on silk fibroin's structure have also been used to create self-assembling hydrogel structures. Another silk gel, a silk fibroin-poly-(vinyl alcohol) gel was created by freeze- or air-drying an aqueous solution, then reconstituting in water and allowing to self-assemble. Silk hydrogels have also been generated by either exposing the silk solution to temperature condition of 4° C. (Thermgel) or by adding thirty percent (v/v) glycerol (Glygel). Silk hydrogels created via a freeze-thaw process have not only been generated but also used in vitro as a cell culture scaffold.

The use of silk hydrogels as biomaterial matrices has also been explored in a number of ways. General research on hydrogels as platforms for drug delivery, specifically the release behavior of benfotiamine (a synthetic variant of vitamin $B_1$) coupled to silk hydrogel was investigated. The study revealed both silk concentration and addition of other compounds may factor in to the eventual release profile of the material. Similarly, the release of FITC-labeled dextran from a silk hydrogel could be manipulated by altering the silk concentrations within the gel.

Further studies of silk hydrogels have been performed in vivo as well. For example, the material has been used in vivo to provide scaffolding for repair of broken bones in rabbits and showed an accelerated healing rate relative to control animals. Of particular interest, the in situ study also illustrated that the particular formulation of silk hydrogel did not elicit an extensive immune response from the host.

Despite early promise with silk hydrogel formulations in vivo, sericin contamination remains a concern in their generation and use just as with native fibroin for reasons of biocompatibility as well as the potential for sericin to alter gelation kinetics. The existence of sericin molecules in the silk solution intermediate prior to gelation may also compromise final gel structural quality, i.e., the distribution of β-sheet structure. For these reasons the removal of sericin from silk fibroin material prior to hydrogel manufacture remains a concern. The potential for disruption of gelation kinetics and structure by contaminants also presents the need for development of a process which consistently ensures structural uniformity and biocompatibility.

SUMMARY

The present specification provides novel dermal fillers useful for treating skin conditions.

Thus, aspects of the present specification disclose a composition comprising hydrogel particles comprising a silk fibroin. In aspect of the present specification, the hydrogel particles comprise a silk fibroin and a second matrix polymer including an elastic protein. An elastic protein includes, without limitation, a resilin, a resilin-like polypeptide, an elastin, an elastin-like polypeptide, a silk protein-elastin-like polypeptide, an abductin, a byssus, a gliadin, a glutenin, abductin, or a collagen. In other aspects of the present specification disclose a composition comprising a gel phase, wherein the gel phase includes hydrogel particles comprising a silk fibroin. In yet other aspects of the present specification disclose a composition comprising a gel phase and a carrier phase, wherein the gel phase includes hydrogel particles comprising a silk fibroin.

Other aspects of the present specification disclose a composition comprising a) hydrogel particles comprising a silk fibroin and b) hydrogel particles comprising a matrix polymer including an elastic protein. An elastic protein useful to make such compositions include, without limitation, a resilin, a resilin-like polypeptide, an elastin, an elastin-like polypeptide, a silk protein-elastin-like polypeptide, an abductin, a byssus, a gliadin, a glutenin, abductin, or a collagen. In other aspects of the present specification disclose a composition comprising a gel phase, wherein the gel phase includes hydrogel particles comprising a silk fibroin. In yet other aspects of the present specification disclose a composition comprising a gel phase and a carrier phase, wherein the gel phase includes hydrogel particles comprising a silk fibroin.

Yet other aspects of the present specification provide a method of treating a skin condition in an individual in need thereof, the method comprising the steps of administering a composition disclosed herein into a dermal region of the individual, wherein the administration improves the skin condition. Skin conditions treated by the disclosed compositions include, without limitation, augmentations, reconstructions, diseases, disorders, defects, or imperfections of a body part, region or area. In one aspect, a skin condition treated by the disclosed compositions include, without limitation, a facial augmentation, a facial reconstruction, a facial disease, a facial disorder, a facial defect, or a facial imperfection. In one aspect, a skin condition treated by the disclosed compositions include, without limitation, skin dehydration, a lack of skin elasticity, skin roughness, a lack of skin tautness, a skin stretch line or mark, skin paleness, a dermal divot, a sunken check, a thin lip, a retro-orbital defect, a facial fold, or a wrinkle.

DETAILED DESCRIPTION

Figure 1A:
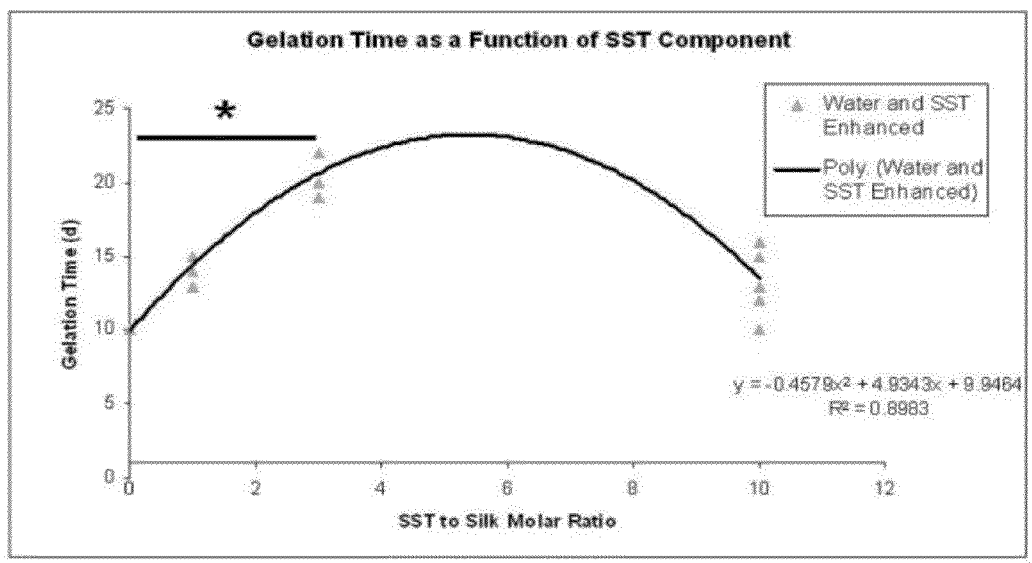
FIG. 1 illustrates the impact of 23RGD on the gelation times of silk hydrogels manufactured under various circumstances for example without enhancers or with a water/23RGD enhancer (FIG. 1A), or with an ethanol enhancer or combined ethanol-23RGD enhancers (FIG. 1B). Depending upon the ratio of 23RGD to silk used and the specific enhancer solvents, the peptide may function as either an accelerant or decelerant of the process.

Aspects of the present specification provide, in part, a composition comprising a hydrogel comprising a silk fibroin. As used herein, the term "silk fibroin" is synonymous with "polymerized silk fibroin" and refers to silk fibroin existing primarily as a polymer. A hydrogel comprising polymerized silk fibroin or silk fibroin is made by, e.g., a gelation process disclosed herein.

Aspects of the present specification provide, in part, a depolymerized silk fibroin. As used herein, the term "depolymerized silk fibroin" is synonymous with "dissolved silk" and "dissolved silk fibroin" and refers to silk fibroin existing primarily as monomers or other lower oligomeric units. Treatment of naturally-occurring fibrous silk with a dissolution agent, such as, e.g., a chaotropic agent results in depolymerized silk fibroin. The depolymerized silk fibroin used for preparing silk fibroin hydrogel is an intermediate in the silk hydrogel production process and a direct precursor to the hydrogel material. The depolymerized silk fibroin can be made from raw cocoons, previously degummed silk or any other partially cleaned silk. This may also include material commonly termed as "waste" from the reeling process, i.e. short fragments of raw or degummed silk, the sole precaution being that the silk must be substantially cleaned of sericin prior to making fibroin solution and inducing gel formation. A particular source of raw silk is from common domesticated silkworm *B. mori*, though several other sources of silk may be appropriate. This includes other strains of Bombycidae including *Antheraea pemyi, Antheraea yamamai, Antheraea mylitta, Antheraea assama*, and *Philosamia cynthia ricini*, as well as silk producing members of the families Saturniidae, Thaumetopoeidae, and silk-producing members of the order Araneae. The material may also be obtained from other spider, caterpillar, or recombinant sources.

A hydrogel disclosed herein provide for a depolymerized silk fibroin and/or silk fibroin that are substantially free of sericin. Methods for performing sericin extraction have been described in pending U.S. patent application Ser. No. 10/008, 924, U.S. Publication No. 2003/0100108, Matrix for the production of tissue engineered ligaments, tendons and other tissue. That application refers to cleaned fibroin fibers spun into yarns, used to create a porous, elastic matrix suitable as a substrate for applications requiring very high tensile strength, such as bioengineered ligaments and tendons.

Extractants such as urea solution, hot water, enzyme solutions including papain among others which are known in the art to remove sericin from fibroin would also be acceptable for generation of the silk. Mechanical methods may also be used for the removal of sericin from silk fibroin. This includes but is not limited to ultrasound, abrasive scrubbing and fluid flow. The rinse post-extraction is conducted preferably with vigorous agitation to remove substantially any ionic contaminants, soluble, and insoluble debris present on the silk as monitored through microscopy and solution electrochemical measurements. A criterion is that the extractant predictably and repeatably remove the sericin coat of the source silk without significantly compromising the molecular structure of the fibroin. For example, an extraction may be evaluated for sericin removal via mass loss, amino acid content analysis, and scanning electron microscopy. Fibroin degradation may in turn be monitored by FTIR analysis, standard protein gel electrophoresis and scanning electron microscopy.

In certain cases, the silk utilized for generation of a silk hydrogel has been substantially depleted of its native sericin content (i.e., 4% (w/w) residual sericin in the final extracted silk). Alternatively, higher concentrations of residual sericin may be left on the silk following extraction or the extraction step may be omitted. In aspects of this embodiment, the sericin-depleted silk fibroin has, e.g., about 1% (w/w) residual sericin, about 2% (w/w) residual sericin, about 3% (w/w) residual sericin, or about 4% (w/w) residual sericin. In other aspects of this embodiment, the sericin-depleted silk fibroin has, e.g., at most 1% (w/w) residual sericin, at most 2% (w/w) residual sericin, at most 3% (w/w) residual sericin, or at most 4% (w/w) residual sericin. In yet other aspects of this embodiment, the sericin-depleted silk fibroin has, e.g., about 1% (w/w) to about 2% (w/w) residual sericin, about 1% (w/w) to about 3% (w/w) residual sericin, or about 1% (w/w) to about 4% (w/w) residual sericin.

In certain cases, the silk utilized for generation of a silk hydrogel is entirely free of its native sericin content. As used herein, the term "entirely free (i.e. "consisting of" terminology) means that within the detection range of the instrument or process being used, the substance cannot be detected or its presence cannot be confirmed.

In certain cases, the silk utilized for generation of a silk hydrogel is essentially free of its native sericin content. As used herein, the term "essentially free" (or "consisting essentially of") means that only trace amounts of the substance can be detected.

Additionally, the possibility exists for deliberately modifying hydrogel properties through controlled partial removal of silk sericin or deliberate enrichment of source silk with sericin. This may function to improve hydrogel hydrophilicity and eventual host acceptance in particular biological settings despite sericin antigenicity.

After initial degumming or sericin removal from fibrous silk used for generation of a hydrogel, the silk is rinsed free of gross particulate debris. It is of concern to remove such particles as either solvent (i.e., specific solvent of interest for device generation) soluble or insoluble compounds may profoundly affect the outcome of the hydrogel generated from the intermediate solution. Insoluble compounds may serve as nucleation points, accelerating the gelation phenomenon and potentially altering subsequent hydrogel protein structure. Soluble compounds may also serve to interface with the protein network of the hydrogel, altering the organizational state of the device. Either type of compound could also compromise biocompatibility of the device.

Prior to dissolution, the prepared silk may be subjected to association of various molecules. The binding between these compounds and the silk molecules may be unaffected by the dissolving agent used for preparation of silk solution intermediate. The method for coupling the modifying compound to the prepared silk may vary dependent upon the specific nature of the bond desired between silk sequence and the modifier. Methods are not limited to but may include hydrogen bonding through affinity adsorption, covalent crosslinking of compounds or sequential binding of inactive and active compounds. These molecules may include, but would not be limited to, inorganic compounds, peptides, proteins, glycoproteins, proteoglycans, ionic compounds, natural, and synthetic polymers. Such peptides, proteins, glycoproteins and proteoglycans may include classes of molecules generally referred to as "growth factors", "cytokines", "chemokines", and "extracellular matrix compounds". These compounds might include such things as surface receptor binding motifs like arginine-glycine-aspartic acid (RGD), growth factors like basic fibroblast growth factor (bFGF), platelet derived growth factor (PDGF), transforming growth factor (TGF), cytokines like tumor necrosis factor (TNF), interferon (IFN), interleukins (IL), and structural sequences including collagen, elastin, hyaluronic acid and others. Additionally recombinant, synthetic, or non-native polymeric compounds might be used as decoration including chitin, poly-lactic acid (PLA), and poly-glycolic acid (PGA). Other compounds linked to the material may include classes of molecules generally referred to as tracers, contrasting agents, aptamers, avimers, peptide nucleic acids and modified polysaccharide coatings.

For example, the initially dissolved silk may be generated by a 4 hour digestion at 60° C. of pure silk fibroin at a concentration of 200 g/L in a 9.3 M aqueous solution of lithium bromide to a silk concentration of 20% (w/v). This process may be conducted by other means provided that they deliver a similar degree of dissociation to that provided by a 4 hour digestion at 60° C. of pure silk fibroin at a concentration of 200 g/L in a 9.3 M aqueous solution of lithium bromide. The primary goal of this is to create uniformly and repeatably dissociated silk fibroin molecules to ensure similar fibroin solution properties and, subsequently, device properties. Less substantially dissociated silk solution may have altered gelation kinetics resulting in differing final gel properties. The degree of dissociation may be indicated by Fourier-transform Infrared Spectroscopy (FTIR) or x-ray diffraction (XRD) and other modalities that quantitatively and qualitatively measure protein structure. Additionally, one may confirm that heavy and light chain domains of the silk fibroin dimer have remained intact following silk processing and dissolution. This may be achieved by methods such as standard protein sodium-dodecyl-sulfate polyacrylamide gel electrophoresis (SDS-PAGE) which assess molecular weight of the independent silk fibroin domains.

System parameters which may be modified in the initial dissolution of silk include but are not limited to solvent type, silk concentration, temperature, pressure, and addition of mechanical disruptive forces. Solvent types other than aqueous lithium bromide may include but are not limited to aqueous solutions, alcohol solutions, 1,1,1,3,3,3-hexafluoro-2-propanol, and hexafluoroacetone, 1-butyl-3-methylimidazolium. These solvents may be further enhanced by addition of urea or ionic species including lithium bromide, calcium chloride, lithium thiocyanate, zinc chloride, magnesium salts, sodium thiocyanate, and other lithium and calcium halides would be useful for such an application. These solvents may also be modified through adjustment of pH either by addition of acidic of basic compounds.

Further tailoring of the solvent system may be achieved through modification of the temperature and pressure of the solution, as ideal dissolution conditions will vary by solvent selected and enhancers added. Mechanical mixing methods employed may also vary by solvent type and may vary from general agitation and mixing to ultrasonic disruption of the protein aggregates. Additionally, the resultant dissolved silk concentration may be tailored to range from about 1% (w/v) to about 30% (w/v). It may be possible to expand this range to include higher fractions of dissolved silk depending upon the specific solvent system utilized. In one example, following initial dissolution of the processed silk, the silk protein may be left in a pure aqueous solution at 8% (w/v) silk. This is accomplished by removal of the residual solvent system while simultaneously ensuring that the aqueous component of the silk solution is never fully removed nor compromised. In a situation which involves an initial solution of 200 g/L silk in a 9.3 M aqueous solution of lithium bromide, this end is accomplished by a dialysis step.

In aspects of this embodiment, the depolymerized silk fibroin (dissolved silk fibroin) has a concentration of, e.g., about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 12% (w/v), about 15% (w/v), about 18% (w/v), about 20% (w/v), about 25% (w/v), or about 30% (w/v). In other aspects of this embodiment, the depolymerized silk fibroin (dissolved silk fibroin) has a concentration of, e.g., at least 1% (w/v), at least 2% (w/v), at least 3% (w/v), at least 4% (w/v), at least 5% (w/v), at least 6% (w/v), at least 7% (w/v), at least 8% (w/v), at least 9% (w/v), at least 10% (w/v), at least 12% (w/v), at least 15% (w/v), at least 18% (w/v), at least 20% (w/v), at least 25% (w/v), or at least 30% (w/v). In yet other aspects of this embodiment, the depolymerized silk fibroin (dissolved silk fibroin) has a concentration of, e.g., about 1% (w/v) to about 5% (w/v), about 1% (w/v) to about 10% (w/v), about 1% (w/v) to about 15% (w/v), about 1% (w/v) to about 20% (w/v), about 1% (w/v) to about 25% (w/v), about 1% (w/v) to about 30% (w/v), about 5% (w/v) to about 10% (w/v), about 5% (w/v) to about 15% (w/v), about 5% (w/v) to about 20% (w/v), about 5% (w/v) to about 25% (w/v), about 5% (w/v) to about 30% (w/v), about 10% (w/v) to about 15% (w/v), about 10% (w/v) to about 20% (w/v), about 10% (w/v) to about 25% (w/v), or about 10% (w/v) to about 30% (w/v).

Example dialysis conditions include a 3 mL-12 mL sample volume dialysis cassettes with 3.5 kD molecular weight cut-off cellulose membranes dialyzed for three days against ultra-pure water with a series of six changes at regular intervals while stirring constantly. Each cassette, 3 mL-12 mL cartridge size, may be loaded (for example via 20-mL syringe) with 12 mL of a 20% solution of silk dissolved in 9.3 M lithium bromide via an 18 gauge needle. The resultant silk solution may be 8%±0.5% (w/v). The silk solution may be stored at a range of −80° C. to 37° C., such as 4° C. prior to use. One method is to dialyze the solution against water using a 3.5 kD molecular weight cutoff cellulose membrane, for example, at one 12 mL cartridge per 1 L water in a 4 L beaker with stirring for 48 hours or 72 hours. Water may be changed several times during the dialysis, for example at 1 hour, 4 hours, 12 hours, 24 hours, and 36 hours (total of six rinses). In other embodiments, this membrane may take the shape of a cassette, tubing or any other semi-permeable membrane in a batch, semi-continuous or continuous system. If desired, the concentration of silk in solution may be raised following the original dialysis step by inclusion of a second dialysis against a hygroscopic polymer such as PEG, a poly(ethylene oxide) or amylase.

The parameters applied to the dialysis step may be altered according to the specific needs or requirements of the particular solution system involved. Although it may be undesirable to change membrane composition or pore size in the interests of maintaining efficiency of the process, it would be possible to change the structuring of the dialysis barrier, as a dialysis tube or any large semi-permeable membrane of similar construction should suffice. Additionally it should be considered that any alteration in the nature of the physical dialysis interface between solution and buffer might alter rates of ion flux and thereby create membrane-localized boundary conditions which could affect solution dialysis and gelation rate kinetics. The duration and volume ratios associated with this dialysis process must be tailored to any new system as well, and removal of the solvent phase should be ensured after purification before proceeding.

It is also possible to change the buffer phase in the dialysis system, altering water purity or adding hygroscopic polymers to simultaneously remove ions and water from the initial silk solution. For example, if necessary, the silk solution can be concentrated by dialysis against a hygroscopic polymer, for example, PEG, a polyethylene oxide or amylase. The apparatus used for dialysis can be cassettes, tubing, or any other semi-permeable membrane.

Insoluble debris may be removed from the dialyzed silk solution by centrifugation or filtration. For example, the dialyzed silk may be removed from the cassette with a needle and syringe (e.g., an 18 g needle at 20 mL syringe), and placed into a clean centrifuge tube with sufficient volume (e.g., 40 mL). The centrifuge may be run at 30,000 g relative centrifugal force (RCF) for 30 minutes at 4° C. The resulting supernatant may be collected and centrifuged again under identical conditions, and the remaining supernatant collected (e.g., in a 50 mL test tube) and stored at 4° C. The silk solution may also be evaluated via X-ray photoelectron spectroscopy (to check for lithium bromide residue) and dry mass (to check solution for dry protein mass, concentration w/v).

Additionally, dependent upon the initial silk solvent, it might be desirable to remove portions of either the silk phase or solvent phase from the solution via an affinity column separation. This could be useful in either selectively binding specific solvent molecules or specific solute molecules to be eluted later in a new solvent. The possibility also exists for a lyophilization of the depolymerized silk fibroin (dissolved silk) followed by a reconstitution step. This would be most useful in a case where removing a solvent is unlikely to leave residue behind. In the case of a lyophilized solution, either used as a purification step or as a procedure subsequent to purification, the type of solvent used for reconstitution might be tailored for the process at hand. Desirable solvents might include but are not limited to aqueous alcohol solutions, aqueous solutions with altered pH, and various organic solutions. These solvents may be selected based upon a number of parameters which may include but are not limited to an enhanced gelation rate, altered gel crystalline structure, altered solution intermediate shelf-life, altered silk solubility, and ability to interact with environmental milieu such as temperature and humidity.

In certain embodiments, a silk hydrogel is prepared from dissolved silk fibroin solution that uses an agent to enhance gelation and an agent to improve the gel's biocompatibility. In some instances, the same agent both enhances gelation and improves biocompatibility. An example agent that both improves gel biocompatibility and serves as a gelation enhancer is an amphiphilic peptide which binds to silk molecules through hydrophobic interactions, such as, e.g., a non-RGD integrin or a RGD motif containing peptide like 23RGD. In other instances, different agents serve these purposes. An example of an agent that serves as a gelation enhancer is an alcohol, such as, e.g., ethanol, methanol, and isopropanol; glycerol; and acetone.

Regarding gelation enhancers, to accelerate the phenomenon of silk gelation, a depolymerized silk fibroin solution (dissolved silk solution) may be mixed with pure alcohol or aqueous alcohol solution at varied volume ratios accompanied by mixing, either through stirring, shaking or any other form of agitation. This alcohol solution enhancer may then have a quantity of an amphiphilic peptide added as a further enhancer of the final gel outcome. The extent of acceleration may be heightened or lessened by adding a larger or smaller enhancer component to the system.

In addition to organics, the gelation rate may be enhanced by increasing the concentration of the depolymerized silk fibroin (dissolved silk). This is done by methods including but not limited to dialysis of intermediate silk solution against a buffer incorporating a hygroscopic species such as polyethylene glycol, a lyophilization step, and an evaporation step. Increased temperature may also be used as an enhancer of the gelation process. In addition to this, manipulation of intermediate silk solution pH by methods including but not limited to direct titration and gas exchange may be used to enhance the gelation process. Introduction of select ionic species including calcium and potassium in particular may also be used to accelerate gelation rate.

Nucleating agents including organic and inorganic species, both soluble and insoluble in an aqueous silk solution intermediate may be used to enhance the gelation process. These may include but are not limited to peptide sequences which bind silk molecules, previously gelled silk, and poorly soluble β-sheet rich structures. A further means of accelerating the gelation process is through the introduction of mechanical excitation. This might be imparted through a shearing device, ultrasound device, or mechanical mixer. It should be borne in mind that any of these factors might conceivably be used in concert with any other or group of others and that the regime would need to be tailored to the desired outcome.

Figure 1B:
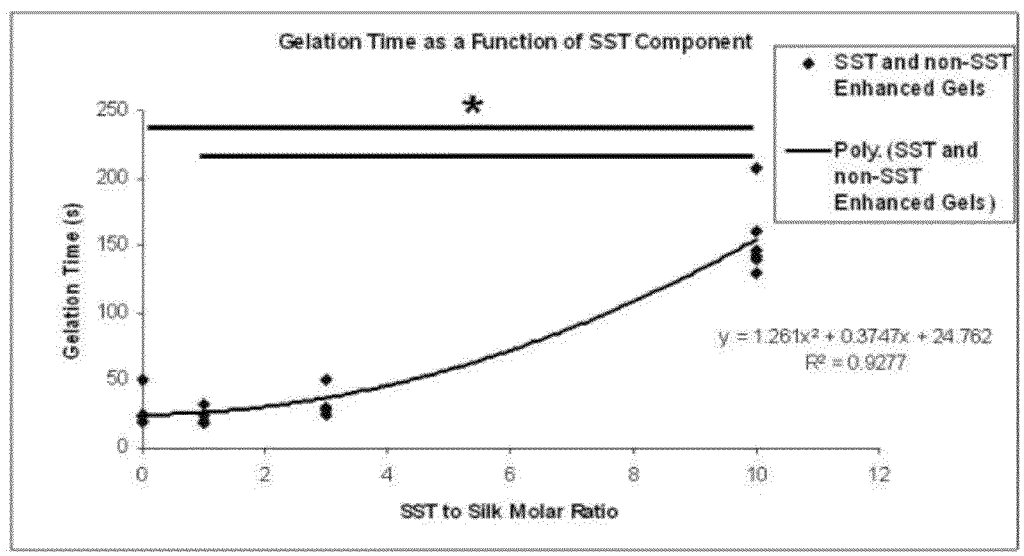

The time necessary for complete silk solution gelation may vary from seconds to hours or days, depending on the values of the above mentioned parameters as well as the initial state of aggregation and organization found in the silk solution (FIG. 1). The volume fraction of added enhancer may vary from about 0% to about 99% of the total system volume (i.e., either component may be added to a large excess of the other or in any relative concentration within the interval). The concentration of silk solution used can range from about 1% (w/v) to about 20% (w/v). The enhancer can be added to silk solution or the silk solution can be added to enhancer. The formed silk hydrogel may be further chemically or physically cross-linked to gain altered mechanical properties.

In aspects of this embodiment, an enhancer solution is added to a depolymerized silk fibroin (dissolved silk fibroin) solution, the depolymerized silk fibroin solution having a concentration of depolymerized silk fibroin of, e.g., about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 12% (w/v), about 15% (w/v), about 18% (w/v), about 20% (w/v), about 25% (w/v), or about 30% (w/v). In other aspects of this embodiment, an enhancer solution is added to a depolymerized silk fibroin (dissolved silk fibroin) solution, the depolymerized silk fibroin solution having a concentration of depolymerized silk fibroin of, e.g., at least 1% (w/v), at least 2% (w/v), at least 3% (w/v), at least 4% (w/v), at least 5% (w/v), at least 6% (w/v), at least 7% (w/v), at least 8% (w/v), at least 9% (w/v), at least 10% (w/v), at least 12% (w/v), at least 15% (w/v), at least 18% (w/v), at least 20% (w/v), at least 25% (w/v), or at least 30% (w/v). In yet other aspects of this embodiment, an enhancer solution is added to a depolymerized silk fibroin (dissolved silk fibroin) solution, the depolymerized silk fibroin solution having a concentration of depolymerized silk fibroin of, e.g., about 1% (w/v) to about 5% (w/v), about 1% (w/v) to about 10% (w/v), about 1% (w/v) to about 15% (w/v), about 1% (w/v) to about 20% (w/v), about 1% (w/v) to about 25% (w/v), about 1% (w/v) to about 30% (w/v), about 5% (w/v) to about 10% (w/v), about 5% (w/v) to about 15% (w/v), about 5% (w/v) to about 20% (w/v), about 5% (w/v) to about 25% (w/v), about 5% (w/v) to about 30% (w/v), about 10% (w/v) to about 15% (w/v), about 10% (w/v) to about 20% (w/v), about 10% (w/v) to about 25% (w/v), or about 10% (w/v) to about 30% (w/v).

Aspects of the present specification provide, in part, a hydrogel comprising an amphiphilic peptide. As used herein, the term "amphiphilic peptide" refers to a peptide that includes both hydrophobic and hydrophilic properties. Many other amphiphilic molecules interact strongly with biological membranes by insertion of the hydrophobic part into the lipid membrane, while exposing the hydrophilic part to the aqueous environment. Particular embodiments of hydrogels include silk fibroin, silk fibroin with 23RGD, silk fibroin with alcohol and 23RGD, and silk fibroin with alcohol, 23RGD, and saline/PBS. The amount, relative ratio and sequence of adding the components will change according to the specific requirement for the device.

Additionally, an amphiphilic peptide may accelerate the phenomenon of silk gelation under certain circumstances. Such gel may be produced through combination of dissolved silk fibroin solution and an enhancer solution of amphiphilic peptide in alcohol across the silk concentration ranges from about 1% (w/v) to about 20% (w/v), amphiphilic peptide concentration ranges from about 1:100 to 100:1 moles 23RGD:moles silk, and alcohol concentration ranges from about 1% (v/v) to about 99% (v/v) before removal. Thus, for example, a particular silk gel is produced through direct contact between an aqueous solution of depolymerized silk fibroin and an enhancer solution comprising 23RGD in ethanol. For example, the dissolved silk solution may be mixed with a 23RGD suspended in pure ethanol or aqueous ethanol solution at varied volume ratios accompanied by mixing, either through stirring, shaking or any other form of agitation.

More specifically, as a non-limiting example, to infuse the silk fibroin hydrogel with 23RGD, the 23RGD is first dissolved in a solution of ethanol and water (e.g., 90% ethanol in purified water) in an amount to generate the planned silk and 23RGD concentrations of the final gel, and mixed (e.g., vortexed until there is no visible 23RGD particulate). This solution is then mixed with dissolved silk solution (e.g., by pipetting rapidly for 1-2 seconds). The gelling mixture may be allowed to stand covered under ambient conditions for a suitable period, for example 24 hours (or 24 hours after the gel has solidified depending on enhancer conditions).

The amount of time required for dissolved silk solutions to gel may vary from seconds to hours or days, depending on the ratio of silk solution volume and enhancer solution volume, dissolved silk fibroin concentration, enhancer solution concentration, enhancer type and amphiphilic peptide concentration. The amphiphilic peptide may be mixed into the dissolved silk solution in a variety of ways, for example water-dissolved amphiphilic peptide can be added to a dissolved silk solution to form a gel; an amphiphilic peptide can be added to water, blended with an alcohol, then added to a dissolved silk solution; or an amphiphilic peptide can be added to a silk fibroin hydrogel. The molar ratio of amphiphilic peptide:silk fibroin can range from 100 to 0.01, the dissolved silk solution concentration can be from about 1% to about 20%.

An example of an amphiphilic peptide is a 23RGD peptide having the amino acid sequence: HOOC-Gly-Arg-Gly-Asp-Ile-Pro-Ala-Ser-Ser-Lys-Gly-Gly-Gly-Gly-Ser-Arg-Leu-Leu-Leu-Leu-Leu-Leu-Arg-NH$_2$ (abbreviated HOOC-GRGDIPASSKG$_4$SRL$_6$R—NH$_2$) (SEQ ID NO: 1). Optionally, each of the arginine residues may be of the D-form, which may stabilize the RG bond to serine proteases. Additionally, the COO-terminus may be acylated to block proteolysis. This example 23RGD has the amino acid sequence Ac-GdRGDIPASSKG$_4$SdRL$_{6d}$R—NH$_2$ (SEQ ID NO: 2). It may be advantageous to include a spacer domain in the RGD peptide, for example, a peptide such as SG$_4$KSSAP (SEQ ID NO: 3) may present the RGD on the surface of the silk biomaterial by optimally separating the cell attachment domain from the bonding sequence at the end of the peptide. The optional leucine tails of this example may interact in a fashion analogous to a leucine zipper, and be driven by entropy from an aqueous solution to form an approximation of a Langmuir-Blodgett (LB), monomolecular film on the surface of materials exposed to such solutions, thus presenting a 'carpet' of RGD attachment sites on those surfaces.

Other proteins or peptides may be used instead of 23RGD if such proteins or peptides have the desired characteristics. Example characteristics include hydrophilic domains that can interfere/enhance/affect silk gelation, and/or cell integrin binding domains that enhance cell adhesion, spreading, and migration. Non-limiting examples of such non-RGD integrins include, KQAGDV (SEQ ID NO: 4), PHSRN (SEQ ID NO: 5), YIGSR (SEQ ID NO: 6), CDPGYIGSR (SEQ ID NO: 7), IKVAV (SEQ ID NO: 8), RNIAEIIKDI (SEQ ID NO: 9), YFQRYLI (SEQ ID NO: 10), PDSGR (SEQ ID NO: 11), FHRRIKA (SEQ ID NO: 12), PRRARV (SEQ ID NO: 13), and WQPPRAR1 (SEQ ID NO: 14). See also Hersel et al., 24 Biomaterials 4285-415 (2003).

In aspects of this embodiment, a hydrogel comprises a molar ratio of amphiphilic peptide to silk fibroin of, e.g., about 100:1, about 90:1, about 80:1, about 70:1, about 60:1, about 50:1, about 40:1, about 30:1, about 20:1, about 10:1, about 7:1, about 5:1, about 3:1, about 1:1, about 1:3, about 1:5, about 1:7, about 1:10, about 1:20, about 1:30, about 1:40, about 1:50, about 1:60, about 1:70, about 1:80, or about 1:90, or about 1:100. In other aspects of this embodiment, a hydrogel comprises a molar ratio of amphiphilic peptide to silk fibroin of, e.g., at least 100:1, at least 90:1, at least 80:1, at least 70:1, at least 60:1, at least 50:1, at least 40:1, at least 30:1, at least 20:1, at least 10:1, at least 7:1, at least 5:1, at least 3:1, at least 1:1, at least 1:3, at least 1:5, at least 1:7, at least 1:10, at least 1:20, at least 1:30, at least 1:40, at least 1:50, at least 1:60, at least 1:70, at least 1:80, or at least 1:90, or at least 1:100. In yet other aspects of this embodiment, a hydrogel comprises a molar ratio of amphiphilic peptide to silk fibroin of, e.g., at most 100:1, at most 90:1, at most 80:1, at most 70:1, at most 60:1, at most 50:1, at most 40:1, at most 30:1, at most 20:1, at most 10:1, at most 7:1, at most 5:1, at most 3:1, at most 1:1, at most 1:3, at most 1:5, at most 1:7, at most 1:10, at most 1:20, at most 1:30, at most 1:40, at most 1:50, at most 1:60, at most 1:70, at most 1:80, or at most 1:90, or at most 1:100. In still other aspects of this embodiment, a hydrogel comprises a molar ratio of amphiphilic peptide to silk fibroin of, e.g., about 100:1 to about 1:100; about 90:1 to about 1:90; about 80:1 to about 1:80; about 70:1 to about 1:70; about 60:1 to about 1:60; about 50:1 to about 1:50; about 40:1 to about 1:40; about 30:1 to about 1:30; about 20:1 to about 1:20; about 10:1 to about 1:10; about 7:1 to about 1:7; about 5:1 to about 1:5; or about 3:1 to about 1:3.

The use of an amphiphilic peptide not only alters the protein structure characteristics of silk fibroin protein, but in so doing alters its resistance to proteolytic bioresorption in vitro. These alterations in proteolytic bioresorption resistance stem from aspects of the protein structure alteration as α-helix and random coil are typically thought to be less stable and therefore more susceptible to proteolytic bioresorption than β-sheet regions of silk. β-turn and β-strand regions of the hydrogel disclosed herein are most resistant to proteolytic bioresorption as opposed to regions of α-helixes and random coils. Through deliberate manipulation of this protein structure by means of controlled solution concentration and addition of enhancer factors (type, concentration, and driving gradient), gelation kinetics and resultant gel properties might be controlled to deliver optimal outcomes in terms of degradative and resultant biological behaviors. The impact of amphiphilic peptide addition to silk hydrogel in a silk hydrogel is evident upon examination of data obtained through implantation studies conducted in vivo, both subcutaneously in rats and intradermally in the dermis of guinea pigs. See Example 10.

Aspects of the present specification provide, in part, a hydrogel comprising a five-amino acid peptide "tail" capable of linking or conjugating a molecule X to a silk molecule or fibroin when the molecule X is attached to the tail. A molecule X is any entity, natural or synthetic, that can be useful and can be use in the context of silk hydrogels. As used herein, the term "linking" or "conjugating" in the context of molecule X refers to an indirect physical attachment of a molecule X to a silk fibroin via a third entity, the five-amino acid peptide "tail" being that entity. In one embodiment, the tail binds to silk fibroin by hydrophobic interaction to the silk fibroin. Alternatively, the "tail" binds the silk molecules by hydrogen bonding and/or covalent bonding. It is envisioned that the "tail" can bind silk fibroins by a combination of hydrophobic interactions, hydrogen bonds, and covalent bonds. By attaching a molecule X to a "tail" described herein, it is possible to indirectly link the molecule X to silk fibroin via the tail, and thus to the silk hydrogels described herein.

In one embodiment, the molecule X is attached to a tail at the carboxyl (COOH) end of the five-amino acid peptide. In another embodiment, the molecule X is attached to a tail at the amino (NH$_2$) end of the five-amino acid peptide.

In one embodiment, the five-amino acid peptide "tail" comprises hydrophobic and/or apolar (non polar) amino acid residues such as valine, leucine, isoleucine, phenylalanine, tryptophan, methionine, cysteine, alanine, tyrosine, serine, proline, histidine, threonine and glycine. Various combinations of hydrophobic and/or apolar amino acid residues are possible, for e.g. LLLLL (SEQ ID NO: 15), LLFFL (SEQ ID NO: 16), LFLWL (SEQ ID NO: 17), FLWLL (SEQ ID NO: 18) and LALGL (SEQ ID NO: 19). In other embodiments, the tail comprises any combination of the twenty standard conventional amino acid residues. In other embodiments, the tail comprises hydrophobic and/or apolar (non polar) and amino acids residues with hydrophobic side chains, e.g. arginine and lysine. As used herein, the term "comprising" or "comprises" means that other elements can also be present in addition to the defined elements presented. The use of "comprising" indicates inclusion rather than limitation.

In one embodiment, the five-amino acid peptide "tail" capable of linking or conjugating a molecule X to a silk molecule or fibroin when the molecule X is attached to the tail comprise more than five amino acid residues, e.g. six or seven hydrophobic and/or apolar amino acid residues, such as LLLLLL (SEQ ID NO: 20).

In one embodiment, the five-amino acid peptide "tail" comprises amino acid residues that are part hydrophobic (i.e. the part of the side-chain nearest to the protein main-chain), for e.g. arginine and lysine. In one embodiment, the part hydrophobic amino acid residues flank the five-amino acid peptide "tail" such as in RLLLLLR (SEQ ID NO: 21), KLLLLLR (SEQ ID NO: 22) and KLLLLLK (SEQ ID NO: 23).

In one embodiment, the five-amino acid peptide "tail" is separated from a molecule X by a spacer peptide. Spacer peptides should generally have non-polar amino acid residues, such as, glycine and proline. In one embodiment, the spacer comprises unnatural amino acid residues such as nor amino acids and keto-substituted amino acids. Such unnatural amino acid residues are well known to one skilled in the art. In one embodiment, the spacer peptide is attached to a tail at the carboxyl (COOH) end of the five-amino acid peptide. In another embodiment, the spacer is attached to a tail at the amino ($NH_2$) end of the five-amino acid peptide.

The length of the space peptide is variable. The spacer serves to link the molecule X and tail together and also to provide steric freedom to the molecule X, allowing for proper orientation of a molecule X (e.g. cell binding domains such as the RGD domain) and the correct interaction of the molecule X with cells in vivo. A spacer which is too short can prevent the molecule X from being properly functional (i.e., holding it too tight to the silk molecules and away from cells), a spacer which is too long can cause undesired effects as well (i.e., non-specific association of peptides or shortened efficacy from peptide due to spacer breakage). In one embodiment, the number of amino acid residues in a spacer can range from 1 to 300. In one embodiment, the spacer comprises a single amino acid residue, such as a G or a P. Examples of spacers with more amino acid residues are GSPGISGGGGGILE (SEQ ID NO: 24) and SGGGGKSSAPI (SEQ ID NO: 25).

In one embodiment, the molecule X is any biological molecule or fragment thereof. Examples biological molecules include but are not limited to growth factors, hormones, cytokines, chemokines, extracellular matrix compounds, osteogenic protein (OP), bone morphogenetic protein (BMP), growth and differentiation factor (GDF), transforming growth factor (TGF), epidermal growth factor (EGF), vascular endothelial growth factor (VEGF), interleukin (IL), platelet derived growth factor (PDGF), fibroblast growth factor (FGF), insulin-like growth factor (IGF), basic fibroblast growth factor (BFGF), fibroblast activation protein (FAP), disintegrin, metalloproteinase (ADAM), matrix metalloproteinase (MMP), connective tissue growth factor (CTGF), stromal derived growth factor (SDGF), keratinocyte growth factor (KGF), tumor necrosis factor (TNF), interferon (IFN), erythropoietin (EPO), hepatocyte growth factor (HGF), thrombopoietin (TPO), granulocyte colony stimulating factor (GCSF), granulocyte macrophage colony stimulating factor (GMCSF), myostatin (GDF-8), collagen, resilin, elastin, laminin, hyaluronic acid, decorin, actin, and tubulin. Examples fragments of biological molecules include but are not limited to known cell integrin binding domains including but not limited to RGD, KQAGDV (SEQ ID NO: 4), PHSRN (SEQ ID NO: 5), YIGSR (SEQ ID NO: 6), CDPGYIGSR (SEQ ID NO: 7), IKVAV (SEQ ID NO: 8), RNIAEIIKDI (SEQ ID NO: 9), YFQRYLI (SEQ ID NO: 10), PDSGR (SEQ ID NO: 11), FHRRIKA (SEQ ID NO: 12), PRRARV (SEQ ID NO: 13), and WQPPRAR1 (SEQ ID NO: 14).

In other embodiments, the molecule X is any recombinant, synthetic, or non-native polymeric compounds. Examples include but are not limited to chitin, poly-lactic acid (PLA), poly-glycolic acid (PGA), as tracers (e.g. radioisotopes), contrasting agents (e.g. imaging dyes), aptamers, avimers, peptides, nucleic acids, modified polysaccharide coatings, drugs (chemotherapy drugs), and recombinant antibodies or antibody-based moieties.

In one embodiment, the present specification provides a synthetic molecule having the formula: (molecule X)$_n$-(spacer peptide)$_{0-300}$-(tail)-$NH_2$ for linking with silk molecule or fibroin, wherein "n" is a whole integer ranging from 1-30, and wherein the amino acid residues of the spacer ranges from 0-300. Examples of such synthetic molecule capable for linking to silk molecule or fibroin are: GRGDIPASSKG$_4$SRL$_6$R—$NH_2$ (SEQ ID NO: 1), Ac-GdRGDIPASSKG$_4$SdRL$_6$dR-$NH_2$ (SEQ ID NO: 2), (VEGF)-(VEGF)-GSPGISGGGGGILEKLLLLLK-$NH_2$ (SEQ ID NO: 26), (HIV-C-peptide)$_3$-GSPGISGGGGGILE-KLALWLLR-$NH_2$ (SEQ ID NO: 27), (taxol)$_2$-GSPGISGGGGGILERLLLLR-$NH_2$ (SEQ ID NO: 28), and (EPO)$_2$-GSPGISGGGGGILERLLWLLR-$NH_2$ (SEQ ID NO: 29). When used in the context of the silk hydrogel described herein, the synthetic molecule of SEQ ID NO: 1 enable better tissue attachment of the hydrogel construct in vivo, the synthetic molecule of SEQ ID NO: 26 can promote blood vessel generation (neo-angiogenesis) in tissue engineered constructs, the synthetic molecule of SEQ ID NO: 28 can provide a slow release anti-HIV medication in the form of a transdermal delivery patch, the synthetic molecule of SEQ ID. NO: 28 can provide sustained dosage of anti-cancer drug in vivo, and the synthetic molecule of SEQ ID NO: 29 can provide a slow release EPO during cancer chemotherapy treatment.

Aspects of the present specification disclose, in part, a hydrogel comprising a synthetic molecule having the formula: (molecule X)$_n$-(spacer peptide)$_{0-300}$-(tail)-$NH_2$ or a synthetic molecule having the formula: (molecule X)$_n$-(spacer peptide)$_{0-300}$-(tail)-$NH_2$ and an amphiphilic peptide. In one embodiment, the amphiphilic peptide is 23RGD. In one embodiment, the present specification provides a method of conjugating a molecule X to a silk molecule or fibroin comprising mixing a synthetic molecule having the formula: (molecule X)$_n$-(spacer peptide)$_{0-300}$-(tail)-$NH_2$ with a silk molecule or fibroin or silk solution. Conjugation of individual peptide can be effected by a linkage via the N-terminal or the C-terminal of the peptide, resulting in an N-linked peptide oligomer or a C-linked peptide oligomer, respectively.

Methods of peptide synthesis are known to one skilled in the art, for example, the peptides described herein can be synthetically constructed by suitable known peptide polymerization techniques, such as exclusively solid phase techniques, partial solid-phase techniques, fragment condensation or classical solution couplings. For example, the disclosed peptides can be synthesized by the solid phase method using standard methods based on either t-butyloxycarbonyl (BOC) or 9-fluorenylmethoxy-carbonyl (FMOC) protecting groups. This methodology is described by G. B. Fields et al. in Synthetic Peptides: A User's Guide, W. M. Freeman & Company, New York, N.Y., pp. 77-183 (1992) and in the textbook "Solid-Phase Synthesis", Stewart & Young, Freemen & Company, San Francisco, 1969, and is exemplified by the disclosure of U.S. Pat. No. 4,105,603, issued Aug. 8, 1979. Classical solution synthesis is described in detail in "Methoden der Organischen Chemic (Houben-Weyl): Synthese von Peptiden", E. Wunsch (editor) (1974) Georg Thieme Verlag, Stuttgart West Germany. The fragment condensation method of synthesis is exemplified in U.S. Pat. No. 3,972,859. Other available syntheses are exemplified in U.S. Pat. No. 3,842,067, U.S. Pat. No. 3,872,925, issued Jan. 28, 1975, Merrifield B, Protein Science (1996), 5: 1947-1951; The chemical synthesis of proteins; Mutter M, Int J Pept Protein Res 1979 March; 13 (3): 274-7 Studies on the coupling rates in liquid-phase peptide synthesis using competition experiments; and Solid Phase Peptide Synthesis in the series Methods in Enzymology (Fields, G. B. (1997) Solid-Phase Peptide Synthesis. Academic Press, San Diego.#9830). The foregoing disclosures are incorporated herein by reference. Molecular DNA methods can also be used. The coding sequence of the short spacer can be constructed be annealing a complementary pair of primers. One of skill in the art can design and synthesize oligonucleotides that will code for the selected spacer.

Methods of linking peptides are also known in the art. The physical linking of the individual isolated peptides into oligomeric peptides as set forth herein, can be effected by chemical conjugation procedures well known in the art, such as by creating peptide linkages, use of condensation agents, and by employing well known bifunctional cross-linking reagents. The conjugation may be direct, which includes linkages not involving any intervening group, e.g., direct peptide linkages, or indirect, wherein the linkage contains an intervening moiety, such as a protein or peptide, e.g., plasma albumin, or other spacer molecule. For example, the linkage may be via a heterobifunctional or homobifunctional crosslinker, e.g., carbodiimide, glutaraldehyde, N-succinimidyl 3-(2-pyridyldithio)propionate (SPDP) and derivatives, bismaleimide, 4-(N-maleimidomethyl)cyclohexane-1-carboxylate, and the like.

Cross-linking can also be accomplished without exogenous cross-linkers by utilizing reactive groups on the molecules being conjugated. Methods for chemically cross-linking peptide molecules are generally known in the art, and a number of hetero- and homobifunctional agents are described in, e.g., U.S. Pat. Nos. 4,355,023, 4,657,853, 4,676,980, 4,925,921, and 4,970,156, and Immuno Technology Catalogue and Handbook, Pierce Chemical Co. (1989), each of which is incorporated herein by reference. Such conjugation, including cross-linking, should be performed so as not to substantially affect the desired function of the peptide oligomer or entity conjugated thereto, including therapeutic agents, and moieties capable of binding substances of interest.

It will be apparent to one skilled in the art that alternative linkers can be used to link peptides, for example the use of chemical protein crosslinkers. For example homobifunctional crosslinker such as disuccinimidyl-suberimidate-dihydrochloride; dimethyl-adipimidate-dihydrochloride; 1,5,-2,4dinitrobenzene or heterobifunctional crosslinkers such as N-hydroxysuccinimidyl 2,3-dibromopropionate; 1-ethyl-3-[3-dimethylaminopropyl]carbodiimide hydrochloride; and succinimidyl-4-[n-maleimidomethyl]-cyclohexane-1-carboxylate.

A composition disclosed herein is typically a biodegradable, bioerodible, and/or bioresorbable. In an embodiment, a silk fibroin hydrogel disclosed herein has a protein structure that makes the hydrogel resist biodegradation. In aspects of this embodiment, a hydrogel is resistant to biodegradation for, e.g., about 10 days, about 20 days, about 30 days, about 40 days, about 50 days, about 60 days, about 70 days, about 80 days, or about 90 days. In other aspects of this embodiment, a hydrogel is resistant to biodegradation for, e.g., at least 10 days, at least 20 days, at least 30 days, at least 40 days, at least 50 days, at least 60 days, at least 70 days, at least 80 days, or at least 90 days. In yet other aspects of this embodiment, a hydrogel is resistant to biodegradation for, e.g., about 10 days to about 30 days, about 20 days to about 50 days, about 40 days to about 60 days, about 50 days to about 80 days, or about 60 days to about 90 days.

In an embodiment, a silk fibroin hydrogel disclosed herein has a protein structure that makes the hydrogel resist bioerosion. In aspects of this embodiment, a hydrogel is resistant to bioerosion for, e.g., about 10 days, about 20 days, about 30 days, about 40 days, about 50 days, about 60 days, about 70 days, about 80 days, or about 90 days. In other aspects of this embodiment, a hydrogel is resistant to bioerosion for, e.g., at least 10 days, at least 20 days, at least 30 days, at least 40 days, at least 50 days, at least 60 days, at least 70 days, at least 80 days, or at least 90 days. In yet other aspects of this embodiment, a hydrogel is resistant to bioerosion for, e.g., about 10 days to about 30 days, about 20 days to about 50 days, about 40 days to about 60 days, about 50 days to about 80 days, or about 60 days to about 90 days.

In an embodiment, a silk fibroin hydrogel disclosed herein has a protein structure that makes the hydrogel resist bioresorption. In aspects of this embodiment, a hydrogel is resistant to bioresorption for, e.g., about 10 days, about 20 days, about 30 days, about 40 days, about 50 days, about 60 days, about 70 days, about 80 days, or about 90 days. In other aspects of this embodiment, a hydrogel is resistant to bioresorption for, e.g., at least 10 days, at least 20 days, at least 30 days, at least 40 days, at least 50 days, at least 60 days, at least 70 days, at least 80 days, or at least 90 days. In yet other aspects of this embodiment, a hydrogel is resistant to bioresorption for, e.g., about 10 days to about 30 days, about 20 days to about 50 days, about 40 days to about 60 days, about 50 days to about 80 days, or about 60 days to about 90 days.

In yet another embodiment, a silk fibroin hydrogel disclosed herein has a protein structure that substantially includes β-turn and β-strand regions. In aspects of this embodiment, a hydrogel has a protein structure including, e.g., about 10% β-turn and β-strand regions, about 20% β-turn and β-strand regions, about 30% β-turn and β-strand regions, about 40% β-turn and β-strand regions, about 50% β-turn and β-strand regions, about 60% β-turn and β-strand regions, about 70% β-turn and β-strand regions, about 80% β-turn and β-strand regions, about 90% β-turn and β-strand regions, or about 100% β-turn and β-strand regions. In other aspects of this embodiment, a hydrogel has a protein structure including, e.g., at least 10% β-turn and β-strand regions, at least 20% β-turn and β-strand regions, at least 30% β-turn and β-strand regions, at least 40% β-turn and β-strand regions, at least 50% β-turn and β-strand regions, at least 60% β-turn and β-strand regions, at least 70% β-turn and β-strand regions, at least 80% β-turn and β-strand regions, at least 90% β-turn and β-strand regions, or at least 95% β-turn and β-strand regions. In yet other aspects of this embodiment, a hydrogel has a protein structure including, e.g., about 10% to about 30% β-turn and β-strand regions, about 20% to about 40% β-turn and β-strand regions, about 30% to about 50% β-turn and β-strand regions, about 40% to about 60% β-turn and β-strand regions, about 50% to about 70% β-turn and β-strand regions, about 60% to about 80% β-turn and β-strand regions, about 70% to about 90% β-turn and β-strand regions, about 80% to about 100% β-turn and β-strand regions, about 10% to about 40% β-turn and β-strand regions, about 30% to about 60% β-turn and β-strand regions, about 50% to about 80% β-turn and β-strand regions, about 70% to about 100% β-turn and β-strand regions, about 40% to about 80% β-turn and β-strand regions, about 50% to about 90% β-turn and β-strand regions, about 60% to about 100% β-turn and β-strand regions, or about 50% to about 100% β-turn and β-strand regions.

In yet another embodiment, a silk fibroin hydrogel disclosed herein has a protein structure that is substantially-free of α-helix and random coil regions. In aspects of this embodiment, a hydrogel has a protein structure including, e.g., about 5% α-helix and random coil regions, about 10% α-helix and random coil regions, about 15% α-helix and random coil regions, about 20% α-helix and random coil regions, about 25% α-helix and random coil regions, about 30% α-helix and random coil regions, about 35% α-helix and random coil regions, about 40% α-helix and random coil regions, about 45% α-helix and random coil regions, or about 50% α-helix and random coil regions. In other aspects of this embodiment, a hydrogel has a protein structure including, e.g., at most 5% α-helix and random coil regions, at most 10% α-helix and random coil regions, at most 15% α-helix and random coil regions, at most 20% α-helix and random coil regions, at most 25% α-helix and random coil regions, at most 30% α-helix and random coil regions, at most 35% α-helix and random coil regions, at most 40% α-helix and random coil regions, at most 45% α-helix and random coil regions, or at most 50% α-helix and random coil regions. In yet other aspects of this embodiment, a hydrogel has a protein structure including, e.g., about 5% to about 10% α-helix and random coil regions, about 5% to about 15% α-helix and random coil regions, about 5% to about 20% α-helix and random coil regions, about 5% to about 25% α-helix and random coil regions, about 5% to about 30% α-helix and random coil regions, about 5% to about 40% α-helix and random coil regions, about 5% to about 50% α-helix and random coil regions, about 10% to about 20% α-helix and random coil regions, about 10% to about 30% α-helix and random coil regions, about 15% to about 25% α-helix and random coil regions, about 15% to about 30% α-helix and random coil regions, or about 15% to about 35% α-helix and random coil regions.

Aspects of the present specification provide, in part, a silk fibroin hydrogel having hardness. Hardness refers to various properties of an object in the solid phase that gives it high resistance to various kinds of shape change when force is applied. Hardness is measured using a durometer and is a unitless value that ranges from zero to 100. The ability or inability of a hydrogel to be easily compressed will affect its suitability for application in different tissue replacement roles, i.e., mechanical compliance as bone, fat, connective tissue. Hardness will also affect the ability of a hydrogel to be effectively comminuted, the reason being that a hard material may be more easily and consistently comminuted. Hardness will also affect extrudability, as a soft material may be more readily able to be slightly compressed during injection to pack with other particles or change shape to pass through a syringe barrel or needle.

In an embodiment, a silk fibroin hydrogel exhibits low hardness. In aspects of this embodiment, a silk fibroin hydrogel exhibits a hardness of, e.g., about 5, about 10, about 15, about 20, about 25, about 30, or about 35. In other aspects of this embodiment, a silk fibroin hydrogel exhibits a hardness of, e.g., at most 5, at most 10, at most 15, at most 20, at most 25, at most 30, or at most 35. In yet other aspects of this embodiment, a silk fibroin hydrogel exhibits a hardness of, e.g., about 5 to about 35, about 10 to about 35, about 15 to about 35, about 20 to about 35, or about 25 to about 35, about 5 to about 40, about 10 to about 40, about 15 to about 40, about 20 to about 40, about 25 to about 40, or about 30 to about 40.

In an embodiment, a silk fibroin hydrogel exhibits medium hardness. In aspects of this embodiment, a silk fibroin hydrogel exhibits a hardness of, e.g., about 40, about 45, about 50, about 55, or about 60. In other aspects of this embodiment, a silk fibroin hydrogel exhibits a hardness of, e.g., at least 40, at least 45, at least 50, at least 55, or at least 60. In yet other aspects of this embodiment, a silk fibroin hydrogel exhibits a hardness of, e.g., at most 40, at most 45, at most 50, at most 55, or at most 60. In still other aspects of this embodiment, a silk fibroin hydrogel exhibits a hardness of, e.g., about 35 to about 60, about 35 to about 55, about 35 to about 50, about 35 to about 45, about 40 to about 60, about 45 to about 60, about 50 to about 60, about 55 to about 60, about 40 to about 65, about 45 to about 65, about 50 to about 65, about 55 to about 65.

In another embodiment, a silk fibroin hydrogel exhibits high hardness. In aspects of this embodiment, a silk fibroin hydrogel exhibits a hardness of, e.g., about 65, about 70, about 75, about 80, about 85, about 90, about 95, or about 100. In other aspects of this embodiment, a silk fibroin hydrogel exhibits a hardness of, e.g., at least 65, at least 70, at least 75, at least 80, at least 85, at least 90, at least 95, or at least 100. In yet other aspects of this embodiment, a silk fibroin hydrogel exhibits a hardness of, e.g., about 65 to about 100, about 70 to about 100, about 75 to about 100, about 80 to about 100, about 85 to about 100, about 90 to about 100, about 65 to about 75, about 65 to about 80, about 65 to about 85, about 65 to about 90, about 65 to about 95, about 60 to about 75, about 60 to about 80, about 60 to about 85, about 60 to about 90, or about 60 to about 95.

In an embodiment, a silk fibroin hydrogel exhibits high resistant to deformation. In aspects of this embodiment, a silk fibroin hydrogel exhibits resistant to deformation of, e.g., about 100%, about 99%, about 98%, about 97%, about 96%, about 95%, about 94%, about 93%, about 92%, about 91%, about 90%, about 89%, about 88%, about 87%, about 86%, or about 85%. In other aspects of this embodiment, a silk fibroin hydrogel exhibits resistant to deformation of, e.g., at least 99%, at least 98%, at least 97%, at least 96%, at least 95%, at least 94%, at least 93%, at least 92%, at least 91%, at least 90%, at least 89%, at least 88%, at least 87%, at least 86%, or at least 85%. In yet other aspects of this embodiment, a silk fibroin hydrogel exhibits resistant to deformation of, e.g., at most 99%, at most 98%, at most 97%, at most 96%, at most 95%, at most 94%, at most 93%, at most 92%, at most 91%, at most 90%, at most 89%, at most 88%, at most 87%, at most 86%, or at most 85%. In still aspects of this embodiment, a silk fibroin hydrogel exhibits resistant to deformation of, e.g., about 85% to about 100%, about 87% to about 100%, about 90% to about 100%, about 93% to about 100%, about 95% to about 100%, or about 97% to about 100%.

A silk fibroin hydrogel exhibits an elastic modulus. Elastic modulus, or modulus of elasticity, refers to the ability of a hydrogel material to resists deformation, or, conversely, an object's tendency to be non-permanently deformed when a force is applied to it. The elastic modulus of an object is defined as the slope of its stress-strain curve in the elastic deformation region: λ=stress/strain, where λ is the elastic modulus in Pascal's; stress is the force causing the deformation divided by the area to which the force is applied; and strain is the ratio of the change caused by the stress to the original state of the object. Specifying how stresses are to be measured, including directions, allows for many types of elastic moduli to be defined. The three primary elastic moduli are tensile modulus, shear modulus, and bulk modulus.

Tensile modulus (E) or Young's modulus is an objects response to linear strain, or the tendency of an object to deform along an axis when opposing forces are applied along that axis. It is defined as the ratio of tensile stress to tensile strain. It is often referred to simply as the elastic modulus. The shear modulus or modulus of rigidity refers to an object's tendency to shear (the deformation of shape at constant volume) when acted upon by opposing forces. It is defined as shear stress over shear strain. The shear modulus is part of the derivation of viscosity. The shear modulus is concerned with the deformation of a solid when it experiences a force parallel to one of its surfaces while its opposite face experiences an opposing force (such as friction). The bulk modulus (K) describes volumetric elasticity or an object's resistance to uniform compression, and is the tendency of an object to deform in all directions when uniformly loaded in all directions. It is defined as volumetric stress over volumetric strain, and is the inverse of compressibility. The bulk modulus is an extension of Young's modulus to three dimensions.

In another embodiment, a silk fibroin hydrogel exhibits a tensile modulus. In aspects of this embodiment, a silk fibroin hydrogel exhibits a tensile modulus of, e.g., about 1 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 750 MPa, about 1 GPa, about 5 GPa, about 10 GPa, about 15 GPa, about 20 GPa, about 25 GPa, or about 30 GPa. In other aspects of this embodiment, a silk fibroin hydrogel exhibits a tensile modulus of, e.g., at least 1 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 750 MPa, at least 1 GPa, at least 5 GPa, at least 10 GPa, at least 15 GPa, at least 20 GPa, at least 25 GPa, or at least 30 GPa In yet other aspects of this embodiment, a silk fibroin hydrogel exhibits a tensile modulus of, e.g., about 1 MPa to about 30 MPa, about 10 MPa to about 50 MPa, about 25 MPa to about 75 MPa, about 50 MPa to about 100 MPa, about 100 MPa to about 300 MPa, about 200 MPa to about 400 MPa, about 300 MPa to about 500 MPa, about 100 MPa to about 500 MPa, about 250 MPa to about 750 MPa, about 500 MPa to about 1 GPa, about 1 GPa to about 30 GPa, about 10 GPa to about 30 GPa.

In another embodiment, a silk fibroin hydrogel exhibits shear modulus. In aspects of this embodiment, a silk fibroin hydrogel exhibits a shear modulus of, e.g., about 1 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 750 MPa, about 1 GPa, about 5 GPa, about 10 GPa, about 15 GPa, about 20 GPa, about 25 GPa, or about 30 GPa. In other aspects of this embodiment, a silk fibroin hydrogel exhibits a shear modulus of, e.g., at least 1 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 750 MPa, at least 1 GPa, at least 5 GPa, at least 10 GPa, at least 15 GPa, at least 20 GPa, at least 25 GPa, or at least 30 GPa In yet other aspects of this embodiment, a silk fibroin hydrogel exhibits a shear modulus of, e.g., about 1 MPa to about 30 MPa, about 10 MPa to about 50 MPa, about 25 MPa to about 75 MPa, about 50 MPa to about 100 MPa, about 100 MPa to about 300 MPa, about 200 MPa to about 400 MPa, about 300 MPa to about 500 MPa, about 100 MPa to about 500 MPa, about 250 MPa to about 750 MPa, about 500 MPa to about 1 GPa, about 1 GPa to about 30 GPa, about 10 GPa to about 30 GPa.

In another embodiment, a silk fibroin hydrogel exhibits a bulk modulus. In aspects of this embodiment, a silk fibroin hydrogel exhibits a bulk modulus of, e.g., about 5 GPa, about 6 GPa, about 7 GPa, about 8 GPa, about 9 GPa, about 10 GPa, about 15 GPa, about 20 GPa, about 25 GPa, about 30 GPa, about 35 GPa, about 40 GPa, about 45 GPa, about 50 GPa, about 60 GPa, about 70 GPa, about 80 GPa, about 90 GPa, about 100 GPa. In other aspects of this embodiment, a silk fibroin hydrogel exhibits a bulk modulus of, e.g., at least 5 GPa, at least 6 GPa, at least 7 GPa, at least 8 GPa, at least 9 GPa, at least 10 GPa, at least 15 GPa, at least 20 GPa, at least 25 GPa, at least 30 GPa, at least 35 GPa, at least 40 GPa, at least 45 GPa, at least 50 GPa, at least 60 GPa, at least 70 GPa, at least 80 GPa, at least 90 GPa, at least 100 GPa. In yet other aspects of this embodiment, a silk fibroin hydrogel exhibits a bulk modulus of, e.g., about 5 GPa to about 50 GPa, about 5 GPa to about 100 GPa, about 10 GPa to about 50 GPa, about 10 GPa to about 100 GPa, or about 50 GPa to about 100 GPa.

A silk fibroin hydrogel exhibits high tensile strength. Tensile strength has three different definitional points of stress maxima. Yield strength refers to the stress at which material strain changes from elastic deformation to plastic deformation, causing it to deform permanently. Ultimate strength refers to the maximum stress a material can withstand when subjected to tension, compression or shearing. It is the maximum stress on the stress-strain curve. Breaking strength refers to the stress coordinate on the stress-strain curve at the point of rupture, or when the material pulls apart.

In another embodiment, a silk fibroin hydrogel exhibits high yield strength relative to other polymer classes. In aspects of this embodiment, a silk fibroin hydrogel exhibits a yield strength of, e.g., about 0.1 MPa, about 0.5 MPa, about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa. In other aspects of this embodiment, a silk fibroin hydrogel exhibits a yield strength of, e.g., at least 0.1 MPa, at least 0.5 MPa, at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa. In yet other aspects of this embodiment, a silk fibroin hydrogel exhibits a yield strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a silk fibroin hydrogel exhibits a yield strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 10 MPa to about 200 MPa, about 10 MPa to about 300 MPa, or about 100 MPa to about 300 MPa.

In another embodiment, a silk fibroin hydrogel exhibits high ultimate strength. In aspects of this embodiment, a silk fibroin hydrogel exhibits an ultimate strength of, e.g., about 0.1 MPa, about 0.5 MPa, about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa. In other aspects of this embodiment, a silk fibroin hydrogel exhibits an ultimate strength of, e.g., at least 0.1 MPa, at least 0.5 MPa, at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa. In yet other aspects of this embodiment, a silk fibroin hydrogel exhibits an ultimate strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a silk fibroin hydrogel exhibits an ultimate strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 10 MPa to about 200 MPa, about 10 MPa to about 300 MPa, or about 100 MPa to about 300 MPa.

In another embodiment, a silk fibroin hydrogel exhibits high breaking strength. In aspects of this embodiment, a silk fibroin hydrogel exhibits a breaking strength of, e.g., about 0.1 MPa, about 0.5 MPa, about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa. In other aspects of this embodiment, a silk fibroin hydrogel exhibits a breaking strength of, e.g., at least 0.1 MPa, at least 0.5 MPa, at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa. In yet other aspects of this embodiment, a silk fibroin hydrogel exhibits a breaking strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a silk fibroin hydrogel exhibits a breaking strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 10 MPa to about 200 MPa, about 10 MPa to about 300 MPa, or about 100 MPa to about 300 MPa.

Aspects of the present specification provide, in part, a silk fibroin hydrogel having a transparency and/or translucency. Transparency (also called pellucidity or diaphaneity) is the physical property of allowing light to pass through a material, whereas translucency (also called translucence or translucidity) only allows light to pass through diffusely. The opposite property is opacity. Transparent materials are clear, while translucent ones cannot be seen through clearly. The silk fibroin hydrogels disclosed herein may, or may not, exhibit optical properties such as transparency and translucency. In certain cases, e.g., superficial line filling, it would be an advantage to have an opaque hydrogel. In other cases such as development of a lens or a "humor" for filling the eye, it would be an advantage to have a translucent hydrogel. These properties could be modified by affecting the structural distribution of the hydrogel material. Factors used to control a hydrogel's optical properties include, without limitation, silk fibroin concentration, gel crystallinity, and hydrogel homogeneity.

When light encounters a material, it can interact with it in several different ways. These interactions depend on the nature of the light (its wavelength, frequency, energy, etc.) and the nature of the material. Light waves interact with an object by some combination of reflection, and transmittance with refraction. As such, an optically transparent material allows much of the light that falls on it to be transmitted, with little light being reflected. Materials which do not allow the transmission of light are called optically opaque or simply opaque.

In an embodiment, a silk fibroin hydrogel is optically transparent. In aspects of this embodiment, a silk fibroin hydrogel transmits, e.g., about 75% of the light, about 80% of the light, about 85% of the light, about 90% of the light, about 95% of the light, or about 100% of the light. In other aspects of this embodiment, a silk fibroin hydrogel transmits, e.g., at least 75% of the light, at least 80% of the light, at least 85% of the light, at least 90% of the light, or at least 95% of the light. In yet other aspects of this embodiment, a silk fibroin hydrogel transmits, e.g., about 75% to about 100% of the light, about 80% to about 100% of the light, about 85% to about 100% of the light, about 90% to about 100% of the light, or about 95% to about 100% of the light.

In another embodiment, a silk fibroin hydrogel is optically opaque. In aspects of this embodiment, a silk fibroin hydrogel transmits, e.g., about 5% of the light, about 10% of the light, about 15% of the light, about 20% of the light, about 25% of the light, about 30% of the light, about 35% of the light, about 40% of the light, about 45% of the light, about 50% of the light, about 55% of the light, about 60% of the light, about 65% of the light, or about 70% of the light. In other aspects of this embodiment, a silk fibroin hydrogel transmits, e.g., at most 5% of the light, at most 10% of the light, at most 15% of the light, at most 20% of the light, at most 25% of the light, at most 30% of the light, at most 35% of the light, at most 40% of the light, at most 45% of the light, at most 50% of the light, at most 55% of the light, at most 60% of the light, at most 65% of the light, at most 70% of the light, or at most 75% of the light. In other aspects of this embodiment, a silk fibroin hydrogel transmits, e.g., about 5% to about 15%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 5% to about 65%, about 5% to about 70%, about 5% to about 75%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 15% to about 75%, about 25% to about 35%, about 25% to about 40%, about 25% to about 45%, about 25% to about 50%, about 25% to about 55%, about 25% to about 60%, about 25% to about 65%, about 25% to about 70%, or about 25% to about 75%, of the light.

In an embodiment, a silk fibroin hydrogel is optically translucent. In aspects of this embodiment, a silk fibroin hydrogel diffusely transmits, e.g., about 75% of the light, about 80% of the light, about 85% of the light, about 90% of the light, about 95% of the light, or about 100% of the light. In other aspects of this embodiment, a silk fibroin hydrogel diffusely transmits, e.g., at least 75% of the light, at least 80% of the light, at least 85% of the light, at least 90% of the light, or at least 95% of the light. In yet other aspects of this embodiment, a silk fibroin hydrogel diffusely transmits, e.g., about 75% to about 100% of the light, about 80% to about 100% of the light, about 85% to about 100% of the light, about 90% to about 100% of the light, or about 95% to about 100% of the light.

After formation of a hydrogel described herein, the hydrogel can further processed. For example, to remove enhancer species and become a more complete, the formed hydrogel may be leeched against a solvent, such as, e.g., water, under ambient temperature and pressure conditions for three days with five changes of water. The hydrogel may be leeched against ultra-pure water of a volume at least 100-times that of the gel. More specifically, for example, the gels may be placed in a bulk of purified water and the rinse changed at hours 12, 24 and 48 with 15 mL gel per 1.5 L water. The number of rinses and volume ratios involved may be altered so long as the resultant hydrogel is substantially free of residual gelation enhancer.

A hydrogel may be further processed by pulverizing the hydrogel into particles and mixed with a carrier phase such as, e.g., water or a saline solution to form an injectable or topical substance like a solution, oil, lotion, gel, ointment, cream, slurry, salve, or paste. A hydrogel may be milled to a particle size from about 0.1 μm to about 1000 μm in diameter, such as 15 μm to 30 μm. Saline is then added as a carrier phase by first determining the bulk volume of a hydrogel, then vigorously pulverizing the hydrogel into particles while incorporating an appropriate volume of saline to achieve a desired carrier to hydrogel particle ratio. For example, hydrogel milling may be accomplished by means of a forced sieving of bulk hydrogel through a series of stainless steel cloth sieves of decreasing pore sizes. In another example, a hydrogel may be loaded into a syringe and pulverized with a spatula to a fine paste with saline. In another example, a hydrogel may be comminuted into particles in a range of 0.5 to 2 μm diameter using a planetary ball mill and appropriate grinding media.

A composition disclosed herein may be formulated using material processing constraints such as silk concentration and saline concentration to tailor material longevity in vivo. In one example, a silk hydrogel might be tailored for a persistence of five weeks to six weeks in vivo by using a 1%-3% (w/v) silk gel with 25%-50% (v/v) saline carrier. In another example, a silk hydrogel might be tailored for a persistence of two months to three months in vivo by using a 3%-5% (w/v) silk gel with 20%-40% (v/v) saline. In another example, a silk hydrogel might be tailored for a persistence of 5-6 months by using 4-6% (w/v) silk gel with 20-40% (v/v) saline. In another example, a silk hydrogel might be tailored for a persistence of 7-10 months by using a 6-8% (w/v) silk gel with 20-30% (v/v) saline. The persistence of these materials might also be increased or decreased by increasing or decreasing particle size respectively.

Gel emulsion saline content and gel silk concentration could be used to modify the mechanical profile of the silk gel materials for particular applications. For example, a gel emulsion of about 1% (w/v) to about 5% (w/v) silk gel concentration with 5%-95% lubricant (e.g., 5%-95% (w/v) saline/PBS) may be useful as a dermal filler, bulking agent, camouflage agent, intramuscular or sub-Q filler, or pharmaceutical delivery vector. A gel emulsion of, for example, about 5% (w/v) to about 8% (w/v) silk gel concentration with 0% to about 30% lubricant fluid may be useful in bone defects or cartilage defects.

Aspects of the present specification provide, in part, a composition comprising a hydrogel comprising a matrix polymer. The compositions disclosed herein can further comprise a hydrogel comprising one or more matrix polymers in addition to hydrogel particles comprising silk fibroin, or a hydrogel comprising one or more matrix polymers and silk fibroin. As used herein, the term "matrix polymer" refers to a polymer that can become part of and/or function as an extracellular matrix polymer and pharmaceutically acceptable salts thereof. Non-limiting examples of a matrix polymer include a glycosaminoglycan like chondroitin sulfate, dermatan sulfate, keratan sulfate, hyaluronan; a lubricin; a polysaccharide, and an elastic protein (like silk protein, resilin, resilin-like polypeptides (RLPs), elastin (including tropoelastin, fibrillin and fibullin), elastin-like polypeptides (ELPs), silk protein-elastin-like polypeptides (SELPs), gluten (including gliadin and glutenin), abductin, byssus, and collagen. Non-limiting examples of a pharmaceutically acceptable salt of a matrix polymer includes sodium salts, potassium salts, magnesium salts, calcium salts, and combinations thereof. Matrix polymers useful in the compositions and methods disclosed herein are described in, e.g., Piron and Tholin, Polysaccharide Crosslinking, Hydrogel Preparation, Resulting Polysaccharides(s) and Hydrogel(s), uses Thereof, U.S. Patent Publication 2003/0148995; Lebreton, Cross-Linking of Low and High Molecular Weight Polysaccharides Preparation of Injectable Monophase Hydrogels; Lebreton, Viscoelastic Solutions Containing Sodium Hyaluronate and Hydroxypropyl Methyl Cellulose, Preparation and Uses, U.S. Patent Publication 2008/0089918; Lebreton, Hyaluronic Acid-Based Gels Including Lidocaine, U.S. Patent Publication 2010/0028438; and Polysaccharides and Hydrogels thus Obtained, U.S. Patent Publication 2006/0194758; and Di Napoli, Composition and Method for Intradermal Soft Tissue Augmentation, International Patent Publication WO 2004/073759, each of which is hereby incorporated by reference in its entirety.

Aspects of the present specification provide, in part, a composition comprising a hydrogel comprising an elastic protein. As used herein, the term "elastic protein" is synonymous with "bioelastomer" and refers to a polypeptide possessing rubber-like elasticity. An elastic protein can undergo high deformation without rupture, storing the energy involved in deformation and then returning to its original state when the stress is removed. The latter phase is passive and returns all, or nearly all, of the energy used in deformation. As such, an elastic protein has high resilience in that the polypeptide can be deformed reversibly without little loss of energy. Additionally, an elastic protein can be deformed to large strains with little force, and/or has low stiffness in that the polypeptide can be stretched. In general, properties useful to characterize elastic protein include stiffness, as evaluated by the modulus of elasticity ($E_{init}$, $Nm^{-2}$); strength, as evaluated by the stress at fracture ($\sigma_{max, Nm}^{-2}$); toughness, as evaluated by the energy to break work of fracture (Jm$^{-3}$, Jm$^{-2}$); extensibility, as evaluated by the strain at fracture ($\epsilon_{max}$, no units); spring efficiency, as evaluated by resilience (%); durability, as evaluated by lifetime fatigue (s to failure or cycles of failure); and spring capacity, as evaluated by energy storage capacity ($W_{out}$, Jkg$^{-1}$). For example, elastic proteins like elastin and resilin have a combination of high resilience, large strains and low stiffness is characteristic of rubber-like proteins that function in the storage of elastic-strain energy. Other elastic proteins, like collagens, provide exceptional energy storage capacity but are not very stretchy. Mussel byssus threads and spider dragline silks are also elastic proteins because they are remarkably stretchy, in spite of their considerable strength, low resilience, and stiffness. The silk fibroin disclosed herein is another elastic protein.

Non-limiting examples of elastic proteins include silk proteins (including silk fibroin disclosed herein), resilin, resilin-like polypeptides (RLPs), elastin (including tropoelastin, fibrillin and fibullin), elastin-like polypeptides (ELPs), gluten (including gliadin and glutenin), abductin, byssus, and collagen. In general, elastic proteins have at least one domain containing elastic repeat motifs and another non-elastic domain where crosslinks can be formed. See, e.g., Tatham and Shewry, Comparative Structures and Properties of Elastic Proteins, Phil. Trans. R. Soc. Lond. B 357: 229-234 (2002), which is hereby incorporated by reference in its entirety. However, both resilin and abductin are exceptions since crosslinking can occur within the elastic repeat motif.

Resilin is found in specialized regions of the cuticle of most insects, providing low stiffness, high strain and efficient energy storage; it is best known for its roles in insect flight and the remarkable jumping ability of fleas and spittle bugs. It has no regular structure but its randomly coiled chains are crosslinked by di- and tri-tyrosine links at the right spacing to confer elasticity. Resilin must last for the lifetime of adult insects and must therefore operate for hundreds of millions of extension and contraction; its elastic efficiency ensures performance over the insect's lifetime. Resilin exhibits unusual elastomeric behavior only when swollen in polar solvents such as water. The soluble precursor of resilin is proresilin. Proresilin is about 600 amino acids in length and has an amino-terminal domain comprising one type of elastic repeat motifs, a central non-repetitive domain, and an amino-terminal domain comprising another type of elastic repeat motifs. In insects, proresilin is secreted in the subcuticular space where it undergoes rapid crosslinking at tyrosine residues, through di- and trityrosine crosslink formations. Crosslinking appears to involve enzymatic reactions involving peroxidases. Exemplary resilin amino acid sequences include SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, or SEQ ID NO: 50.

Resilin fragments comprising elastic repeat motifs as well as fragments comprising the amino acid segment encoded by first exon produce resilin proteins useful as compositions and in the methods disclosed herein. Resilin, and resilin fragments useful to the compositions and methods disclosed herein, can be produced recombinantly by expressing a genetic construct encoding this protein in a standard expression system like a bacterial, yeast, insect or mammalian expression system and purifying the resulting resilin using routine procedures. Such expression constructs encoding resilin and functional resilin fragments and purification methods are described in, e.g., Elvin, et al., Synthesis and Properties of Crosslinked Recombinant Proresilin, Nature 437: 999-1002 (2005); Lyons, et al, Design and Facile Production of Recombinant Resilin-Like Polypeptides: Gene construction and a Rapid Protein Purification Method, Protein Eng. Des. Sel. 20: 25-32 (2007); Nairn, et al., A Synthetic Resilin is Largely Unstructured, Biophys. J. 95: 3358-3365 (2008), each of which is incorporated by reference in its entirety. Resilin can be crosslinked using standard procedures, like rapid photochemical, to produce a resilin hydrogel. Such a resilin hydrogel can be processed to contain additional components such as, e.g., amphiphilic and synthetic peptides disclosed herein, protease cleavage sites to facilitate biodegradation, and used in a manner and in the methods as disclosed herein for a silk fibroin hydrogel.

Resilin-like polypeptides (RLPs) are derived from an elastic repeat motif found within resilin and can be 5 to 1,500 amino acids in length. The most common elastic repeat motifs include YGAP (SEQ ID NO. 51), AQTPSSQYGAP (SEQ ID NO. 52), GGRPSDSYGAPGGGN (SEQ ID NO. 53), GYSGGRPGGQDLG (SEQ ID NO. 54), PGGGN (SEQ ID NO. 55), PGGGNGGRP (SEQ ID NO. 56), SDTYGAPGGGNGGRP (SEQ ID NO. 57), and PGGGNGGRPSDTYGAPGGGNGGRP (SEQ ID NO. 58). In one embodiment, the RLP has the general formula of (SEQ ID NO. 51)$_m$, (SEQ ID NO. 52)$_m$, (SEQ ID NO. 53)$_m$, (SEQ ID NO. 54)$_m$, (SEQ ID NO. 55)$_m$, (SEQ ID NO. 56)$_m$, (SEQ ID NO. 57)$_m$, and (SEQ ID NO. 58)$_m$, or any combination thereof, where m is the number of repeats comprising the RLP. In an aspect of this embodiment, m is 0-200. RLPs comprising these elastic repeat motifs exhibit properties similar to resilin. RLPs can be designed at the molecular level and genetically synthesized to add unique properties that can be introduced by incorporating other biologically active peptide sequences. As such, RLP hydrogels can be formed by crosslinking using a variety of methods including, without limitation, irradiation, photoinitiation, amine-reactive chemical crosslinking and enzymatic crosslinking. Such an RLP hydrogel can be processed to contain additional components such as, e.g., amphiphilic and synthetic peptides disclosed herein, protease cleavage sites to facilitate biodegradation, and used in a manner and in the methods as disclosed herein for a silk fibroin hydrogel. Exemplary RLP amino acid sequences include SEQ ID NO. 59, SEQ ID NO. 60, and SEQ ID NO. 61. Other RLPs are described in, e.g., Elvin, Bioelastomers, U.S. Patent Publication 2007/0099231 and Elvin, Synthetic Bioelastomers, U.S. Patent Publication 2007/0275408, each of which is hereby incorporated by reference in its entirety.

One of the most abundant extracellular matrix proteins, elastin is an insoluble crosslinked polymer that forms massive complex arrays. Elastin is composed of monomeric subunits of a soluble precursor called tropoelastin that has a molecular weight of about 66-70 kDa. Tropoelastin is about 760 amino acids in length and composed of alternating hydrophobic domains rich in glycine, valine and praline residues; and hydrophilic domains rich in lysine and arginine residues. Elastin is formed and stabilized by crosslinking tropoelastin monomers at lysine residues, in a reaction catalyzed by lysyl oxidase or transglutaminase. Exemplary tropoelastin amino acid sequences include SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, or SEQ ID NO: 82. Like proresilin, tropoelastin can be recombinantly made by expressing a genetic construct encoding this protein in a standard expression system and purifying the resulting tropoelastin using routine procedures. Such expression constructs encoding tropoelastin and functional tropoelastin fragments and purification methods are described in, e.g., Urry, et al., Elastic Protein-Based Polymers in Soft Tissue Augmentation and Generation, J. Biomater. Sci. Polym. Ed. 9: 1015-1048 (1998), which is hereby incorporated by reference in its entirety. These monomeric subunits can then be enzymatically crosslinked using lysyl oxidase or transglutaminase to form an elastin hydrogel. See, e.g., Betre, et al., Characterization of a Genetically-Engineered Elastin-Like Polypeptide for Cartilaginous Tissue Repair, Biomolecules 3: 910-916 (2003); Ong, Epitope-Tagging for Tracking Elastin-Like Polypeptides, Biomaterials 27: 1930-1935 (2006); Strokowski and Woodhouse, Development and Characterization of Novel Cross-Linked Bioelastomeric Materials, J. Biomater. Sci. Polym. Ed. 19: 785-799 (2008), each of which is incorporated by reference in its entirety. Such a elastin hydrogel can be processed to contain additional components such as, e.g., amphiphilic and synthetic peptides disclosed herein, protease cleavage sites to facilitate biodegradation, and used in a manner and in the methods as disclosed herein for a silk fibroin hydrogel.

Elastin-like polypeptides (ELPs) can be 5 to 1,500 amino acids in length and are generally made from an elastic repeat motif found within a hydrophobic domain of tropoelastin. See, e.g., Banta, et al., *Protein Engineering in the Development of Functional Hydrogels*, Annu. Rev. Biomed. Eng. 12: 167-186 (2010), which is hereby incorporated by reference in its entirety. The most common elastic motif has the amino acid sequence VPGXG (SEQ ID NO: 83), where X can be any amino acid other than proline. However, other elastic repeat motifs include KGGVG (SEQ ID NO: 84), LGGVG (SEQ ID NO: 85), LGAGGAG (SEQ ID NO: 86), and LGAGGAGVL (SEQ ID NO: 87), where m is the number of repeats comprising the ELP. Any combination of these elastin elastic repeat motifs can be used to design an ELP. In one embodiment, the ELP has the general formula of (SEQ ID NO: 83)$_m$, (SEQ ID NO: 84)$_m$, (SEQ ID NO: 85)$_m$, (SEQ ID NO: 86)$_m$, and (SEQ ID NO: 87)$_m$, or any combination thereof, where m is the number of repeats comprising the ELP. In an aspect of this embodiment, m is 0-200. In an aspect of this embodiment, an ELP has the formula (m) (SEQ ID NO: 88) (SEQ ID NO: 83)$_m$WP, where X is Valine, Alanine, or Glycine in a ratio of 5:2:3 and m is 1-200. In another aspect of this embodiment, an ELP has the formula (m) (SEQ ID NO: 88) (SEQ ID NO: 83)$_m$WP, where X is Valine, Alanine, or Glycine in a ratio of 1:8:7 and m is 1-200. In yet another aspect of this embodiment, an ELP has the formula (m) (SEQ ID NO: 88) (SEQ ID NO: 83)$_m$WP, where X is Valine, Isoleucine, or Glutamine in a ratio of 1:3:1 and m is 1-200. ELPs comprising these repeating motifs exhibit elastin-like properties. Exemplary ELP amino acid sequences include SEQ ID NO: 89, SEQ ID NO: 90, and SEQ ID NO: 91. Other ELPs are described in, e.g., Masters, Protein Matrix Materials, Devices and Methods of Making and Using Thereof, U.S. Pat. No. 7,662,409; Chaikof, et al., Native Protein Mimetic Fibers, Fiber Networks and Fabrics for Medical Use, U.S. Patent Publication 2004/0110439, each of which is hereby incorporated by reference in its entirety.

ELPs are highly soluble in an aqueous solution below their transition temperature ($T_t$), but aggregate rapidly above their $T_t$ in a process called inverse phase transition. ELPs are good candidates for chemical crosslinking because a chemically active amino acid, like lysine or glutamine, can be easily to incorporate into the X site of the repeating motif. In addition, because ELPs can be designed at the molecular level and genetically synthesized, unique properties can be introduced by incorporating other biologically active peptide sequences. As such, ELP hydrogels can be formed by irradiation, photoinitiation, amine-reactive chemical crosslinking and enzymatic crosslinking. Like tropoelastin, ELPs can be recombinantly made by expressing a genetic construct encoding this protein in a standard expression system and purifying the resulting tropoelastin using routine procedures. Such ELPs, expression constructs encoding ELPs purification methods, and crosslinking procedures are described in, e.g., Urry, et al. Elastic protein-based polymers in soft tissue augmentation and generation, J. Biomater. Sci. Polym. Ed. 9(10): 1015-1048 (1998); Betre, et al., Characterization of a genetically engineered elastin-like polypeptide for cartilaginous tissue repair, Biomacromolecules 3(5): 910-916 (2002); Haider, et al., Molecular engineering of silk elastin-like polymers for matrix-mediated gene delivery: biosynthesis and characterization, Mol. Pharm. 2(2): 139-150 (2005); McHale, et al., Synthesis and in vitro evaluation of enzymatically crosslinked elastin-like polypeptide gels for cartilaginous tissue repair, Tissue Eng. 11(11-12): 1768-1779 (2005); Srokowski and Woodhouse, Development and characterisation of novel cross-linked bio-elastomeric materials, J. Biomater. Sci. Polym. Ed. 19(6): 785-799 (2008); and MacEwan and Chilkoti, Elastin-Like Polypeptides: Biomedical Applications of Tunable Biopolymers, Peptide Sci. 94(1): 60-77 (2010), each of which is hereby incorporated by reference in its entirety. Such an ELP hydrogel can be processed to contain additional components such as, e.g., amphiphilic and synthetic peptides disclosed herein, protease cleavage sites to facilitate biodegradation, and used in a manner and in the methods as disclosed herein for a silk fibroin hydrogel.

Silk-elastin-like polypeptides (SELPs) comprise tandem repeats of silk-like elastic repeat motifs and elastin elastic repeat motifs. See, e.g., Haider, et al., Molecular Engineering of Silk Elastin-like Polymers for Matrix-Mediated Gene Delivery Biosynthesis and Characterization, Mol. Pharmaceutics. 2(2): 139-150 (2005), which is hereby incorporated by reference in its entirety. The most common elastic motif from silk proteins has the amino acid sequence (GAGAGS)$_m$, (SEQ ID NO: 95), where m is the number of repeats comprising the SELP, whereas elastic motif from elastins are as disclosed herein. Other elastic motifs from silk proteins useful in designing a SELP include, without limitation, GAAGY (SEQ ID NO: 96), AGAGAGPEG (SEQ ID NO: 97), AGAGAGEG (SEQ ID NO: 98), GAGAGSGAAG-GAGAGSGAGAGSGAGAGSGAGAGS GAGAGS-GAGAGSGAGAGSGAGAGSY (SEQ ID NO: 99), and YGGLGSQGAGRGG (SEQ ID NO: 100). By combining the silk and elastin elastic motifs in various ratios and sequences, it is possible to produce a variety of SELPs with diverse material properties. The formation of hydrogen binds between the silk elastic motifs appears to be the primary driving force behind gelation. The inclusion of elastin elastic motifs increases flexibility and aqueous solubility of the SELP. Exemplary SELP amino acid sequences include SEQ ID NO: 101, SEQ ID NO: 102, SEQ ID NO: 103, and SEQ ID NO: 104. Other SELPs as described in, e.g., Masters, Protein Matrix Materials, Devices and Methods of Making and Using Thereof, U.S. Pat. No. 7,662,409; Cappello, Synthetic Protein as Implantables, U.S. Pat. No. 5,606,019, Kumar, et al., Controlled Release of Active Agents Utilizing Repeat Sequence Protein Polymers, U.S. Patent Publication 2004/0228913, Kumar, et al., Use of Repeat Sequence Protein Polymers in Personal Care Compositions, U.S. Patent Publication 2005/0142094, Collier, et al., Repeat Sequence Protein Polymer Active Ingredient Conjugates, Methods and Uses, U.S. Patent Publication 2006/0153791, each of which is hereby incorporated by reference in its entirety.

SELPs are good candidates for chemical crosslinking because a chemically active amino acid, like lysine or glutamine, can be easily to incorporate into the X site of the repeating elastin elastic motif. In addition, because SELPs can be designed at the molecular level and genetically synthesized, unique properties can be introduced by incorporating other biologically active peptide sequences. As such, ELP hydrogels can be formed by irradiation, photoinitiation, amine-reactive chemical crosslinking and enzymatic crosslinking. Like tropoelastin, SELPs can be recombinantly made by expressing a genetic construct encoding this protein in a standard expression system and purifying the resulting tropoelastin using routine procedures. SELPs can be crosslinked using standard procedures, like rapid photochemical, to produce a SELP hydrogel. Such a SELP hydrogel can be processed to contain additional components such as, e.g., amphiphilic and synthetic peptides disclosed herein, protease cleavage sites to facilitate biodegradation, and used in a manner and in the methods as disclosed herein for a silk fibroin hydrogel.

Abductin is a rubber-like protein from the internal triangular hinge ligament of bivalve mollusks, acting as an elastic pivot that antagonizes the action of the adductor muscle. Abductin is an about 136 residue polypeptide comprising two domains. An alanine-rich amino-terminal domain of 20 residues in length contains two tyrosine residues believed to be involved in crosslinking. The second domain comprises 11 glycine-methionine-rich decapeptide repeats. This 10 amino acid elastic repeat motif has the acid sequence GGFG-GMGGGX (SEQ ID NO: 105), where X is any amino acid. Exemplary Abductin amino acid sequences include SEQ ID NO: 106, SEQ ID NO: 107, SEQ ID NO: 108, and SEQ ID NO: 109.

Gluten comprises two proteins, gliadin and glutenin that exist, conjoined with starch, in the endosperms of some grass-related grains, notably wheat, rye, and barley. Gliadins are glycoprotein present in wheat and several other cereals within the grass genus *Triticum*. Gliadins are prolamins that are slightly soluble in ethanol, and are separated on the basis of electrophoretic mobility and isoelectric focusing, with α-/β-gliadins, γ-gliadins, and ω-gliadin. Exemplary gliadin amino acid sequences include SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, and SEQ ID NO: 140.

Glutenin consists of 20% High-Molecular-Weight (HMW) subunits, which are relatively low in sulfur and 80% are Low-Molecular-Weight (LMW) subunits and are high in sulfur. The HMW subunit is about 825 amino acids in length and comprises a large central repetitive domain comprising hexapeptide PGQGQQ (SEQ ID NO: 141), nonapeptide GYYPTSPQQ (SEQ ID NO: 142), and tripeptide GQQ elastic repeat motifs. Because it is insoluble in water, gluten can be obtained by simply washing slurry of flour in water by stirring vigorously to dissolve the associated starch. The resulting gummy mass, which is about 70% to about 80% gluten, may then be centrifuged to collect the gluten. If a saline solution is used instead of water a purer gluten fraction is obtained. Gluten is also commercially available. Exemplary gliadin amino acid sequences include SEQ ID NO: 143.

Byssus is a major protein component present in the byssal threads used to attach mussels to hard surfaces in water. One form of byssus, Col-P comprises a central collagen-like domain of about 430 amino acids flanked by an amino-terminal elastic domain of about 100 amino acids and by a carboxyl-terminal elastic domain of about 160 amino acids. See, e.g., Tatham and Shewry, Comparative Structures and Properties of Elastic Proteins, Phil. Trans. R. Soc. Lond. B 257: 229-234 (2002), which is hereby incorporated by reference in its entirety. The elastic domains comprise a pentapeptide repeat motif and histidine-rich domains. This 5 amino acid elastic repeat motif has the acid sequence GPGGG (SEQ ID NO: 144).

The collagen superfamily contains at least 29 different types of collagen, designated COL1A1-COL29A1. Some collagens have several isoforms, such as, e.g., COL1A1, COL1A2, COL4A1, COL4A2, COL4A3, COL4A4, COL4A5, COL4A6, COL5A1, COL5A2, COL5A3, COL6A1, COL6A2, COL6A3, COL8A1, COL8A2, COL9A1, COL9A2, COL9A3, COL11A1, and COL11A2. Collagens are found in all connective tissue and are a major component of the extracellular matrix. Collagens can be purified from animal sources or produced recombinantly. Although 29 types of collagen have been identified, over 90% of the collagen in the body is of type I, II, III, and IV. Collagen I is found in skin, tendon, vascular, ligature, organs, and is the main component of bone; collagen II is the main component of cartilage; collagen III is the main component of reticular fibers; collagen IV forms bases of cell basement membrane; and collagen V is present on cells surfaces, hair and placenta. Gelatin is a protein produced by partial hydrolysis of collagen extracted from the boiled bones, connective tissues, organs and intestines of animals such as cattle, pigs, and horses. Collagens are also commercially available. The elastic domain comprises a tripeptide repeat motif of either GXP or GXHyp, where X is any amino acid and Hyp is hydroxyproline. Collagen-based elastic proteins are described in, e.g., Masters, Protein Matrix Materials, Devices and Methods of Making and Using Thereof, U.S. Pat. No. 7,662,409, which is hereby incorporated by reference in its entirety.

Other elastic proteins useful in the compositions and methods disclosed herein are described in, e.g., Masters, Protein Matrix Materials, Devices and Methods of Making and Using Thereof, U.S. Pat. No. 7,662,409; and Kaplan, et al., Fibrous Protein Fusions and Use Thereof in the Formation of Advanced Organic/Inorganic Composite Materials, U.S. Patent Publication 2008/0293919, each of which is hereby incorporated by reference in its entirety.

Aspects of the present specification provide, in part, a composition comprising a hydrogel comprising crosslinked matrix polymer. As used herein, the term "crosslinked" refers to the intermolecular bonds joining the individual polymer molecules, or monomer chains, into a more stable structure like a gel. As such, a crosslinked matrix polymer has at least one intermolecular bond joining at least one individual polymer molecule to another one. Matrix polymers disclosed herein may be crosslinked using dialdehydes and disulfides crosslinking agents including, without limitation, multifunctional PEG-based crosslinking agents, divinyl sulfones, diglycidyl ethers, and bis-epoxides. Non-limiting examples of hyaluronan crosslinking agents include divinyl sulfone (DVS), 1,4-butanediol diglycidyl ether (BDDE), 1,2-bis(2,3-epoxypropoxy)ethylene (EGDGE), 1,2,7,8-diepoxyoctane (DEO), biscarbodiimide (BCD), pentaerythritol tetraglycidyl ether (PETGE), adipic dihydrazide (ADH), bis(sulfosuccinimidyl)suberate (BS), hexamethylenediamine (NMDA), 1-(2,3-epoxypropyl)-2,3-epoxycyclohexane, or combinations thereof.

Aspects of the present specification provide, in part, a composition comprising a hydrogel comprising a crosslinked matrix polymer having a degree of crosslinking. As used herein, the term "degree of crosslinking" refers to the percentage of matrix polymer monomeric units that are bound to a cross-linking agent, such as, e.g., the disaccharide monomer units of hyaluronan. Thus, a composition that that has a crosslinked matrix polymer with a 4% degree of crosslinking means that on average there are four crosslinking molecules for every 100 monomeric units. Every other parameter being equal, the greater the degree of crosslinking, the harder the gel becomes. Non-limiting examples of a degree of crosslinking include about 1% to about 15%.

In an embodiment, a composition comprises a crosslinked matrix polymer. In other aspects of this embodiment, a composition comprises a crosslinked matrix polymer where the partially crosslinked matrix polymer represents, e.g., about 1% by weight, about 2% by weight, about 3% by weight, about 4% by weight, about 5% by weight, about 6% by weight, about 7% by weight, about 8% by weight, or about 9%, or about 10% by weight, of the total matrix polymer present in the composition. In yet other aspects of this embodiment, a composition comprises a crosslinked matrix polymer where the partially crosslinked matrix polymer represents, e.g., at most 1% by weight, at most 2% by weight, at most 3% by weight, at most 4% by weight, at most 5% by weight, at most 6% by weight, at most 7% by weight, at most 8% by weight, at most 9% by weight, or at most 10% by weight, of the total matrix polymer present in the composition. In still other aspects of this embodiment, a composition comprises a crosslinked matrix polymer where the partially crosslinked matrix polymer represents, e.g., about 0% to about 10% by weight, about 1% to about 10% by weight, about 3% to about 10% by weight, or about 5% to about 10% by weight, of the total matrix polymer present in the composition.

In other aspects of this embodiment, a composition comprises a crosslinked matrix polymer where the degree of crosslinking is about 1%, about 2%, about 3%, about 4%, about 5%, about 6%, about 7%, about 8%, about 9%, about 10%, about 11%, about 12%, about 13%, about 14%, or about 15%. In yet other aspects of this embodiment, a composition comprises a crosslinked matrix polymer where the degree of crosslinking is at most 1%, at most 2%, at most 3%, at most 4%, at most 5%, at most 6%, at most 7%, at most 8%, at most 9%, at most 10%, at most 11%, at most 12%, at most 13%, at most 14%, or at most 15%. In still other aspects of this embodiment, a composition comprises a crosslinked matrix polymer where the degree of crosslinking is about 1% to about 15%, about 2% to about 11%, about 3% to about 10%, about 1% to about 5%, about 10% to about 15%, about 11% to about 15%, about 6% to about 10%, or about 6% to about 8%.

In still another embodiment, a composition comprises a crosslinked elastic protein. In aspect of this embodiment, a composition comprises a crosslinked silk protein, a crosslinked resilin, a crosslinked RLP, a crosslinked elastin, a crosslinked ELP, a crosslinked SELP, a crosslinked abductin, a crosslinked byssus, a crosslinked gliadin, a crosslinked, glutenin, or a crosslinked collagen. In other aspects of this embodiment, a composition comprises a crosslinked elastic protein where the crosslinked elastic protein represents, e.g., about 1% by weight, about 2% by weight, about 3% by weight, about 4% by weight, about 5% by weight, about 6% by weight, about 7% by weight, about 8% by weight, or about 9%, or about 10% by weight, of the total elastic protein present in the composition. In yet other aspects of this embodiment, a fluid composition comprises a crosslinked elastic protein where the crosslinked elastic protein represents, e.g., at most 1% by weight, at most 2% by weight, at most 3% by weight, at most 4% by weight, at most 5% by weight, at most 6% by weight, at most 7% by weight, at most 8% by weight, at most 9% by weight, or at most 10% by weight, of the total elastic protein present in the composition. In still other aspects of this embodiment, a composition comprises a crosslinked elastic protein where the crosslinked elastic protein represents, e.g., about 0% to about 10% by weight, about 1% to about 10% by weight, about 3% to about 10% by weight, or about 5% to about 10% by weight, of the total elastic protein present in the composition.

In other aspects of this embodiment, a composition comprises a crosslinked elastic protein where the degree of crosslinking is about 1%, about 2%, about 3%, about 4%, about 5%, about 6%, about 7%, about 8%, about 9%, about 10%, about 11%, about 12%, about 13%, about 14%, or about 15%. In yet other aspects of this embodiment, a composition comprises a crosslinked elastic protein where the degree of crosslinking is at most 1%, at most 2%, at most 3%, at most 4%, at most 5%, at most 6%, at most 7%, at most 8%, at most 9%, at most 10%, at most 11%, at most 12%, at most 13%, at most 14%, or at most 15%. In still other aspects of this embodiment, a composition comprises a crosslinked elastic protein where the degree of crosslinking is about 1% to about 15%, about 2% to about 11%, about 3% to about 10%, about 1% to about 5%, about 10% to about 15%, about 11% to about 15%, about 6% to about 10%, or about 6% to about 8%.

Aspects of the present specification provide, in part, a composition comprising a hydrogel comprising an uncrosslinked matrix polymer. As used herein, the term "uncrosslinked" refers to a lack of intermolecular bonds joining the individual matrix polymer molecules, or monomer chains. As such, an uncrosslinked matrix polymer is not linked to any other matrix polymer by an intermolecular bond.

Aspects of the present specification provide, in part, a composition comprising a hydrogel comprising a substantially uncrosslinked matrix polymer. As sued herein, the term "substantially uncrosslinked" refers to the presence of uncrosslinked matrix polymers in a composition disclosed herein at a level of at least 90% by weight of the composition, with the remaining at most 10% by weight of the composition being comprised of other components including crosslinked matrix polymers.

In an embodiment, a composition comprises a substantially uncrosslinked matrix polymer. In other aspects of this embodiment, a composition comprises an uncrosslinked matrix polymer where the uncrosslinked matrix polymer represents, e.g., about 90% by weight, about 91% by weight, about 92% by weight, about 93% by weight, about 94% by weight, about 95% by weight, about 96% by weight, about 97% by weight, about 98% by weight, or about 99%, or about 100% by weight, of the total matrix polymer present in the composition. In yet other aspects of this embodiment, a composition comprises an uncrosslinked matrix polymer where the uncrosslinked matrix polymer represents, e.g., at least 90% by weight, at least 91% by weight, at least 92% by weight, at least 93% by weight, at least 94% by weight, at least 95% by weight, at least 96% by weight, at least 97% by weight, at least 98% by weight, or at least 99% by weight, of the total matrix polymer present in the composition. In still other aspects of this embodiment, a composition comprises an uncrosslinked matrix polymer where the uncrosslinked matrix polymer represents, e.g., about 90% to about 100% by weight, about 93% to about 100% by weight, about 95% to about 100% by weight, or about 97% to about 100% by weight, of the total matrix polymer present in the composition.

In still another embodiment, a composition comprises a substantially uncrosslinked elastic protein. In aspects of this embodiment, a composition comprises a substantially uncrosslinked resilin, a substantially uncrosslinked RLP, a substantially uncrosslinked elastin, a substantially uncrosslinked ELP, a substantially uncrosslinked SELP, a substantially uncrosslinked abductin, a substantially uncrosslinked byssus, a substantially uncrosslinked gliadin, a substantially uncrosslinked, glutenin, or a substantially uncrosslinked collagen. In other aspects of this embodiment, a composition comprises an uncrosslinked elastic protein where the uncrosslinked elastic protein represents, e.g., about 90% or more by weight, about 91% or more by weight, about 92% or more by weight, about 93% or more by weight, about 94% or more by weight, about 95% or more by weight, about 96% or more by weight, about 97% or more by weight, about 98% or more by weight, or about 99% or more, or about 100% by weight, of the total elastic protein present in the composition. In yet other aspects of this embodiment, a composition comprises an uncrosslinked elastic protein where the uncrosslinked elastic protein represents, e.g., about 90% to about 100% by weight, about 93% to about 100% by weight, about 95% to about 100% by weight, or about 97% to about 100% by weight, of the total elastic protein present in the composition.

Aspects of the present specification provide, in part, a composition that is essentially free of a crosslinked matrix polymer. As used herein, the term "essentially free" (or "consisting essentially of") refers to a composition where only trace amounts of cross-linked matrix polymers can be detected.

In still another embodiment, a composition comprises an elastic protein that is essentially free of a crosslinked elastic protein. In an aspect of this embodiment, a composition comprises a resilin that is essentially free of a crosslinked resilin, a RLP that is essentially free of a crosslinked RLP, an elastin essentially free of a crosslinked elastin, an ELP that is essentially free of a crosslinked ELP, a SELP that is essentially free of a crosslinked SELP, an abductin essentially free of a crosslinked abductin, a byssus essentially free of a crosslinked byssus, a gliadin essentially free of a crosslinked gliadin, a glutenin essentially free of a crosslinked glutenin, or a collagen essentially free of a crosslinked collagen.

Aspects of the present specification provide, in part, a composition that is entirely free of a crosslinked matrix polymer. As used herein, the term "entirely free" refers to a fluid composition that within the detection range of the instrument or process being used, crosslinked matrix polymers cannot be detected or its presence cannot be confirmed.

In still another embodiment, a composition comprises an elastic protein that is entirely free of a crosslinked elastic protein. In an aspect of this embodiment, a composition comprises a resilin that is entirely free of a crosslinked resilin, a RLP that is entirely free of a crosslinked RLP, an elastin entirely free of a crosslinked elastin, an ELP that is entirely free of a crosslinked ELP, a SELP that is entirely free of a crosslinked SELP, an abductin entirely free of a crosslinked abductin, a byssus entirely free of a crosslinked byssus, a gliadin entirely free of a crosslinked gliadin, a glutenin entirely free of a crosslinked, glutenin, or a collagen entirely free of a crosslinked collagen.

Aspects of the present specification provide, in part, a composition comprising a ratio of uncrosslinked polymer and a hydrogel comprising crosslinked matrix polymer. This ratio of uncrosslinked polymer and a hydrogel comprising crosslinked matrix polymer is also known as the fluid:gel ratio. Any fluid:gel ratio is useful in making the compositions disclosed herein with the proviso that such ratio produces a composition disclosed herein that improves a skin condition as disclosed herein. Non-limiting examples of fluid:gel ratios include 100:0, 98:2, 90:10, 75:25, 70:30, 60:40, 50:50, 40:60, 30:70, 25:75, 10:90; 2:98, and 0:100.

In an aspect of this embodiment, a composition comprising an uncrosslinked matrix polymer and a hydrogel comprising a crosslinked matrix polymer has a fluid:gel ratio sufficient to form a fluid. In other aspects of this embodiment, a composition comprising an uncrosslinked matrix polymer and a hydrogel comprising a crosslinked matrix polymer has a fluid:gel ratio of, e.g., about 0:100, about 1:99, about 2:98, about 3:97, about 4:96, about 5:95, about 6:94, about 7:93, about 8:92, about 9:91, or about 10:90. In yet other aspects of this embodiment, a composition comprising an uncrosslinked matrix polymer and a hydrogel comprising a crosslinked matrix polymer has a fluid:gel ratio of, e.g., at most 1:99, at most 2:98, at most 3:97, at most 4:96, at most 5:95, at most 6:94, at most 7:93, at most 8:92, at most 9:91, or at most 10:90. In still other aspects of this embodiment, a composition comprising an uncrosslinked matrix polymer and a hydrogel comprising a crosslinked matrix polymer has a fluid:gel ratio of, e.g., about 0:100 to about 3:97, about 0:100 to about 5:95, or about 0:100 to about 10:90.

In other aspects of this embodiment, a composition comprising an uncrosslinked matrix polymer and a hydrogel comprising a crosslinked matrix polymer has a fluid:gel ratio of, e.g., about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, about 98:2, or about 100:0. In yet other aspects of this embodiment, a composition comprising an uncrosslinked matrix polymer and a hydrogel comprising a crosslinked matrix polymer has a fluid:gel ratio of, e.g., at most 15:85, at most 20:80, at most 25:75, at most 30:70, at most 35:65, at most 40:60, at most 45:55, at most 50:50, at most 55:45, at most 60:40, at most 65:35, at most 70:30, at most 75:25, at most 80:20, at most 85:15, at most 90:10, at most 95:5, at most 98:2, or at most 100:0. In still other aspects of this embodiment, a composition comprising an uncrosslinked matrix polymer and a hydrogel comprising a crosslinked matrix polymer has a fluid:gel ratio of, e.g., about 10:90 to about 70:30, about 15:85 to about 70:30, about 10:90 to about 55:45, about 80:20 to about 95:5, about 90:10 to about 100:0, about 75:25 to about 100:0, or about 60:40 to about 100:0.

In still another embodiment, a composition comprises an uncrosslinked matrix polymer where the uncrosslinked matrix polymer is present in an amount sufficient to improve a condition of the skin, such as, e.g., hydration or elasticity. In aspects of this embodiment, a composition comprises an uncrosslinked matrix polymer where the uncrosslinked matrix polymer is present at a concentration of, e.g., about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 13.5 mg/mL, about 14 mg/mL, about 15 mg/mL, about 16 mg/mL, about 17 mg/mL, about 18 mg/mL, about 19 mg/mL, or about 20 mg/mL. In other aspects of this embodiment, a composition comprises an uncrosslinked matrix polymer where the uncrosslinked matrix polymer is present at a concentration of, e.g., at least 1 mg/mL, at least 5 mg/mL, at least 10 mg/mL, at least 15 mg/mL, at least 20 mg/mL, or at least 25 mg/mL. In yet other aspects of this embodiment, a composition comprises an uncrosslinked matrix polymer where the uncrosslinked matrix polymer is present at a concentration of, e.g., at most 1 mg/mL, at most 5 mg/mL, at most 10 mg/mL, at most 15 mg/mL, at most 20 mg/mL, or at most 25 mg/mL. In still other aspects of this embodiment, a composition comprises an uncrosslinked matrix polymer where the uncrosslinked matrix polymer is present at a concentration of, e.g., about 7.5 mg/mL to about 19.5 mg/mL, about 8.5 mg/mL to about 18.5 mg/mL, about 9.5 mg/mL to about 17.5 mg/mL, about 10.5 mg/mL to about 16.5 mg/mL, about 11.5 mg/mL to about 15.5 mg/mL, or about 12.5 mg/mL to about 14.5 mg/mL.

In aspects of this embodiment, a composition comprises an uncrosslinked elastic protein where the uncrosslinked elastic protein is present at a concentration of, e.g., about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 13.5 mg/mL, about 14 mg/mL, about 15 mg/mL, about 16 mg/mL, about 17 mg/mL, about 18 mg/mL, about 19 mg/mL, or about 20 mg/mL. In other aspects of this embodiment, a composition comprises an uncrosslinked elastic protein where the uncrosslinked elastic protein is present at a concentration of, e.g., at least 1 mg/mL, at least 2 mg/mL, at least 3 mg/mL, at least 4 mg/mL, at least 5 mg/mL, at least 10 mg/mL, at least 15 mg/mL, at least 20 mg/mL, or at least 25 mg/mL. In yet other aspects of this embodiment, a composition comprises an uncrosslinked elastic protein where the uncrosslinked elastic protein is present at a concentration of, e.g., at most 1 mg/mL, at most 2 mg/mL, at most 3 mg/mL, at most 4 mg/mL, at most 5 mg/mL, at most 10 mg/mL, at most 15 mg/mL, at most 20 mg/mL, or at most 25 mg/mL. In still other aspects of this embodiment, a composition comprises an uncrosslinked elastic protein where the uncrosslinked elastic protein is present at a concentration of, e.g., about 7.5 mg/mL to about 19.5 mg/mL, about 8.5 mg/mL to about 18.5 mg/mL, about 9.5 mg/mL to about 17.5 mg/mL, about 10.5 mg/mL to about 16.5 mg/mL, about 11.5 mg/mL to about 15.5 mg/mL, or about 12.5 mg/mL to about 14.5 mg/mL.

A composition disclosed herein comprises a gel phase that may include a hydrogel comprising a silk fibroin and a second matrix polymer including an elastic protein. In aspects of this embodiment, the elastic protein is a resilin, a resilin-like polypeptide, an elastin, an elastin-like polypeptide, a silk protein-elastin-like polypeptide, an abductin, a byssus, a gliadin, a glutenin, abductin, or a collagen. In other aspects of this embodiment, the percent amount of silk fibroin present in a hydrogel relative to a second matrix polymer is from about 0.1% (v/v) to about 25% (v/v). In yet other aspects of this embodiment, the percent amount of silk fibroin present in a hydrogel relative to a second matrix polymer is from about 99.9% (v/v) to about 75% (v/v). In still other aspects of this embodiment, the ratio of silk fibroin to matrix polymer in the hydrogel comprises, e.g., about 0.1% (v/v) silk fibroin and about 99.9% (v/v) matrix polymer, about 1% (v/v) silk fibroin and about 99% (v/v) matrix polymer, about 5% (v/v) silk fibroin and about 95% (v/v) matrix polymer, about 10% (v/v) silk fibroin and about 90% (v/v) matrix polymer, about 15% (v/v) silk fibroin and about 85% (v/v) matrix polymer, about 20% (v/v) silk fibroin and about 80% (v/v) matrix polymer, or about 25% (v/v) silk fibroin and about 75% (v/v) matrix polymer.

A composition disclosed herein comprises a gel phase that may include a silk fibroin hydrogel component and matrix polymer hydrogel component. In an aspect of this embodiment, the hydrogel comprising a matrix polymer is an elastic protein. In aspects of this embodiment, the elastic protein is a resilin, a resilin-like polypeptide, an elastin, an elastin-like polypeptide, a silk protein-elastin-like polypeptide, an abductin, a byssus, a gliadin, a glutenin, abductin, or a collagen. In other aspects of this embodiment, the percent amount of silk fibroin hydrogel present in a composition relative to matrix polymer hydrogel is from about 0.1% (v/v) to about 25% (v/v). In yet other aspects of this embodiment, the percent amount of matrix polymer hydrogel present in a composition relative to silk fibroin hydrogel is from about 99.9% (v/v) to about 75% (v/v). In still other aspects of this embodiment, the ratio of silk fibroin hydrogel to matrix polymer hydrogel in the gel phase of a composition comprises, e.g., about 0.1% (v/v) silk fibroin hydrogel and about 99.9% (v/v) matrix polymer hydrogel, about 1% (v/v) silk fibroin hydrogel and about 99% (v/v) matrix polymer hydrogel, about 5% (v/v) silk fibroin hydrogel and about 95% (v/v) matrix polymer hydrogel, about 10% (v/v) silk fibroin hydrogel and about 90% (v/v) matrix polymer hydrogel, about 15% (v/v) silk fibroin hydrogel and about 85% (v/v) matrix polymer hydrogel, about 20% (v/v) silk fibroin hydrogel and about 80% (v/v) matrix polymer hydrogel, or about 25% (v/v) silk fibroin hydrogel and about 75% (v/v) matrix polymer hydrogel.

A composition disclosed herein may comprise a gel phase where the silk fibroin hydrogel component and matrix polymer hydrogel component are processed separately. The resulting processed hydrogel materials, e.g., hydrogel particles of both types, are then mixed together, such as, e.g., after a milling step and/or after re-homogenization in a carrier phase, to form the final composition. In addition, a matrix polymer may be initially mixed with depolymerized silk fibroin solution, with subsequent polymerization occurring only after the completion of the mixing step to form an integrated matrix polymer/silk fibroin composite hydrogel. Similarly, the silk fibroin and matrix polymers may be linked together to form a hydrogel composite that is then subsequently processed into the gel phase of the composition. Such linkage can occur by a typical crosslinking method or by linking the matrix polymer to the silk fibroin hydrogel via a peptide linker disclosed herein, such as, e.g., a five-amino acid peptide "tail" and synthetic molecule. As disclosed herein, a composition may comprise a gel phase that comprises both separately processed hydrogel components as well as particles of hydrogel composites.

As a non-limiting example, a solution comprising about 1% to about 30% depolymerized silk fibroin may be mixed with about 6 mg/g to about 30 mg/g of elastic protein having a degree of crosslinking of from 0 to about 17% where the percent weight of the silk fibroin component is from about 1% to about 75%. As another non-limiting example, hydrogel particles comprising from about 1% to about 8% silk fibroin are mixed with hydrogel particles comprising about 6 mg/g to about 30 mg/g of elastic protein having a degree of crosslinking of from 0 to about 17% where the percent weight of the silk fibroin component is from about 1% to about 75%. As yet another non-limiting example, a composition comprising hydrogel particles comprising from about 1% to about 8% silk fibroin mixed together with a carrier phase (about 20% (v/v) to about 50% (v/v)) is mixed with a composition comprising hydrogel particles comprising about 6 mg/g to about 30 mg/g of elastic protein having a degree of crosslinking of from 0 to about 17% where the percent weight of the silk fibroin component is from about 1% to about 75%.

Aspects of the present specification provide, in part, a composition disclosed herein having an opacity. Opacity is the measure of impenetrability to electromagnetic or other kinds of radiation, especially visible light. An opaque object is neither transparent (allowing all light to pass through) nor translucent (allowing some light to pass through). In certain applications, it would be an advantage to have an opaque composition. For example, in applications where a composition disclosed herein is administered to a superficial region, an opaque composition provides coloration and appearance of the overlying skin.

In an embodiment, a composition disclosed herein is optically opaque. In aspects of this embodiment, a composition disclosed herein transmits, e.g., about 5% of the light, about 10% of the light, about 15% of the light, about 20% of the light, about 25% of the light, about 30% of the light, about 35% of the light, about 40% of the light, about 45% of the light, about 50% of the light, about 55% of the light, about 60% of the light, about 65% of the light, or about 70% of the light. In other aspects of this embodiment, a composition disclosed herein transmits, e.g., at most 5% of the light, at most 10% of the light, at most 15% of the light, at most 20% of the light, at most 25% of the light, at most 30% of the light, at most 35% of the light, at most 40% of the light, at most 45% of the light, at most 50% of the light, at most 55% of the light, at most 60% of the light, at most 65% of the light, at most 70% of the light, or at most 75% of the light. In other aspects of this embodiment, a composition disclosed herein transmits, e.g., about 5% to about 15%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 5% to about 65%, about 5% to about 70%, about 5% to about 75%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 15% to about 75%, about 25% to about 35%, about 25% to about 40%, about 25% to about 45%, about 25% to about 50%, about 25% to about 55%, about 25% to about 60%, about 25% to about 65%, about 25% to about 70%, or about 25% to about 75%, of the light.

In aspects of this embodiment, a composition disclosed herein exhibits, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100% reduction in tyndalling. In other aspects of this embodiment, a composition disclosed herein exhibits, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, reduction in tyndalling. In other aspects of this embodiment, a composition disclosed herein exhibits, e.g., about 20% to about 100%, about 50% to about 100%, about 70% to about 100%, about 15% to about 35%, about 20% to about 40%, about 25% to about 45%, about 30% to about 50%, about 35% to about 55%, about 40% to about 60%, about 45% to about 65%, about 50% to about 70%, about 55% to about 75%, about 60% to about 80%, about 65% to about 85%, about 70% to about 90%, about 75% to about 95%, or about 80% to about 100%, reduction in tyndalling.

Aspects of the present specification provide, in part, a composition comprising a carrier phase. A composition disclosed herein may include a carrier phase. As such, the disclosed compositions can be monophasic or multiphasic compositions. As used herein, the term "carrier phase" is synonymous with "carrier" and refers to a material used to increase fluidity of a hydrogel. A carrier is advantageously a physiologically-acceptable carrier and may include one or more conventional excipients useful in pharmaceutical compositions. As used herein, the term "a physiologically-acceptable carrier" refers to a carrier in accord with, or characteristic of, the normal functioning of a living organism. As such, administration of a composition comprising a hydrogel and a carrier has substantially no long term or permanent detrimental effect when administered to a mammal. The present compositions include a carrier where a major of the volume is water or saline. However, other useful carriers include any physiologically tolerable material which improves upon extrudability or intrudability of the hydrogel through a needle or into a target host environment. Potential carriers could include but are not limited to physiological buffer solutions, serum, other protein solutions, gels composed of polymers including proteins, glycoproteins, proteoglycans, or polysaccharides. Any of the indicated potential carriers may be either naturally derived, wholly synthetic, or combinations of both.

The volume of carrier per volume of hydrogel may be increased or decreased in a range between 0% to about 100% depending upon the desired physical properties of the resultant composition including dose delivery, viscosity, injectability, and desired in vivo behavioral characteristics. This carrier is then mixed with the hydrogel until achieving a "uniform" consistency which may be termed an emulsion or suspension. More specifically, for example, a hydrogel may be passed through an 18 g needle several times to create hydrogel particles, injecting back and forth between a pair of syringes, then this procedure repeated with 22 g needles affixed to 1 mL syringes. Advantages derived from adding a carrier to a hydrogel or hydrogel particles include decreased viscosity in the extracellular in vivo microenvironment; release of local mechanical stress loading after drug delivery platform administration; and improved ionic composition resulting in improved biocompatibility.

Aspects of the present specification provide, in part, a composition disclosed herein exhibiting a dynamic viscosity. Viscosity is resistance of a fluid to shear or flow caused by either shear stress or tensile stress. Viscosity describes a fluid's internal resistance to flow caused by intermolecular friction exerted when layers of fluids attempt to slide by one another and may be thought of as a measure of fluid friction. The less viscous the fluid, the greater its ease of movement (fluidity).

Viscosity can be defined in two ways; dynamic viscosity ($\mu$, although $\eta$ is sometimes used) or kinematic viscosity ($v$). Dynamic viscosity, also known as absolute or complex viscosity, is the tangential force per unit area required to move one horizontal plane with respect to the other at unit velocity when maintained a unit distance apart by the fluid. The SI physical unit of dynamic viscosity is the Pascal-second (Pa·s), which is identical to N·m-2·s. Dynamic viscosity can be expressed as $\tau = \mu \, dvx/dz$, where $\tau$=shearing stress, $\mu$=dynamic viscosity, and $dvx/dz$ is the velocity gradient over time. For example, if a fluid with a viscosity of one Pa·s is placed between two plates, and one plate is pushed sideways with a shear stress of one Pascal, it moves a distance equal to the thickness of the layer between the plates in one second. Dynamic viscosity symbolize by is also used, is measured with various types of rheometers, devices used to measure the way in which a liquid, suspension or slurry flows in response to applied forces.

Kinematic viscosity ($v$) is the ratio of dynamic viscosity to density, a quantity in which no force is involved and is defined as follows: $v = \mu/\rho$, where $\mu$ is the dynamic viscosity $\rho$ is density with the SI unit of kg/m³. Kinematic viscosity is usually measured by a glass capillary viscometer as has an SI unit of m²/s.

The viscosity of a fluid is highly temperature dependent and for either dynamic or kinematic viscosity to be meaningful, the reference temperature must be quoted. For the viscosity values disclosed herein, a dynamic viscosity is measured at 1 Pa with a cone/plane geometry 2°/40 cm and a temperature of 20° C. Examples of the dynamic viscosity of various fluids at 20° C. is as follows: water is about $1.0 \times 10^{-3}$ Pa·s, blood is about $3-4 \times 10^{-3}$ Pa·s, vegetable oil is about $60-85 \times 10^{-3}$ Pa·s, motor oil SE 30 is about 0.2 Pa·s, glycerin is about 1.4 Pa·s, maple syrup is about 2-3 Pa·s, honey is about 10 Pa·s, chocolate syrup is about 10-25 Pa·s, peanut butter is about 150-250 Pa·s, lard is about 1,000 Pa·s, vegetable shortening is about 1,200 Pa·s, and tar is about 30,000 Pa·s.

In aspects of this embodiment, a composition disclosed herein exhibits a dynamic viscosity of, e.g., about 10 Pa·s, about 20 Pa·s, about 30 Pa·s, about 40 Pa·s, about 50 Pa·s, about 60 Pa·s, about 70 Pa·s, about 80 Pa·s, about 90 Pa·s, about 100 Pa·s, about 125 Pa·s, about 150 Pa·s, about 175 Pa·s, about 200 Pas, about 225 Pa·s, about 250 Pa·s, about 275 Pa·s, about 300 Pa·s, about 400 Pa·s, about 500 Pa·s, about 600 Pa·s, about 700 Pa·s, about 750 Pa·s, about 800 Pa·s, about 900 Pa·s, about 1,000 Pa·s, about 1,100 Pa·s, or about 1,200 Pa·s. In other aspects of this embodiment, a composition disclosed herein exhibits a dynamic viscosity of, e.g., at most 10 Pa·s, at most 20 Pa·s, at most 30 Pa·s, at most 40 Pa·s, at most 50 Pa·s, at most 60 Pa·s, at most 70 Pa·s, at most 80 Pa·s, at most 90 Pa·s, at most 100 Pa·s, at most 125 Pa·s, at most 150 Pa·s, at most 175 Pa·s, at most 200 Pa·s, at most 225 Pa·s, at most 250 Pa·s, at most 275 Pa·s, at most 300 Pa·s, at most 400 Pa·s, at most 500 Pa·s, at most 600 Pa·s, at most 700 Pa·s, at most 750 Pa·s, at most 800 Pa·s, at most 900 Pa·s, or at most 1000 Pa·s. In yet other aspects of this embodiment, a composition disclosed herein exhibits a dynamic viscosity of, e.g., about 10 Pa·s to about 100 Pa·s, about 10 Pa·s to about 150 Pa·s, about 10 Pa·s to about 250 Pa·s, about 50 Pa·s to about 100 Pa·s, about 50 Pa·s to about 150 Pa·s, about 50 Pa·s to about 250 Pa·s, about 100 Pa·s to about 500 Pa·s, about 100 Pa·s to about 750 Pa·s, about 100 Pa·s to about 1,000 Pa·s, about 100 Pa·s to about 1,200 Pa·s, about 300 Pa·s to about 500 Pa·s, about 300 Pa·s to about 750 Pa·s, about 300 Pa·s to about 1,000 Pa·s, or about 300 Pa·s to about 1,200 Pa·s.

Aspects of the present specification provide, in part, a composition disclosed herein is injectable. As used herein, the term "injectable" refers to a material having the properties necessary to administer the composition into a skin region of an individual using an injection device with a fine needle. As used herein, the term "fine needle" refers to a needle that is 27 gauge or smaller. Injectability of a composition disclosed herein can be accomplished by sizing the hydrogel particles as discussed above.

In aspect of this embodiment, a composition disclosed herein is injectable through a fine needle. In other aspects of this embodiment, a composition disclosed herein is injectable through a needle of, e.g., about 27 gauge, about 30 gauge, or about 32 gauge. In yet other aspects of this embodiment, a composition disclosed herein is injectable through a needle of, e.g., 27 gauge or smaller, 30 gauge or smaller, or 32 gauge or smaller. In still other aspects of this embodiment, a composition disclosed herein is injectable through a needle of, e.g., about 27 gauge to about 32 gauge.

In aspects of this embodiment, a composition disclosed herein can be injected with an extrusion force of about 60 N, about 55 N, about 50 N, about 45 N, about 40 N, about 35 N, about 30 N, about 25 N, about 20 N, or about 15 N. In other aspects of this embodiment, a composition disclosed herein can be injected through a 27 gauge needle with an extrusion force of about 60 N or less, about 55 N or less, about 50 N or less, about 45 N or less, about 40 N or less, about 35 N or less, about 30 N or less, about 25 N or less, about 20 N or less, about 15 N or less, about 10 N or less, or about 5 N or less. In yet other aspects of this embodiment, a composition disclosed herein can be injected through a 30 gauge needle with an extrusion force of about 60 N or less, about 55 N or less, about 50 N or less, about 45 N or less, about 40 N or less, about 35 N or less, about 30 N or less, about 25 N or less, about 20 N or less, about 15 N or less, about 10 N or less, or about 5 N or less. In still other aspects of this embodiment, a composition disclosed herein can be injected through a 32 gauge needle with an extrusion force of about 60 N or less, about 55 N or less, about 50 N or less, about 45 N or less, about 40 N or less, about 35 N or less, about 30 N or less, about 25 N or less, about 20 N or less, about 15 N or less, about 10 N or less, or about 5 N or less.

Aspects of the present specification provide, in part, a composition disclosed herein exhibits cohesiveness. Cohesion or cohesive attraction, cohesive force, or compression force is a physical property of a material, caused by the intermolecular attraction between like-molecules within the material that acts to unite the molecules. A composition should be sufficiently cohesive as to remain localized to a site of administration. Additionally, in certain applications, a sufficient cohesiveness is important for a composition to retain its shape, and thus functionality, in the event of mechanical load cycling. As such, in one embodiment, a composition exhibits strong cohesive attraction, on par with water. In another embodiment, a composition exhibits low cohesive attraction. In yet another embodiment, a composition exhibits sufficient cohesive attraction to remain localized to a site of administration. In still another embodiment, a composition exhibits sufficient cohesive attraction to retain its shape. In a further embodiment, a composition exhibits sufficient cohesive attraction to retain its shape and functionality.

In aspects of this embodiment, a composition disclosed herein has a compression force of about 10 grams-force, about 20 grams-force, about 30 grams-force, about 40 grams-force, about 50 grams-force, about 60 grams-force, about 70 grams-force, about 80 grams-force, about 90 grams-force, about 100 grams-force, about 200 grams-force, about 300 grams-force, about 400 grams-force, about 500 grams-force, about 600 grams-force, about 700 grams-force, or about 800 grams-force. In other aspects of this embodiment, a composition disclosed herein has a compression force of at least 500 grams-force, at least 600 grams-force, at least 700 grams-force, at least 800 grams-force, at least 900 grams-force, at least 1000 grams-force, at least 1250 grams-force, at least 1500 grams-force, at least 1750 grams-force, at least 2000 grams-force, at least 2250 grams-force, at least 2500 grams-force, at least 2750 grams-force, or at least 3000 grams-force. In other aspects of this embodiment, a composition disclosed herein has a compression force of at most 10 grams-force, at most 20 grams-force, at most 30 grams-force, at most 40 grams-force, at most 50 grams-force, at most 60 grams-force, at most 70 grams-force, at most 80 grams-force, at most 90 grams-force, at most 100 grams-force, at most 200 grams-force, at most 300 grams-force, at most 400 grams-force, at most 500 grams-force, at most 600 grams-force, at most 700 grams-force, or at most 800 grams-force.

In yet other aspects of this embodiment, a composition disclosed herein has a compression force of about 10 grams-force to about 50 grams-force, about 25 grams-force to about 75 grams-force, about 50 grams-force to about 150 grams-force, about 100 grams-force to about 200 grams-force, about 100 grams-force to about 300 grams-force, about 100 grams-force to about 400 grams-force, about 100 grams-force to about 500 grams-force, about 200 grams-force to about 300 grams-force, about 200 grams-force to about 400 grams-force, about 200 grams-force to about 500 grams-force, about 200 grams-force to about 600 grams-force, about 200 grams-force to about 700 grams-force, about 300 grams-force to about 400 grams-force, about 300 grams-force to about 500 grams-force, about 300 grams-force to about 600 grams-force, about 300 grams-force to about 700 grams-force, about 300 grams-force to about 800 grams-force, about 400 grams-force to about 500, about 400 grams-force to about 600, about 400 grams-force to about 700, about 400 grams-force to about 800, about 500 grams-force to about 600 grams-force, about 500 grams-force to about 700 grams-force, about 500 grams-force to about 800 grams-force, about 600 grams-force to about 700 grams-force, about 600 grams-force to about 800 grams-force, about 700 grams-force to about 800 grams-force, about 1000 grams-force to about 2000 grams-force, about 1000 grams-force to about 3000 grams-force, or about 2000 grams-force to about 3000 grams-force.

Aspects of the present hydrogel formulations provide, in part, a surfactant. As used herein, the term "surfactant" refers to a natural or synthetic amphiphilic compound. A surfactant can be non-ionic, zwitterionic, or ionic. It is envisioned that any surfactant is useful in making a hydrogel formulation disclosed in the present specification, with the proviso that a therapeutically effective amount of the hydrogel formulation is recovered using this surfactant amount. Non-limiting examples of surfactants include polysorbates like polysorbate 20 (TWEEN® 20), polysorbate 40 (TWEEN® 40), polysorbate 60 (TWEEN® 60), polysorbate 61 (TWEEN® 61), polysorbate 65 (TWEEN® 65), polysorbate 80 (TWEEN® 80), and polysorbate 81 (TWEEN® 81); poloxamers (polyethylene-polypropylene copolymers), like Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), Poloxamer 407 (PLURONIC® F127), polyoxyethyleneglycol dodecyl ethers, like BRIJ® 30, and BRIJ® 35; 2-dodecoxyethanol (LUBROL®-PX); polyoxyethylene octyl phenyl ether (TRITON® X-100); sodium dodecyl sulfate (SDS); 3-[(3-Cholamidopropyl)dimethylammonio]-1-propanesulfonate (CHAPS); 3-[(3-Cholamidopropyl)dimethylammonio]-2-hydroxy-1-propanesulfonate (CHAPSO); sucrose monolaurate; and sodium cholate. Other non-limiting examples of surfactant excipients can be found in, e.g., Pharmaceutical Dosage Forms and Drug Delivery Systems (Howard C. Ansel et al., eds., Lippincott Williams & Wilkins Publishers, 7$^{th}$ ed. 1999); Remington: The Science and Practice of Pharmacy (Alfonso R. Gennaro ed., Lippincott, Williams & Wilkins, 20$^{th}$ ed. 2000); Goodman & Gilman's The Pharmacological Basis of Therapeutics (Joel G. Hardman et al., eds., McGraw-Hill Professional, 10$^{th}$ ed. 2001); and Handbook of Pharmaceutical Excipients (Raymond C. Rowe et al., APhA Publications, 4$^{th}$ edition 2003), each of which is hereby incorporated by reference in its entirety.

In aspects of this embodiment, a hydrogel formulation comprises a polysorbate, a poloxamer, a polyoxyethyleneglycol dodecyl ether, 2-dodecoxyethanol, polyoxyethylene octyl phenyl ether, sodium dodecyl sulfate, 3-[(3-Cholamidopropyl)dimethylammonio]-1-propanesulfonate, 3-[(3-Cholamidopropyl)dimethylammonio]-2-hydroxy-1-propanesulfonate, sucrose monolaurate; or sodium cholate.

Aspects of the present specification provide, in part, a method of treating a soft tissue condition of an individual by administering a composition disclosed herein. As used herein, the term "treating," refers to reducing or eliminating in an individual a cosmetic or clinical symptom of a soft tissue condition characterized by a soft tissue imperfection, defect, disease, and/or disorder; or delaying or preventing in an individual the onset of a cosmetic or clinical symptom of a condition characterized by a soft tissue imperfection, defect, disease, and/or disorder. For example, the term "treating" can mean reducing a symptom of a condition characterized by a soft tissue defect, disease, and/or disorder by, e.g., at least 20%, at least 30%, at least 40%, at least 50%, at least 60%, at least 70%, at least 80%, at least 90% or at least 100%. The effectiveness of a compound disclosed herein in treating a condition characterized by a soft tissue defect, disease, and/or disorder can be determined by observing one or more cosmetic, clinical symptoms, and/or physiological indicators associated with the condition. An improvement in a soft tissue defect, disease, and/or disorder also can be indicated by a reduced need for a concurrent therapy. Those of skill in the art will know the appropriate symptoms or indicators associated with specific soft tissue defect, disease, and/or disorder and will know how to determine if an individual is a candidate for treatment with a compound or composition disclosed herein.

A composition or compound is administered to an individual. An individual is typically a human being. Typically, any individual who is a candidate for a conventional procedure to treat a soft tissue condition is a candidate for a method disclosed herein. In addition, the presently disclosed compositions and methods may apply to individuals seeking a small/moderate enlargement, shape change or contour alteration of a body part or region, which may not be technically possible or aesthetically acceptable with existing soft tissue implant technology. Pre-operative evaluation typically includes routine history and physical examination in addition to thorough informed consent disclosing all relevant risks and benefits of the procedure.

The composition and methods disclosed herein are useful in treating a soft tissue condition. A soft tissue condition includes, without limitation, a soft tissue imperfection, defect, disease, and/or disorder. Non-limiting examples of a soft tissue condition include breast imperfection, defect, disease and/or disorder, such as, e.g., a breast augmentation, a breast reconstruction, mastopexy, micromastia, thoracic hypoplasia, Poland's syndrome, defects due to implant complications like capsular contraction and/or rupture; a facial imperfection, defect, disease or disorder, such as, e.g., a facial augmentation, a facial reconstruction, Parry-Romberg syndrome, lupus erythematosus profundus, dermal divots, sunken checks, thin lips, nasal imperfections or defects, retro-orbital imperfections or defects, a facial fold, line and/or wrinkle like a glabellar line, a nasolabial line, a perioral line, and/or a marionette line, and/or other contour deformities or imperfections of the face; a neck imperfection, defect, disease or disorder; a skin imperfection, defect, disease and/or disorder; other soft tissue imperfections, defects, diseases and/or disorders, such as, e.g., an augmentation or a reconstruction of the upper arm, lower arm, hand, shoulder, back, torso including abdomen, buttocks, upper leg, lower leg including calves, foot including plantar fat pad, eye, genitals, or other body part, region or area, or a disease or disorder affecting these body parts, regions or areas; urinary incontinence, fecal incontinence, other forms of incontinence; and gastroesophageal reflux disease (GERD).

The amount of a composition used with any of the methods as disclosed herein will typically be determined based on the alteration and/or improvement desired, the reduction and/or elimination of a soft tissue condition symptom desired, the clinical and/or cosmetic effect desired by the individual and/or physician, and the body part or region being treated. The effectiveness of composition administration may be manifested by one or more of the following clinical and/or cosmetic measures: altered and/or improved soft tissue shape, altered and/or improved soft tissue size, altered and/or improved soft tissue contour, altered and/or improved tissue function, tissue ingrowth support and/or new collagen deposition, sustained engraftment of composition, improved patient satisfaction and/or quality of life, and decreased use of implantable foreign material.

For example, for breast augmentation procedures, effectiveness of the compositions and methods may be manifested by one or more of the following clinical and/or cosmetic measures: increased breast size, altered breast shape, altered breast contour, sustained engraftment, reduction in the risk of capsular contraction, decreased rate of liponecrotic cyst formation, improved patient satisfaction and/or quality of life, and decreased use of breast implant.

As another example, effectiveness of the compositions and methods in treating a facial soft tissue may be manifested by one or more of the following clinical and/or cosmetic measures: increased size, shape, and/or contour of facial feature like increased size, shape, and/or contour of lip, cheek or eye region; altered size, shape, and/or contour of facial feature like altered size, shape, and/or contour of lip, cheek or eye region shape; reduction or elimination of a wrinkle, fold or line in the skin; resistance to a wrinkle, fold or line in the skin; rehydration of the skin; increased elasticity to the skin; reduction or elimination of skin roughness; increased and/or improved skin tautness; reduction or elimination of stretch lines or marks; increased and/or improved skin tone, shine, brightness and/or radiance; increased and/or improved skin color, reduction or elimination of skin paleness; sustained engraftment of composition; decreased side effects; improved patient satisfaction and/or quality of life.

As yet another example, for urinary incontinence procedures, effectiveness of the compositions and methods for sphincter support may be manifested by one or more of the following clinical measures: decreased frequency of incontinence, sustained engraftment, improved patient satisfaction and/or quality of life, and decreased use of implantable foreign filler.

The amount of a composition used with any of the methods disclosed herein will typically be a therapeutically effective amount. As used herein, the term "therapeutically effective amount" is synonymous with "effective amount", "therapeutically effective dose", and/or "effective dose" and refers to the amount of compound that will elicit the biological, cosmetic or clinical response being sought by the practitioner in an individual in need thereof. As a non-limiting example, an effective amount is an amount sufficient to achieve one or more of the clinical and/or cosmetic measures disclosed herein. The appropriate effective amount to be administered for a particular application of the disclosed methods can be determined by those skilled in the art, using the guidance provided herein. For example, an effective amount can be extrapolated from in vitro and in vivo assays as described in the present specification. One skilled in the art will recognize that the condition of the individual can be monitored throughout the course of therapy and that the effective amount of a composition disclosed herein that is administered can be adjusted accordingly.

In aspects of this embodiment, the amount of a composition administered is, e.g., 0.01 g, 0.05 g, 0.1 g, 0.5 g, 1 g, 5 g, 10 g, 20 g, 30 g, 40 g, 50 g, 60 g, 70 g, 80 g, 90 g, 100 g, 150 g, or 200 g. In other aspects of this embodiment, the amount of a composition administered is, e.g., about 0.01 g to about 0.1 g, about 0.1 g to about 1 g, about 1 g to about 10 g, about 10 g to about 100 g, or about 50 g to about 200 g. In yet other aspects of this embodiment, the amount of a composition administered is, e.g., 0.01 mL, 0.05 mL, 0.1 mL, 0.5 mL, 1 mL, 5 mL, 10 mL, 20 mL, 30 mL, 40 mL, 50 mL, 60 mL, 70 g, 80 mL, 90 mL, 100 mL, 150 mL, or 200 mL. In other aspects of this embodiment, the amount of a composition administered is, e.g., about 0.01 mL to about 0.1 mL, about 0.1 mL to about 1 mL, about 1 mL to about 10 mL, about 10 mL to about 100 mL, or about 50 mL to about 200 mL.

Aspects of the present invention provide, in part, administering a composition disclosed herein. As used herein, the term "administering" means any delivery mechanism that provides a composition disclosed herein to an individual that potentially results in a clinically, therapeutically, or experimentally beneficial result. The actual delivery mechanism used to administer a composition to an individual can be determined by a person of ordinary skill in the art by taking into account factors, including, without limitation, the type of skin condition, the location of the skin condition, the cause of the skin condition, the severity of the skin condition, the degree of relief desired, the duration of relief desired, the particular composition used, the rate of excretion of the particular composition used, the pharmacodynamics of the particular composition used, the nature of the other compounds included in the particular composition used, the particular route of administration, the particular characteristics, history and risk factors of the individual, such as, e.g., age, weight, general health and the like, or any combination thereof. In an aspect of this embodiment, a composition disclosed herein is administered to a skin region of an individual by injection.

The route of administration of composition administered to an individual patient will typically be determined based on the cosmetic and/or clinical effect desired by the individual and/or physician and the body part or region being treated. A composition disclosed herein may be administered by any means known to persons of ordinary skill in the art including, without limitation, syringe with needle, catheter, topically, or by direct surgical implantation. The composition disclosed herein can be administered into a skin region such as, e.g., a dermal region or a hypodermal region. In addition, a composition disclosed herein can be administered once, or over a plurality of times. Ultimately, the timing used will follow quality care standards.

For a breast soft tissue replacement procedure, the route of administration may include axillary, periareolar, and/or inframammary routes. Alternatively or in addition, a composition may be delivered through a transaxillary endoscopic subpectoral approach. For a facial soft tissue replacement procedure, the route of administration can be frontal, temporal, zygomatic, periocular, mandibula, perioral or chin routes. In urinary incontinence procedures, the route of administration may include transurethral or periurethral routes. Alternatively or in addition, administration may be delivered via an antegrade route. The routes discussed herein do not exclude the use of multiple routes to achieve the desired clinical effect.

Aspects of the present invention provide, in part, a dermal region. As used herein, the term "dermal region" refers to the region of skin comprising the epidermal-dermal junction and the dermis including the superficial dermis (papillary region) and the deep dermis (reticular region). The skin is composed of three primary layers: the epidermis, which provides waterproofing and serves as a barrier to infection; the dermis, which serves as a location for the appendages of skin; and the hypodermis (subcutaneous adipose layer). The epidermis contains no blood vessels, and is nourished by diffusion from the dermis. The main type of cells which make up the epidermis are keratinocytes, melanocytes, Langerhans cells and Merkels cells.

The dermis is the layer of skin beneath the epidermis that consists of connective tissue and cushions the body from stress and strain. The dermis is tightly connected to the epidermis by a basement membrane. It also harbors many Mechanoreceptor/nerve endings that provide the sense of touch and heat. It contains the hair follicles, sweat glands, sebaceous glands, apocrine glands, lymphatic vessels and blood vessels. The blood vessels in the dermis provide nourishment and waste removal from its own cells as well as from the Stratum basale of the epidermis. The dermis is structurally divided into two areas: a superficial area adjacent to the epidermis, called the papillary region, and a deep thicker area known as the reticular region.

The papillary region is composed of loose areolar connective tissue. It is named for its fingerlike projections called papillae that extend toward the epidermis. The papillae provide the dermis with a "bumpy" surface that interdigitates with the epidermis, strengthening the connection between the two layers of skin. The reticular region lies deep in the papillary region and is usually much thicker. It is composed of dense irregular connective tissue, and receives its name from the dense concentration of collagenous, elastic, and reticular fibers that weave throughout it. These protein fibers give the dermis its properties of strength, extensibility, and elasticity. Also located within the reticular region are the roots of the hair, sebaceous glands, sweat glands, receptors, nails, and blood vessels. Tattoo ink is held in the dermis. Stretch marks from pregnancy are also located in the dermis.

The hypodermis lies below the dermis. Its purpose is to attach the dermal region of the skin to underlying bone and muscle as well as supplying it with blood vessels and nerves. It consists of loose connective tissue and elastin. The main cell types are fibroblasts, macrophages and adipocytes (the hypodermis contains 50% of body fat). Fat serves as padding and insulation for the body.

In an aspect of this embodiment, a composition disclosed herein is administered to a skin region of an individual by injection into a dermal region or a hypodermal region. In aspects of this embodiment, a composition disclosed herein is administered to a dermal region of an individual by injection into, e.g., an epidermal-dermal junction region, a papillary region, a reticular region, or any combination thereof.

Aspects of the present specification disclose, in part, a method of treating a soft tissue condition of an individual, the method comprising the steps of administering a composition disclosed herein to a site of the soft tissue condition of the individual, wherein the administration of the composition improves the soft tissue condition, thereby treating the soft tissue condition. In aspects of this embodiment, a soft tissue condition is a breast tissue condition, a facial tissue condition, a neck condition, a skin condition, an upper arm condition, a lower arm condition, a hand condition, a shoulder condition, a back condition, a torso including abdominal condition, a buttock condition, an upper leg condition, a lower leg condition including calf condition, a foot condition including plantar fat pad condition, an eye condition, a genital condition, or a condition effecting another body part, region or area.

Other aspects of the present specification disclose, in part, a method of treating a skin condition comprises the step of administering to an individual suffering from a skin condition a composition disclosed herein, wherein the administration of the composition improves the skin condition, thereby treating the skin condition. In an aspect of this embodiment, a skin condition is a method of treating skin dehydration comprises the step of administering to an individual suffering from skin dehydration a composition disclosed herein, wherein the administration of the composition rehydrates the skin, thereby treating skin dehydration. In another aspect of this embodiment, a method of treating a lack of skin elasticity comprises the step of administering to an individual suffering from a lack of skin elasticity a composition disclosed herein, wherein the administration of the composition increases the elasticity of the skin, thereby treating a lack of skin elasticity. In yet another aspect of this embodiment, a method of treating skin roughness comprises the step of administering to an individual suffering from skin roughness a composition disclosed herein, wherein the administration of the composition decreases skin roughness, thereby treating skin roughness. In still another aspect of this embodiment, a method of treating a lack of skin tautness comprises the step of administering to an individual suffering from a lack of skin tautness a composition disclosed herein, wherein the administration of the composition makes the skin tauter, thereby treating a lack of skin tautness.

In a further aspect of this embodiment, a method of treating a skin stretch line or mark comprises the step of administering to an individual suffering from a skin stretch line or mark a composition disclosed herein, wherein the administration of the composition reduces or eliminates the skin stretch line or mark, thereby treating a skin stretch line or mark. In another aspect of this embodiment, a method of treating skin paleness comprises the step of administering to an individual suffering from skin paleness a composition disclosed herein, wherein the administration of the composition increases skin tone or radiance, thereby treating skin paleness. In another aspect of this embodiment, a method of treating skin wrinkles comprises the step of administering to an individual suffering from skin wrinkles a composition disclosed herein, wherein the administration of the composition reduces or eliminates skin wrinkles, thereby treating skin wrinkles. In yet another aspect of this embodiment, a method of treating skin wrinkles comprises the step of administering to an individual a composition disclosed herein, wherein the administration of the composition makes the skin resistant to skin wrinkles, thereby treating skin wrinkles.

Aspects of the present specification provide, in part, administration of a composition disclosed herein wherein such administration promotes new collagen deposition. The compositions comprising a silk fibroin hydrogel component or particle and matrix polymer hydrogel component or particle support tissue ingrowth and new deposition of collagen (Example 21).

In an embodiment, administration of a composition disclosed herein increases new collagen deposition. In aspects of this embodiment, administration of a composition disclosed herein increases new collagen deposition by about 10%, about 20%, about 30%, about 40%, about 50%, about 60%, about 70%, about 80%, about 90%, or about 100%, relative to the same or similar composition comprising hydrogel particles including a matrix polymer, but lacking a silk fibroin; or a composition comprising a matrix polymer hydrogel component, but lacking a silk fibroin hydrogel component. In other aspects of this embodiment, administration of a composition disclosed herein increases new collagen deposition by at least 25%, at least 50%, at least 75%, at least 100%, at least 125%, at least 150%, at least 175%, at least 200%, at least 225%, at least 250%, at least 275%, or at least 300%, relative to the same or similar composition comprising hydrogel particles including a matrix polymer, but lacking a silk fibroin; or a composition comprising a matrix polymer hydrogel component, but lacking a silk fibroin hydrogel component. In yet other aspects of this embodiment, administration of a composition disclosed herein increases new collagen deposition by about 10% to about 100%, about 50% to about 150%, about 100% to about 200%, about 150% to about 250%, about 200% to about 300%, about 350% to about 450%, about 400% to about 500%, about 550% to about 650%, about 600% to about 700%, relative to the same or similar composition comprising hydrogel particles including a matrix polymer, but lacking a silk fibroin; or a composition comprising a matrix polymer hydrogel component, but lacking a silk fibroin hydrogel component.

Aspects of the present specification can also be described as follows:

1. A composition comprising a) hydrogel particles comprising a substantially sericin-depleted silk fibroin; and b) hydrogel particles comprising a matrix polymer including an elastic protein; and
2. The composition of 1, wherein the silk fibroin hydrogel particles and elastic protein hydrogel particles have a cross-sectional area from about 20 $\mu m^2$ to about 50 $\mu m^2$, a cross-sectional area from about 0.1 $\mu m^2$ to about 10 $\mu m^2$, or a cross-sectional area from about 0.1 $\mu m^2$ to about 1000 $\mu m^2$.
3. The composition of 1 or 2, wherein the hydrogel particles are part of a gel phase.
4. A composition comprising hydrogel particles comprising a substantially sericin-depleted silk fibroin and a matrix polymer including an elastic protein.
5. The composition of 3, wherein the hydrogel particles have a cross-sectional area from about 20 $\mu m^2$ to about 50 $\mu m^2$, a cross-sectional area from about 0.1 $\mu m^2$ to about 10 $\mu m^2$, or a cross-sectional area from about 0.1 $\mu m^2$ to about 1000 $\mu m^2$.
6. The composition of 4 or 5, wherein the hydrogel particles are part of a gel phase.
7. The composition of 1 or 4, wherein the silk fibroin comprises about 1% (w/v) to about 10% (w/v) of the hydrogel.
8. The composition of 1 or 4, wherein the final concentration of the silk fibroin is from about 3 mg/g to about 30 mg/g.
9. The composition of 1 or 4, wherein the silk fibroin comprises a protein structure having a β-sheet conformation of at least 20%, at least 50%, or at least 80%.
10. The composition of 1 or 4, wherein the silk fibroin comprises a protein structure having an α-helical and random coil conformation of at most 20%.
11. The composition of 1 or 4, wherein the elastic protein is a resilin, a resilin-like polypeptide, an elastin, an elastin-like polypeptide, a silk protein-elastin-like polypeptide, an abductin, a byssus, a gliadin, a glutenin, abductin, or a collagen.
12. The composition of 1 or 4, wherein the elastic protein is crosslinked.
13. The composition of 1 or 4, wherein the crosslinked elastic protein has a degree of crosslinking of at least 1%.
14. The composition of 1 or 4, wherein the crosslinked elastic protein has a degree of crosslinking of at most 17%.
15. The composition of 1 or 4, wherein the crosslinked elastic protein has a degree of crosslinking of about 1% to about 17%.
16. The composition of 1 or 4, wherein the uncrosslinked elastic protein represents about 90% or more by weight of the total matrix polymer present in the composition.
17. The composition of 16, wherein the hydrogel particles further comprises an amphiphilic peptide.
18. The composition of 16, wherein the amphiphilic peptide comprising a RGD motif or a non-RGD integrin.
19. The composition of 16, wherein the amphiphilic peptide is 23 RGD.
20. The composition of 16, wherein the amphiphilic peptide comprises of a tail region, followed by a spacer region and finally a RGD motif.
21. The composition of 16, wherein the silk fibroin hydrogel particles comprises a molar ratio of 1:10 to 10:1 moles of the amphiphilic peptide per mole of the silk fibroin.
22. The composition of 16, wherein the silk fibroin hydrogel particles comprises a molar ratio of 3:1 moles of the amphiphilic peptide per mole of the silk fibroin.
23. The composition of 1 or 4, wherein the silk fibroin hydrogel particles further comprise a synthetic molecule having the formula: (molecule X)$_n$-(spacer peptide)$_{0-300}$-(five-amino-acid peptide tail) is conjugated to the silk fibroin.
24. The composition of 1 or 4, wherein the composition further comprises a carrier phase.
25. The composition of 24, wherein the carrier phase comprises saline.
26. The composition of 24, wherein the carrier phase comprises a surfactant solution.
27. The composition of 24, wherein the gel phase is 50% to 99% of the total formulation volume, the remainder being a carrier solution.
28. The composition of 27, wherein the gel phase is 75% of the total formulation volume, the remainder being a carrier solution.
29. The composition of 1 or 4, wherein the composition further comprising lidocaine.
30. The composition of 1 or 4, wherein, upon injection, the hydrogel particles remains substantially at the injection site for one month to eighteen months.
31. A method of treating a soft tissue condition in an individual in need thereof, the method comprising the step of administering a composition of 1 or 4 into a skin region of the individual, wherein the administration improves the condition.
32. The method of 31, wherein the soft tissue condition is wherein the soft tissue condition is a breast tissue condition, a facial tissue condition, a neck condition, a skin condition, an upper arm condition, a lower arm condition, a hand condition, a shoulder condition, a back condition, a torso including abdominal condition, a buttock condition, an upper leg condition, a lower leg condition including calf condition, a foot condition including plantar fat pad condition, an eye condition, a genital condition, or a condition effecting another body part, region or area.
33. The method of 32, wherein the breast tissue condition is a breast imperfection, a breast defect, a breast augmentation, or a breast reconstruction.
34. The method of 32, wherein the facial tissue condition is a facial imperfection, a facial defect, a facial augmentation, or a facial reconstruction.
35. The method of 32, wherein the facial soft tissue condition is a dermal divot, a sunken check, a thin lip, a nasal imperfection or defect, a retro-orbital imperfection or defect, a facial fold, a facial line, a facial wrinkle, or other size, shape or contour imperfection or defect of the face.
36. The method of 35, wherein the wrinkle is a glabellar line, a nasolabial line, a perioral line, or a marionette line.
37. The method of 32, wherein the facial soft tissue condition is skin dehydration, a lack of skin elasticity, skin roughness, a lack of skin tautness, a skin stretch line or mark, or skin paleness.

38. The method of 32, wherein the skin condition is Parry-Romberg syndrome or lupus erythematosus profundus.
39. The method of 31, wherein the soft tissue condition is urinary incontinence, fecal incontinence, or gastroesophageal reflux disease (GERD).

EXAMPLES

The following examples illustrate representative embodiments now contemplated, but should not be construed to limit the disclosed purified silk fibroin and method for purifying such silk fibroins, hydrogels comprising such silk fibroin with or without an amphiphilic peptide and methods for making hydrogels comprising such silk fibroin and the use of silk fibroin hydrogels in a variety of medical uses.

Example 1

Silk Sericin Extraction

Silk fibroin for generation of the hydrogel was obtained in the form of degummed *B. mori* silk at a size of 20 denier-22 denier (38 μm±5.6 μm diameter). This degummed silk was further processed in order to remove the inherently present and potentially antigenic protein glue, sericin that conjoins independent fibroin filaments. This was done as described previously herein. Following removal of sericin, the pure fibroin was dried carefully to ambient humidity levels using a laminar flow hood.

Example 2

Generation of Silk Fibroin Solution

Silk fibroin filaments, cleaned of their sericin and rinsed free of insoluble debris and ionic contaminants were used for the generation of an aqueous silk solution. These silk fibers were added to a solution of 9.3M LiBr and purified water (e.g., MILLI-Q® Ultrapure Water Purification Systems) (Millipore, Billerica, Mass.) to make a solution consisting of 20% pure silk (% w/v). This mixture was then heated to a temperature of 60° C. and digested for a period of four hours. A total of 12 mL of the resultant solution was then loaded into a 3 mL-12 mL Slide-A-Lyzer dialysis cassette (Pierce Biotechnology, Inc., Rockford, Ill.) (molecular weight cutoff of 3.5 kD) and placed into a beaker containing purified water as a dialysis buffer at a volume of 1 L water per 12 mL cassette of silk solution. The beakers were placed on stir plates and stirred continuously for the duration of the dialysis. Changes of dialysis buffer occurred at 1, 4, 12, 24, and 36 hours of processing time.

Following dialysis, the solution was removed from the cassettes by means of a syringe and needle and centrifuged at 30,000 g relative centrifugal force (RCF) at 4° C. for 30 minutes, decanting the supernatant (silk solution) into a clean centrifuge tube, then repeating the centrifugation for a further 30 minutes. This process of centrifugation is beneficial for removal of insoluble particulate debris associated with the silk solution both prior to and following after dialysis. It is believed that such insoluble debris could serve as antigens in vivo or perhaps nucleation points about which gelation of the silk could occur, shortening storage life of the solution and compromising the uniformity of the gelation system. After completion of the second centrifugation, the supernatant was again collected and stored at 4° C. until needed. To confirm uniformity of the dialysis product, known volumes of the solution were collected, massed, and then dried completely through lyophilization. These lyophilized samples were then massed and the dry mass of solution compared to initial solution volume to determine percent silk present per unit volume of solution. Additionally, the solution was assessed via X-ray Photoelectron Spectroscopy (XPS) analysis to ensure that no detectable quantities of $Li^+$ or $Br^-$ ions were present in the solution.

Example 3

Induction of Gelation

A variety of different methods were employed in the course of hydrogel development for the purposes of contrasting and comparing certain relevant properties of various formulae. Regardless of the nature in which the gelation process was carried out, the final determination that a "gel" state had been reached was applied uniformly to all groups. A solution or composite of solutions (i.e., silk solution blended with an enhancer or enhancer solution) was considered a gel after observing formation of a uniform solid phase throughout the entire volume, generally opaque and white in appearance.

Samples to be produced by passive gelation were not exposed to any enhancer additives. These gels were produced by measuring a volume of silk solution into a casting vessel, for the purposes of these experiments, polypropylene tubes sealed against air penetration and water loss, and the sample allowed to stand under ambient room conditions (nominally 20-24° C., 1 atm, 40% relative humidity) until fully gelled. Care was taken to ensure uniformity of casting vessels material of construction across groups so as to avoid potential influence from surface effects. These effects may serve to enhance or inhibit gelation and may be caused by factors including but not limited to siliconization, surface roughness, surface charge, debris contamination, surface hydrophobicity/hydrophilicity, and altered mass transfer dynamics.

Samples produced by means of a 23RGD-induced process were made in one of two ways, the first being direct addition of 23RGD in a pre-determined ratio to the silk solution without any sort of reconstitution. The 23RGD (obtained as a desiccated fine powder form) was blended into a measured volume of 8% silk solution within the casting vessel by pipetting using a 1000 μL pipette. These gels were then cast in polypropylene tubes, sealed against air penetration and water loss, and the sample was allowed to stand under ambient room conditions (nominally 20-24° C., 1 atm, 40% relative humidity) until fully gelled.

The 23RGD-induced gels were also produced by first dissolving the 23RGD powder in purified water. The concentration of this solution was determined based upon the amount of 23RGD to be introduced into a gel and the final concentration of silk desired in the gel. In the case of 4% silk gels enhanced with 23RGD, quantities of water equal to the amount of 8% silk solution to be used in the gel were used for the dissolution of appropriate quantities of 23RGD. In the case of gels induced by addition of 23RGD to be generated at a molar ratio of 3:1 23RGD:silk, a quantity of 23RGD was dissolved in 1 mL of water per 1 mL of 8% silk solution to be gelled. This mixing was performed in the casting vessel as well, being accomplished by means of rapid pipetting with a 1000 μL pipette when appropriate. These gels were then cast in polypropylene tubes, sealed against air penetration and water loss, and the sample was allowed to stand under ambient room conditions (nominally 20-24° C., 1 atm, 40% relative humidity) until fully gelled.

Samples produced by means of ethanol-enhanced gelation (EEG) were generated by means of directly adding ethanol to a measured volume of 8% silk solution in the casting vessel. The ethanol is added in a quantity such that the volume added should yield a volumetric dilution of the 8% silk solution resulting in the final required concentration of silk within the gel, assuming minimal volume loss due to miscibility of the organic added. The mixture of ethanol and silk solution is then mixed by means of pipetting with a 1000 µL pipette when appropriate. These gels were then cast in polypropylene tubes, sealed against air penetration and water loss, and the sample was allowed to stand under ambient room conditions (nominally 20-24° C., 1 atm, 40% relative humidity) until fully gelled.

Samples produced by a combined 23RGD-ethanol effect (RGDEEG) were generated using a solution of 90% ethanol, 10% purified water and appropriate quantities of 23RGD dissolved in this solvent. It was not possible to readily dissolve 23RGD in pure ethanol and it was believed that undissolved 23RGD might cause poor distribution of the peptide throughout the gel phase. As a result, it was determined that since a solution of ethanol and water offering similar gelation acceleration characteristics to a pure ethanol solution and reasonable 23RGD solubility would be an acceptable alternative. A solution of 90% ethanol and 10% water met both of these criteria and as a result was used for generation of these gels. The 23RGD concentration of this ethanol solution was determined based upon the amount of 23RGD to be introduced into a gel and the final concentration of silk desired in the gel. In the case of 4% silk gels enhanced with 23RGD, quantities of 90% ethanol equal to the amount of 8% silk solution to be used in the gel were used for the dissolution of appropriate quantities of 23RGD. In the case of gels induced by addition of 23RGD to be generated at a molar ratio of 3:1 23RGD:silk, a quantity of 23RGD was dissolved in 1 mL of 90& ethanol per 1 mL of 8% silk solution to be gelled. This mixing was performed in the casting vessel as well, being accomplished by means of rapid pipetting with a 1000 µL pipette when appropriate. These gels were then cast in polypropylene tubes, sealed against air penetration and water loss, and the sample was allowed to stand under ambient room conditions (nominally 20-24° C., 1 atm, 40% relative humidity) until fully gelled.

Silk gelation times were determined by casting gels according to the methods above, the exception being that gels were mixed not through pipetting, but through vigorous mechanical shaking. These studies were conducted using 1.5 mL microcentrifuge tubes as casting vessels with sample groups of N=6 used for each gel formulation (FIG. 1). The determination that a "gel" state had been reached was made in the method as described above, based upon observation of a uniform solid phase throughout the entire volume, generally opaque and white in appearance.

Gelation time varied widely depending on specific formulation. The 8P silk samples took 21 days until gelation while the 4P samples required 31±1 day (data not shown). EEG samples gelled significantly faster than PG samples with a 4E sample requiring 27±5.4 seconds for gelation ($p \leq 0.05$). EEG samples gelled more rapidly as the concentration of ethanol added increased with time required gelation times of 1770±600 s, 670.3±101.0 s, 29.8±5.2 s, 9.7±2.0 s, and 4.2±0.8 s for 6.4E, 6E, 4.8E, 4E, and 3.2E respectively. There were significant differences between all times except 4.8E and 4E, 4E and 3.2E, and 4.8E and 3.2E. RGDEEG gels generated a tightly localized white fibrous precipitate instantaneously upon addition of the ethanol solution to the silk and gelled more quickly than PG samples, though they were slower than EEG gels. 4RL, 4RM and 4RH samples took 22.7±2.5 seconds, 38.8±4.5 seconds, and 154.5±5 seconds to gel with 4RH differing significantly from the other RGDEEG formulations.

Gelation timing experiments revealed the time constraints posed by the PG method. Results indicated that, while increased silk concentration decreased gelation time, the total time to gel was decreased only from 31 days for 4P to 21 days for 8P. This may result from the increased frequency of collisions between silk molecules in solution and resultant gel network assembly. Using ethanol directly added to silk solution as an accelerant proved to dramatically decrease the gelation time of the silk by increasing the volume of ethanol added in a fashion well-modeled by a power function. This increasingly rapid gelation is likely caused by greater competition for hydrating water molecules between silk and ethanol coupled with altered electronegativity of the solution, both favoring forced aggregation of the silk molecules. Studies conducted on RGDEEG samples revealed that addition of greater concentrations of RGD led to increasing gelation times modeled by an exponential function. This appears counter-intuitive as it was expected that RGD should function in some capacity to accelerate gelation.

The slowing of gelation in RGDEEG samples may result from difficulties in silk molecular binding to the RGD-coated silk precipitates, perhaps due to stearic interference with hydrophobic regions of silk chains. Upon RGD-ethanol accelerant addition to the silk solution, a large quantity of silk-RGD complexes was precipitated from the solution. It was noted during the gelation of RGDEEG samples that a fibrillar, white, opaque precipitate was consistently formed within the solution mixture immediately upon mixing. This precipitation from solution may be evidence of this rapid assembly of high concentration silk-RGD precipitates. This formation may be caused by association between silk micelles and peptide molecules in solution, disruption of the silk micelles, and rapid assembly of them into a tightly-localized fibrillar structure. This rapid assembly may progress until driving gradients generated by the differing solvent chemistries provided by the ethanol and water reach an equilibrium state. At this point, silk molecules are able to remain stably in solution with further silk network assembly occurring only by slow lengthening of the initially formed precipitates. While this precipitation provided a high number of nucleation points to initiate completion of a gel network, these nucleation points may be of limited utility based upon availability of binding sites. The remaining silk molecules were much slower to assemble as a result. These precipitates also tended to initiate assembly of a peripheral network comprised largely of loose α-helix and random coil motifs, possibly due to interference in silk packing due to the interference of these particles.

The hydrogels produced by the methods described above derive substantial benefit from the ability to more precisely control the time course for its gelation in comparison to that of a conventionally designed and cast gel. It is evident from monitoring the time between casting and gelation of the device and similarly cast, non-enhanced or exclusively ethanol modified gels that 23RGD under certain circumstances may be manipulated to have an additional accelerant effect upon the process of gelation. This observed enhancer effect both mitigates the time constraints and controllability associated with non-modified gels and additionally alters the manner in which the protein aggregate network is formed relative to solely ethanol enhanced gels.

Example 4

Determination of Residual Ethanol by Colorimetric Analysis

Following gelation of a sample produced with either an ethanol or 23RGD component, the gel was removed from the casting vessel and immersed in a bulk of purified water as a rinse buffer. This bulk comprised a volume such that the volumetric ratio of water to gel was 100:1. The gel was permitted to lay static in the rinse buffer for a period of 72 hours, changing the water every 12 hours.

Figure 2:
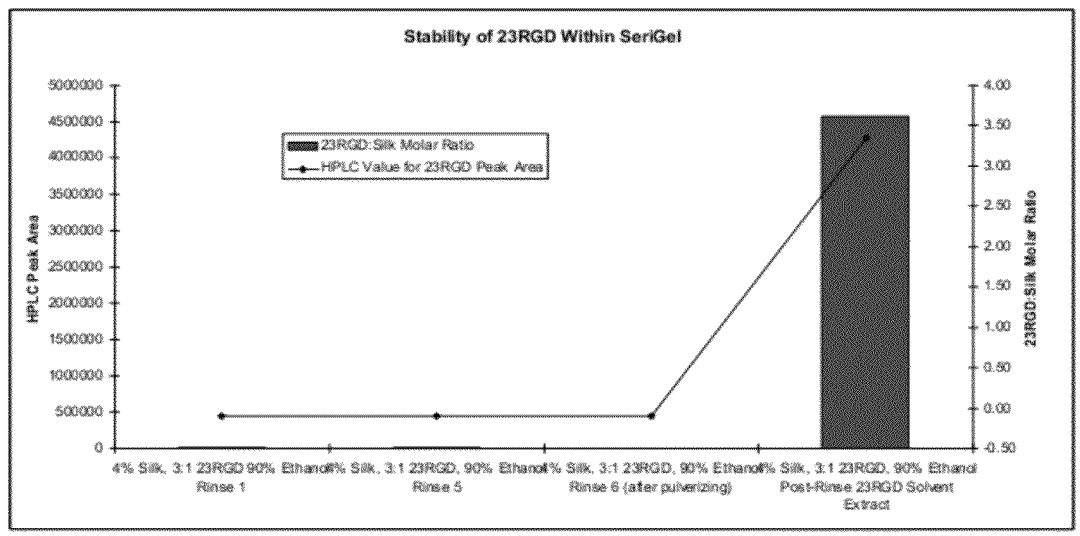
FIG. 2 is a graph of HPLC data illustrating the integration of 23RGD and stability of its binding to 4% silk gel material made with an enhancer solution consisting of a 3:1 molar ratio of 23RGD:silk dissolved in 90% ethanol, 10% water when rinsed multiple times in ultra-purified water over several days. Data are shown for both total peak area and calculated 23RGD:silk molar ratio based on a 23RGD standard curve.

Samples of silk gel were evaluated to determine the total residual content of ethanol in a series of 23RGD-ethanol- and ethanol-enhanced gels. Briefly, samples of gel (N=4 of each type) generated as described above were processed and analyzed using an Ethanol Assay Kit (kit #K620-100 from Bio-Vision Research Prods, Mountain View, Calif.). Samples of gel were cut to a size of approximately 0.3 cm in height by 0.5 cm in diameter (approximately 250 mg). These samples were massed to the nearest 0.1 mg using an APX-60 (Denver Instrument, Denver Colo.) balance as per the manufacturer's instructions. These gel samples were individually ground using a metal spatula and placed into 250 µL of Milli-Q water in microcentrifuge tubes. These gels were incubated at 37° C. for a period of 24 hours. After incubation, the gels were centrifuged on an Eppendorf 5415 microcentrifuge with an HA 45-18-11 rotor (Hamburg, Germany) at 18,000 rpm for 30 minutes. At the conclusion of this centrifugation step, the supernatant was used as the sample of interest according to the instructions provided by the kit manufacturer. Colorimetric analyses of the sample was performed at an absorbance of 570 nm using a spectrophotometer, and in conjunction with a standard curve, residual percentages of ethanol in the gel were calculated (Table 1, FIG. 2). It was shown in this process that the leeching step is capable of substantially removing residual ethanol from the silk gels, as none of these materials exhibited a residual ethanol component of greater than 5% ethanol by mass.

quent to the last rinse, the gel samples were mechanically pulverized by means of a stainless steel stirring rod and the adsorbed 23RGD removed by incubation for 4 hours in a dissolving buffer. This mixture of gel and solvent was then centrifuged on an Eppendorf 5415C at 16,000 g RCF for 30 minutes. The supernatant was collected and centrifuged another 30 minutes at 16,000 g RCF after which time the supernatant was collected in a sample vial for HPLC analysis. Samples of rinse buffer from the first and last rinse were centrifuged in the same fashion after being diluted with the same solvent the gel was extracted with in a volumetric ratio of 1 part rinse buffer to 4 parts solvent. To ensure 23RGD-hydrogel device rinse-exposed surface area was not a limiting factor, the same rinse and extraction process was performed upon devices pulverized after gelation and before rinsing. The peak area consistent with 23RGD for each HPLC sample was taken and these data compared against a standard curve generated for 23RGD on the same HPLC unit under identical handling and run conditions.

The resultant data indicated levels of signal from 23RGD in samples collected from rinse buffer were just slightly higher than values for 23RGD solvent alone and were immeasurable by the standard curve, expected to resolve a relative 23RGD:silk ratio of 0.05:1. By comparison, the assay was able to detect a ratio of 3.35:1 in the final rinsed and extracted 23RGD-enhanced gel.

HPLC data confirmed complete retention of RGD on the silk hydrogel material after the rinse process. This provides not only a functional RGD component to this specific series of hydrogel formulations, but indication for use of amphiphilic peptides as candidates for introduction of other components into silk gels. This knowledge might be applied to a number of other biologically active peptide sequences, though additional work must be done to understand how these specific peptides might influence gelation and how gelation in turn impacts the functionality of these peptides.

TABLE 1

Determination of Residual Ethanol by Colorimetric Analysis

| Silk Concentration | Enhancer Solvent | Enhancer Solute | Initial Ethanol Concentration | Final Ethanol Concentration | |
|---|---|---|---|---|---|
| | | | | Mean | Stdev |
| 2% | 90% | None | 68% | 2.49% | 0.06% |
| | | 3:1 23RDG:Silk | | 4.44% | 0.13% |
| | | 10:1 23RDG:Silk | | 4.77% | 0.29% |
| 4% | | None | 45% | 2.55% | 0.07% |
| | | 3:1 23RDG:Silk | | 2.86% | 0.08% |
| | | 10:1 23RDG:Silk | | 2.97% | 0.07% |
| 6% | | None | 22.5% | 3.12% | 0.05% |
| | | 3:1 23RDG:Silk | | 3.16% | 0.04% |
| | | 10:1 23RDG:Silk | | 2.99% | 0.10% |

Example 5

23RGD Quantification by HPLC

23RGD-infused gels were studied to quantify the amount of 23RGD bound to the silk-hydrogel device as well as the quantity of free 23RGD which might be rinsed free of the device under relevant conditions. Briefly, samples of 23RGD-infused gel were cast and rinsed according to the methods above, with samples of rinse buffer being collected from each rinse for subsequent analysis by HPLC. Additionally, subse-

Example 6

Silk Gel Dry Massing

Silk gel samples of various 23RGD-ethanol- and ethanol-enhanced formulations were cut into sample cylinders (N=4 of each type) of approximately 0.7 cm in height by 0.5 cm in diameter (approximately 500 mg). These samples were massed to the nearest 0.1 mg using an APX-60 (Denver Instrument, Denver Colo.) balance as per the manufacturer's instructions and placed into massed microcentrifuge tubes.

After this, the samples were frozen to −80° C. for 24 hours. At the conclusion of this time, the samples were placed into a lyophilizer unit for a period of 96 hours to remove all water content. Following the completion of this 96 hour drying, the remaining protein components of the silk gel samples were massed again and the mass fraction of water in the samples determined.

Figure 3:
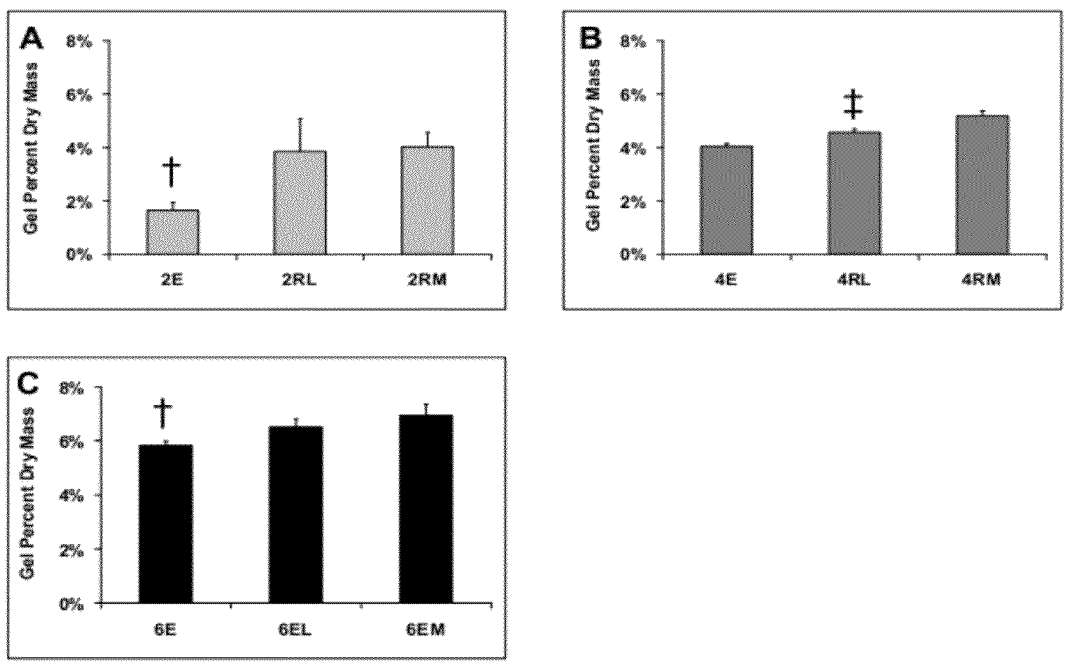
FIG. 3 is a graph comparing gel dry mass component at different RGD concentrations for 2% silk gels (A), 4% silk gels (B), and 6% gels (C). * Samples differ significantly, p<0.05; † sample differs significantly from all others; ‡ all samples differ significantly.

Gel dry massing showed an increasing percentage of dry mass as RGD component increased in each silk concentration group (FIG. 3). The dry mass of 2E was significantly less than 2RL and 2RM ($p \leq 0.05$) at 1.63±0.30%, 3.85±1.23% and 4.03±0.53% respectively (FIG. 3A). The dry masses of 4E, 4RL and 4RM all differed significantly from each other at 4.05±0.10%, 4.56±0.12%, and 5.19±0.18% respectively (FIG. 3B). The dry mass of 6E was significantly less than both 6RL and 6RM at 5.84±0.15%, 6.53±0.28%, and 6.95±0.40% respectively (FIG. 3C).

Figure 4:
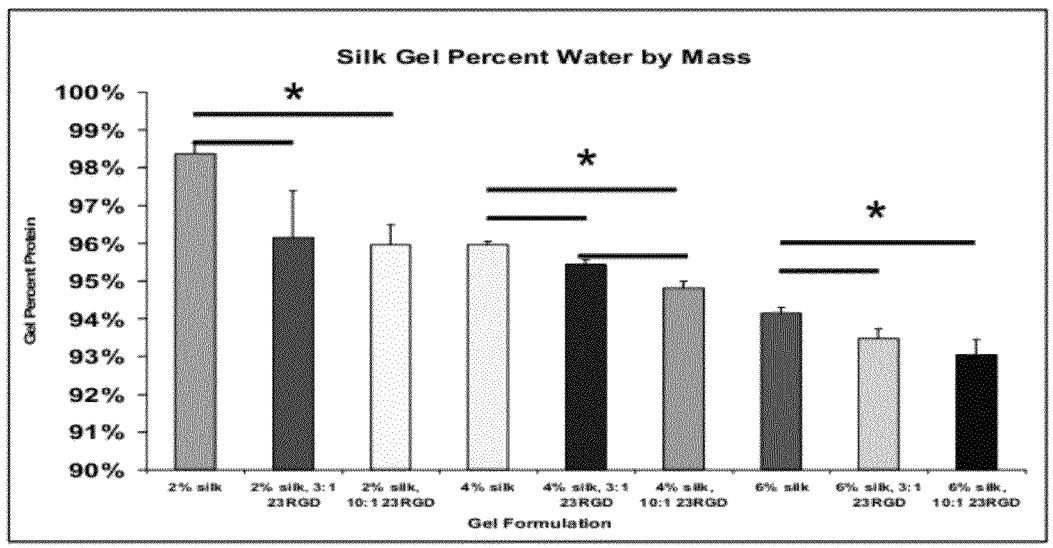
FIG. 4 illustrates the impact upon silk hydrogel water absorption and retention as identified in a gel drying assay. Data are shown as the percentage of mass retained by a silk gel sample (n=4 for each type) after being subjected to a 96-hour lyophilization process. Increasing concentrations of 23RGD enhancer caused increasing dry mass in the gel materials more substantial than the mass of the peptide itself. This phenomenon is likely due to structural differences in 23RGD-enhanced gels which do not permit a level of water entrainment equal to those of gels enhanced only with ethanol.

The gels, regardless of the silk concentration, showed a statistically significant trend toward decreasing percentage of water mass in each gel material as 23RGD component increased as determined by analysis of each silk concentration group with ANOVA (FIG. 4, Tukey post hoc, $p<0.05$). This phenomenon might be explained by the possibility that the 23RGD causes formation of a different secondary structure within the silk hydrogels and that this structure might be less hydrophilic than non-23RGD-enhanced material. It is possible that this may be manifested in a different ratio of β-sheet structure, α-helix structure, and unordered random coil for 23RGD-treated materials than their counterparts, tending to favor the more hydrophobic β-sheet conformation.

Silk gel dry mass data revealed that increasing concentrations of both silk and RGD in the silk gels increased the percentage of dry mass in these materials, though the increase from RGD was too large to attribute solely to additional peptide mass. This phenomenon might be explained by the hypothesized structure of the RGDEEG gels mentioned previously relative to PG and EEG gels. It is likely that the large regions of poorly-associated β-sheet structure in the RGDEEG gels do a poor job at integrating water into the structure. The inter-connecting regions of α-helix structures and unordered random coil are able to entrain water, but do so with less success than in the case of the more homogenous EEG gels. It may also be possible that the hydrophilic RGD sequence interfered with the dry massing procedure, causing rapid gain of water mass upon exposure of the samples to atmospheric conditions.

Example 7

Enzymatic Bioresorption

Gels specified were subjected to in vitro digestion by a solution consisting of non-specific protease mixture. Briefly, gel samples were cast to generate uniform, cylindrical samples of approximately 1 gram total weight (about 1 mL of gel). These samples were digested with a protease obtained from the bacteria *Streptomyces griseus* (Sigma catalog No. P-5147) suspended in phosphate buffered saline at a concentration of 1 mg/ml. A ratio of 3 mL of protease solution per 1 ml of initial gel was used for the purposes of this study. The protease solution was added to a sealed tube containing the gel and incubated for 24 hours at 37° C. with no mechanical mixing. After 24 hours, the solution was drained through a piece of 316 stainless steel woven wire cloth. This permitted retention of all gel particles greater than 50 μm in diameter (gap size was 43 μm by 43 μm), those smaller than that were considered to be "bioresorbed" for the purposes of this assay. After thorough draining of the solution, the mass of the gel was measured wet, but devoid of excess entrained moisture. The protease solution was then replaced and the sample incubated a further 24 hours at 37° C. This process was repeated until the samples were bioresorbed for a total of four days, changing solutions and massing each day.

Figure 5:
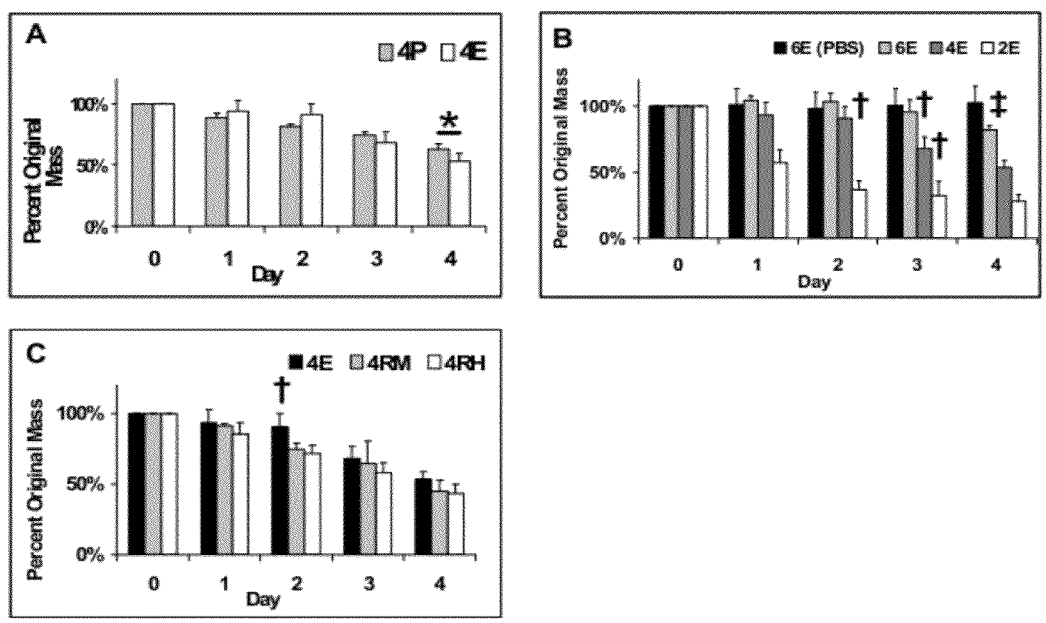
FIG. 5 shows a comparison of the percent mass loss over time due to bioresorption of samples cast by PG and EEG methods (A), cast from increasing silk concentrations (B), and cast using increasing RGD concentrations (C). * Samples differ significantly, p<0.05; † sample differs significantly from all others; ‡ all samples differ significantly.

PG samples and EEG samples bioresorbed similarly, differing significantly only at D4 where 4P samples retained 62.89±4.26% of the original mass and 4E samples retained 53.27±5.45% ($p \leq 0.05$) (FIG. 5A). 6E gels incubated in PBS showed no significant mass loss over the course of the 4 day incubation (FIG. 5B). EEG silk gels with high concentrations of fibroin exhibited higher mass retention than lower concentrations at all days. At Day 1 there were significant differences between 2E and all other gel types with 2E, 4E and 6E gels retaining 57.04±10.03%, 93.21±9.47%, and 103.98±3.65%, respectively while 6E in PBS retained 101.18%±12.01%. At Day 2, there were significant differences again between 2E and all other gel types with 2E, 4E and 6E gels retaining 36.59±7.07%, 90.60±9.24%, and 103.24±6.38% of the original mass while 6E in PBS retained 98.28%±12.38%. At Day 3 there were significant differences between all gel types in protease, with 2E, 4E and 6E gels retaining 32.36±10.48%, 67.85±8.82%, and 95.51±8.97% of the original mass. 6E samples incubated in PBS did not differ from those incubated in protease, retaining 100.39%±12.73% of the original mass. At Day 4 there were significant differences between all gel types with 2E, 4E, and 6E gels retaining 28.14±4.75%, 53.27±5.45%, and 81.76%±3.35% of the original mass while 6E in PBS retained 102.45%±12.50%. Addition of RGD to silk gels appeared to slightly decrease the mass retention of these materials when subjected to proteolytic bioresorption (FIG. 5C). 4E samples retained significantly more mass than 4RM and 4RH at Day 2 as they retained 90.6±9.24%, 74.47±4.55%, and 71.23±6.06% of the initial masses respectively. There were no further significant differences in 4E samples relative to 4RM and 4RH samples over the course of the bioresorption assay.

Figure 6:
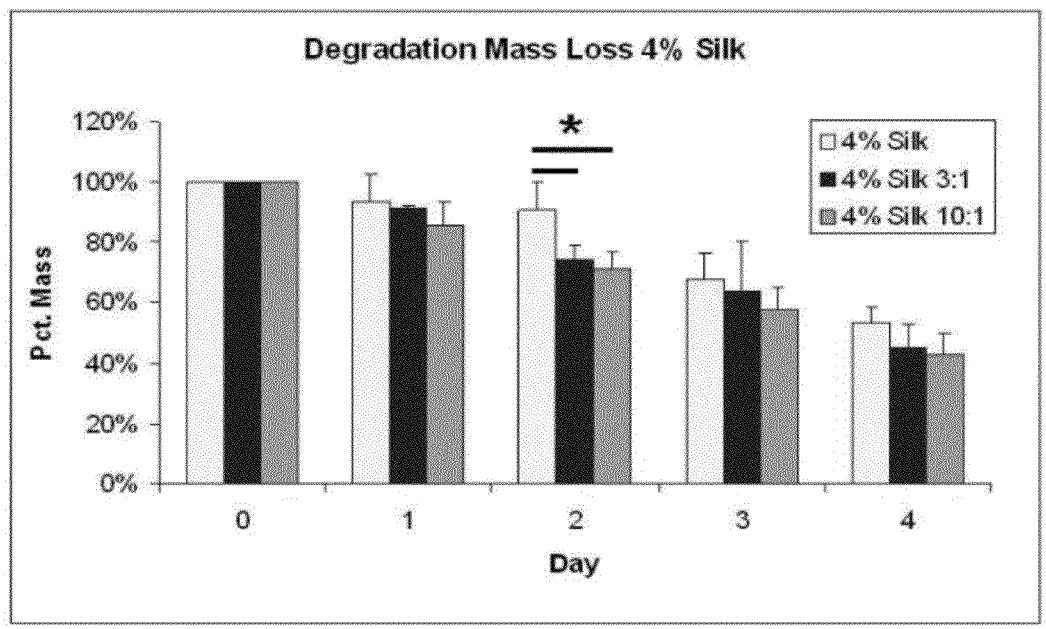
FIG. 6 illustrates wet mass loss due to proteolytic bioresorption of silk hydrogels enhanced by a combination of 23RGD and ethanol at increasing concentrations of 23RGD. As a general trend, gels enhanced with 23RGD tend to be bioresorbed more quickly based upon this assay.
Figure 7:
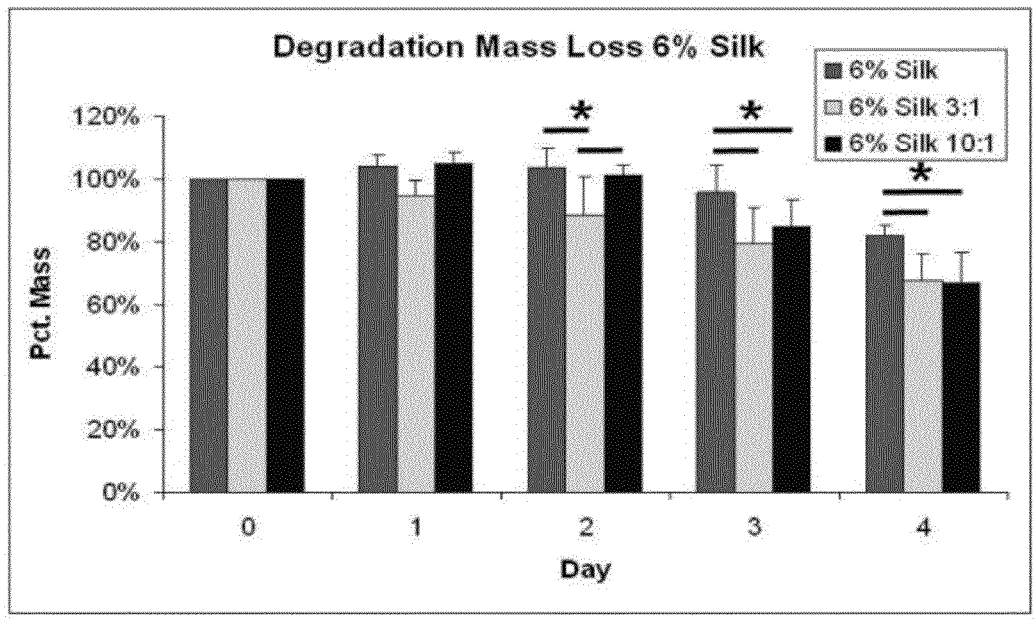
FIG. 7 is a second illustration of the bioresorption behavior of 23RGD-enhanced and non-23RGD-enhanced silk hydrogels when incubated in a protease solution. This bioresorption data serves to reinforce the trend, illustrated in FIG. 5, of a slightly more rapid rate of bioresorption of 23RGD-enhanced hydrogels in comparison to non-23RGD-enhanced gels. The figure also supports the more thorough removal of α-helix and random coil conformations from 23RGD-enhanced gels in FIG. 6 over four days of incubation in protease.
Figure 8A:
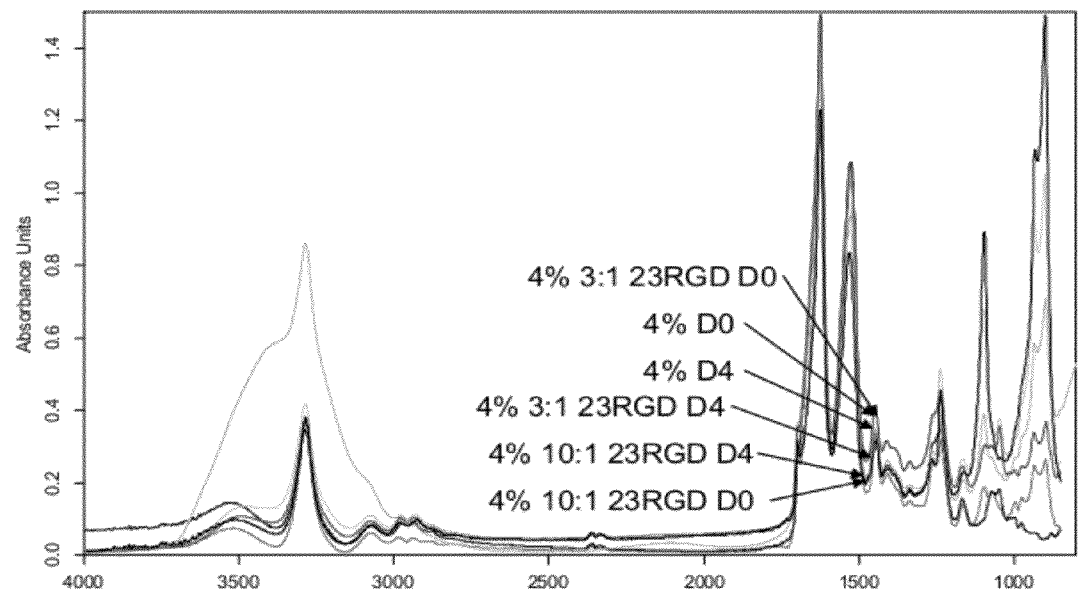
FIG. 8 shows structural features observed by Fourier-Transform Infrared (FTIR) spectroscopy of 4% silk fibroin hydrogel devices which are enhanced by ethanol alone, and two 23RGD-ethanol enhancers. The full spectra (FIG. 8A) of the materials are compared and the Amide I Band (1700-1600 $cm^{-1}$) highlighted for particular attention (FIG. 8B) because of its relevance to secondary protein structure. Of specific interest is the commonality between all gels in their rich β-sheet structure (1700 $cm^{-1}$ and 1622 $cm^{-1}$ respectively, highlighted in FIGS. 8C and 8E) at all time points. These peaks become more pronounced after bioresorption, and begin to differentiate 23RGD-enhanced materials from materials enhanced with ethanol alone. This is evidenced in 23RGD-enhanced gels by a peak shift to lower wave numbers by the 1622 $cm^{-1}$ peak and dramatically increased prominence of the 1700 $cm^{-1}$ peak. Additional differences between bioresorbed and non-bioresorbed gels may be seen in regions of the spectrum known to correlate to α-helix and random coil conformations (1654 $cm^{-1}$ and 1645 $cm^{-1}$ respectively highlighted in FIG. 8D). These conformations are extensively digested in all gel types, but most completely in gels enhanced by 23RGD. This suggests that 23RGD-enhanced gels tend to bioresorb to a very β-sheet rich secondary structure in a more rapid fashion than non-23RGD-enhanced gels. Spectra shown were collected on a Bruker Equinox 55 FTIR unit using a compilation of 128 scans with a resolution of 4 $cm^{-1}$.
Figure 8B:
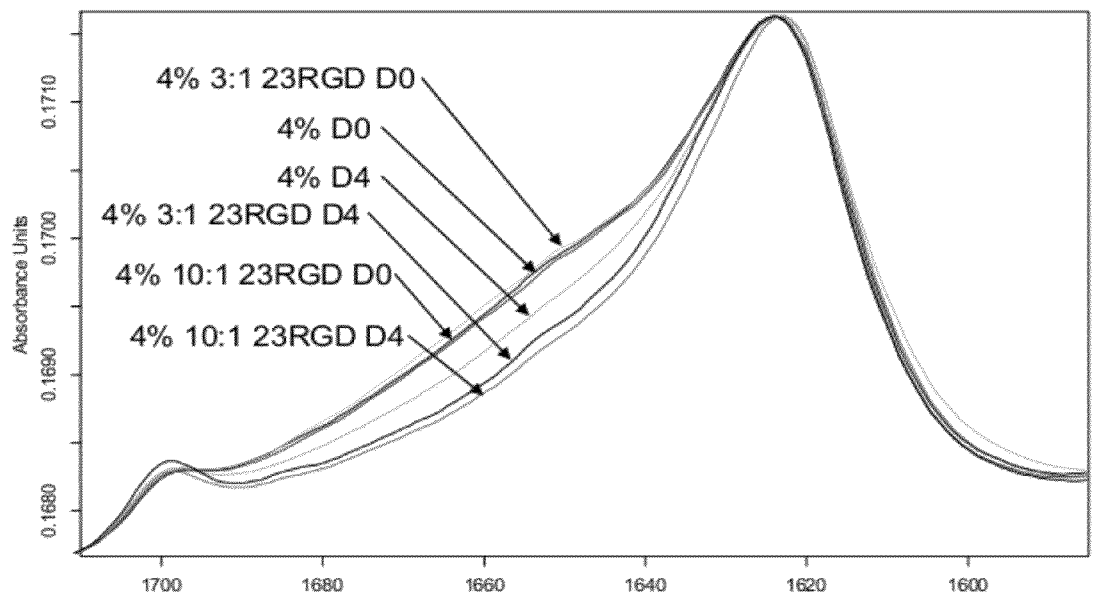
Figure 8C:
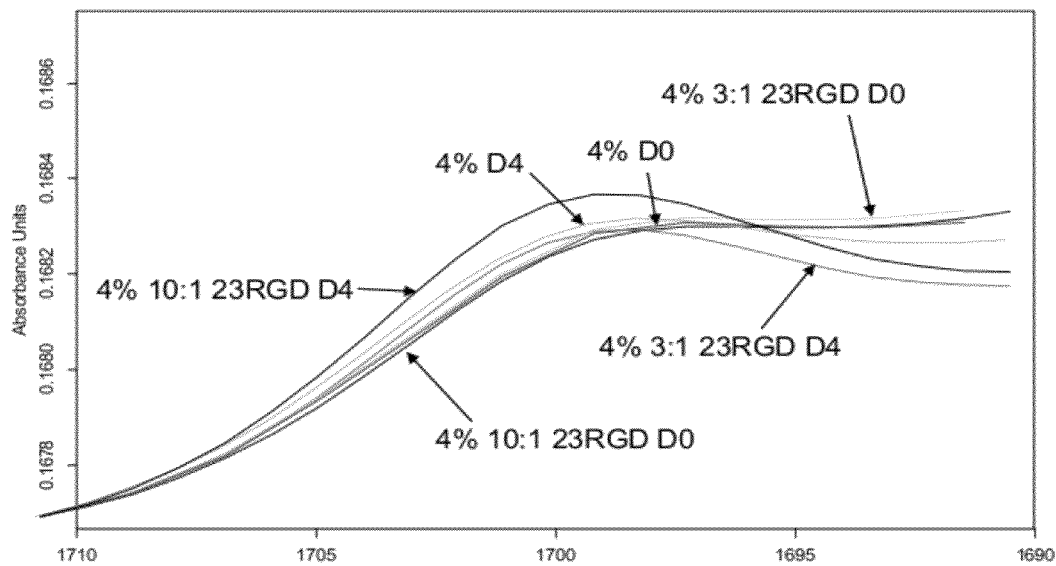
Figure 8D:
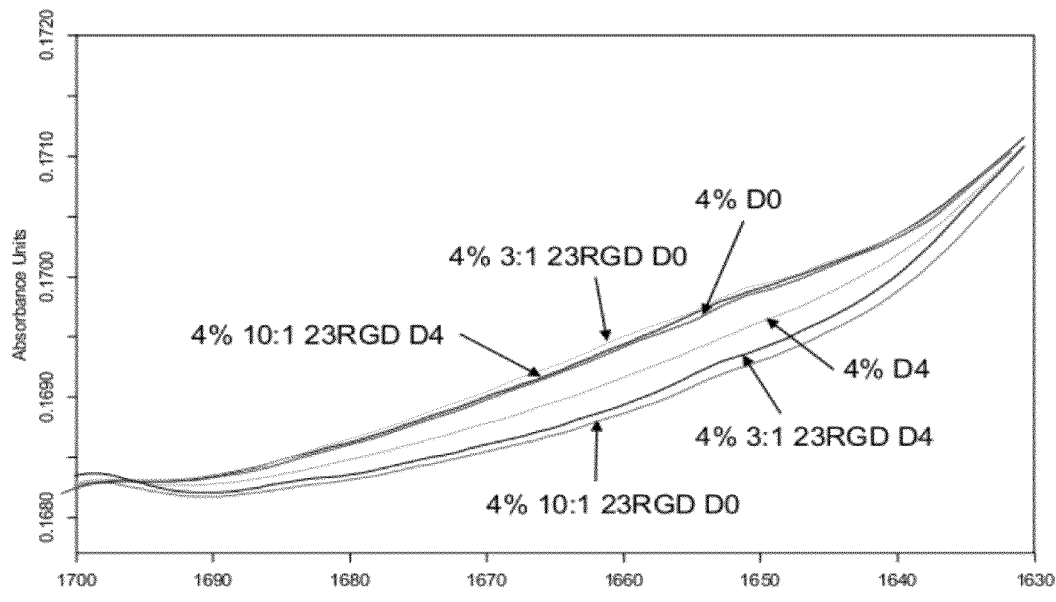
Figure 8E:
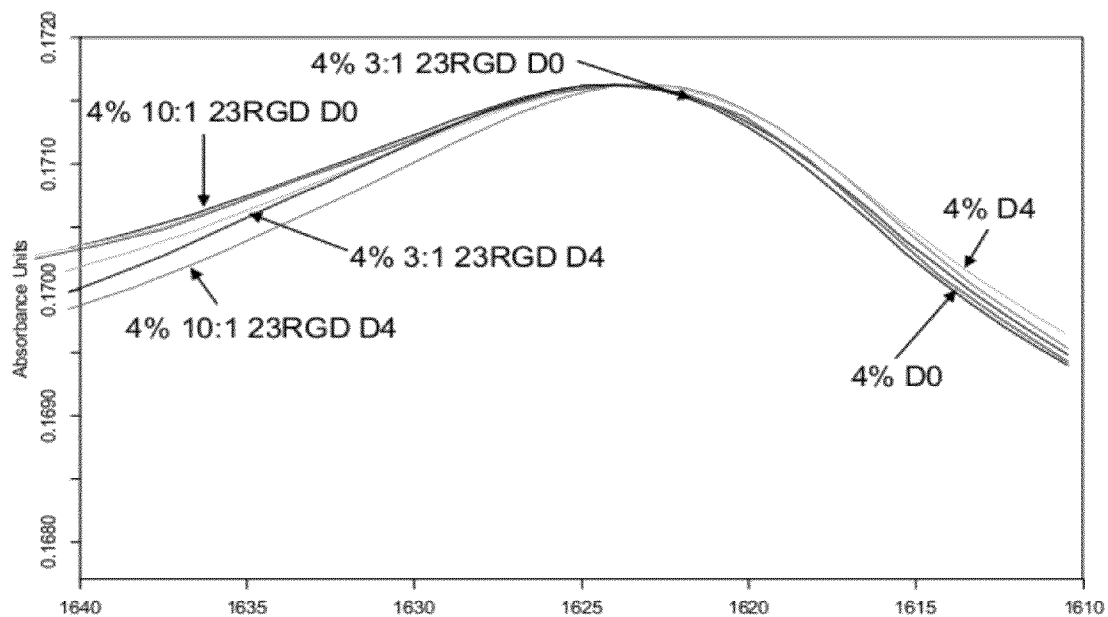

Gel samples treated with 23RGD exhibit a trend toward more rapid bioresorption within the constraints of this particular assay. This was illustrated at the 4% silk concentration (FIG. 6) and then confirmed at a concentration of 6% silk fibroin in the gel materials (FIG. 7). Significant differences in the bioresorption rates of 23RGD enhanced samples recorded by two-way ANOVA using a Bonferroni post test ($p<0.05$), particularly with 6% silk, reinforced the trend. The unique behavior attributed to 23RGD-enhanced materials may be due in part to its unique protein structure, as the bioresorption method considers particles below a size of 50 μm to be bioresorbed, regardless of their stability. It may be possible for a rich beta sheet structure to exist within 23RGD gels which is broken up into small, discrete regions by interfering regions of α-helix structure and random coil which bioresorb more quickly, creating a plethora of tiny, non-resorbed fragments in solution.

In vitro bioresorption of 4P and 4E samples showed both materials had a similar resistance to proteolysis (FIG. 5A). This is indicative that the basic process of ethanol-enhanced gelation is capable of generating a gel structure rapidly without sacrificing important material properties. It was also shown that increasing the concentration of silk in EEG gels from 2% to 4% to 6% in 2E, 4E, and 6E respectively, substantially decreased sample bioresorption mass loss (FIG. 5B). This may correlate to a more homogeneous, stable and resilient gel structure, or simply to a greater quantity of silk molecules to be cleaved by the proteases in order to bioresorb the samples. In either case, these data clearly indicate a potential for tailoring of bioresorption time scale of a silk gel material through alteration of the silk protein content of gels. It was also illustrated that a 4 day exposure to PBS did not appreciably alter the mass of 6E samples, providing a preliminary indication that EEG samples are not substantially degraded by hydrolysis. This is a further reinforcement of the stability and bulk integrity of these silk gels as many gel materials suffer from limited resilience in vivo due to high susceptibility to hydrolysis. Addition of increasing quantities of RGD to silk gels was shown to slightly increase the rates of bioresorption mass loss in comparing 4E, 4RM and 4RH (FIG. 5C). This behavior indicates that there may be some structural differences between RGDEEG and EEG gels which cause less mass loss in EEG gels as compared to RGDEEG in this bioresorption assay. This may relate directly to the previously proposed idea that RGDEEG materials consist of many small regions of robust β-sheet structure loosely bound together by a weak inter-connecting matrix of α-helix and unordered random coil structures. This stands in contrast to EEG materials, which are thought to assemble from similar, though less prominent and numerous, precipitates into a more homogeneous structure than RGDEEG gels as a result. The inter-connecting matrix of the RGDEEG gels is therefore more susceptible to rapid bioresorption through this proteolytic assay than that of EEG gels. While β-sheet regions may remain intact in RGDEEG gels, bulk material integrity is lost as the inter-connecting network is resorbed as are the residual β-sheet particles due to the sieving method used as a cutoff for degradation product particle size. This is indicative that it may be possible to use varying levels of RGD in order to further manipulate the structure and bioresorption profile of a silk gel.

Example 8

Fourier-Transform Infrared Spectrum Capture

Silk hydrogels, 23RGD-ethanol-enhanced 4% silk, 3:1 and 10:1, were cast as described above and subjected to proteolytic bioresorption as described above. Additionally, non-bioresorbed control samples were obtained for sake of analysis via FTIR in quantities of 0.5 ml each. Using a Bruker Equinox 55 spectrophotometer (Bruker Optics, Inc., Billerica, Mass.) coupled with a Pike MIRACLE™ germanium crystal (PIKE Technologies, Madison, Wis.), sample absorbance spectra were obtained. Samples were imaged by pressing them upon the crystal via a pressure arm until single sample scans indicated viable signal from the material then performing a 128-scan integration. Resolution was set to 4 $cm^{-1}$ with a 1 $cm^{-1}$ interval from a range of 4000 $cm^{-1}$ to 400 $cm^{-1}$.

Resultant spectra were subjected to analysis via OPUS 4.2 software (Bruker Optics, Inc). A peak-find feature was used to identify peaks between 4000 $cm^{-1}$ and 600 $cm^{-1}$, with the search criteria being automatic selection of local inflection points of a second-derivative, nine-point smoothing function. Program sensitivity was set to 3.5% for all spectra based upon operator discretion regarding magnitude of peaks identified and likely relevance to compound identification and "fingerprinting".

Each of the samples subjected to FTIR analysis exhibited a spectrum with very pronounced peaks at the Amide I band (1600-1700 $cm^{-1}$) (FIG. 8). Additionally, the specific wave numbers of these peaks are consistent between the 23RGD-infused silk fibroin hydrogel and other silk gel groups. All samples exhibit major peaks at ~1622 $cm^{-1}$ and a minor peak/toe region at ~1700 $cm^{-1}$, a pattern associated with a high degree of β-sheet structure within a sample (FIG. 8). There are also similarities across all samples types at the Amide II band with a major peak at ~1514 $cm^{-1}$.

Figure 9:
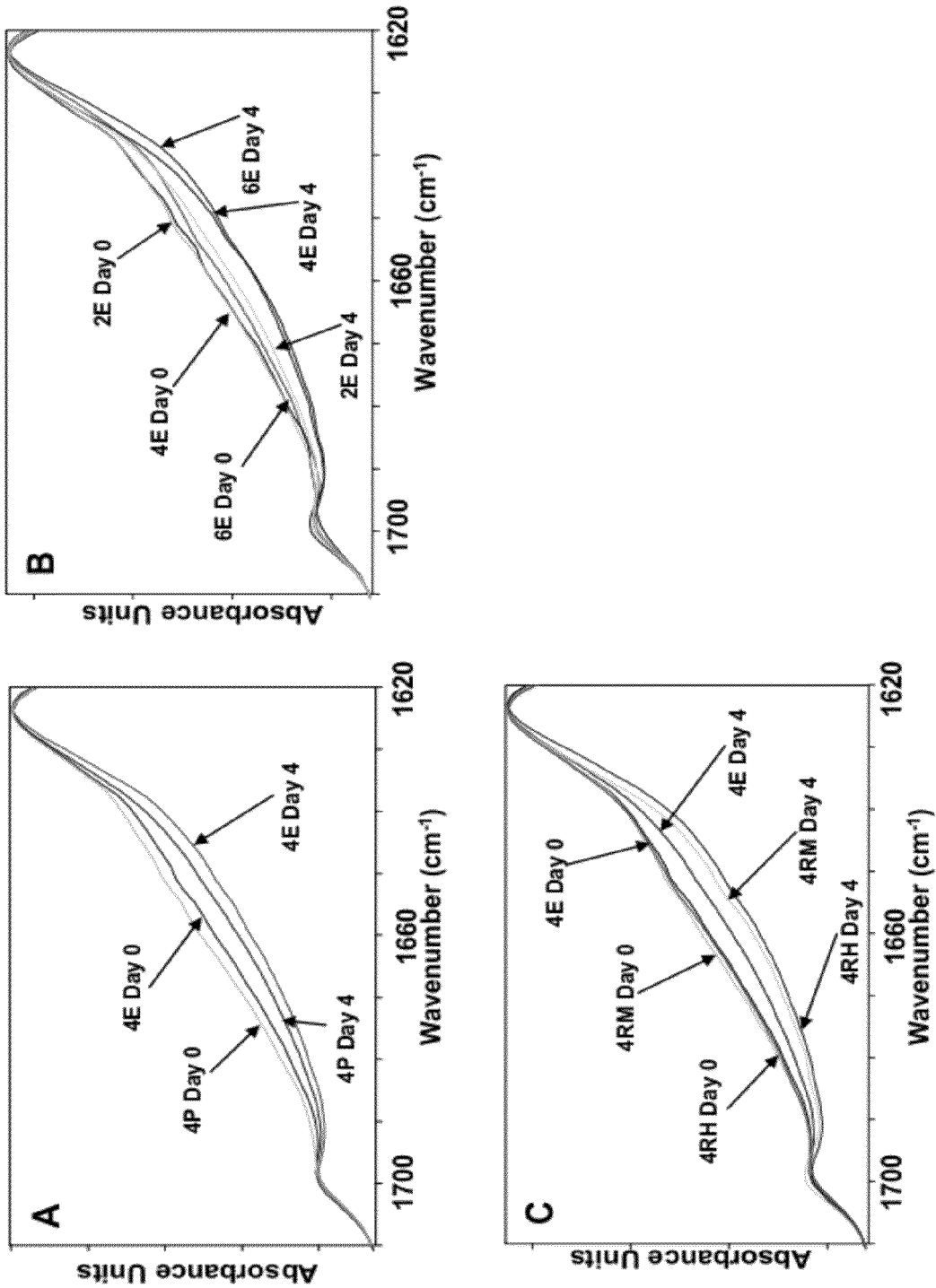
FIG. 9 shows a comparative FTIR spectra illustrating the effects of differing gelation techniques on gel protein structure before (Day 0) and after (Day 4) proteolytic bioresorption. Groups assessed included samples cast by PG and EEG methods (A), cast from increasing silk concentrations (B), and cast using increasing RGD concentrations (C).

Use of the EEG process to produce silk gels did not dramatically impact gel secondary structure but did slightly increase the resistance of the gel formulation to proteolytic bioresorption (FIG. 9A). Evaluation of characteristic FTIR spectra of 4P and 4E gels at Day 0 revealed few distinguishing characteristics as both formulations exhibited a characteristic β-sheet peak around 1622 $cm^{-1}$ and toe region of β-turn at 1700 $cm^{-1}$. Each sample also had additional portions of β-sheet, β-turn, α-helix, and unordered random coil at 1677 $cm^{-1}$, 1663 $cm^{-1}$, 1654 $cm^{-1}$, and 1645 $cm^{-1}$ respectively with higher relative quantities of α-helix and random coil appearing in 4P than 4E at Day 0. At Day 4, both samples showed pronounced decreases in 1677 $cm^{-1}$ β-sheet, β-turn, α-helix and random coil signal, though this 4P exhibited this to a greater extent than 4E, indicating preferential resorption of these motifs and greater resistance to this in 4E gels.

Increasing the final silk concentration of EEG gels had little impact on initial gel secondary structure, though there was a pronounced increase in β-sheet structures at Day 4 with greater silk concentrations (FIG. 9B). At Day 0, 2E, 4E, and 6E gels all showed strong signal for 1622 $cm^{-1}$ β-sheet and 1700 $cm^{-1}$ β-turn strong, with 6E having particularly prominent peaks in these regions. Each sample also had additional portions of 1677 $cm^{-1}$ β-sheet, 1663 $cm^{-1}$ β-turn, α-helix, and unordered random coil. At Day 4 all gels showed decreases in 1677 $cm^{-1}$ β-sheet, 1663 $cm^{-1}$ β-turn, α-helix and random coil peaks relative to 1622 $cm^{-1}$ β-sheet and β-turn peaks with this behavior being more marked in 4E and 6E than 2E. The Day 4 6E sample also showed a more stable β-sheet structure indicated by a peak shift to lower wave number at ~1620 $cm^{-1}$.

Pronounced differences in the 23RGD-ethanol-enhanced and ethanol-enhanced spectra only became evident after a four-day period of bioresorption in protease. The day 4 samples exhibited differences primarily in the order of magnitude of certain secondary structure modalities seen through slight differences in FTIR Amide I band shape. At day 4, the 23RGD-ethanol-enhanced samples exhibit higher levels of β-turn structure evidenced by far more pronounced and distinct peaks at ~1700 $cm^{-1}$ while also showing considerably lower levels of α-helix structure (1654 $cm^{-1}$) and unordered random coil (1645 $cm^{-1}$) structures. For example, FTIR spectra from 4E, 4RM and 4RH all show similar structures featuring 1622 $cm^{-1}$ β-sheet and 1700 $cm^{-1}$ β-turn prominently with indications of 1677 $cm^{-1}$ β-sheet, 1663 $cm^{-1}$ β-turn, α-helix, and unordered random coil secondary structures (FIG. 9C). At Day 4, 4RM and 4RH both show a less pronounced 1677 $cm^{-1}$ β-sheet, 1663 $cm^{-1}$ β-turn, α-helix, and random coil component than the 4E sample with 4RH also showing a more stable β-sheet structure, indicated by a peak shift to lower wave number at ~1620 $cm^{-1}$. Additionally, a peak shift occurred in both the 10:1 23RGD-ethanol-enhanced and ethanol-enhanced samples in the β-strand peak at 1622 $cm^{-1}$, indicative of increased β-sheet stability. Considered as a whole, the collective peak shifts and peak magnitudes observed in the spectra at day 4 compared to day 0, all gel types experienced substantial strengthening of β-sheet component, likely due to removal of less-stable α-helix and random coil. These effects were most pronounced in 23RGD-enhanced gel materials, likely due to intrinsic differences in the initial organization of the structural network of the gel materials.

FTIR analysis and comparison of PG, EEG and RGDEEG showed strong behavioral similarities across all gel groups.

Each material exhibited β-sheet-dominated secondary protein structures, featuring elements of α-helical and random coil structures and each resorbed in such a fashion that the quantities of β-sheet-rich structure increased relative to α-helical and random coil structures. The selective bioresorption of α-helical and random coil structures indicates that they are likely favorably degraded by proteolysis relative to β-sheet structures, thus the bioresorption profile of a gel might be influenced by altering the balance between β-sheet motifs and the combination of α-helical and random coil structures. An evaluation of ethanol as an accelerant revealed a minimal effect on silk gel structure at Day 0 as both 4P and 4E had high β-sheet contents with α-helical and random coil structures (FIG. 9A). At Day 4 though, there was a slightly greater relative β-sheet content in 4E than 4P samples. This may be caused by structural differences in 4E and 4P formulations that were imperceptible at Day 0 by ATR-FTIR, possibly in the uniformity and homogeneity of the silk gels. It is possible that the same differences hypothesized between EEG and RGDEEG gels derived from their different extents of precipitate/nucleation point formation in early-phase gelation causes differences between PG and EEG materials as well. As PG samples are not accelerated, it is likely that very few nucleation points will form quickly and as a result, the gelation process occurs in a very slow but homogeneous fashion, allowing for an optimal stearic packing of silk molecules throughout the solution volume. This results in a consistent protein structure throughout the final gel volume, corresponding to good bulk material integrity. This would contrast with EEG gels, as the previously postulated nucleation phenomenon associated with RGDEEG materials likely occurs with EEG materials as well, though in a less prominent fashion. This results in a non-uniform distribution of highly organized regions of β-sheet held together by α-helical and random coil structures in the EEG materials relative to the PG materials, with α-helical and random coil degraded more rapidly than β-sheet. This is in keeping with previous studies which have shown that more poorly packed β-sheet structures and α-helix structures are more susceptible to degradation. Increasing silk concentration in EEG gels from 2E to 4E to 6E revealed the most prominent β-sheet structures in 6E at both Day 0 and Day 4 while 2E had considerably more α-helix and random coil at both days than 2E and 4E (FIG. 9B). This would seem to indicate that dilute concentrations of silk in the final hydrogel result in a less densely packed secondary structure, possibly due to stearic freedom within the gel volume relative to 4% and 6% states. This indicates that silk concentration may be used to manipulate the secondary structure of silk gel to influence bioresorption. A study of the effect of increasing RGD concentration indicated that while gels were virtually identical at Day 0, the α-helix structure and unordered random coil in 4RM and 4RH gels were less resilient to bioresorption than in 4E as seen at Day 4 (FIG. 9C). This might also be explained by inhomogeneities within the 4RM and 4RH gels relative to 4E as mentioned previously. This may be particularly likely in light of the formation of precipitates observed in RGDEEG samples. This data may be indicative that RGD or a similar peptide could be used to further tailor the nature of the bioresorption profile of silk gels.

These results indicate that silk gels produced through PG, EEG, and RGDEEG result from a two-phase assembly process consisting of nucleation and aggregation. Silk gels contain predominantly β-sheet structure which is more resistant to in vitro bioresorption than α-helix and random coil. EEG gels form more quickly than PG, likely due to a more rapid precipitation and nucleation event mediated by the effects of ethanol on the solution solvent phase. EEG gels form a non-homogeneous structure likely consisting of localized, initially-precipitated β-sheet regions inter-connected by α-helix and random coil assembled subsequently. RGDEEG gels form a non-homogeneous structure likely consisting of localized, initially-precipitated β-sheet regions inter-connected by α-helix and random coil assembled subsequently. RGDEEG gels reach completion more slowly than EEG gels due to stearic RGD-mediated interference encountered in gel assembly following nucleation. RGDEEG gels are less homogeneous than EEG gels due to these difficulties associated with late-phase assembly.

Example 9

Injectable Gel Processing

Silk hydrogels were prepared as described above in Examples 1-4. Gels were then comminuted by grinding the silk gel to a paste using a stainless steel spatula. Gel formulations including PBS were massed with an SI-215 balance (Denver Instrument, Denver Colo.) and the correct volume percentage of PBS (Invitrogen Corporation, Carlsbad, Calif.) was blended in with the assumption that both the gel and PBS had a density of 1 g/ml. Silk hydrogels to be used for in vivo assessment were subjected to vigorous mechanical pulverization by means of a stainless steel stir rod. When specified as containing a saline component, gels were blended with saline at volumetric ratios based upon the original volume of gel (i.e., prior to mechanical disruption) following pulverizing by the stainless steel bar. This addition of phosphate buffered saline serves to regulate tonicity of the gel as well as improve injectability. Following this initial pulverizing, the gel was further disrupted by means of repeated injection through a 26-gauge needle in order to decrease overall particle size within the gel and improve injectability characteristics. In some samples, gel was further disrupted by means of repeated injection first through an 18 g needle repeatedly until the gel flowed readily, and then the material was then cycled in like fashion through a 23 g needle and 26 g needle.

Example 10

In Vivo Investigation of Silk Hydrogel in Rodent Models

Samples of silk gel which had been processed for implantation or injection in vivo as described in Example 9 were double-bagged with appropriate sterilization bags for gamma irradiation and sterilized by exposure to a dose of 25 kGy of gamma radiation.

In one trial silk hydrogel samples, both 23RGD-enhanced and native were implanted subcutaneously in male Lewis rats having an average weight of 400 g. This was done according to protocol#86-04 on file with New England Medical Center's Department of Laboratory Animal Medicine (DLAM) and approved by the Institutional Animal Care and Use Committee (IACUC). On the day of surgery, animals were anesthetized via a ketamine/xylazine solution injected IM in the animals' hind legs. Following administration of anesthesia, the skin of the rats was shaved closely and swabbed with alcohol, allowed to dry, swabbed with BETADINE® microbicide (Purdue Pharma, Stamford, Conn.) then draped with sterile towels. In the case of implanted devices, two dorsal midline incisions were made directly over the spine, the first 0.5 cm below the shoulders and the second 2.5 cm above the pelvic crest, each 1 cm long each. The incisions were expanded into 1 cm deep pockets using a blunt dissection technique beneath the panniculus carnosus at each side yielding 4 potential implant sites. Implants, 3 per animal; each 1 cm×1 cm×0.3 cm in size were inserted into the pockets without fixation with the final site undergoing the same dissection but replacing the implant with 0.5 mL of sterile saline solution. The skin was closed with interrupted absorbable sutures. Depending on study, samples were harvested at 7 days, 14 days, 28 days, and/or 57 days after implantation surgery. Gross observations were collected semi-weekly regarding implant site appearance. After sample harvest, gross observations of the implants were conducted and samples were processed for histological evaluation. Analysis of histology slides was provided by a trained veterinary pathologist.

Sections were scored for presence (0=none, 1=present) of implant mineralization, cyst formation, fibrosis, sebaceous cell hyperplasia, and focal follicular atrophy. Additionally, the density of inflammatory response (0=none . . . 5=extensive) and extent epidermal hyperplasia (0=none . . . 3=extensive) were graded. These data were reported as percentages of the highest score possible for the group of slides. Sections were also examined for presence of any particular characteristic cell types including lymphocytes, neutrophils, eosinophils, mononuclear giant cells, macrophages, and fibroblasts. Additional commentary relevant to the host response was included at the discretion of the reviewing pathologist. Prism 4.03 (GraphPad Software Inc., San Diego, Calif.) was used to perform analysis of variance (ANOVA) with a significance threshold set at p 0.05. One-way ANOVA was used to compare differences average extrusion forces for comminuted gels. For all tests, Tukey's post-hoc test was also performed for multiple comparisons.

Figure 10:
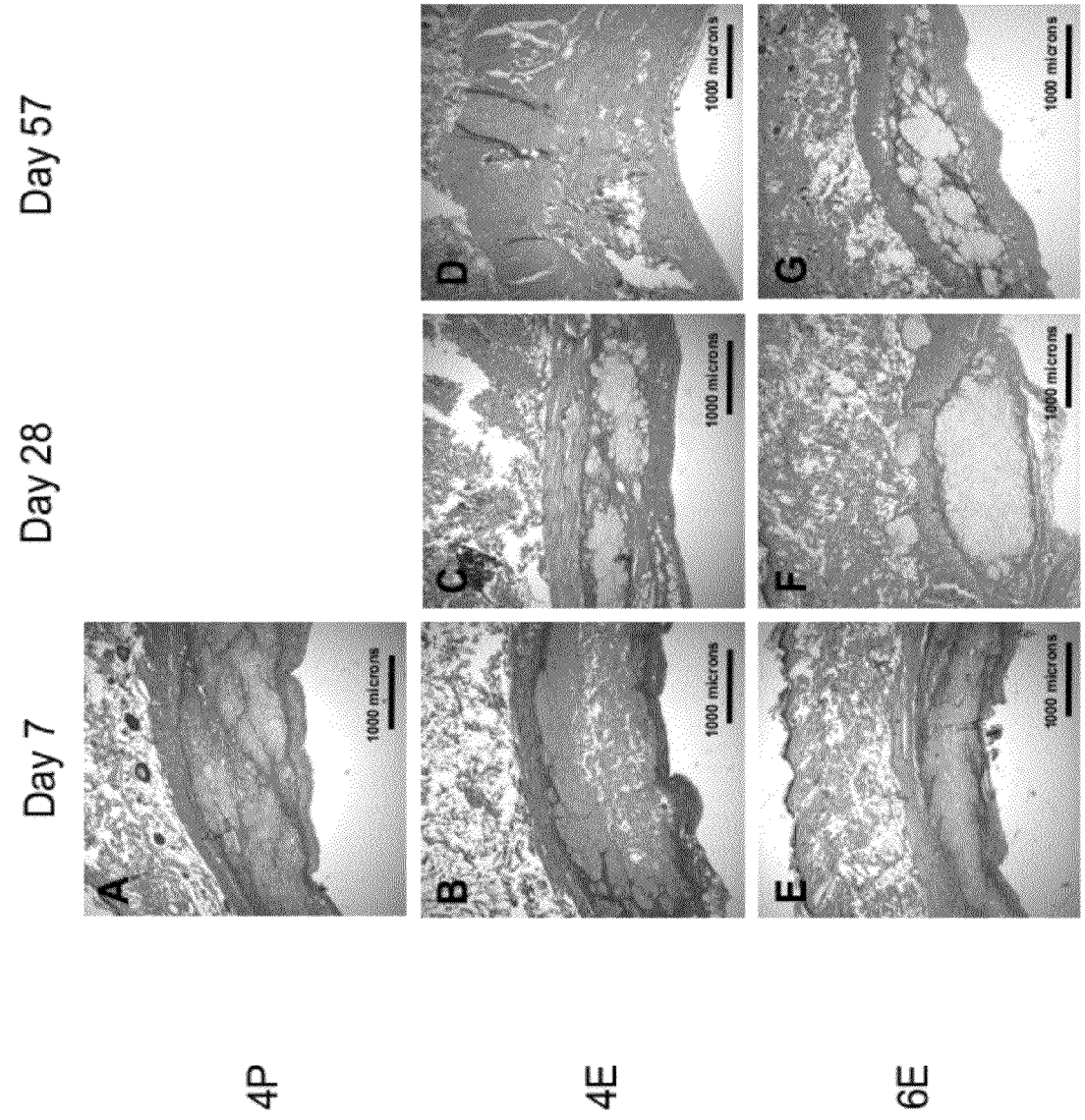
FIG. 10 shows representative micrographs of H&E-stained histological sections collected from silk gels implanted subcutaneously in rats. Samples of 4% silk fibroin hydrogel formed by passive gelation (4P), 4% silk fibroin hydrogel formed by ethanol-enhanced gelation (4E), and 6% silk fibroin hydrogel formed by ethanol-enhanced gelation (6E) were compared at 7 days (A, B, and E respectively) with 4E and 6E samples compared again at days 28 (C and F) and 57 (D and G).

Table 2 lists the formulations of silk gel, both 23RGD-ethanol-enhanced and ethanol-enhanced developed and assessed intradermally in a rat model. Silk gels explanted from rats at Day 7 were visibly well-defined and easily identifiable with no gross indications of edema, erythema, or transdermal elimination of material. It was not possible to differentiate sites of PBS control implantation from surrounding tissue. H&E sections of 4% silk fibroin hydrogels formed by passive gelation (4P), 4% silk fibroin hydrogels formed by ethanol-enhanced gelation (4E) and 6% silk fibroin hydrogels formed by ethanol-enhanced gelation (6E) all appeared similar, with mild inflammation in all cases characterized by lymphocytes, macrophages, some neutrophils and fibroblasts (FIG. 10). Cellular infiltration was observed in all sample types with complete penetration in 4P and peripheral ingrowth to a depth of about 100 μm in both EEG gels with no evidence of cyst formation observed. In all gels, early bioresorption was indicated by implant edge erosion with residual implant material remaining localized into large lakes. Host integration of implanted gel had progressed in Day 28 samples of 4E and 6E evidenced by greater cellular ingrowth into the material with complete implant penetration in 4E samples and robust peripheral ingrowth in 6E samples. The cellular response at this time point was characterized by fibroblasts, lymphocytes and macrophages with the addition of a few multi-nucleated giant cells.

TABLE 2

Silk Hydrogel Formulations

| Group Name | Silk Concentration | Enhancer | Saline Component |
|---|---|---|---|
| 4E10 | 4% | 90% Ethanol | 10% |
| 4R10 | | 90% Ethanol, 1:1 23RGD | |
| 4RH10 | | 90% Ethanol, 3:1 23RGD | |
| 4E25 | | 90% Ethanol | 25% |
| 4R25 | | 90% Ethanol, 1:1 23RGD | |
| 4RH25 | | 90% Ethanol, 3:1 23RGD | |
| 6E10 | 6% | 90% Ethanol | 10% |
| 6R10 | | 90% Ethanol, 1:1 23RGD | |
| 6E25 | | 90% Ethanol | 25% |
| 6R25 | | 90% Ethanol, 1:1 23RGD | |
| 6RH25 | | 90% Ethanol, 3:1 23RGD | |

Day 57 samples of 4E and 6E showed continued host bioresorption of the gel material as there was little residual 4E and while 6E remained visible in large, intact lakes, the gel had been completely penetrated with host tissue. The host response to 4E had dramatically decreased in cellularity between Day 28 and Day 57 with very little evidence of hypercellularity at Day 57 with some scattered macrophages and fibroblasts around the implant site. The pathology of the host response of 6E was similar to the Day 28 response to 4E, with fibroblasts as the predominant cell type and scattered lymphocytes, macrophages and multi-nucleated giant cells. This was viewed as a low-grade, persistent, fibrotic-type inflammatory response to the material.

Figure 11:
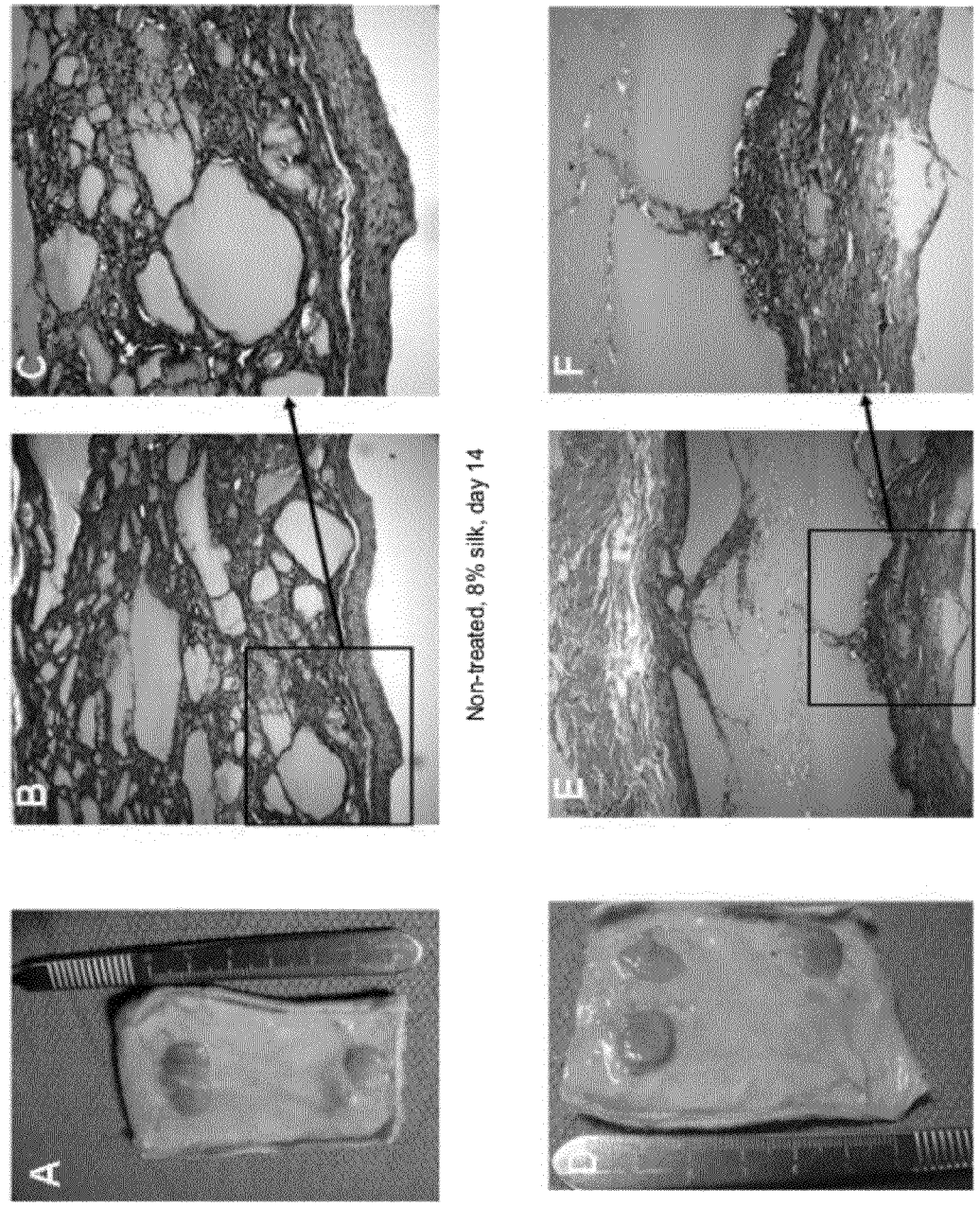
FIG. 11 shows representative gross photographs of 8% silk fibroin hydrogel devices both unmodified (A) and 23RGD-enhanced (D) after a two-week subcutaneous incubation in Lewis rats. Also shown are micrographs resultant from H & E stains of the unmodified (B and C) and 23RGD-coupled (E and F) samples at 10× and 20× magnification. These gross images coupled with the histological micrographs provide evidence of a less extensive inflammatory response during early device integration being associated with 23RGD-enhanced gel than non-23RGD-enhanced gel.

Samples of 23RGD-enhanced gel exhibited a less robust inflammatory response at the 14 day time point in comparison to non-23RGD-enhanced gel (FIG. 11). This is observed through an appreciable decrease in hyper-cellularity proximal to the gel implant and an accompanying decrease in the fragmentation of the implant material. It is possible that this improvement in implant integrity is due to a less robust foreign body response by the host animal and it may also be evidence that there is less mechanical contraction of the implant site, a commonly observed phenomenon with biomaterials including the "RGD" motif. These effects indicate that 23RGD-enhancement of silk gels leads to a more biocompatible material with better implant outcomes.

In a second trial, intradermally-injected samples of silk hydrogel, both ethanol enhanced and 23RGD-ethanol enhanced and relevant control materials were investigated using male Hartley guinea pigs. This was done according to protocol#29-05 on file with New England Medical Center's Department of Laboratory Animal Medicine (DLAM) and approved by the Institutional Animal Care and Use Committee (IACUC). Briefly, male Hartley guinea pigs weighing 300-350 g were anesthetized via a ketamine/xylazine cocktail injected intramuscularly into the animals' hind legs. The dorsal skin of the guinea pigs was then shaved closely and swabbed with alcohol, allowed to dry, swabbed with BETADINE® microbicide or Chloraprep (Enturia, Inc., Leawood, Kans.), then draped with sterile towels. A 50 μL volume of the desired material was injected through a 26 g needle at six different sites along the left side of the animal's back. Further injections of an appropriate silk gel control were made at the six contralateral sites. Explanation of the silk gels was performed at 28 days after implantation. Gross observations were collected semi-weekly regarding implant site appearance. After sample harvest, gross observations of the implants were conducted and samples were processed for histological evaluation. Analysis of histology slides was provided by a trained veterinary pathologist. Scoring and statistical analysis was performed as described above.

Table 3 lists the formulations of silk gel, both 23RGD-ethanol-enhanced and ethanol-enhanced developed and assessed intradermally in a guinea pig model in a twenty-eight day screen. Although no statistically significant differences were identified, the data for both gross observations and histology (Tables 4 and 5) indicate a general trend supporting the previous data that 23RGD-enhancement of gel improves material biocompatibility. Among sites implanted with silk gel, gross outcomes varied. Ulceration and hair loss rates were lower in groups with 25% PBS compared to 10% saline, 6% silk compared to 4% silk and RGDEEG casting as compared to just EEG casting (Table 4). Site redness rates followed a similar pattern with the exception that RGDEEG samples induced more site redness than EEG samples. All silk gels showed evidence of epidermal cyst formation, fibrosis, epidermal hyperplasia and pronounced inflammation with traces of follicular atrophy in all EEG samples. Sebaceous cell hyperplasia was present to a limited extent in all formulations with the exception of 6% silk, 10% saline, 1:1 23RGD (Table 5). This is particularly evident in the case of silk gels of 4% silk with 25% saline added and either enhanced with an ethanol-based enhancer or an 23RGD-ethanol-based enhancer, and more specifically, in the case of site ulcerations (Table 5). This material indicated strong improvements with increasing 23RGD concentration in the number of sites ulcerating throughout the course of the trial. These results are indicative that use of 23RGD in conjunction with an ethanol enhancer provides an improved outcome when compared to an ethanol enhancer alone.

TABLE 3

Silk Hydrogel Formulations

| Group Name | Silk Concentration | Enhancer | Saline Component |
|---|---|---|---|
| 4E10 | 4% | 90% Ethanol | 10% |
| 4R10 | | 90% Ethanol, 1:1 23RGD | |
| 4E25 | | 90% Ethanol | 25% |
| 4R25 | | 90% Ethanol, 1:1 23RGD | |
| 4RH25 | | 90% Ethanol, 3:1 23RGD | |
| 6E10 | 6% | 90% Ethanol | 10% |
| 6R10 | | 90% Ethanol, 1:1 23RGD | |
| 6E25 | | 90% Ethanol | 25% |
| 6R25 | | 90% Ethanol, 1:1 23RGD | |

TABLE 4

Gross Evaluation of Guinea Pigs

| Group Name | Site Redness | Hair Loss | Palpability | Ulceration |
|---|---|---|---|---|
| 4E10 | 38% | 58% | 65% | 33% |
| 4R10 | 57% | 49% | 67% | 33% |
| 4E25 | 28% | 34% | 49% | 28% |
| 4R25 | 44% | 34% | 64% | 17% |
| 4RH25 | 50% | 23% | 66% | 6% |
| 6E10 | 63% | 52% | 68% | 33% |
| 6R10 | 78% | 51% | 68% | 22% |
| 6E25 | 33% | 31% | 69% | 11% |
| 6R25 | 56% | 30% | 68% | 13% |
| HYLAFORM ™ | 6% | 12% | 63% | 0% |
| ZYPLAST ™ | 17% | 10% | 52% | 0% |

TABLE 5

Histological Evaluation of Guinea Pigs

| Group Name | Epidermal Cyst Formation | Fibrosis | Inflammation | Epidermal Hyperplasia | Follicular Atrophy | Sebaceous Hyperplasia |
|---|---|---|---|---|---|---|
| 4E10 | 22% | 100% | 70% | 59% | 11% | 22% |
| 4R10 | 74% | 100% | 62% | 67% | 0% | 14% |
| 4E25 | 50% | 100% | 69% | 67% | 13% | 13% |
| 4R25 | 29% | 100% | 39% | 62% | 0% | 14% |
| 4RH25 | 14% | 100% | 64% | 50% | 0% | 43% |
| 6E10 | 44% | 100% | 70% | 56% | 11% | 33% |
| 6R10 | 25% | 100% | 63% | 38% | 0% | 0% |
| 6E25 | 30% | 100% | 60% | 40% | 10% | 20% |
| 6R25 | 29% | 100% | 64% | 33% | 0% | 14% |
| HYLAFORM ™ | 0% | 0% | 3% | 6% | 0% | 0% |
| ZYPLAST ™ | 0% | 25% | 28% | 31% | 0% | 0% |

Figure 12:
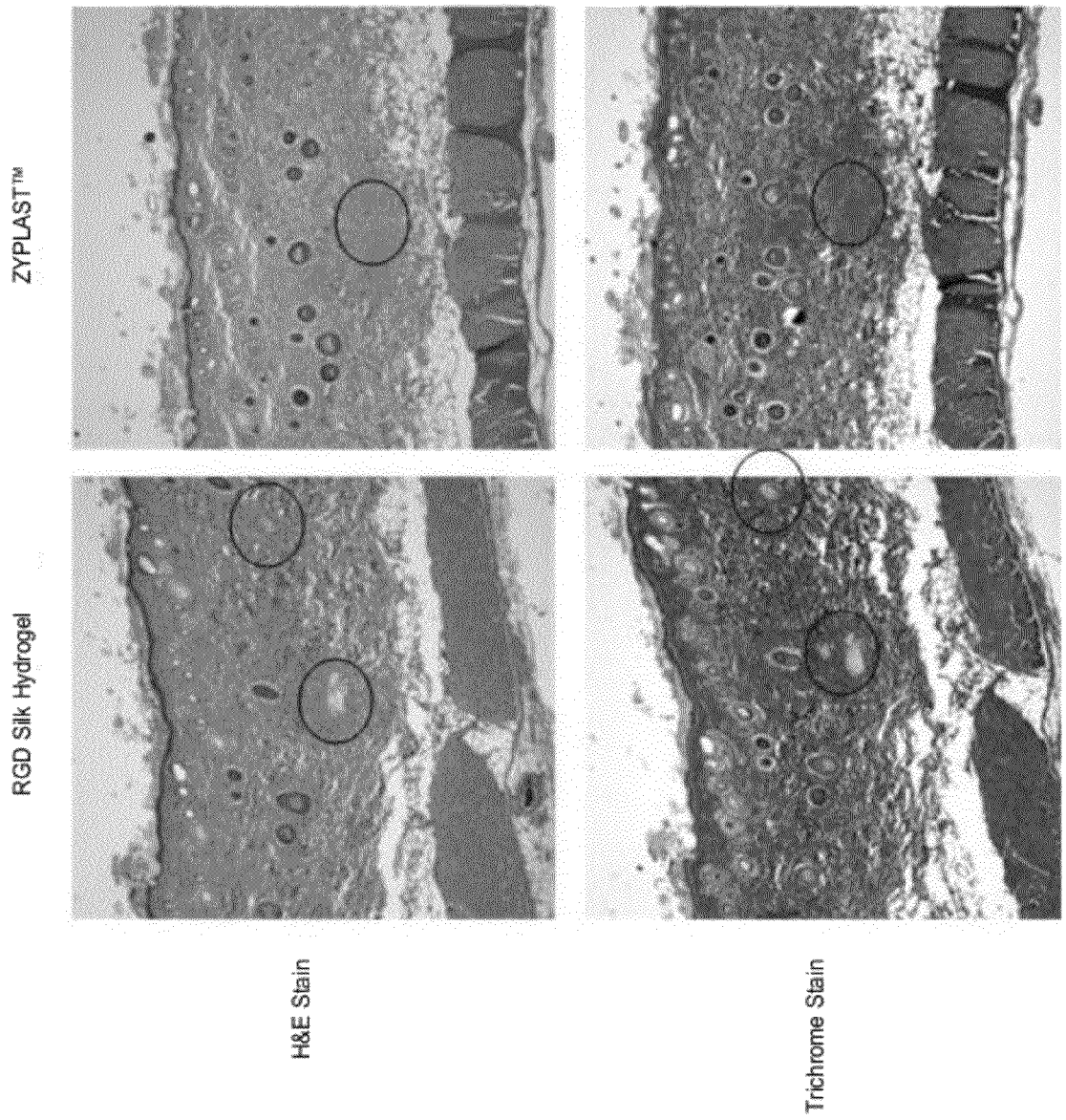
FIG. 12 shows representative histology collected from a thirteen-week study of 4% 3:1 23RGD-enhanced silk hydrogel blended with 25% saline (left panels, H&E stain Trichrome stain) and ZYPLAST™ (right panels H&E stain, Trichrome stain) and injected into the intradermis of guinea pig. Each material type exhibited some clear evidence of implanted device in 75% of their respective implant sites. These micrographs indicate strong similarities not only between the long-term bioresorption characteristics but also long-term host tissue response between collagen-derived biomaterials and this particular 23RGD-enhanced silk hydrogel formulation.

A third trial also used male Hartley guinea pigs to investigate intradermally injected samples of silk hydrogel as described above, comparing samples of 4% and 6% silk, 25% saline 3:1 23RGD-ethanol enhanced silk gels with a collagen-based control material, ZYPLAST™ (Allergan Inc., Irvine Calif.) and HYLAFORM™ (Allergan Inc., Irvine Calif.). Explanation of the silk gels was performed at 92 days after implantation. Gross observations were collected semi-weekly regarding implant site appearance. After sample harvest, gross observations of the implants were conducted and samples were processed for histological evaluation. During the course of the 92 day trial, none of the 24 implant sites, either 23RGD-ethanol-enhanced hydrogel or ZYPLAST™, ulcerated. Histology revealed that 75% of all ZYPLAST™ sites had residual material as did 75% of all 23RGD-ethanol-enhanced silk gel sites (both 4% and 6%). Both materials exhibited very similar chronic phase cellular responses, as the sites were characterized by a mild fibrotic reaction with abundant deposition of collagen in and around the implant site (FIG. 12). The collagen appears less ordered than does that in the surrounding dermal reticulum based upon the color density when viewed with Trichrome staining and also when viewed under polarized light. Silk gel sites had similar palpability scores to both control materials but exhibited higher rates of site redness, hair loss and ulceration than did ZYPLAST™ and HYLAFORM™. These results not only reinforce that 23RGD-ethanol-enhanced silk gel is biocompatible, but also indicate that it is comparable to collagen biomaterials in terms of its persistence and long-term behavior in vivo.

Figure 13:
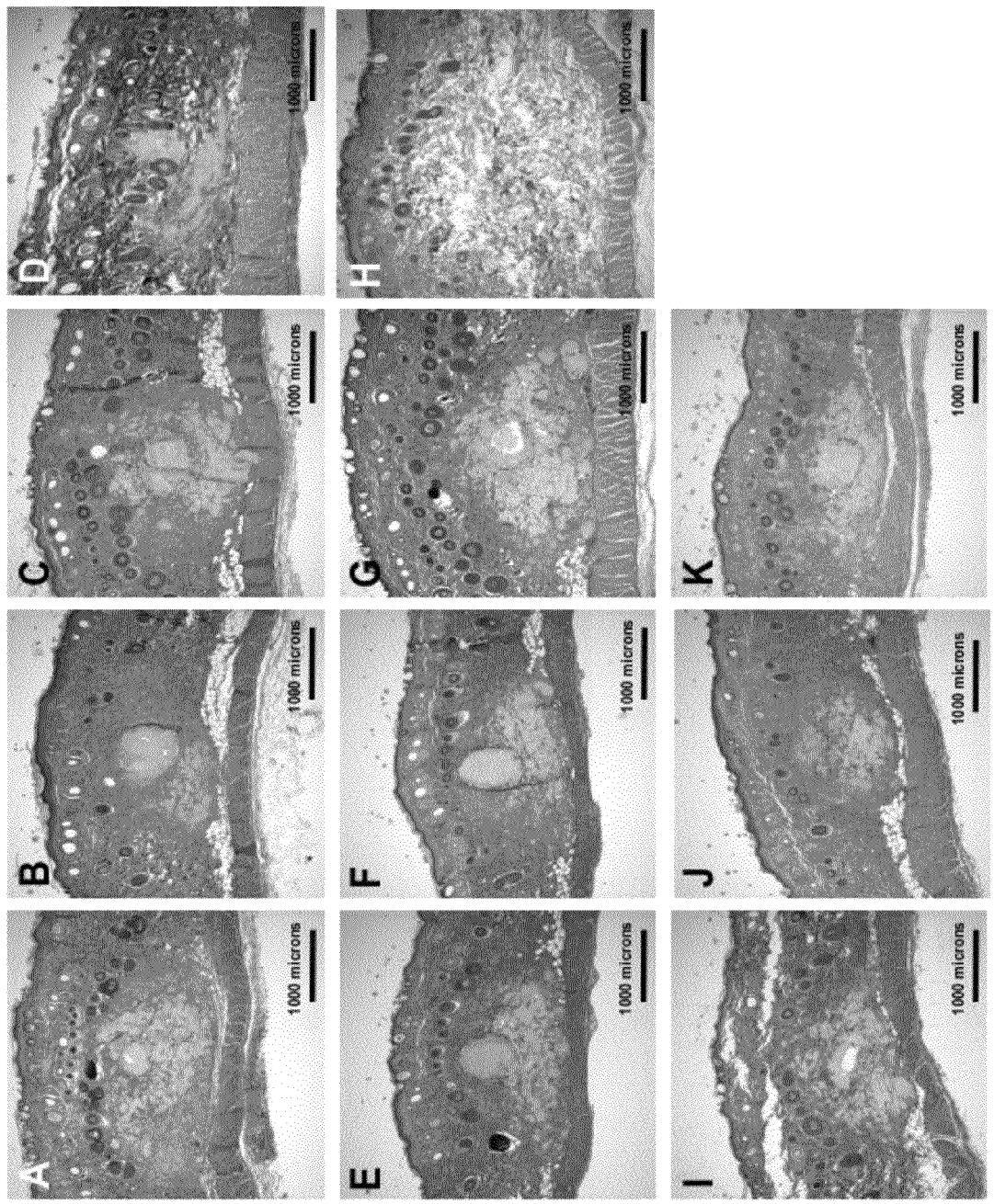
FIG. 13 shows representative micrographs of H&E-stained histological sections collected from Day 28 explants of 4% silk fibroin, 10% saline (A); 4% silk fibroin, 1:1 23RGD, 10% saline (B); 6% silk fibroin, 1:1 23RGD, 10% saline (C); ZYPLAST™ (D); 4% silk fibroin, 25% saline (E); 4% silk fibroin, 1:1 23RGD, 25% saline (F); 6% silk fibroin, 10% saline (G); HYLAFORM™ (H); 6% silk fibroin, 25% saline (I); 4% silk fibroin, 3:1 23RGD, 25% saline (J); and 6% silk fibroin, 1:1 23RGD, 25% saline (K).

ZYPLAST™ exhibited no epidermal cysts, follicular atrophy, or sebaceous cell hyperplasia, though it did show small levels of fibrosis, inflammation and epidermal hyperplasia. Examination of histological sections showed residual silk gel material which stained in a mildly eosinophilic fashion and appeared as large lakes of material at a central location with smaller masses of material distributed more widely throughout the reticular dermis (FIG. 13). These smaller masses were typically surrounded by fibroblasts and macrophages with occasional multi-nucleated giant cells present. Eosinophils were located proximal to these smaller masses of implant as well. In general, host response to the silk fibroin gels was characterized as mildly fibrotic and included populations of fibroblasts, lymphocytes, macrophages, multi-nucleated giant cells and eosinophils. Little difference was evident between silk gel types except in terms of the extent of eosinophilia. Larger eosinophil populations were observed for 6% as compared to 4% silk gels and were also observed to increase with RGD concentration in the silk gel samples in both 4% and 6% groups. ZYPLAST™ exhibited strong eosinophilic staining and was distributed as large lakes in the reticular dermis with smaller masses throughout the area. Hypercellularity near the injection site was lessened in ZYPLAST™ samples when compared to silk gel. Fibroblasts, lymphocytes, macrophages, multi-nucleated giant cells and eosinophils were present with less tendency to localize at the implant periphery. HYLAFORM™ samples examined showed many very small masses of material throughout the reticular dermis. HYLAFORM™ exhibited no epidermal cysts, fibrosis, follicular atrophy, or sebaceous cell hyperplasia with extremely limited instances of inflammation and epidermal hyperplasia. There was no observable hypercellularity near the implanted material or other evidence of inflammation at the implant sites.

Figure 14:
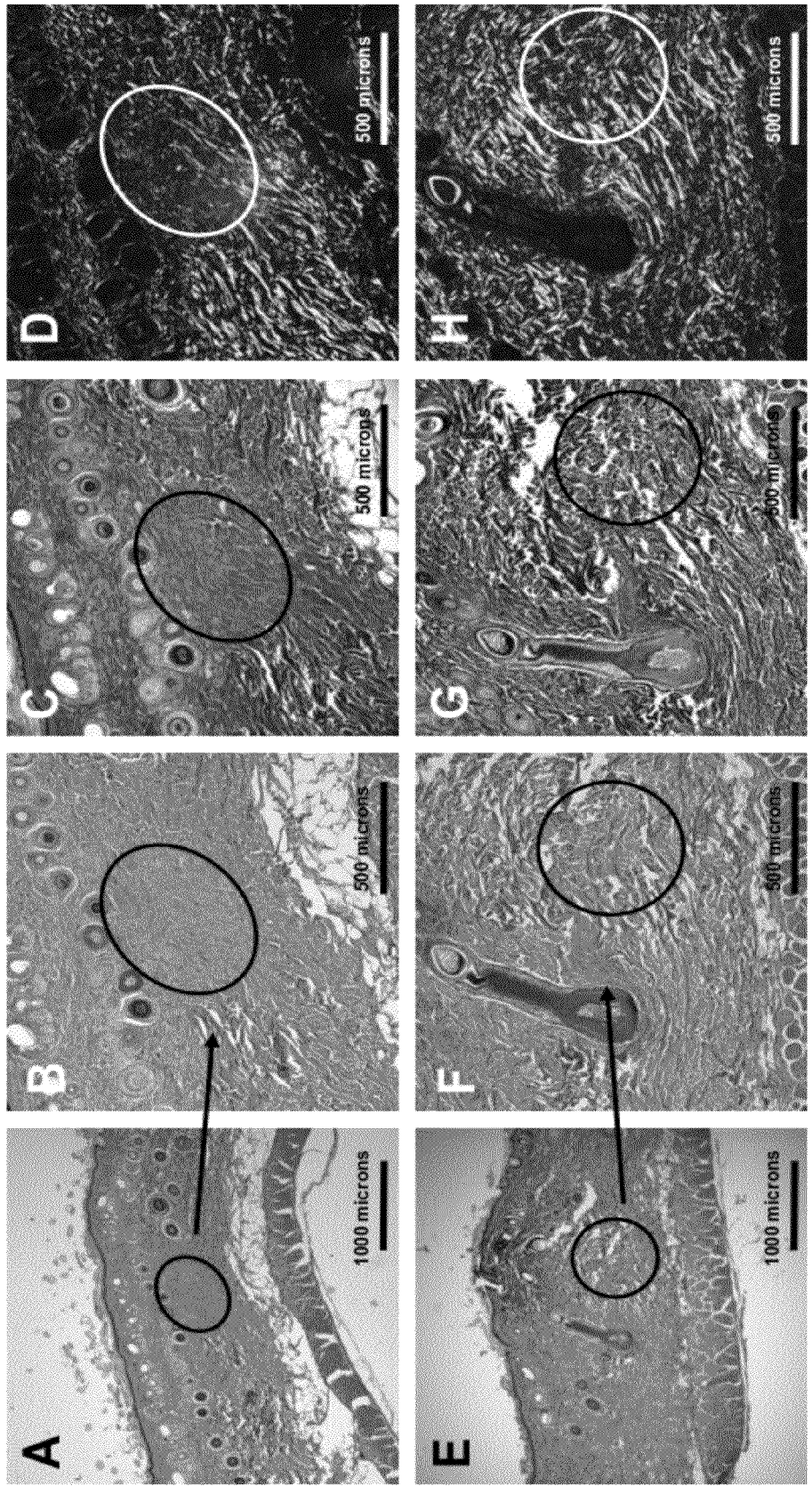
FIG. 14 shows representative micrographs of Day 92 histological sections of 4% silk fibroin, 3:1 23RGD, 25% saline (A-D) and ZYPLAST™ samples (E-H) stained with H&E at 4× (A and E), 10× (B and F), stained with Masson's Trichrome at 10× (C and G) and under polarized light at 10× (D and H).

At day 92, histological evaluation of 4% silk fibroin hydrogel, 3:1 23RGD, 25% saline (4RH25) samples and ZYPLAST™ samples showed similar material persistence and host response (FIG. 14). Very little implant material remained visible in the dermis of the animals with no hypercellularity present at this time point, evidence of hyperplasia or cellular inflammation. The eosinophils found at day 28 in the ZYPLAST™ and silk gel samples were not observed at day 92. Of particular interest, 4RH25 also exhibited residual disruption to the reticular dermis in the form of an irregular collagen pattern near the implant material. The disorganization of the collagen was seen as a region of stained collagen seen to be devoid of the typical cross-hatch pattern of normal reticular dermis (FIG. 14C). This disorganization was confirmed when viewing the histological sections under polarized light with the disorganized collagen appearing as an interruption in the birefringence associated with the surrounding reticular dermis (FIG. 14D).

Example 11

Enhanced Injectable Gel Formulation

Silk hydrogels were prepared as described above in Examples 1-4. Once processed, the gels were sized into coarse or fine particles using a sieving step (Table 6). Gel materials were pressed through a 316SS stainless steel wire cloth sieve with a stainless steel spatula and into clean polystyrene Petri dishes. Sieves with gap sizes of 711 µm×711 µm, 295 µm×295 µm, 104 µm×104 µm and 74 µm×74 µm were used. After passing through the 74 µm×74 µm gap sieve, the material was considered processed to a "coarse" state. Samples to be processed to a "fine" state were further forced through a 43 µm×43 µm sieve in the same fashion. This sieving was conducted four separate times for each sample type, each sieving using an approximate quantity of 0.5 mL of gel material.

TABLE 6

Particle sizing

| Nominal Silk Mass Percentage | 23RGD Molar Ratio with Silk | Fineness | Group Name |
|---|---|---|---|
| 2% | 1:1 | Fine | 2RF |
| 4% | 0 | | 4F |
| | 1:1 | Coarse | 4RC |
| | | Fine | 4RF |
| | 3:1 | | RHRF |
| | 10:1 | | 4VHRF |
| 8% | 1:1 | Coarse | 8RC |
| | | Fine | 8RF |

Samples of silk gel material (N=4 of each type) were evaluated under light microscopy. Briefly, a 100 mg portion of silk gel or control device was massed using an SI-215 Summit series balance. This material was loaded into the open back end of a 3 mL syringe using a stainless steel spatula. The plunger was replaced in the syringe, an 18 g needle was attached to the end of the syringe and approximately 900 µL of ultra-pure water was drawn up. This mixture of water and silk gel was mixed through gentle shaking. After mixing to suspend evenly, a sample of approximately 30 µL of dilute silk gel was placed on a 75 mm×25 mm single frosted, pre-cleaned micro slide (Fisher Scientific Co., Waltham, Mass.) and covered with a 22 mm×40 mm premium cover glass (Corning Inc., Corning, N.Y.). This sample slide was then be imaged with a microscope. Sample slides were imaged using a System Microscope Model BX41 (Olympus, Melville, N.Y.) in conjunction with a Microscope PC MACROFIRE™ Model S99831 Camera (Optronics, Goleta, Calif.) and PICTUREFRAME™ 2.1 software (Optronics, Goleta, Calif.). Briefly, slides were scanned for clearly separated gel particles using the 4× objective lens and locations determined for a series of 3 representative images of the sample slide. Each of these locations was imaged after first switching the microscope objective lens to 10×. Micrograph image files were subjected to analysis with IMAGE-PRO® Plus 5.1 software (Media Cybernetics, Inc., Silver Spring, Md.). Image files were checked for particle size distribution, average particle size, average aspect ratio, maximum particle size, minimum particle size and standard particle size deviation. A compilation of the data is presented in Table 7.

TABLE 7

Particle Comminution Data

| Group Name | Min to Max Object Area (µm$^2$) | Mean Object Area (µm$^2$) |
|---|---|---|
| 2RF | 5.33 to 1.32 × 10$^4$ | 52.43 ± 261.82 |
| 4F | 5.33 to 8.07 × 10$^3$ | 27.82 ± 129.34 |
| 4RC | 5.33 to 8.52 × 10$^3$ | 38.41 ± 196.67 |
| 4RF | 5.33 to 5.29 × 10$^3$ | 34.12 ± 135.31 |
| 4HRF | 5.33 to 7.51 × 10$^3$ | 40.62 ± 166.61 |
| 4VHRF | 5.33 to 3.14 × 10$^3$ | 35.4 ± 105.43 |
| 8RC | 5.33 to 8.04 × 10$^3$ | 46.57 ± 225.43 |
| 8RF | 5.33 to 2.85 × 10$^3$ | 35.26 ± 129.63 |
| ZYPLAST ™ | 5.33 to 1.95 × 10$^3$ | 22.08 ± 41.71 |

Examination of the particles under light microscopy revealed some clumped gel particles which were removed from particle sizing data manually. Particle sizes ranged from 5.3 to 1.3×10$^4$ µm$^2$, comparable in range to commercially available ZYPLAST™ which ranged from 5.3 to $1.95 \times 10^3$ $\mu m^2$. The data also revealed mean particle sizes ranging from 27.8 $\mu m^2$ to 52.4 $\mu m^2$, again, comparable to ZYPLAST™ with a mean particle size of 22.1 $\mu m^2$. These data illustrate that silk gel may be successfully comminuted to small and functionally useful particle sizes in a fashion similar to presently utilized injectable gel materials. The basic forced-sieving method could easily be replaced with more sophisticated, reproducible methods for purposes of scale-up.

After comminution and blending, samples of silk gel emulsions were subjected to extrusion force testing. Gel materials prepared as described in Examples 1-4 were blended with appropriate ratios of saline in order to evaluate injection (extrusion) force profiles relative to a control material, ZYPLAST™ (Table 8). This was accomplished by massing 5 g of gel material in a large weighing boat using an SI-215 balance (Denver Instrument, Denver, Colo.). An appropriate quantity of saline will be added to constitute the correct volume percentage making the assumption that both the gel material and saline have a density of 1 g/mL. This material was then blended to an even consistency using a stainless steel spatula and loaded into the back end of a 10 mL syringe with an 18 g needle attached for subsequent use.

TABLE 8

Silk Gel Injection Force Profile Generation

| Nominal Silk Mass | 23RGD Molar Ratio with Silk | Fineness | Saline Content | Group Name |
|---|---|---|---|---|
| 2% | 1:1 | Fine | 25% | 2RF25 |
| 4% | 0 | | 25% | 4F25 |
| | 1:1 | Coarse | 25% | 4RC25 |
| | | Fine | 0% | 4RF0 |
| | | | 25% | 4RF25 |
| | | | 50% | 4RF50 |
| | 3:1 | | 25% | 4HRF25 |
| | 10:1 | | 25% | 4VHRF25 |
| 8% | | Fine | 25% | 6RF25 |

Figure 15:
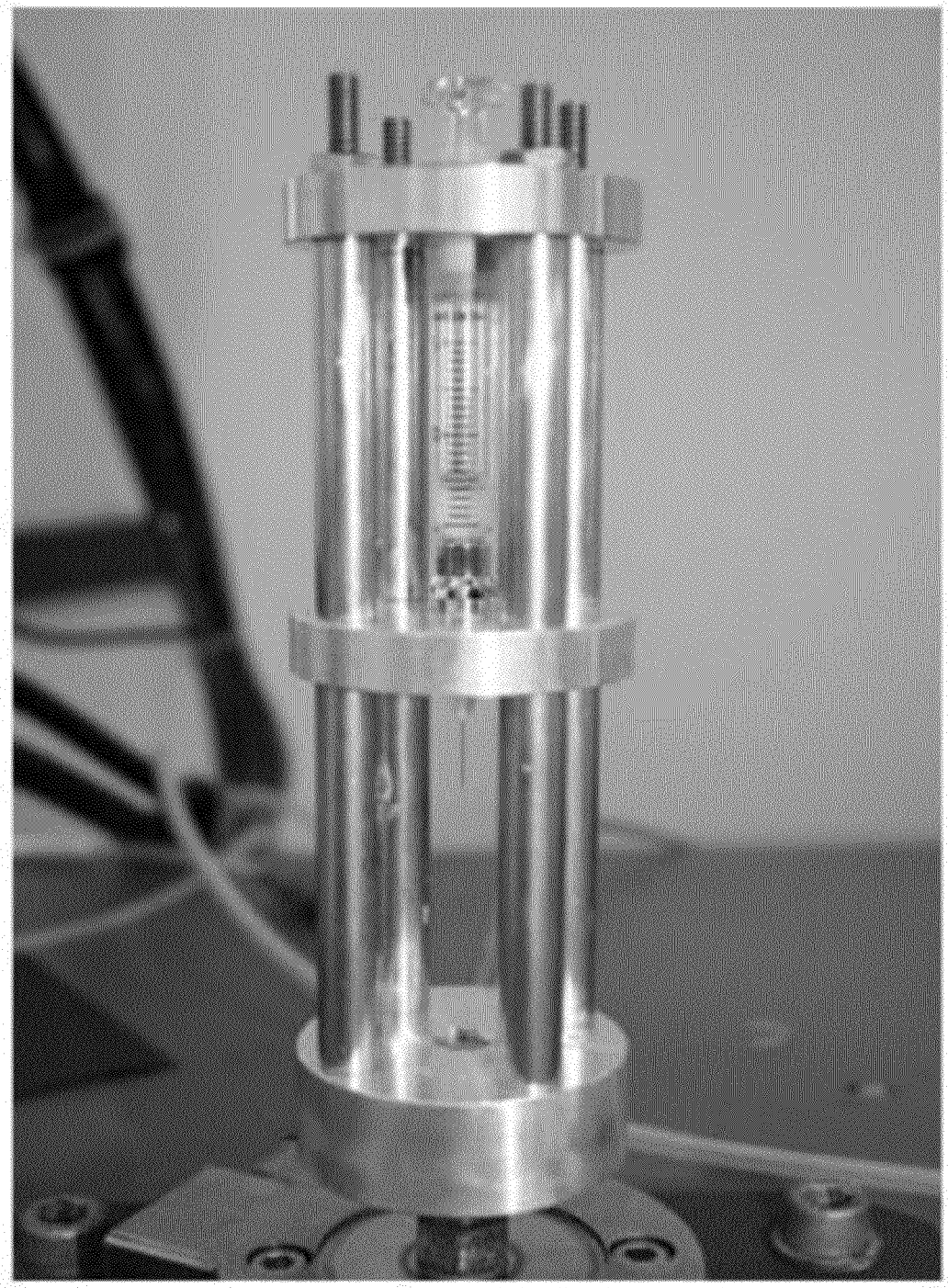
FIG. 15 is a photograph of a custom-built testing jig used in conjunction with an Instron 8511 (Instron Corporation, Canton Mass.) in conjunction with Series IX software and a 100 N load cell for characterizing the injection forces associated with forcing silk gel through a 30 g needle.
Figure 16:
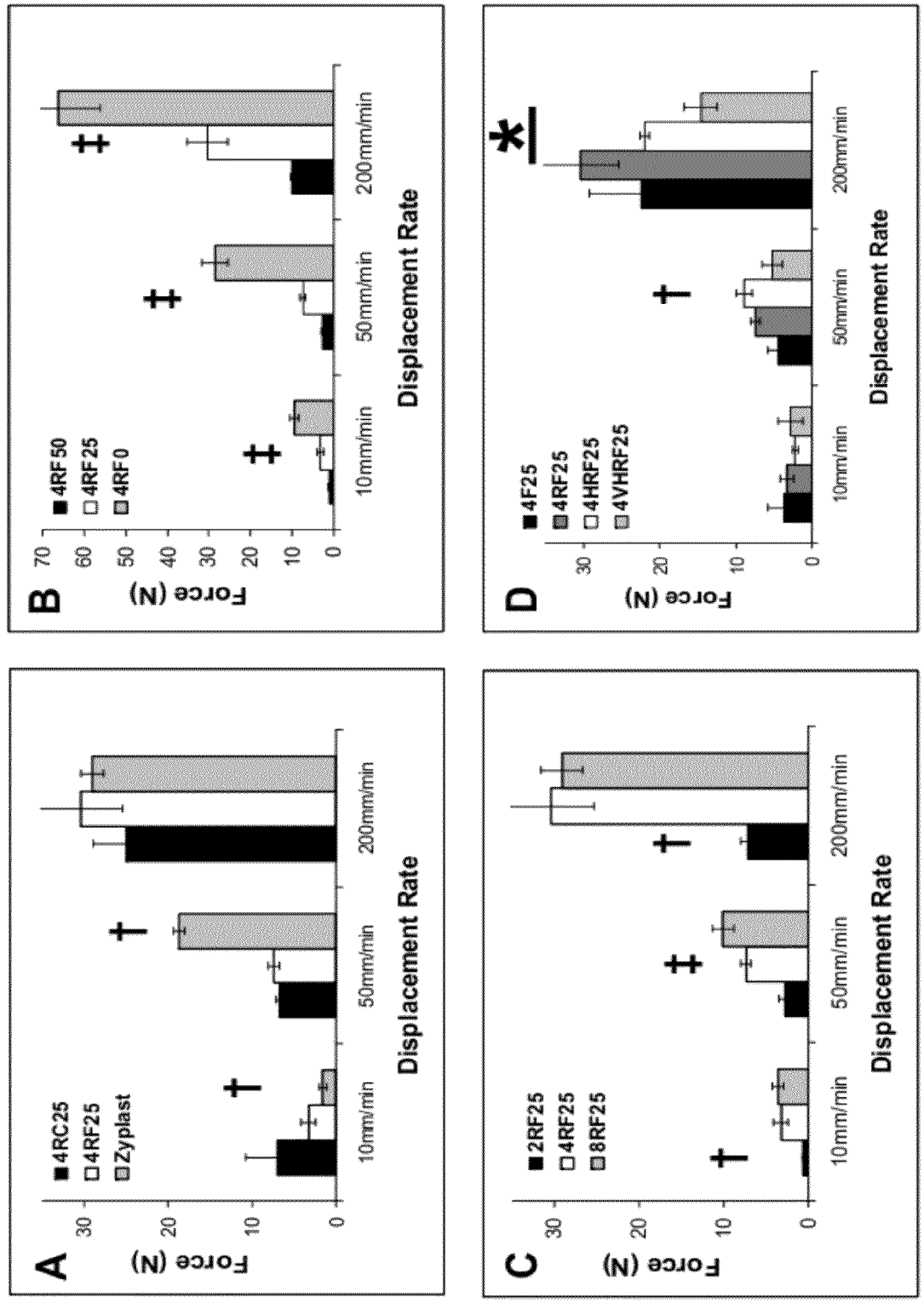
FIG. 16 illustrates the average extrusion force data from mechanical testing of various silk gel formulations illustrating the effects of changing comminution method (A), saline concentration (B), silk concentration (C), and RGD content (D). Values are reported as an average of n=4 tests at each displacement rate with standard deviation illustrated as error bars. * Samples differ significantly, $p<0.05$; † sample differs significantly from all others in group at same strain rate; ‡ all samples in group differ significantly from all others in group at same strain rate.

These samples were tested using an Instron 8511 (Instron Corp., Canton, Mass.) in conjunction with Series IX software and a custom-designed aluminum frame attached to a 100 N load cell (FIG. 15). For the material testing, 1 mL of the sample material of interest was loaded into a 1 mL gas-tight glass syringe. The sample syringe was mounted in the custom-designed aluminum frame mounted on the Instron unit and the material extruded. The sample was then checked for the force required to extrude the gel at each of 3 strain rates, 10 mm/minute, 50 mm/minute, and 200 mm/minute with total actuator displacement set at 7 mm. A series of four tests were run on each material type at each piston displacement rate. Load-displacement data was collected at a frequency of 100 Hz and are presented as the mean±the standard deviation of the 4 average extrusion forces experienced of each gel type at each strain rate. The average extrusion force was defined as the average load measured in the plateau region of the load-displacement curve resultant from each extrusion test. The data were reported as the average amount of force required for extrusion of the sample material and are compiled in Table 9 and FIG. 16.

TABLE 9

Average Force (N) to Extrude Silk Gel from 30 g Needle

| | Plunger Displacement Rate | | | | | |
|---|---|---|---|---|---|---|
| | 10 mm/min | | 50 mm/min | | 200 mm/min | |
| Group Name | Ave | Stdev | Ave | Stdev | Ave | Stdev |
| 2RF25 | 0.6 | 0.0 | 2.9 | 0.6 | 7.3 | 0.7 |
| 4RF25 | 3.7 | 2.0 | 4.5 | 1.3 | 22.4 | 6.7 |
| 4RD25 | 7.1 | 3.7 | 6.7 | 0.5 | 25.1 | 3.9 |
| 4RF0 | 9.5 | 1.0 | 28.5 | 3.1 | 66.2 | 10.0 |
| 4RF26 | 3.2 | 0.9 | 7.4 | 0.6 | 30.4 | 5.0 |
| 4RF50 | 1.2 | 0.2 | 2.7 | 0.1 | 10.1 | 0.3 |
| 4HRF25 | 2.2 | 0.4 | 8.9 | 1.0 | 22.0 | 0.6 |
| 4VHRF25 | 2.8 | 1.6 | 5.2 | 1.4 | 14.6 | 2.1 |
| 8RF25 | 3.6 | 0.7 | 10.1 | 1.3 | 29.2 | 2.4 |
| ZYPLAST ™ | 1.6 | 0.5 | 18.7 | 0.7 | 29.1 | 1.4 |

A comparison between milling techniques revealed that there were no significant differences between 4RC25 and 4RF25, having average extrusion forces of 7.1±3.7N and 3.2±0.9N at 10 mm/min, 6.7±0.5N and 7.4±0.6N at 50 mm/min, and 25.1±3.9N and 30.4±5.0N at 200 mm/min respectively (Table 6, FIG. 16A). Both of these formulations differed significantly ($p \leq 0.05$) from ZYPLAST™ at strain rates of 10 and 50 mm/min, which had extrusion forces of 1.6±0.5 N, 18.7±0.7 N, and 29.1±1.4 N at 10, 50, and 200 mm/min strain rates.

Data regarding the extrudability of silk gel formulations clearly illustrated that the addition of saline as a carrier fluid to the comminuted silk particles offers an improved degree of extrudability, substantially reducing the force necessary to extrude silk gel at all strain rates. Adding increasing concentrations of saline to the comminuted silk gels significantly decreased the extrusion force required for silk gels at each strain rate, with gels again exhibiting shear-thickening behavior (Table 9, FIG. 16B). At all strain rates, 4RF0 required significantly more force to extrude than 4RF25, which in turn required significantly more than 4RF50. At a strain rate of 10 mm/min, 4R0, 4R10, and 4R25 showed a significant decrease ($p \leq 0.05$) in extrusion force with increasing PBS concentration, having average forces of 9.5±3.1 N, 6.1±0.5 N, and 4.7±0.7 N respectively (Table 9). At 50 mm/min, these relationships were more pronounced with average extrusion forces of 14.0±0.9 N, 5.4±0.7 N, and 3.9±0.2 N respectively and all differed significantly (Table 6, FIG. 16). At 200 mm/min, the trend remained as average extrusion forces were 26.4±4.5 N, 10.6±1.6 N, and 6.4±0.5 N respectively with 0% PBS differing significantly from the other two groups. Samples of 6R25 had an average extrusion force of 29.3±4.8 N at 10 mm/min, significantly higher than 4R25 (Table 9). At 50 mm/min and 200 mm/min, the force to extrude the 6R25 was greater than 80 N, causing the test to abort in order prevent damage to the load cell.

The data also illustrate that use of very low concentrations of silk may improve the extrudability of gel relative to higher concentrations as in the case of 2RF25 as compared to 4RF25 and 8RF25. Increasing the concentration of silk in the comminuted silk gels increased the extrusion force required for silk gels at each strain rate, with significant increases between 2RF25 and both 4RF25 and 8RF25 at 10 mm/min and 200 mm/min (Table 9, FIG. 16C). All groups differed significantly at the 50 mm/min strain rate and gels continued to exhibit shear-thickening behavior, seen in the increased extrusion forces associated with increased strain rates. At 10 mm/min 2RF25 and 8RF25 required 0.6±0.0 N and 3.6±0.7 N respectively, at 50 mm/min they required 2.9±0.6 N and 10.1±1.3 N, and at 200 mm/min 7.3±0.6 N and 29.2±2.4 N.

The data further indicated that use of 23RGD to enhance the silk gel material did not appreciably impact the force necessary to extrude silk gel formulations. Adding increasing concentrations of RGD did not have a consistent effect upon the extrusion force necessary for the gel materials (Table 9, FIG. 16D). At a 10 mm/min strain rate there were no significant differences between 4F25 at 3.7±2.0 N, 4R25, 4HR25 at 2.2±0.4 N, and 4VHR25 at 2.8±1.6 N. At a 50 mm/min strain rate 4HR25 was significantly higher than all other extrusion forces at 8.9±1.0 N as compared to 4F25 at 4.5±1.3 N, 4R25, and 4VHR25 at 5.2±1.4N. At a 200 mm/min strain rate 4HR25 at 22.0±0.6 N was significantly higher than only 4VHR25 at 14.6±2.1 N as compared to 4F25 at 22.4±6.7 N and 4R25.

Example 12

Silk Gel Precipitates

The silk gel precipitate materials outlined in Table 10 were generated for analysis. Silk solution of the specified concentration was generated using the stock solution of 8% (w/v) aqueous silk and diluting with purified water (Milli-Q purified). 23RGD/ethanol accelerant was prepared by generating a solution of ethanol and purified water, then dissolving the specified 23RGD quantity by vortexing. Silk precipitates were generated by directly adding the specified volume of accelerant solution to that of silk solution in 50 mL centrifuge tubes, shaking once to mix and allowing the mixture to stand for 5 additional seconds before adding about 45 mL purified water to halt the gelation process. This material stood for 24 hours under ambient conditions and was then strained through stainless steel cloth with 150 μm×150 μm pores to recover precipitates. These precipitates were rinsed twice for 24 hours in 50 mL of purified (Milli-Q) water at room conditions, strained a final time and used for evaluation.

TABLE 10

Silk Gel Precipitate Types Generated

| | Initial Silk Solution | | 23RGD/ethanol Accelerant | | | Final Precipitate | |
| | Silk | | | | Accelerant | | |
| Group Name | Silk Concentration (mg/mL) | Solution Volume (mL) | Ethanol Concentration (%) | 23RGD Concentration (mg/mL) | Solution Volume (mL) | Final Silk Concentration (mg/mL) | RGD:Silk Molar Ratio |
|---|---|---|---|---|---|---|---|
| BASE | 80 | 1 | 90 | 2.45 | 1 | 40 | 5.0 |
| RHI | 80 | 1 | 90 | 4.90 | 1 | 40 | 10.0 |
| RVLO | 80 | 1 | 90 | 0.49 | 1 | 40 | 1.0 |
| RLO | 80 | 1 | 90 | 1.47 | 1 | 40 | 3.0 |
| SCLO | 80 | 1 | 90 | 2.45 | 1 | 30 | 6.7 |
| SCVLO | 80 | 1 | 90 | 2.45 | 1 | 20 | 10.0 |
| ECLO | 80 | 1 | 80 | 2.45 | 1 | 40 | 5.0 |
| ECVLO | 80 | 1 | 70 | 2.45 | 1 | 40 | 5.0 |
| AVHI | 80 | 0.67 | 90 | 2.45 | 1.33 | 27 | 10.0 |
| AVLO | 80 | 1.33 | 90 | 2.45 | 0.67 | 53 | 2.5 |

Lastly, the data showed that silk gels blended with saline had very similar extrudability to ZYPLAST™, a material already proven to be readily handled as an injectable material. Based upon this data it is believed that through careful manipulation of the carrier species associated with the silk gel, modulation of silk concentration, and control of particle size, silk gel materials may be made to behave as a readily injectable material.

These results indicate that silk gels may be comminuted to a particle range of about 25-50 μm² in cross-sectional area. Silk gels may be comminuted to a size similar to ZYPLAST™. Silk gel particle size can be decreased by increasing silk concentration or by changing the method of comminution. Increasing concentrations of RGD did not develop a clear trend in silk particle size. Silk gels may be extruded at a relevant strain rate of 50 mm/min at a force comparable to or less than ZYPLAST™. Silk gel extrusion force may be decreased by adding increased quantities of saline carrier or decreased concentrations of silk in the original gel. Changes of comminution method attempted in this study did not substantially affect the amount of force necessary for silk extrusion. Increasing concentrations of RGD did not develop a clear trend in silk gel extrusion force.

Figure 17:
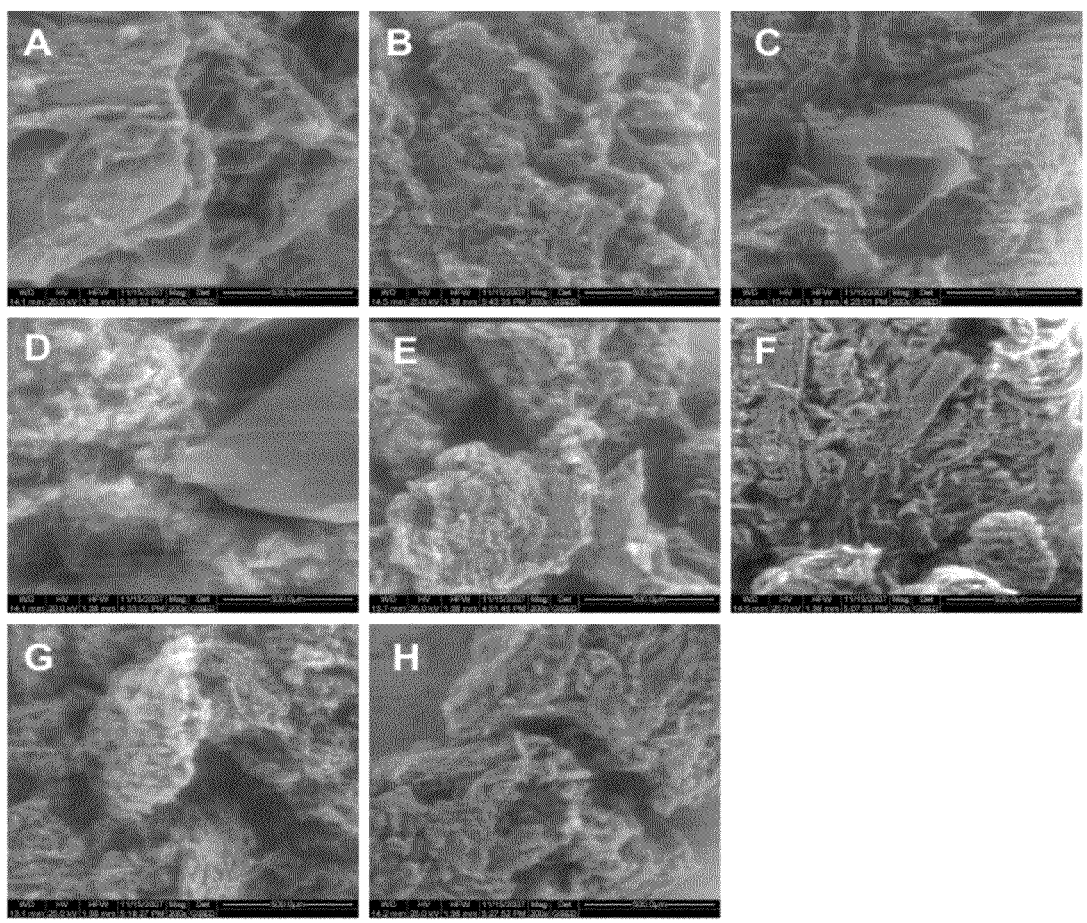
FIG. 17 shows representative ESEM micrographs of selected RGD/ethanol-induced silk precipitates generated from the previously mentioned formulations. BASE (A), SCVLO (B), RHI (C), RLO (D), AVHI (E), ECLO (F), AVLO (G), and 3R 6.7:1 (H) are shown at 200× magnification.

Samples of gel were examined under low-vacuum conditions (~1 Torr) on a Quanta 200 (FEI Co., Hillsboro, Oreg.) environmental scanning electron microscope with images collected at magnifications of 200×. Representative images were taken to illustrate surface topography characteristics of silk precipitate samples (FIG. 17). All silk precipitate types appeared similar under ESEM analysis. Each sample exhibited a mixture of both granular and filamentous regions with occasional appearance of large, contiguous masses of smooth material.

Example 13

Silk Gel Precipitate Massing

Silk precipitate samples, as described in Example 12, were isolated after rinsing by straining through stainless steel wire cloth with a pore size of 104 μm×104 μm and gently blotted with a clean, lint-free wipe. Samples were massed to the nearest 0.01 mg using an S-215 balance (Denver Instrument, Denver, Colo.). These samples were frozen to −80° C. for 24 hours and placed into a Labconco lyophilizer unit (Labconco Corp., Kansas City, Mo.) for 96 hours to remove all water content. The precipitate residual solids were massed again and the dry mass fraction in the samples determined. One-Way analysis of variance (ANOVA) was used to test for significant differences caused by changing silk concentration, 23RGD concentration and accelerant volume. A Student's t-test was used to test the significance of differences resulting from altered ethanol concentrations.

Increasing silk fibroin concentration increased precipitate dry mass with Increasing the percentage of ethanol in the accelerant solution also increased dry mass of the precipitates with ECVLO produced only trace quantities of precipitate (visible, but not recoverable in measurable quantities).

Figure 18:
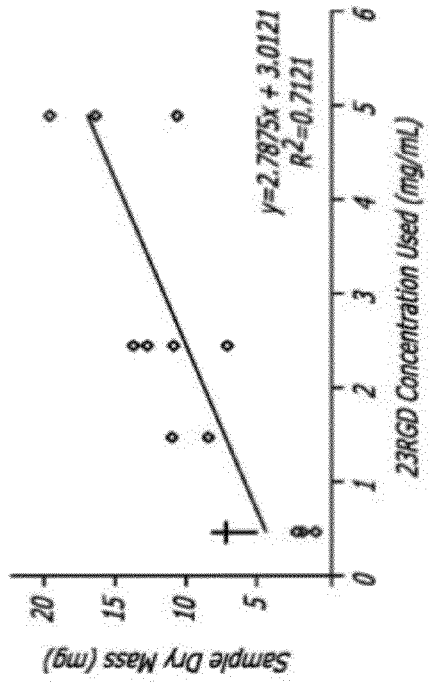
FIG. 18 shows a comparison of the total dry mass of precipitate recovered from each silk precipitate formulation (n=4 for each type) after being subjected to a 96-hour lyophilization process. Data are grouped to compare the effects of changing volume ratio of accelerant added (A), concentration of 23RGD in the accelerant (B), changing the initial silk concentration (C), and changing the concentration of ethanol in the accelerant (D). It was shown that increasing any of these volumes or concentrations resulted in greater quantities of precipitate, though none appear to have substantially greater impact than another. This phenomenon is likely due to basic kinetics of the assembly reaction, with each reagent in turn appearing both as an excess and as limiting dependent upon the specific formulation. *—significant difference, $p<0.05$; †—Group differs significantly from all others.
Figure 18:
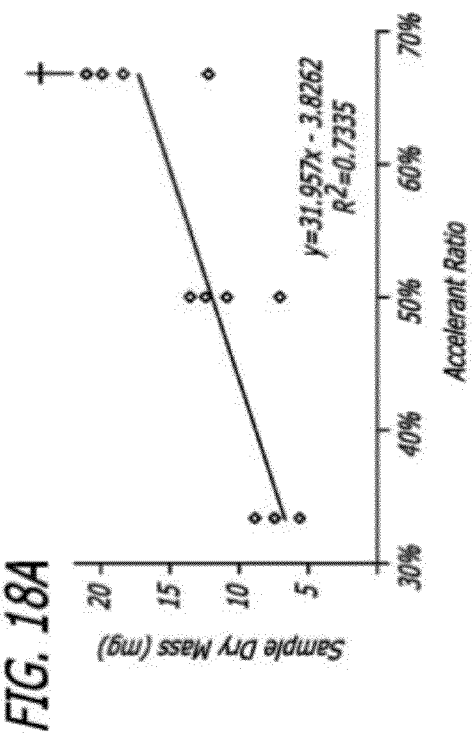
Figure 18:
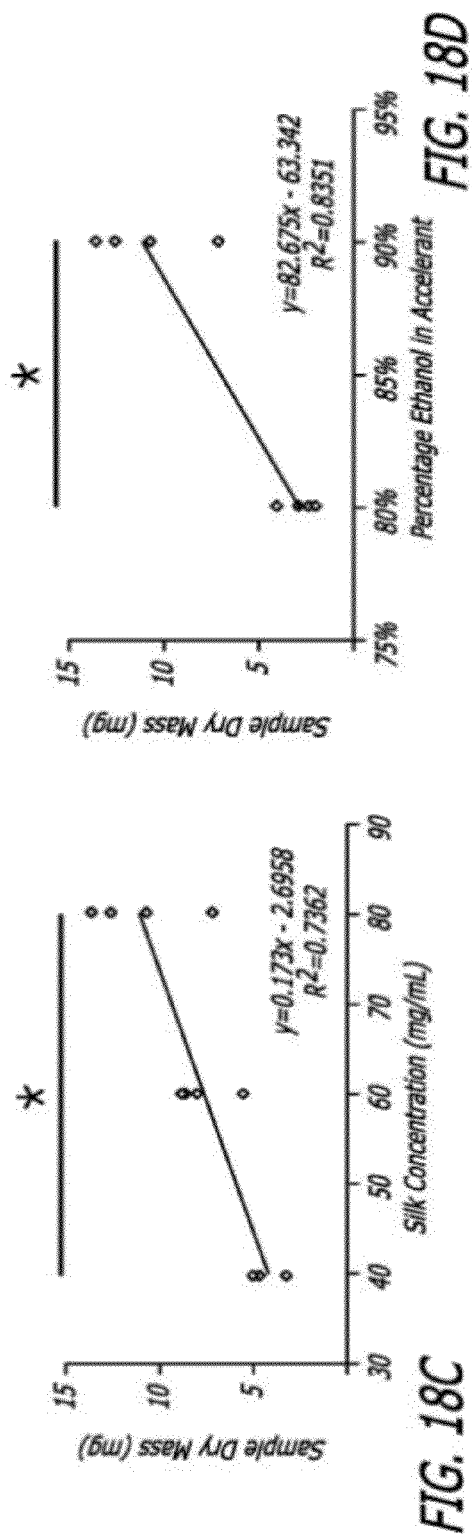

Increasing accelerant volume significantly increased precipitate dry mass as AVHI was significantly greater than both AVLO and BASE (p≦0.05, FIG. 18A). For example, AVHI (18.02±3.9 mg) was significantly greater than both AVLO (7.37±1.33 mg) and BASE (11.07±2.86 mg). Increasing concentrations of 23RGD in the accelerant also increased the dry mass of precipitate with BASE and RHI both significantly higher than RVLO at (FIG. 18B). For example, BASE at 11.07±2.86 mg, RHI at 15.61±3.62 mg, and RMED at 10.2±1.42 mg were all significantly higher than RLO at 1.9±0.6 mg. Increasing silk fibroin concentration increased precipitate dry mass with BASE being greater than SCLO and significantly greater than SCVLO (FIG. 18C). For example, BASE was greater than SCLO at 7.84±1.49 mg and significantly greater than SCVLO at 4.15±1.0 mg. Increasing the percentage of ethanol in the accelerant solution also increased dry mass of the precipitates with BASE producing significantly more than ECLO (FIG. 18D). For example, BASE produced significantly more than ECLO at 2.8±0.91 mg. ECVLO produced only trace quantities of precipitate (visible, but not recoverable in measurable quantities). These results indicate that greater concentrations of reactants (i.e., accelerant solution, RGD, silk and ethanol) all increased the quantity of precipitant resultant.

Figure 19:
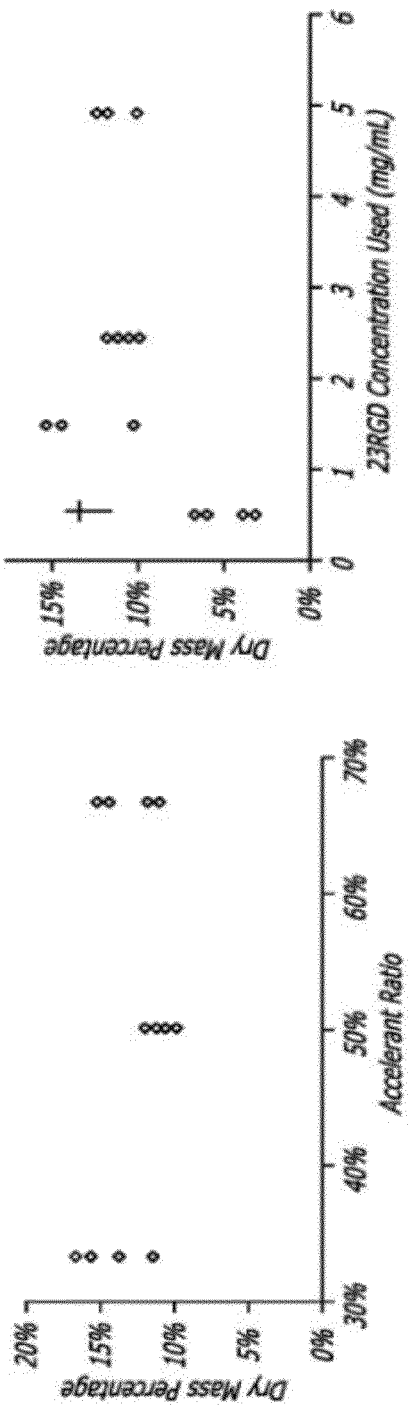
FIG. 19 shows a comparison of the percentage of dry mass in each of precipitate recovered (n=4 for each type) after being subjected to a 96-hour lyophilization process. Data are grouped to compare the effects of changing volume ratio of accelerant added (A), concentration of 23RGD in the accelerant (B), changing the initial silk concentration (C), and changing the concentration of ethanol in the accelerant (D). Increasing the concentration of 23RGD used increased the dry mass percentage of precipitates, while increasing the ethanol percentage in the accelerant decreased dry mass. These changes may stem from formation of altered gel network structures caused by manipulation of these variables, likely more crystalline in the case of 23RGD increases and less crystalline in the case of ethanol concentration increases. *—significant difference, p<0.05; †—Group differs significantly from all others.
Figure 19:
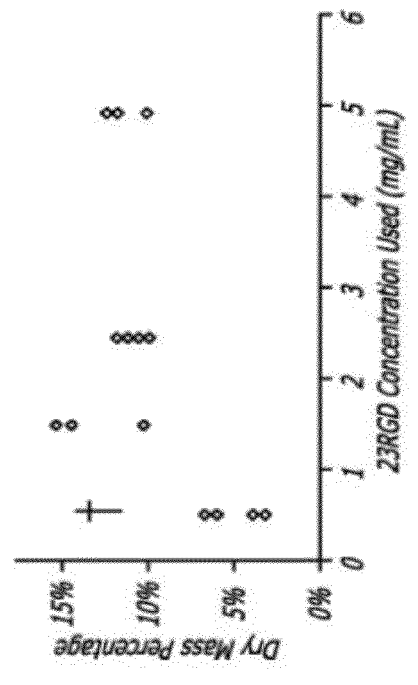
Figure 19:
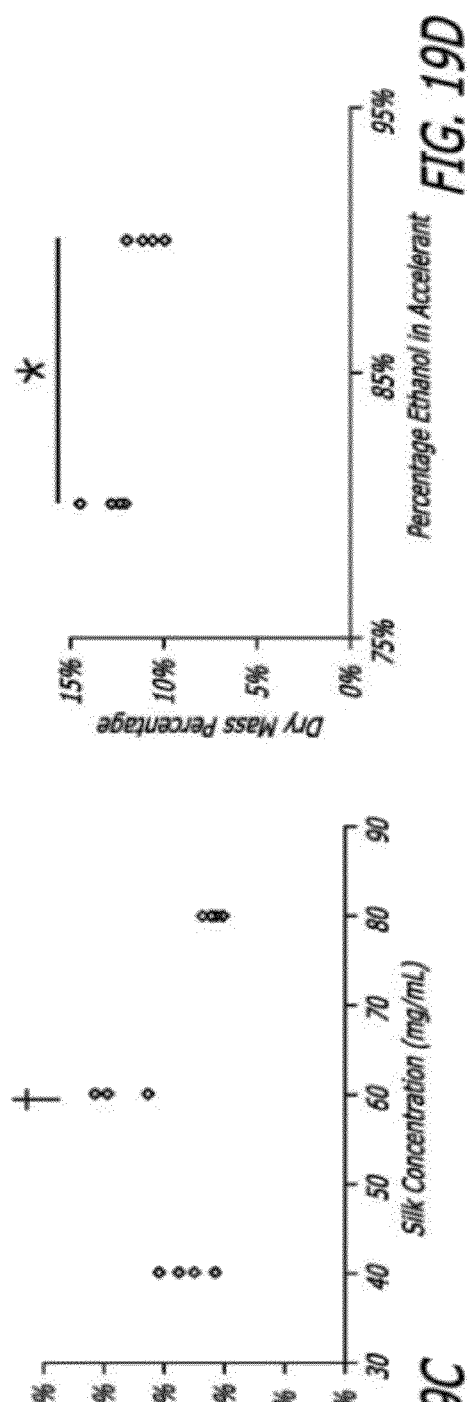
Figure 19:

The percent water in silk precipitates was determined as the percentage of mass lost after silk precipitates of each formulation types were subjected to a lyophilization step. Increasing the volumetric fraction of accelerant added to make silk precipitates did not significantly (p≦0.05) affect the dry mass fraction of the resultant precipitates (FIG. 19A). For example, AVLO at (85.57±2.32%, BASE at 88.99±0.8%, and AVHI was 86.83±1.95%. Increasing concentrations of 23RGD in the accelerant showed a significant increase in dry mass percentage with RVLO significantly less than RLO, RHI, and BASE (FIG. 19B). For example, RLO at 95.01±1.76% retained significantly more water than RMED at 86.52±2.67%, RHI at 88.39±0.98%, and BASE. Increasing concentrations of silk fibroin did not result in a clear trend although SCLO was significantly greater than both SCVLO and BASE (FIG. 19C). For example, SCLO at 80.77±1.97% was significantly less than both SCVLO at 86.94±1.98% and BASE. Increasing the percentage of ethanol in the accelerant solution significantly decreased the dry mass percentage with ECLO compared to BASE (FIG. 19D). For example, ECLO at 86.97±1.16% compared to BASE. In summary, greater concentrations of reactants (i.e., accelerant solution, 23RGD, silk and ethanol) increased the quantity of resultant precipitate. It is also of interest that there were significant differences between the dry mass fractions of BASE and both RVLO and ECLO, possibly indicating different protein structures. These differing protein structures might be more hydrophobic than BASE in the case of ECLO and more hydrophilic in the case of RVLO. These properties might used to affect the stability of the gels in an in vivo environment with more hydrophilic materials being more readily bioresorbed by the host while more hydrophobic materials prove more resistant.

In examining the percent of water in the precipitates it is of particular interest that there were significant differences between BASE and both RLO and ECLO. This may result from structural motifs different than other precipitate types generated by RLO and ECLO. With respect to ECLO, it has a greater proportion of β-sheet structure than BASE and would be expected to entrain less water. However, the difference observed between RLO and base is difficult to explain. RLO has a greater extent of β-sheet structure with less α-helix and random coil motifs than BASE, yet it entrains a greater quantity of water. In fact, this same trend is seen when comparing RLO to RMED, BASE, and RHI. The situation is further confounded in examining the relationship between the initial secondary structures of RMED, BASE and RHI, as all initially exhibit greater quantities of α-helix and random coil than RLO, yet all entrain significantly less water. SCLO samples also had a significantly higher dry mass percentage as compared to BASE and SCVLO sample with no clear trend or reason for this occurrence. These data indicate that there may be a structural difference in these precipitates not apparent in the secondary structure of the materials which is affecting the manner in which the precipitates associate with water. It may be the case that the RGD bound to these precipitates has altered in some fashion the manner in which the silk molecules are presented to water, enhancing their ability to associate with it.

Example 14

Gel Precipitate FTIR Spectrum Capture

Gel precipitates of each type, as described in Example 12, were analyzed by attenuated total reflectance Fourier-transform infrared (ATR-FTIR) spectroscopy using a Bruker Equinox 55 spectrophotometer (Bruker Optics, Inc., Billerica, Mass.) coupled with a Pike MIRACLE™ germanium crystal (PIKE Technologies, Madison, Wis.). Sample ATR signal spectra were obtained by performing a 128-scan integration. Resolution was set to 4 $cm^{-1}$ with a 1 $cm^{-1}$ interval from a range of 4000 to 400 $cm^{-1}$. FTIR spectra of pure water were also collected and subtracted manually from the gel spectra to remove confounding water signal at a ratio conducive to flattening the region between 1800 $cm^{-1}$ and 1700 $cm^{-1}$ on the spectrum. After subtraction, the Amide I bands (1700-1600 $cm^{-1}$) of representative spectra were evaluated against characteristic peaks commonly accepted to be associated with secondary protein structures.

Figure 20:
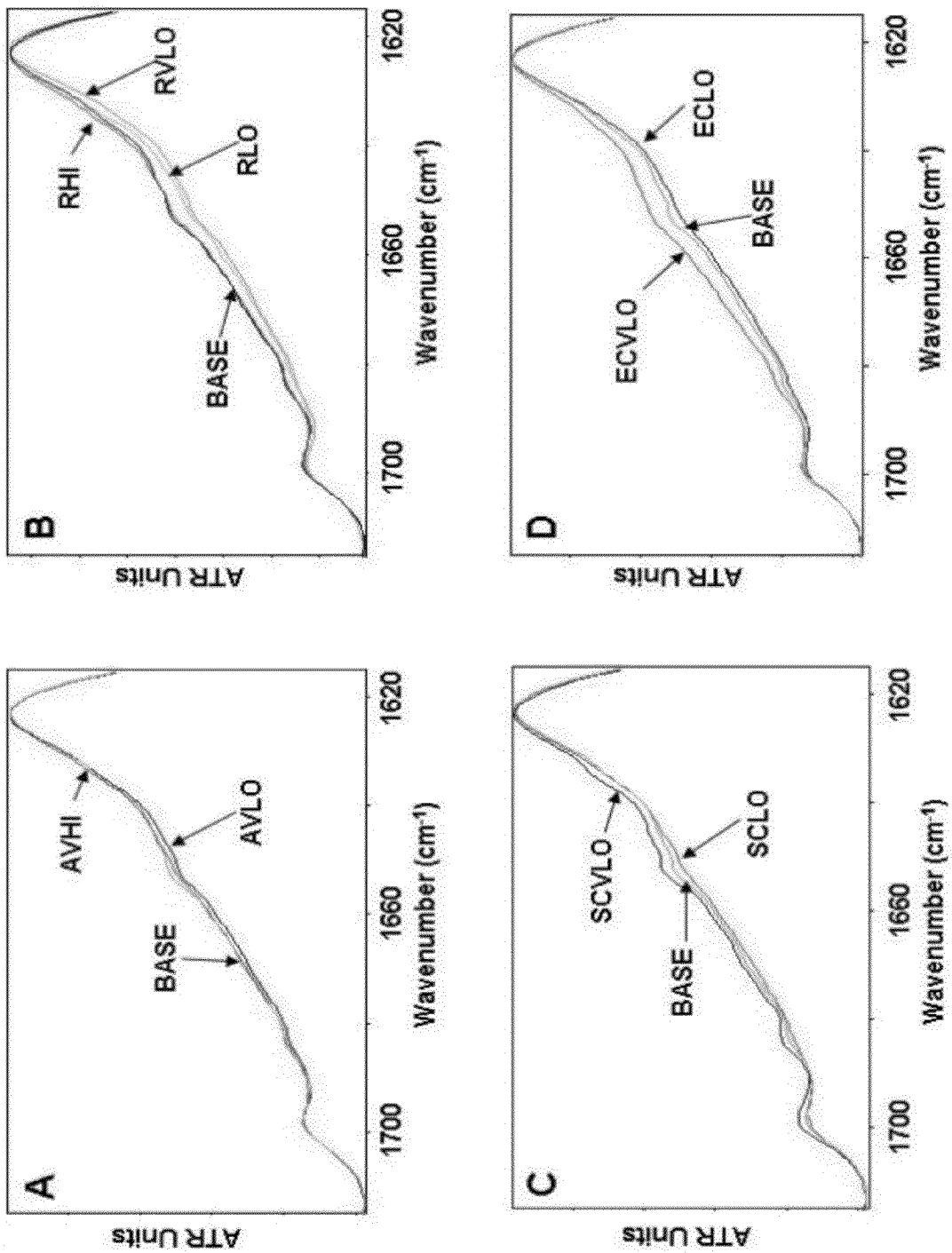
FIG. 20 shows representative FTIR spectra of the Amide I band for 23RGD/ethanol-induced silk precipitates immediately after processing (D0). Spectra are grouped to compare the effects of changing volume ratio of accelerant added (A), concentration of 23RGD in the accelerant (B), changing the initial silk concentration (C), and changing the concentration of ethanol in the accelerant (D). These spectra illustrate that similarities exist between all groups although changing 23RGD concentrations and ethanol concentrations may substantially impact precipitate structure. Increasing concentrations of decreased β-sheet seen in a peak shift from ~1621 $cm^{-1}$ in RVLO to ~1624 $cm^{-1}$ in RLO. A further increase in 23RGD concentration in both BASE and RHI caused this weakened β-sheet again along with increased signal values in the 1654 $cm^{-1}$ and 1645 $cm^{-1}$ range, correlating to increased random coil and α-helical content. An increased percentage of ethanol decreased the content of α-helical and random coil shown by decreased signal between 1670 $cm^{-1}$ and 1630 $cm^{-1}$ in both ECLO and BASE samples relative to ECVLO. This decrease in α-helical and random coil is accompanied by an increase in β-sheet structure. The findings relating to 23RGD and ethanol concentrations reinforce the trends observed in the percent dry mass of the precipitates, supposing that α-helical and random coil motifs entrain more water than β-sheet regions.

Examination of the silk precipitates under FTIR revealed that increasing the volumetric ratio of accelerant added to the silk solution had little effect on their protein secondary structure (FIG. 20A). AVLO, BASE, and AVHI all exhibited similar characteristics with characteristic peaks around 1624 $cm^{-1}$ and a toe region at 1698 $cm^{-1}$ indicating a predominance of β-sheet and β-turn structure respectively. Each sample also exhibited additional structures at 1677 $cm^{-1}$, 1663 $cm^{-1}$, 1654 $cm^{-1}$ and 1645 $cm^{-1}$ denoting additional interspersed β-sheet, β-turn, α-helical and random coil conformations respectively. Increasing concentrations of 23RGD in the accelerant decreased β-sheet stability indicated by a peak shift from ~1621 $cm^{-1}$ in RVLO to ~1624 $cm^{-1}$ in RLO (FIG. 20B). Further increasing the concentration of 23RGD in BASE and RHI caused this weakened β-sheet again accompanied by an increase in higher signal values in the 1654 $cm^{-1}$ and 1645 cm ranges, indicating increased random coil and α-helical constituents. Otherwise, RVLO, RLO, BASE, and RHI revealed similar structures with dominant peaks in the 1620 $cm^{-1}$ range and a toe region at 1698 $cm^{-1}$ with additional structures at 1654 $cm^{-1}$ and 1645 $cm^{-1}$. Increasing concentrations of silk fibroin had little perceptible effect on protein secondary structure (FIG. 20C). The spectra for SCVLO, SCLO, and BASE each exhibited similar characteristic peaks around 1624 cm$^{-1}$ with toe regions at 1698 cm$^{-1}$ indicating a predominant β-sheet structure with additional α-helical and random coil conformations interspersed. Increasing the percentage of ethanol in the accelerant solution resulted in less evidence of α-helical and random coil conformations indicated by a decrease in the signal between 1670 cm$^{-1}$ and 1630 cm$^{-1}$ in both ECLO and BASE samples relative to ECVLO (FIG. 20D). This decrease in α-helical and random coil is accompanied by an increase in β-sheet structure.

Substantial similarity existed between all groups except for RVLO and ECVLO, which each differ from BASE formulation. Each of these material types exhibited a different secondary structure from both each other and from BASE, reinforcing the trend observed previously in the percent dry mass of the precipitates. Higher concentrations of 23RGD yielded less organized β-sheet structures and lower concentrations of ethanol yielded greater quantities of α-helix and random coil motifs. It is possible that used in conjunction with one another, these two phenomena could be adjusted to develop silk structures resulting from silk solutions in any of a variety of different protein conformations. These conformations could, in turn, be tailored based upon the desired ultimate bulk properties of the silk material.

It is expected that higher β-sheet components might provide the gel with greater resistance to bioresorption and compressive loading, while at the same time, making the material more rigid.

Example 15

Congo Red Staining of Gel Precipitates

Silk precipitate samples were stained with 100 µM Congo red in purified water. Silk precipitate samples weighing 5-10 mg were vortexed with 500 µL of this solution for 15 seconds, allowed to stand at room temperature (~20-24° C.) for 10 minutes, then centrifuged at 16,000 g (RCF) for 10 minutes. The supernatant was discarded and the pellet re-suspended by vortexing for 30 seconds in 1 mL of purified water. The process of soaking, centrifugation, aspirating and rinsing was repeated 3 times. The final pellet was removed, smeared on a glass microscope slide, and imaged under white and polarized light using a Microscope PC MACROFIRE™ Model S99831 Camera (Optronics, Goleta, Calif.) and PICTUREFRAME™ 2.1 software (Optronics, Goleta, Calif.) and a System Microscope Model BX41 (Olympus, Melville, N.Y.).

Figure 21:
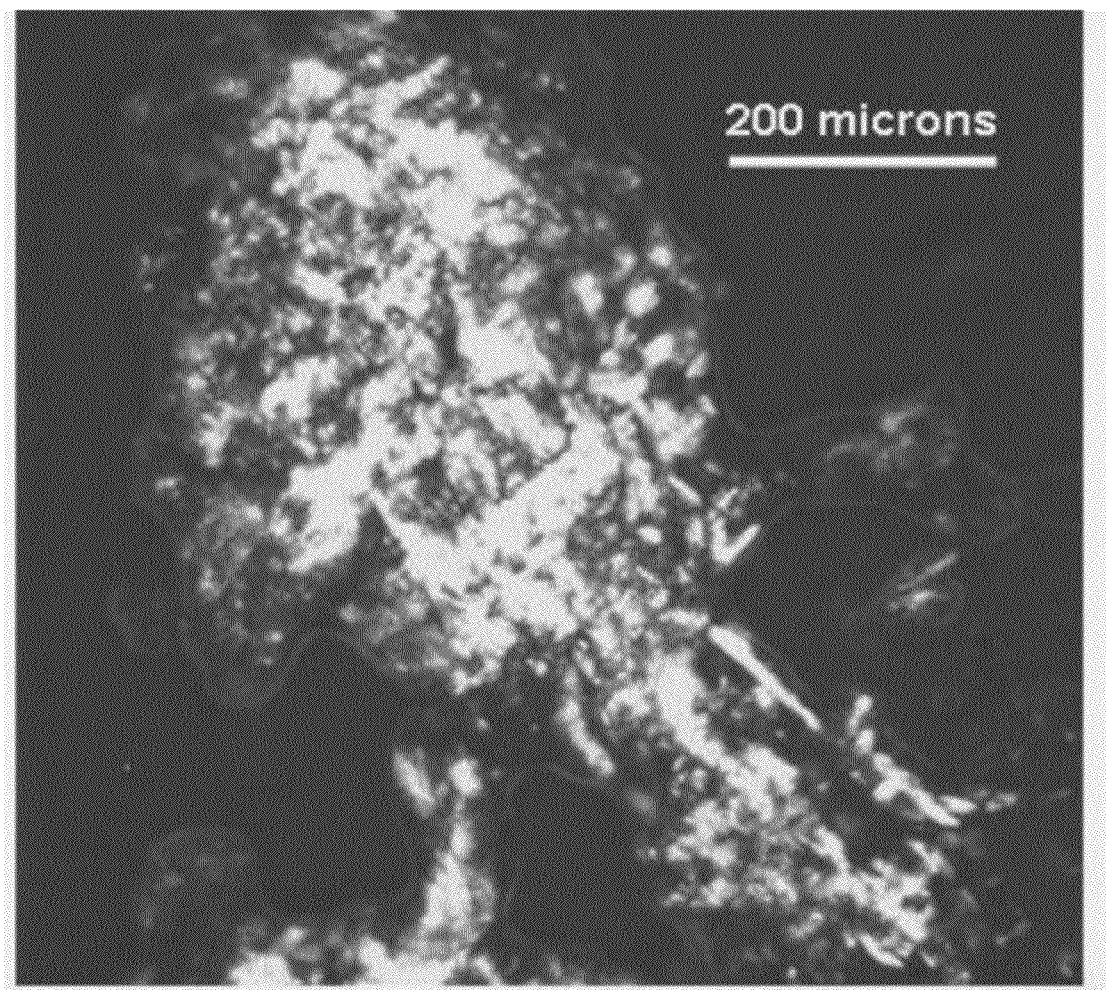
FIG. 21 is a representative micrograph of Congo red-stained 23RGD/ethanol-induced silk precipitates under polarized light at 20× magnification. A lack of emerald-green birefringence indicates a negative result in testing for amyloid fibril formation.

None of the silk precipitate types exhibited the emerald luminescence typically associated with amyloid fibrillar structures (FIG. 21). All precipitate types did exhibit bright white luminescence, indicative of a robust crystalline structure. The extent of this brightness does not appear to vary substantially by formulation, but only by sample quantity on the slide. Based on these results, it is unlikely that any of these precipitate types is amyloid in nature, a positive sign, as amyloid fibrils are associated with a number of negative pathologies in humans.

Example 16

23RGD Quantification in Gel Precipitates by HPLC

The amount of 23RGD bound to silk precipitates was quantified by analyzing lyophilized samples. The 23RGD was removed by incubating the samples for 4 hours in a dissolving buffer, then centrifuging on an Eppendorf 5415C (Eppendorf North America Inc., Westbury, N.Y.) at 16,000 g (RCF) for 30 minutes and the supernatant collected. This supernatant was then centrifuged in identical fashion and the final supernatant collected for HPLC analysis using a PerkinElmer Series 200 (PerkinElmer, Waltham, Mass.). The 23RGD peak areas from each curve were compared against a standard curve. 1-Way ANOVA was used to test for significant differences caused by changing silk concentration, 23RGD concentration, and accelerant volume. A Student's t-test was used to test the significance of differences resulting from altered ethanol concentrations.

Figure 22:
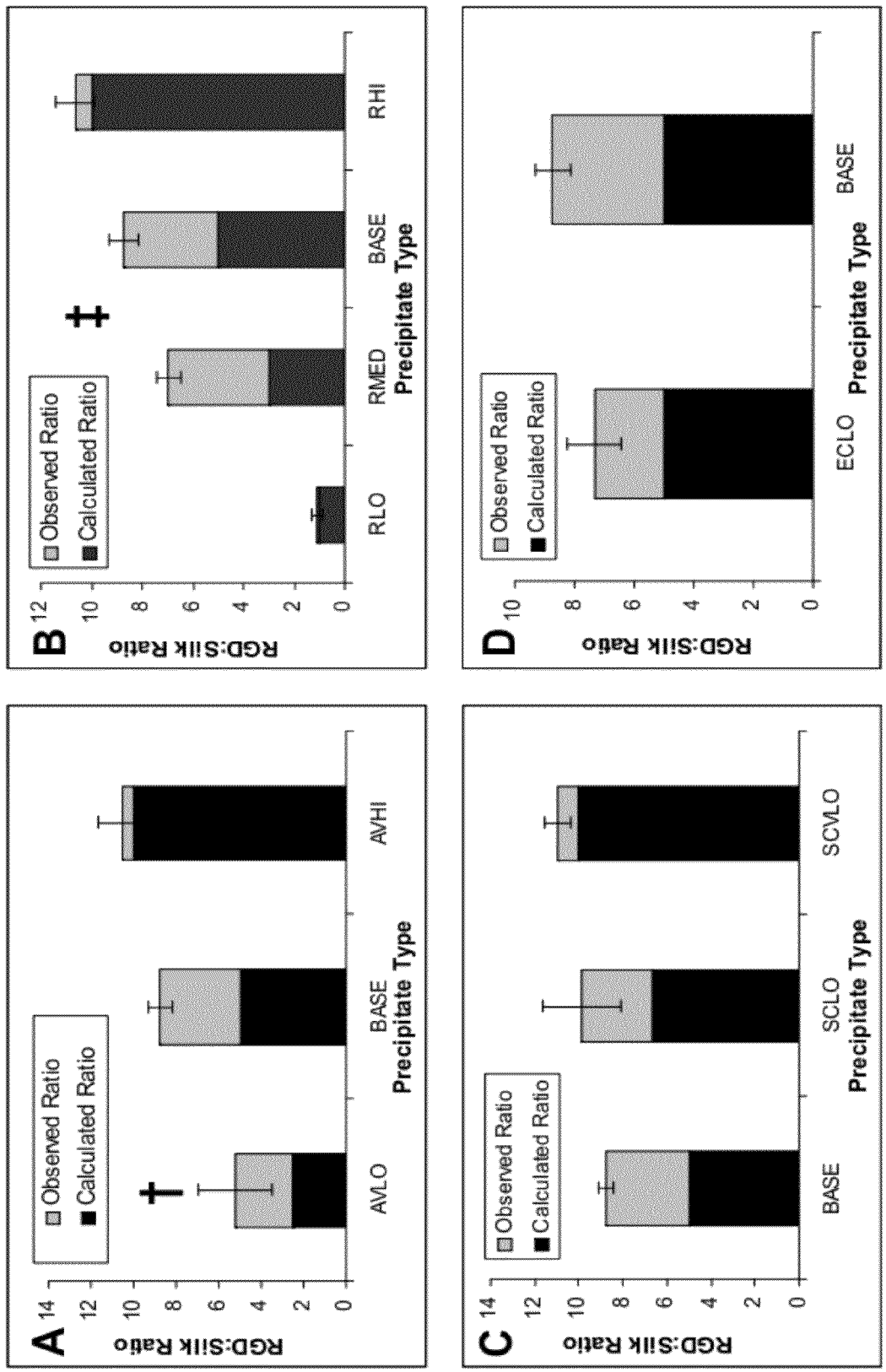
FIG. 22 shows comparison of 23RGD:silk molar ratio in each of precipitate recovered. Data are grouped to compare the effects of changing volume ratio of accelerant added (A), concentration of 23RGD in the accelerant (B), changing the initial silk concentration (C), and changing the concentration of ethanol in the accelerant (D). In examining the 23RGD bound to the precipitates, all materials contained more 23RGD than predicted by initial calculations aside of AVHI, RVLO, RHI, and SCVLO. In the cases of AVHI and ECLO the 23RGD quantity was substantially more than was expected. In the cases of BASE, RLO, SCVLO, and SCLO the 23RGD quantities were approximately double that expected. This may be indicative of the formation of a 23RGD dimer in the 90% ethanol accelerant solution. The RVLO samples were made with a 23RGD concentration of 0.49 mg/mL in the accelerant, the lowest used in this study and potentially within the solubility range of 23RGD in 90% ethanol. RLO samples used 1.47 mg/mL and most other formulations were made with a 23RGD accelerant concentration of 2.45 mg/mL, above the 23RGD concentration at which dimerization became favorable in the solution. Further highlighting the possibility of 23RGD dimerizing in the ethanol solution is the behavior of ECLO precipitation. The 23RGD concentration remains 2.45 mg/mL as with BASE and AVLO but the water concentration in the accelerant is increased to 20% and results in a binding of about 1.5-fold the expected total of 23RGD instead of 2-fold. This may be due to dissolution of a greater quantity of 23RGD, causing coexistence between dimeric and monomeric 23RGD in solution reflected in the subsequent binding ratios. *—significant difference, p<0.05; †—Group differs significantly from all others; ‡—All groups differ significantly.

Increasing the quantity of 23RGD/ethanol accelerant added resulted in a significant increase (p≦0.05) in 23RGD: silk ratio for both BASE and AVHI as compared to AVLO (FIG. 22A). For example, BASE at 8.7±0.6 and AVHI at 10.5±1.2 were significantly increased as compared to AVLO at 5.2±1.8. Increasing the quantity of 23RGD in the accelerant solution resulted in significant increases in 23RGD:silk ratio for each of RVLO, RLO, BASE, and RHI relative to each other (FIG. 22B). For example, RLO at 1.1±0.2, RMED at 6.95±0.49, BASE and RHI at 10.7±0.8 relative to each other. Changing the starting concentration of silk in solution prior to precipitation did not affect 23RGD:silk ratio as those in SCVLO, SCLO, and BASE did not differ significantly (FIG. 22C). For example, SCVLO at 11.0±0.4, SCLO at 9.9±1.8, and BASE did not differ significantly. Decreasing the ethanol content in the accelerant did not produce a significant effect as observed by comparing ECLO and BASE (FIG. 22D).

Reviewing this data in light of the precipitate dry massing data, none of the conditions explored resulted in isolation of silk (~10-35% precipitated) nor 23RGD (~5-30% precipitated) as limiting reagents in the reaction. Precipitate samples generated at a calculated 10:1 23RGD:silk ratio consistently generated a "correct" molecular binding ratio. In the case of AVHI, this runs contrary to the trend of bound 23RGD concentrations being approximately double the projected values as indicated by AVLO and BASE (about 5:1 and about 9:1, respectively). This might be explained by saturation of the silk with 23RGD in the case of 10:1 23RGD precipitates. This is further reinforced by the behavior of SCVLO and 0.6S 3R 10:1, both of which were produced using 2.45 mg/mL 23RGD in 90% ethanol as the AVHI was. Both materials projected to have greater than 10:1 ratios of bound 23RGD (20:1 and 13.4:1, respectively) based on the behavior of AVLO and BASE, but which both reached only about 10:1 ratios. RHI, generated using a 4.5 mg/mL 23RGD concentration in the accelerant which conceivably should have been high enough to induce the postulated dimeric 23RGD reached only the expected 23RGD ratio of about 10:1 not the postulated 20:1.

Figure 23:
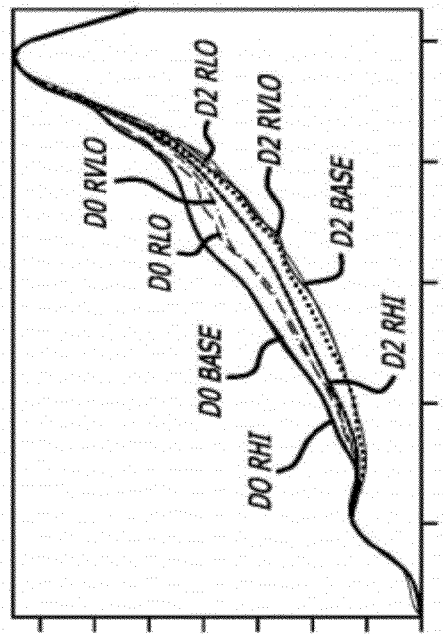
FIG. 23 shows a representative FTIR spectra of the Amide I band are shown for 23RGD/ethanol-induced silk precipitates initially (D0) and after proteolytic bioresorption (D2). Spectra are grouped to compare the effects of changing volume ratio of accelerant added (A), concentration of 23RGD in the accelerant (B), changing the initial silk concentration (C), and changing the concentration of ethanol in the accelerant (D). Accelerant quantity added did not substantially affect the bioresorption behavior of the materials as BASE, AVHI and AVLO all featured decreased levels of α-helix and random coil motifs. This decrease was slightly larger in the case of AVLO which also featured a peak shift from 1624 $cm^{-1}$ to 1622 $cm^{-1}$, indicating a more stable β-sheet structure. 23RGD concentration did not appear to affect bioresorption behavior of the materials either as RVLO, RLO, BASE and RHI all showed decreased in α-helix and random coil motifs, though a greater portion of α-helix and random coil remained intact in RHI. Silk concentration did not substantially affect the bioresorption behavior of the materials as BASE and SCLO exhibited decreased levels of α-helix and random coil motifs and featured slight peak shifts from 1624 $cm^{-1}$ to 1623 $cm^{-1}$.
Figure 23:
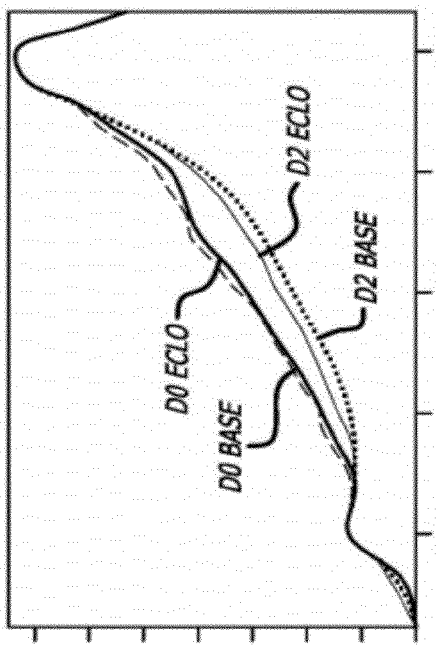
Figure 23:
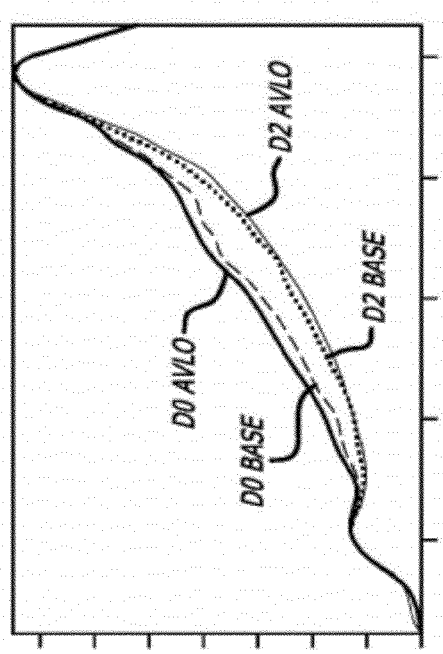
Figure 23:
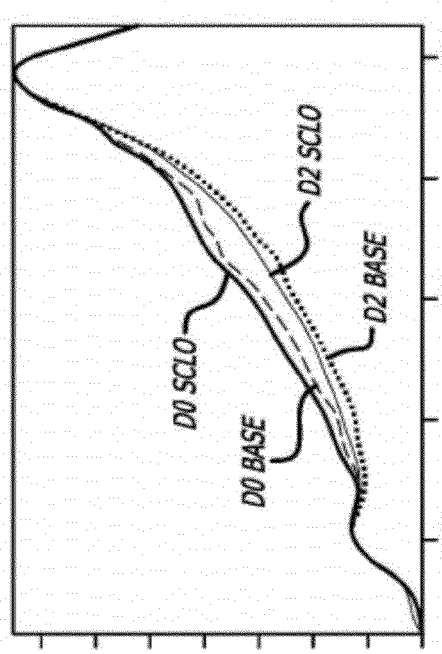

Few of the silk precipitates entrained a molar ratio similar to what was initially calculated (FIG. 23). Four groups, SCVLO, AVHI, RHI, and RLO contained ratios similar to their calculated values of RGD per mole of silk. The six remaining groups contained ratios substantially greater than their calculated values. In the cases of AVLO, BASE, RMED, and SCLO, the RGD quantities were about 2-fold greater than expected. Although not wishing to be limited by theory, this greater observed molar ratio may be indicative of the formation of a RGD bi-layer. It may be the case that either micelles or lamellar structures of RGD existed in the 90% ethanol solution prior to addition to the silk, upon contacting the aqueous phase, micellar stability was disrupted. As a result, a bi-layer of RGD was formed at the solution interface, where these molecules began to interact with the silk molecules. The RLO samples were made with a RGD concentration of 0.49 mg/mL in the accelerant, the lowest used in this study and potentially within the solubility range of RGD in 90% ethanol. RMED samples used 1.47 mg/mL and most other formulations were made with a RGD accelerant concentration of 2.45 mg/mL, above the RGD concentration at which dimerization became favorable in the solution. Further highlighting the possibility of RGD dimerizing in the ethanol solution is the behavior of ECLO precipitation. The RGD concentration remains 2.45 mg/mL as with BASE and AVLO but the water concentration in the accelerant is increased to 20% and results in a binding of about 1.5-fold the expected total of RGD. This may be due to a decreased driving force for RGD bi-layer formation at the solution interface caused by the lower ethanol content. This might in turn cause disruption to fewer micellar structures in the initial accelerant solution. It could also be explained by altered micellar structure, varying between a single peptide layer and a multi-lamellar structure depending upon the concentrations of water and ethanol in the accelerant phase.

Precipitate samples generated at a calculated 10:1 RGD:silk ratio consistently generated a "correct" molecular binding ratio. In the case of AVHI, this runs contrary to the trend of bound RGD concentrations being approximately double the projected values as indicated by AVLO and BASE (about 5:1 and about 9:1 respectively). It is possible that this might be explained by saturation of the silk with RGD in the case of 10:1 RGD precipitates. This is further reinforced by the behavior of SCVLO and 0.6S 3R 10:1, both of which were produced using 2.45 mg/mL RGD in 90% ethanol as was AVHI. Both materials projected to have greater than 10:1 ratios of bound RGD (20:1 and 13.4:1 respectively) based on the behavior of AVLO and BASE, but which both reached only about 10:1 ratios. RHI, generated using a 4.5 mg/mL RGD concentration in the accelerant which conceivably should have been high enough to induce the postulated dimeric RGD, reached only the expected RGD ratio of about 10:1 not the postulated 20:1. This may be attributed to the mode of binding between the silk molecules and the RGD molecules. It is expected that RGD will bind through a hydrophobic association mechanism and despite the largely hydrophobic sequence of silk, it may be possible that there are approximately 5 sites which offer preferable RGD binding stability. This presumption stems from the apparent saturation at 10:1 RGD molecules per molecule of silk. Dependent upon the nature of RGD self-association at the solution boundary, it may be a case where single RGD molecules or RGD dimers bind to these sites.

There are a series of properties further indicating the possibility of a specific molecular assembly interaction between the silk and 23RGD accelerant. Conspicuously, that 23RGD does localize to the precipitates in a greater-than-calculated ratio but that it binds at intuitive concentrations which can be related quickly to the initially calculated molar ratios. The fact that this occurs without fully depleting either the 23RGD or the silk fibroin molecules is of further interest. The FTIR data also indicated that use of 0.49 mg/mL 23RGD in RVLO precipitates induced formation of distinctly different structures than use of 2.45 mg/mL in BASE or 4.9 mg/mL in RHI which appeared similar to each other. RMED precipitates generated with 1.47 mg/mL of 23RGD contained characteristics of both RVLO and BASE/RHI material spectra. FTIR indicated a different structure from a 2.45 mg/mL of 23RGD in 70% ethanol accelerant in the case of ECVLO. These outcomes were both reinforced in examining the percentage of dry mass from the resultant precipitates (though ECLO is used to illustrate the trend in 23RGD solubility in ethanol solution instead of ECVLO). Both of these assays indicate the formation of different precipitate structures based upon the extent of 23RGD saturation in the ethanol solution, conceivably resulting from dimeric 23RGD binding or monomeric 23RGD binding.

This phenomenon likely results from the amphiphilic nature of 23RGD and the varied chemistry of the solution phase between heavily ethanolic and heavily aqueous. It is possible that the hydrophilic ends of two 23RGD molecules associate in the 90% ethanol solution, exposing the two hydrophobic ends to solution. Addition of this accelerant solution with dimeric 23RGD causes rapid association of the exposed hydrophobic ends of the 23RGD with hydrophobic domains of the silk molecules, rapidly precipitating them. This process occurs until the 90% ethanol accelerant solution is sufficiently diluted with the aqueous silk solution to cause the dimeric assembly of the 23RGD molecules to no longer be favorable, as a result stopping precipitation. Based upon the apparent saturation at about 10 for 23RGD:silk ratio, there may also be a maximum of 5 binding sites for the 23RGD dimer per molecule of silk. This knowledge may be used to bind specific quantities of 23RGD to silk, while at the same time dictating silk gel structure and resultant behavior. Additionally, this method may also potentially be applied to other amphiphilic peptides of interest during their integration into a silk gel material.

These results indicate that silk precipitate quantity may be increased by increasing the quantity of any reactant in the RGDEEG system. Silk precipitates occurring during RGDEEG gelation are unlikely to be amyloid. Silk precipitate β-sheet structure may be increased by higher concentrations of ethanol accelerant or lower concentrations of RGD. RGD molecules may self-associate into micelles, lamellar structures, or dimers when placed into a strongly ethanolic solution, in turn, assembling with silk in a dimeric fashion during RGDEEG gelation. Silk molecules may become saturated with RGD once they have bound about 10 molecules. Silk precipitate structures may be altered by changing RGD concentrations added, though the extent and nature of these changes remains unclear, as they are not perceptible in material secondary structure. These altered structures may account for otherwise unexplained increased appearance of α-helix and random coil motifs at high RGD concentrations in precipitates. These altered structures may account for otherwise unexplained increased resistance to proteolytic bioresorption of α-helix and random coil motifs at high RGD concentrations in precipitates.

Example 17

Enzymatic Bioresorption of Gel Precipitates

A single sample of precipitate types selected for distinctly different behaviors from BASE in the previously listed assays including RVLO, RLO, BASE, RHI, ECLO, 0.6S 3R 5:1 weighing approximately 60 mg were massed using an S-215 balance. These samples were placed in a solution of Protease Type XIV from *Streptomyces griseus* (Sigma catalog no. P-5147) in phosphate buffered saline (PBS) was generated at a concentration of 0.3 mg/mL (activity was 4.5 U/mg) at a ratio of 1 mL of protease solution per 100 mg of silk precipitate. The gel and protease solution were incubated for 24 hours at 37° C. with no mechanical mixing. After 24 hours, the residual precipitate was isolated by straining through stainless steel cloth as before and the specimens analyzed by FTIR as described.

Accelerant quantity added did not substantially affect the bioresorption behavior of the materials as BASE, AVHI and AVLO all featured decreased levels of α-helix and random coil motifs (FIG. 23A). This decrease was slightly larger in the case of AVLO which also featured a peak shift from 1624 cm$^{-1}$ to 1622 cm$^{-1}$, indicating a more stable β-sheet structure. The 23RGD concentration did not appear to affect bioresorption behavior of the materials either as RVLO, RLO, BASE and RHI all showed decreased in α-helix and random coil motifs, though a greater portion of α-helix and random coil remained intact in RHI (FIG. 23B). However, a greater portion of α-helix and random coil remained intact in RHI at Day 2 relative to the other samples. Silk concentration did not substantially affect the bioresorption behavior of the materials as BASE and SCLO exhibited decreased levels of α-helix and random coil motifs and featured slight peak shifts from 1624 cm$^{-1}$ to 1623 cm$^{-1}$ (FIG. 23C).

Despite differences in initial structures, all precipitate types bioresorbed in a similar fashion with α-helix and random coil motifs degraded preferentially to β-sheet. Only increasing the concentration of 23RGD, as in the case of RHI, appeared to have any appreciable effect on the final secondary structure of the precipitates. This appears to be a case where there is simply more α-helix and random coil structure upon initial formation of these materials and they take more time to degrade to a similar extent of β-sheet structure as the other formulations. Use of this knowledge in conjunction with an ability to manipulate the secondary protein structures of these materials could lead to biomaterials with very specific lifetimes in vivo.

Example 18

Composition Comprising Silk Fibroin Hydrogel Particles and Matrix Polymer

Silk fibroin hydrogels were cast according to the methods described above in Examples 1-4. A silk hydrogel consisting of 6% silk fibroin by dry mass percent with a 23RGD molar ratio of 1:1 with silk molecules was generated for particle comminution. This material was subjected to the forced sieving method described above to generate silk gel particles ranging nominally between 0.1 μm$^2$ and 5 μm$^2$. These materials were blended with crosslinked hyaluronan at various volumetric ratios for evaluation as a potential filler material. The blends were made at volumetric percentages of 5% silk fibroin hydrogel with 95% hyaluronan, 25% silk fibroin hydrogel with 75% hyaluronan, 50% silk fibroin hydrogel with 50% hyaluronan.

Example 19

Composition Comprising Silk Fibroin Hydrogel Particles and Matrix Polymer

The composition described above in Example 18 are modified in terms of the 23RGD component (0 to 3:1), silk fibroin concentration (1% to 8%), particle size (0.1 μm$^2$ to 500 μm$^2$), and silk format (may be silk solution intermediate mentioned above added directly to hyaluronan). Materials also vary in the percent composition of silk hydrogel in hyaluronan between 0.1% and 99.9% depending upon application and desired material properties.

Example 20

Extrudability Characteristics of Composition Comprising Silk Fibroin Hydrogel Particles and Matrix Polymer To assess the extrusion force necessary to inject a composition disclosed herein through a needle, the dermal fillers comprising silk fibroin hydrogel particles in Table 11 were compared with JUVÉDERM® Ultra Plus (Allergan, Inc., Irvine Calif.), a crosslinked hyaluronan dermal filler sample lacking silk fibroin hydrogel particles (6PUR00). The extrusion force test was performed by measuring the force necessary to extrude a hydrogel through a 27 gauge or 30 gauge needle using a 0.8 mL syringe.

To prepare the compositions listed in Table 11, a 6% silk fibroin hydrogel was prepared according to Examples 1-4. Some of it was used as component for the filler formulation, and another batch was mixed with 25% (v/v) PBS (saline buffer) according to Example 9, for a final silk fibroin content of around 4.5%. These hydrogels were mixed with a commercial crosslinked hyaluronan in various proportions using a mechanic mixer. This hyaluronan hydrogel had the following characteristics: 24 mg/g sodium hyaluronate (with an average molecular weight of 3,000,000 Da before crosslinking), a degree of crosslinking of 5%-6% (crosslinker: 1,4-butanediol diglycidyl ether). Table 11 lists the formulations prepared by mixing silk fibroin hydrogels with hyaluronan gels in 100 g pots by using several homogenization cycles of 1 minute at 3500 rpm in the mixer. The pH was adjusted to about 7.0 by addition of small volumes of a diluted sodium hydroxide solution between homogenization cycles.

TABLE 11

Examples of filler formulations containing silk fibroin and crosslinked hyaluronan

| Composition Name | Silk Fibroin Hydrogel | Silk Component Weight % | Final Silk Fibroin Concentration | Final HA Concentration |
|---|---|---|---|---|
| 6PUR00 | no silk (blank) | 0% | 0 mg/g | 24.0 mg/g |
| 6PUR05 | 6% silk fibroin gel | 5% | 3.0 mg/g | 22.8 mg/g |
| 6PUR25 | | 25% | 15.0 mg/g | 18.0 mg/g |
| 6PUR50 | | 50% | 30.0 mg/g | 12 mg/g |
| 6PBS05 | 4.5% silk fibroin gel | 5% | 2.25 mg/g | 22.8 mg/g |
| 6PBS25 | (made from 6% gel + | 25% | 11.25 mg/g | 18.0 mg/g |
| 6PBS50 | 25% (v/v) saline buffer) | 50% | 22.5 mg/g | 12 mg/g |
| 6PBS75 | | 75% | 33.75 mg/g | 6 mg/g |

Analysis of these compositions indicate that compositions comprising about 5% to about 50% silk fibroin hydrogel particles exhibited extrudability characteristics similar to a composition comprising 0% silk fibroin hydrogel particles. For example, at a plunger displacement rate of about 13 mm/min, compositions comprising 0% to about 50% silk fibroin hydrogel particles all exhibited an extrusion force of about 10N. Similarly, at a plunger displacement rate of about 50 mm/min, compositions comprising 0%, about 5%, and about 50% silk fibroin hydrogel particles all exhibited an extrusion force of about 17N, with compositions comprising 25% silk fibroin hydrogel particles exhibiting an extrusion force of about 20N.

Example 21

In Vivo Evaluation of Composition

Comprising Silk Fibroin Hydrogel Particles and Matrix Polymer

To examine the in vivo effects of the compositions disclosed herein, the compositions disclosed in Table 12 were subcutaneously injected into Sprague Dawley rats.

To prepare the compositions listed in Table 12, a 8% silk fibroin hydrogel was prepared according to Examples 1-4. The silk fibroin hydrogel was milled into particles of a mean cross-sectional area of about 1 μm and blended with the saline component indicated in Table 12. Saline was added by first mixing by spatula into a bulk of silk fibroin hydrogel, then shearing 60 times through a 1.5 mm orifice. After saline blending, the material was sterilized by gamma irradiation at a dose of 25-40 kgy. The sterilized silk fibroin hydrogel particles were blended with JUVÉDERM® Ultra Plus (Allergan, Inc., Irvine Calif.), a hyaluronan dermal filler, in ratios according to Table 12 immediately prior to surgery. Blending was conducted by means of shearing back and forth between a pair of syringes connected by a stopcock until combined gel appearance was uniform.

TABLE 12

Examples of filler formulations containing silk fibroin and crosslinked hyaluronan

| Group | Sample Name | Silk Fibroin Component | Hyaluronan Component | Saline Component | Silk Fibroin Percent Silk | SST:Silk Ratio |
| --- | --- | --- | --- | --- | --- | --- |
| 1 | JUVÉDERM ® Ultra Plus | N/A | 100% | N/A | N/A | N/A |
| 2 | 5% Base Silk Fibroin | 3.75% | 95% | 1.25% | 6% | 1:1 molar |
| 3 | 25% Base Silk Fibroin | 18.75% | 75% | 6.25% | 6% | 1:1 molar |
| 4 | 50% Base Silk Fibroin | 37.5% | 50% | 12.5% | 6% | 1:1 molar |
| 5 | 75% Base Silk Fibroin | 56.25% | 5% | 18.75% | 6% | 1:1 molar |
| 6 | Base Silk Fibroin | 75% | 0% | 25% | 6% | 1:1 molar |

Eight male Sprague Dawley rats weighing 250-275 grams, acclimated for one week at the animal facility prior to surgery, were anesthetized with 4% isoflurane and maintained at 1-2% isoflurane on a heated pad. The back of the animal was shaved and cleaned with alcohol. The animals were injected at four different sites on the back with a volume of 50 μL/injection. Compositions were distributed across multiple animals in a successive and cyclical pattern. Material Group 1 will be injected into Animal 1, Site 1; Material Group 2 into Animal 1, Site 2; Material Group 3 into Animal 1, Site 3; Material Group 4 into Animal 1, Site 4; Material Group 5 will be injected into Animal 2, Site 1, Material Group 6 will be injected into Animal 2, Site 2; Material Group 1 will be injected into Animal 2, Site 3; Material Group 2 will be injected into Animal 2, Site 4; etc. A total of 24 sites will be injected in 6 rats. On Day 42, animals were euthanized via carbon dioxide asphyxiation and all sample sites were identified, harvested, and prepared for subsequent sectioning and staining.

Figure 24:
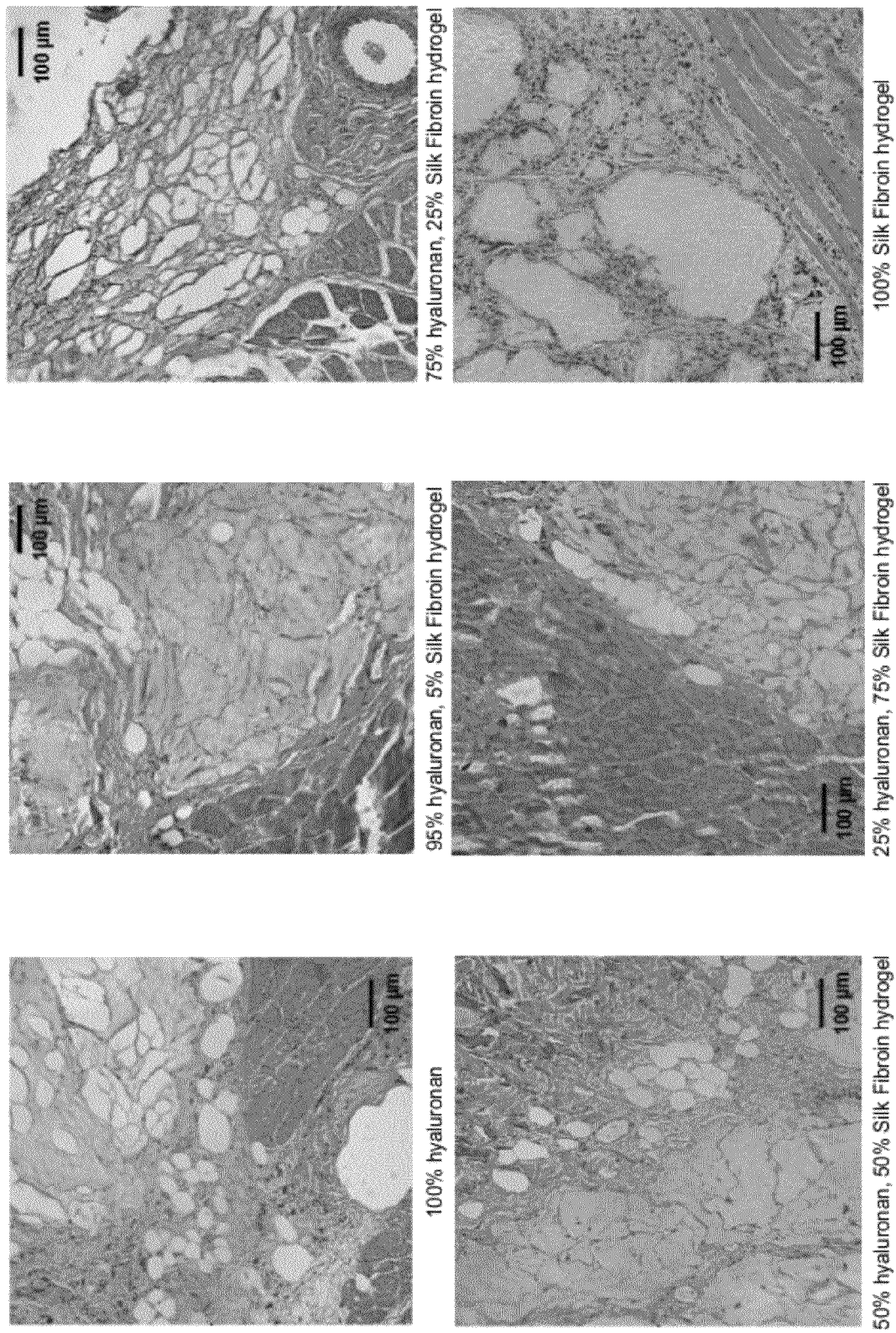
FIG. 24 shows a H&E staining of tissue samples injected with a dermal filler comprising 100% hyaluronan, a dermal filler comprising 95% hyaluronan and 5% silk fibroin hydrogel, a dermal filler comprising 75% hyaluronan and 25% silk fibroin hydrogel, a dermal filler comprising 50% hyaluronan and 50% silk fibroin hydrogel, a dermal filler comprising 25% hyaluronan and 75% silk fibroin hydrogel, and a dermal filler comprising 100% silk fibroin hydrogel.
Figure 25:
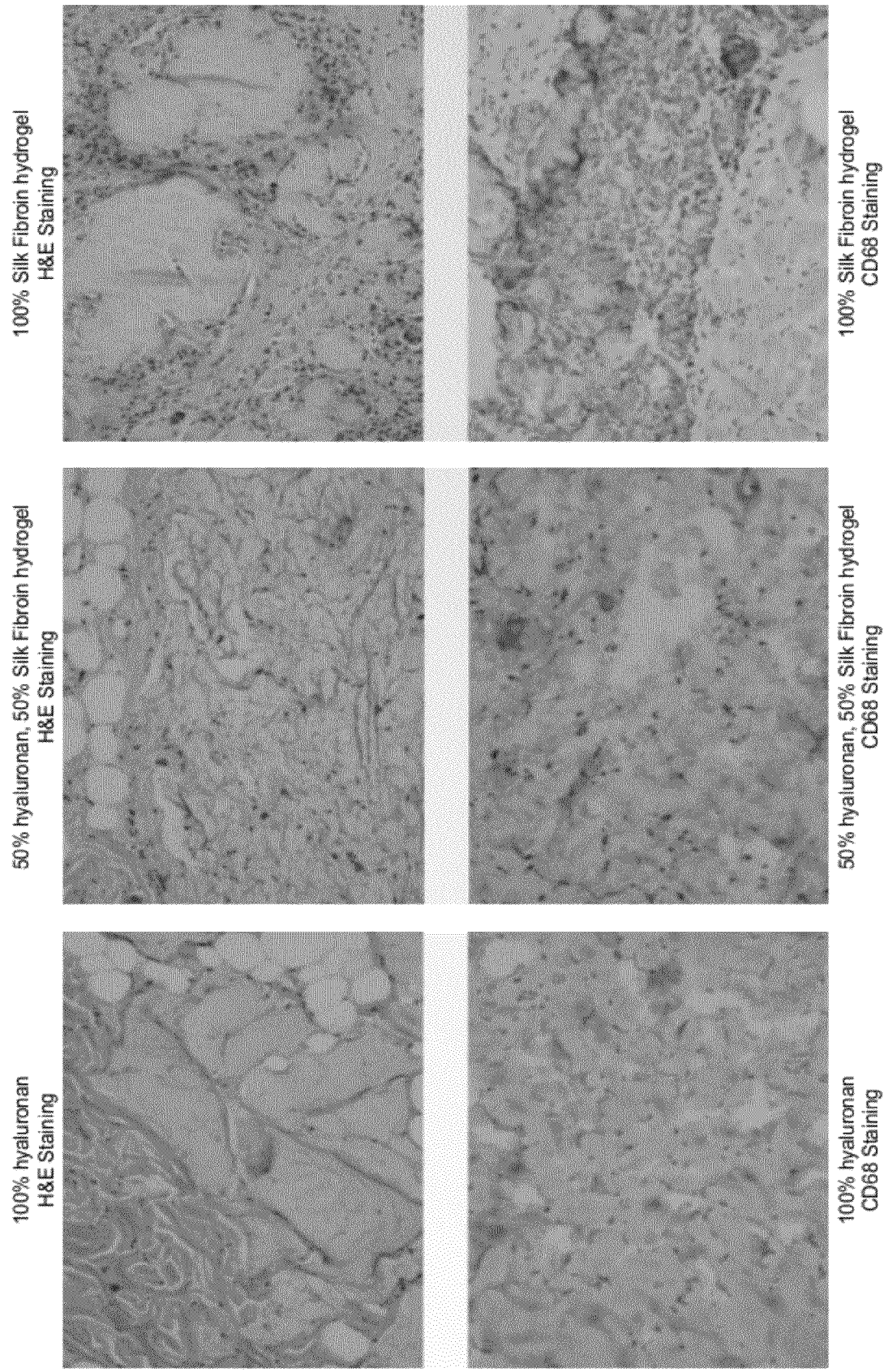
FIG. 25 shows on the tope row, a H&E staining of tissue samples injected with a dermal filler comprising 100% hyaluronan, a dermal filler comprising 50% hyaluronan and 50% silk fibroin hydrogel, and a dermal filler comprising 100% silk fibroin hydrogel; and on the bottom row a CD-68 staining of tissue samples injected with a dermal filler comprising 100% hyaluronan, a dermal filler comprising 50% hyaluronan and 50% silk fibroin hydrogel, and a dermal filler comprising 100% silk fibroin hydrogel.

Material cross-sections mounted on slides were stained with H&E and CD-68 according to standard methods (FIG. 24 and FIG. 25). It was observed that all sample types infiltrated the animal dermis and appeared as lakes of material. Pure JUVÉDERM® Ultra Plus control elicited a minimal extent of cellular response, very consistent with ambient cellularity in the surrounding tissue (FIG. 24). The extent of cellular infiltrate and total presence was increased by adding silk fibroin hydrogel particles to the HA dermal filler (FIG. 24). Base silk fibroin hydrogel particle material by comparison, exhibited significant cellular response which tended to occur circumferentially around smaller agglomerated lakes of material (FIG. 24). Staining with CD-68 revealed the presence of small populations of CD-68+ cells in all silk fibroin hydrogel particle containing samples but in none of the pure JUVÉDERM® Ultra Plus control samples (FIG. 25). This suggests increased macrophage activity in the silk fibroin hydrogel particle-containing samples as compared to the pure JUVÉDERM® Ultra Plus control.

The results reveal the potential for increasing the extent of cellular interaction with a pure crosslinked hyaluronan material through introduction of a silk fibroin hydrogel component. This increased cellularity at the implant site could ultimately correlate to an alternative host response to the hyaluronan including a wound-healing-type response involving neo-collagen deposition during implant bioresorption. Taken together, the data here suggest that the combination hyaluronan/silk fibroin hydrogel material not only acts as a dermal filler for intradermal defects, but also encourages neo-collagen deposition through a native healing response.

Example 22

Use of Dermal Filler Composition for Treating a Facial Defect of the Cheek

This example illustrates the use of compositions and methods disclosed herein for treating a facial defect of the cheek.

A 28-year-old woman presents with a lean face. She felt her face looked old, sad and bitter because of the less fullness of her check contour. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A composition comprising silk fibroin hydrogel component and a hyaluronan component is administered subcutaneously and under superficial musculoaponeurotic system into the checks regions; about 15 mL of composition into the left and right cheeks. The individual is monitored for approximately 7 days. The physician evaluates the cheeks tissue and determines that the treatment was successful. Both the woman and her physician are satisfied with the results of the procedure because she looked younger. Approximately one month after the procedure, the woman indicates that his quality of life has improved.

Example 23

Use of Dermal Filler Composition for Treating Facial Imperfection of Eyelids

This example illustrates the use of compositions and methods disclosed herein for treating a facial imperfection of the eyelids.

A 37-year-old woman presents with sunken eyes and this appearance made her look old and fierce. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A composition comprising silk fibroin hydrogel component and a hyaluronan component is administered subcutaneously and under superficial musculoaponeurotic system into the upper eyelid regions; about 2.5 mL of composition into the left and right eyelid regions. The individual is monitored for approximately 7 days. The physician evaluates the eyelid regions and determines that the treatment was successful. Both the woman and her physician are satisfied with the results of the procedure because she looked younger. Approximately one month after the procedure, the woman indicates that his quality of life has improved.

Example 24

Use of Dermal Filler Composition for Treating Wrinkles

This example illustrates the use of compositions and methods disclosed herein for treating wrinkles.

A 55-year-old woman presents with wrinkles around the eyes and cheek areas. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A composition comprising silk fibroin hydrogel component and a hyaluronan component is administered subcutaneously and under superficial musculoaponeurotic system into the upper eyelid and cheek regions; about 1.5 mL of composition into the left and right eyelid and cheek regions. The individual is monitored for approximately 7 days. The physician evaluates the facial regions and determines that the treatment was successful. Both the woman and her physician are satisfied with the results of the procedure because she looked younger. Approximately one month after the procedure, the woman indicates that his quality of life has improved.

Example 25

Use of Dermal Filler Composition for Treating a Breast Defect

This example illustrates the use of compositions and methods disclosed herein for treating a breast defect.

A 32-year-old woman presents with complaints that the medial portions of her breast implants are visible, which accentuated the "bony" appearance of her sternum. In addition she felt her breast are too far apart. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A composition comprising silk fibroin hydrogel component and a hyaluronan component is administered subcutaneously over the lateral sternum and medial breast bilaterally, 15 mL on the right and 10 mL on the left. The composition is administered in a tear like fashion to increase the surface area to volume ratio. The individual is monitored for approximately 7 days. The physician evaluates the breasts and determines that the treatment was successful. Both the woman and her physician are satisfied with the results of the procedure. Approximately one month after the procedure, the woman indicates that his quality of life has improved.

Example 26

Use of Dermal Filler Composition for Breast Augmentation

This example illustrates the use of compositions and methods disclosed herein for breast augmentation.

A 28-year-old woman presents micromastia or breast hypoplasia. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A composition comprising silk fibroin hydrogel component and a hyaluronan component is administered subcutaneously using axillary, periareolar, and inframammary routes bilaterally, 90 mL on the right and 145 mL on the left. The composition is administered in a tear like fashion to increase the surface area to volume ratio. The individual is monitored for approximately 7 days. The physician evaluates the breasts and determines that the treatment was successful. Both the woman and her physician are satisfied with the results of the procedure. Approximately one month after the procedure, the woman indicates that his quality of life has improved.

Example 27

Adipose Tissue Transplant for Breast Disorder

This example illustrates the use of compositions and methods disclosed herein for treating a breast disorder.

A 29-year-old woman presents with bilateral tuberous breast deformity. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A composition comprising silk fibroin hydrogel component and a hyaluronan component is administered subcutaneously in multiple planes axillary, periareolar, and inframammary routes bilaterally, 180 mL on the right and 170 mL on the left. The composition is administered in a tear like fashion to increase the surface area to volume ratio. The individual is monitored for approximately 7 days. The physician evaluates the breasts and determines that the treatment was successful. Both the woman and her physician are satisfied with the results of the procedure. Approximately one month after the procedure, the woman indicates that his quality of life has improved.

In closing, it is to be understood that although aspects of the present specification have been described with reference to the various embodiments, one skilled in the art will readily appreciate that the specific examples disclosed are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing quantities of ingredients, properties such as molecular weight, reaction conditions, and so forth used in the specification and claims are to be understood as being modified in all instances by the term "about." As used herein, the term "about" means that the item, parameter or term so qualified encompasses a range of plus or minus ten percent above and below the value of the stated item, parameter or term. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A dermal filler composition comprising a gel phase and a carrier phase that increases the fluidity of the gel phase, the gel phase including
   a) first hydrogel particles comprising a substantially sericin-depleted silk fibroin; and
   b) second hydrogel particles comprising a matrix polymer including an elastic protein;
      wherein the first hydrogel particles has a protein structure that makes the hydrogel particles resist biodegradation.

2. The composition of claim 1, wherein the silk fibroin hydrogel particles comprises about 1% (w/v) to about 10% (w/v) of silk fibroin.

3. The composition of claim 1, wherein the elastic protein is an elastin.

4. The composition of claim 1, wherein the silk fibroin hydrogel particles and elastic protein hydrogel particles have a cross-sectional area from about 0.1 $\mu m^2$ to about 1000 $\mu m^2$.

5. The composition of claim 1, wherein the silk fibroin hydrogel particles further comprises an amphiphilic peptide.

6. The composition of claim 1, wherein the carrier phase is water, a saline solution, or a buffered solution.

7. The composition of claim 1, wherein the carrier phase further comprises lidocaine.

8. A method of treating a soft tissue condition in an individual in need thereof, the method comprising the step of administering a composition of claim 1 into a skin region of the individual, wherein the administration improves the condition.

9. The method of claim 8, wherein the soft tissue condition is a breast tissue condition, a facial tissue condition, a neck condition, a skin condition, an upper arm condition, a lower arm condition, a hand condition, a shoulder condition, a back condition, a torso including abdominal condition, a buttock condition, an upper leg condition, a lower leg condition including calf condition, a foot condition including plantar fat pad condition, an eye condition, a genital condition, or a condition effecting another body part, region or area.

10. The method of claim 9, wherein the breast tissue condition is a breast imperfection, a breast defect, a breast augmentation, or a breast reconstruction.

11. The method of claim 9, wherein the facial tissue condition is a facial imperfection, a facial defect, a facial augmentation, or a facial reconstruction.

12. The method of claim 9, wherein the facial tissue condition is a dermal divot, a sunken cheek, a thin lip, a nasal imperfection or defect, a retro-orbital imperfection or defect, a facial fold, a facial line, a facial wrinkle, or other size, shape or contour imperfection or defect of the face.

13. The method of claim 9, wherein the facial tissue condition is skin dehydration, a lack of skin elasticity, skin roughness, a lack of skin tautness, a skin stretch line or mark, or skin paleness.

* * * * *

UNITED STATES PATENT AND TRADEMARK OFFICE
CERTIFICATE OF CORRECTION

| | | |
|---|---|---|
| PATENT NO. | : 8,288,347 B2 | Page 1 of 2 |
| APPLICATION NO. | : 12/906777 | |
| DATED | : October 16, 2012 | |
| INVENTOR(S) | : Adam L. Collette et al. | |

It is certified that error appears in the above-identified patent and that said Letters Patent is hereby corrected as shown below:

On the Title Page

On first page, item (75), in "Inventor", in column 1, line 1, delete "Westminister," and insert -- Westminster, --, therefor.

On first page, item (56), under "OTHER PUBLICATIONS", in column 2, line 2, delete "Plypeptide" and insert -- Polypeptide --, therefor.

On first page, item (56), under "OTHER PUBLICATIONS", in column 2, line 15, delete "Biomatericals" and insert -- Biomaterials --, therefor.

On first page, item (56), under "OTHER PUBLICATIONS", in column 2, line 16, delete "Biomatericals," and insert -- Biomaterials, --, therefor.

In the Specification

In column 9, line 1, delete "pemyi," and insert -- pernyi, --, therefor.

In column 15, line 24-25, delete "Leu- Leu" and insert -- Leu-Leu --, therefor.

In column 15, line 54, delete "WQPPRAR1" and insert -- WQPPRARI --, therefor.

In column 18, line 14, delete "WQPPRAR1" and insert -- WQPPRARI --, therefor.

In column 28, line 67, delete "$_{Nm}{}^{-2}$);" and insert -- $Nm^{-2}$); --, therefor.

In column 35, line 1, delete "(NMDA)," and insert -- (HMDA), --, therefor.

In column 35, line 62, delete "crosslinked," and insert -- crosslinked --, therefor.

In column 37, line 15, delete "uncrosslinked," and insert -- uncrosslinked --, therefor.

In column 37, line 66, delete "crosslinked," and insert -- crosslinked --, therefor.

In column 57 (TABLE 1), line 5, delete "RDG:" and insert -- RGD: --, therefor.

In column 57 (TABLE 1), line 6, delete "RDG:" and insert -- RGD: --, therefor.

In column 57 (TABLE 1), line 8, delete "RDG:" and insert -- RGD: --, therefor.

Signed and Sealed this
Twentieth Day of May, 2014

Michelle K. Lee
*Deputy Director of the United States Patent and Trademark Office*

In column 57 (TABLE 1), line 9, delete "RDG:" and insert -- RGD: --, therefor.

In column 57 (TABLE 1), line 11, delete "RDG:" and insert -- RGD: --, therefor.

In column 57 (TABLE 1), line 12, delete "RDG:" and insert -- RGD: --, therefor.

SEQUENCE LISTING

<160> NUMBER OF SEQ ID NOS: 144

<210> SEQ ID NO 1
<211> LENGTH: 23
<212> TYPE: PRT
<213> ORGANISM: Artificial Sequence
<220> FEATURE:
<223> OTHER INFORMATION: Chemically synthesized RGD peptide

<400> SEQUENCE: 1

Gly Arg Gly Asp Ile Pro Ala Ser Ser Lys Gly Gly Gly Ser Arg
1               5                   10                  15

Leu Leu Leu Leu Leu Leu Arg
            20

<210> SEQ ID NO 2
<211> LENGTH: 23
<212> TYPE: PRT
<213> ORGANISM: Artificial Sequence
<220> FEATURE:
<223> OTHER INFORMATION: Chemically synthesized acylated RGD peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: D form
<220> FEATURE:
<221> NAME/KEY: MOD_RES
<222> LOCATION: (16)..(16)
<223> OTHER INFORMATION: D form
<220> FEATURE:
<221> NAME/KEY: MOD_RES
<222> LOCATION: (23)..(23)
<223> OTHER INFORMATION: D form

<400> SEQUENCE: 2

Gly Arg Gly Asp Ile Pro Ala Ser Ser Lys Gly Gly Gly Ser Arg
1               5                   10                  15

Leu Leu Leu Leu Leu Leu Arg
            20

<210> SEQ ID NO 3
<211> LENGTH: 10
<212> TYPE: PRT
<213> ORGANISM: Artificial Sequence
<220> FEATURE:
<223> OTHER INFORMATION: Chemically synthesized spacer peptide
      SGGGGKSSAP

<400> SEQUENCE: 3

Ser Gly Gly Gly Gly Lys Ser Ser Ala Pro
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Chemically synthesized hydrophilic domain

<400> SEQUENCE: 4

Lys Gln Ala Gly Asp Val
1               5

```
<210> SEQ ID NO 5
<211> LENGTH: 5
<212> TYPE: PRT
<213> ORGANISM: Artificial Sequence
<220> FEATURE:
<223> OTHER INFORMATION: Chemically synthesized hydrophilic domain

<400> SEQUENCE: 5

Pro His Ser Arg Asn
1               5

<210> SEQ ID NO 6
<211> LENGTH: 5
<212> TYPE: PRT
<213> ORGANISM: Artificial Sequence
<220> FEATURE:
<223> OTHER INFORMATION: Chemically synthesized hydrophilic domain YIGSR

<400> SEQUENCE: 6

Tyr Ile Gly Ser Arg
1               5

<210> SEQ ID NO 7
<211> LENGTH: 9
<212> TYPE: PRT
<213> ORGANISM: Artificial Sequence
<220> FEATURE:
<223> OTHER INFORMATION: Chemically synthesized hydrophilic domain
      CDPGYIGSR

<400> SEQUENCE: 7

Cys Asp Pro Gly Tyr Ile Gly Ser Arg
1               5

<210> SEQ ID NO 8
<211> LENGTH: 5
<212> TYPE: PRT
<213> ORGANISM: Artificial Sequence
<220> FEATURE:
<223> OTHER INFORMATION: Chemically synthesized hydrophilic domain IKVAV

<400> SEQUENCE: 8

Ile Lys Val Ala Val
1               5

<210> SEQ ID NO 9
<211> LENGTH: 10
<212> TYPE: PRT
<213> ORGANISM: Artificial Sequence
<220> FEATURE:
<223> OTHER INFORMATION: Chemically synthesized hydrophilic domain
      RNIAEIIKDI

<400> SEQUENCE: 9

Arg Asn Ile Ala Glu Ile Ile Lys Asp Ile
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Chemically synthesized hydrophilic domain
      YFQRYLI

<400> SEQUENCE: 10

Tyr Phe Gln Arg Tyr Leu Ile
1               5
```

```
<210> SEQ ID NO 11
<211> LENGTH: 5
<212> TYPE: PRT
<213> ORGANISM: Artificial Sequence
<220> FEATURE:
<223> OTHER INFORMATION: Chemically synthesized hydrophilic domain PDSGR

<400> SEQUENCE: 11

Pro Asp Ser Gly Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Chemically synthesized hydrophilic domain
      FHRRIKA

<400> SEQUENCE: 12

Phe His Arg Arg Ile Lys Ala
1               5

<210> SEQ ID NO 13
<211> LENGTH: 6
<212> TYPE: PRT
<213> ORGANISM: Artificial Sequence
<220> FEATURE:
<223> OTHER INFORMATION: Chemically synthesized hydrophilic domain
      PRRARV

<400> SEQUENCE: 13

Pro Arg Arg Ala Arg Val
1               5

<210> SEQ ID NO 14
<211> LENGTH: 8
<212> TYPE: PRT
<213> ORGANISM: Artificial Sequence
<220> FEATURE:
<223> OTHER INFORMATION: Chemically synthesized hydrophilic domain
      WQPPRARI

<400> SEQUENCE: 14

Trp Gln Pro Pro Arg Ala Arg Ile
1               5

<210> SEQ ID NO 15
<211> LENGTH: 5
<212> TYPE: PRT
<213> ORGANISM: Artificial Sequence
<220> FEATURE:
<223> OTHER INFORMATION: Chemically synthesized hydrophobic/apolar tail
      LLLLL

<400> SEQUENCE: 15

Leu Leu Leu Leu Leu
1               5

<210> SEQ ID NO 16
<211> LENGTH: 5
<212> TYPE: PRT
<213> ORGANISM: Artificial Sequence
<220> FEATURE:
<223> OTHER INFORMATION: Chemically synthesized hydrophobic/apolar tail
      LLFFL

<400> SEQUENCE: 16
```

```
Leu Leu Phe Phe Leu
1               5

<210> SEQ ID NO 17
<211> LENGTH: 5
<212> TYPE: PRT
<213> ORGANISM: Artificial Sequence
<220> FEATURE:
<223> OTHER INFORMATION: Chemically synthesized hydrophobic/apolar tail
      LFLWL

<400> SEQUENCE: 17

Leu Phe Leu Trp Leu
1               5

<210> SEQ ID NO 18
<211> LENGTH: 5
<212> TYPE: PRT
<213> ORGANISM: Artificial Sequence
<220> FEATURE:
<223> OTHER INFORMATION: Chemically synthesized hydrophobic/apolar tail
      FLWLL

<400> SEQUENCE: 18

Phe Leu Trp Leu Leu
1               5

<210> SEQ ID NO 19
<211> LENGTH: 5
<212> TYPE: PRT
<213> ORGANISM: Artificial Sequence
<220> FEATURE:
<223> OTHER INFORMATION: Chemically synthesized hydrophobic/apolar tail
      LALGL

<400> SEQUENCE: 19

Leu Ala Leu Gly Leu
1               5

<210> SEQ ID NO 20
<211> LENGTH: 6
<212> TYPE: PRT
<213> ORGANISM: Artificial Sequence
<220> FEATURE:
<223> OTHER INFORMATION: Chemically synthesized hydrophobic/apolar tail
      LLLLLL

<400> SEQUENCE: 20

Leu Leu Leu Leu Leu Leu
1               5

<210> SEQ ID NO 21
<211> LENGTH: 7
<212> TYPE: PRT
<213> ORGANISM: Artificial Sequence
<220> FEATURE:
<223> OTHER INFORMATION: Chemically synthesized hydrophobic/apolar tail
      RLLLLLR

<400> SEQUENCE: 21

Arg Leu Leu Leu Leu Leu Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Chemically synthesized hydrophobic/apolar tail
```

```
      KLLLLLR

<400> SEQUENCE: 22

Lys Leu Leu Leu Leu Leu Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Chemically synthesized hydrophobic/apolar tail
      KLLLLLK

<400> SEQUENCE: 23

Lys Leu Leu Leu Leu Leu Lys
1               5

<210> SEQ ID NO 24
<211> LENGTH: 14
<212> TYPE: PRT
<213> ORGANISM: Artificial Sequence
<220> FEATURE:
<223> OTHER INFORMATION: Chemically synthesized spacer GSPGISGGGGGILE

<400> SEQUENCE: 24

Gly Ser Pro Gly Ile Ser Gly Gly Gly Gly Ile Leu Glu
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Chemically synthesized spacer SGGGGKSSAPI

<400> SEQUENCE: 25

Ser Gly Gly Gly Gly Lys Ser Ser Ala Pro Ile
1               5                   10

<210> SEQ ID NO 26
<211> LENGTH: 21
<212> TYPE: PRT
<213> ORGANISM: Artificial Sequence
<220> FEATURE:
<223> OTHER INFORMATION: Chemically synthesized spacer-tail peptide
      GSPGISGGGGGILEKLLLLLK

<400> SEQUENCE: 26

Gly Ser Pro Gly Ile Ser Gly Gly Gly Gly Ile Leu Glu Lys Leu
1               5                   10                  15

Leu Leu Leu Lys
            20

<210> SEQ ID NO 27
<211> LENGTH: 22
<212> TYPE: PRT
<213> ORGANISM: Artificial Sequence
<220> FEATURE:
<223> OTHER INFORMATION: Chemically synthesized spacer-tail peptide
      GSPGISGGGGGILEKLALWLLR

<400> SEQUENCE: 27

Gly Ser Pro Gly Ile Ser Gly Gly Gly Gly Ile Leu Glu Lys Leu
1               5                   10                  15

Ala Leu Trp Leu Leu Arg
            20
```

```
<210> SEQ ID NO 28
<211> LENGTH: 20
<212> TYPE: PRT
<213> ORGANISM: Artificial Sequence
<220> FEATURE:
<223> OTHER INFORMATION: Chemically synthesized spacer-tail peptide
      GSPGISGGGGGILERLLLLR

<400> SEQUENCE: 28

Gly Ser Pro Gly Ile Ser Gly Gly Gly Gly Ile Leu Glu Arg Leu
1               5                   10                  15

Leu Leu Leu Arg
            20

<210> SEQ ID NO 29
<211> LENGTH: 21
<212> TYPE: PRT
<213> ORGANISM: Artificial Sequence
<220> FEATURE:
<223> OTHER INFORMATION: Chemically synthesized spacer-tail peptide
      GSPGISGGGGGILERLLWLLR

<400> SEQUENCE: 29

Gly Ser Pro Gly Ile Ser Gly Gly Gly Gly Ile Leu Glu Arg Leu
1               5                   10                  15

Leu Trp Leu Leu Arg
            20

<210> SEQ ID NO 30
<211> LENGTH: 620
<212> TYPE: PRT
<213> ORGANISM: Drosophila melanogaster

<400> SEQUENCE: 30

Met Phe Lys Leu Leu Gly Leu Thr Leu Leu Met Ala Met Val Val Leu
1               5                   10                  15

Gly Arg Pro Glu Pro Pro Val Asn Ser Tyr Leu Pro Pro Ser Asp Ser
                20                  25                  30

Tyr Gly Ala Pro Gly Gln Ser Gly Pro Gly Gly Arg Pro Ser Asp Ser
            35                  40                  45

Tyr Gly Ala Pro Gly Gly Gly Asn Gly Gly Arg Pro Ser Asp Ser Tyr
        50                  55                  60

Gly Ala Pro Gly Gln Gly Gln Gly Gln Gly Gln Gly Gln Gly Gly Tyr
65                  70                  75                  80

Ala Gly Lys Pro Ser Asp Thr Tyr Gly Ala Pro Gly Gly Gly Asn Gly
                85                  90                  95

Asn Gly Gly Arg Pro Ser Ser Tyr Gly Ala Pro Gly Gly Gly Asn
                100                 105                 110

Gly Gly Arg Pro Ser Asp Thr Tyr Gly Ala Pro Gly Gly Gly Asn Gly
            115                 120                 125

Gly Arg Pro Ser Asp Thr Tyr Gly Ala Pro Gly Gly Gly Asn Gly
        130                 135                 140

Asn Gly Gly Arg Pro Ser Ser Tyr Gly Ala Pro Gly Gln Gly Gln
145                 150                 155                 160

Gly Asn Gly Asn Gly Gly Arg Ser Ser Ser Tyr Gly Ala Pro Gly
                165                 170                 175

Gly Gly Asn Gly Gly Arg Pro Ser Asp Thr Tyr Gly Ala Pro Gly Gly
            180                 185                 190

Gly Asn Gly Gly Arg Pro Ser Asp Thr Tyr Gly Ala Pro Gly Gly Gly
```

-continued

```
                 195                 200                 205
Asn Asn Gly Gly Arg Pro Ser Ser Tyr Gly Ala Pro Gly Gly Gly
    210                 215                 220

Asn Gly Gly Arg Pro Ser Asp Thr Tyr Gly Ala Pro Gly Gly Asn
225                 230                 235                 240

Gly Asn Gly Ser Gly Gly Arg Pro Ser Ser Tyr Gly Ala Pro Gly
                245                 250                 255

Gln Gly Gln Gly Gly Phe Gly Gly Arg Pro Ser Asp Ser Tyr Gly Ala
            260                 265                 270

Pro Gly Gln Asn Gln Lys Pro Ser Asp Ser Tyr Gly Ala Pro Gly Ser
        275                 280                 285

Gly Asn Gly Asn Gly Gly Arg Pro Ser Ser Tyr Gly Ala Pro Gly
    290                 295                 300

Ser Gly Pro Gly Gly Arg Pro Ser Asp Ser Tyr Gly Pro Pro Ala Ser
305                 310                 315                 320

Gly Ser Gly Ala Gly Gly Ala Gly Gly Ser Gly Pro Gly Gly Ala Asp
                325                 330                 335

Tyr Asp Asn Asp Glu Pro Ala Lys Tyr Glu Phe Asn Tyr Gln Val Glu
            340                 345                 350

Asp Ala Pro Ser Gly Leu Ser Phe Gly His Ser Glu Met Arg Asp Gly
        355                 360                 365

Asp Phe Thr Thr Gly Gln Tyr Asn Val Leu Leu Pro Asp Gly Arg Lys
    370                 375                 380

Gln Ile Val Glu Tyr Glu Ala Asp Gln Gln Gly Tyr Arg Pro Gln Ile
385                 390                 395                 400

Arg Tyr Glu Gly Asp Ala Asn Asp Gly Ser Gly Pro Ser Gly Pro Gly
                405                 410                 415

Gly Pro Gly Gly Gln Asn Leu Gly Ala Asp Gly Tyr Ser Ser Gly Arg
            420                 425                 430

Pro Gly Asn Gly Asn Gly Asn Gly Gly Tyr Ser Gly Gly Arg
        435                 440                 445

Pro Gly Gly Gln Asp Leu Gly Pro Ser Gly Tyr Ser Gly Gly Arg Pro
    450                 455                 460

Gly Gly Gln Asp Leu Gly Ala Gly Gly Tyr Ser Asn Gly Lys Pro Gly
465                 470                 475                 480

Gly Gln Asp Leu Gly Pro Gly Gly Tyr Ser Gly Gly Arg Pro Gly Gly
                485                 490                 495

Gln Asp Leu Gly Arg Asp Gly Tyr Ser Gly Gly Arg Pro Gly Gly Gln
            500                 505                 510

Asp Leu Gly Ala Ser Gly Tyr Ser Asn Gly Arg Pro Gly Gly Asn Gly
        515                 520                 525

Asn Gly Gly Ser Asp Gly Gly Arg Val Ile Ile Gly Gly Arg Val Ile
    530                 535                 540

Gly Gly Gln Asp Gly Gly Asp Gln Gly Tyr Ser Gly Gly Arg Pro Gly
545                 550                 555                 560

Gly Gln Asp Leu Gly Arg Asp Gly Tyr Ser Ser Gly Arg Pro Gly Gly
                565                 570                 575

Arg Pro Gly Gly Asn Gly Gln Asp Ser Gln Asp Gly Gln Gly Tyr Ser
            580                 585                 590

Ser Gly Arg Pro Gly Gln Gly Gly Arg Asn Gly Phe Gly Pro Gly Gly
        595                 600                 605

Gln Asn Gly Asp Asn Asp Gly Ser Gly Tyr Arg Tyr
    610                 615                 620
```

```
<210> SEQ ID NO 31
<211> LENGTH: 575
<212> TYPE: PRT
<213> ORGANISM: Drosophila melanogaster

<400> SEQUENCE: 31
```

| | | | | | | | | | | | | | | |
|---|---|---|---|---|---|---|---|---|---|---|---|---|---|---|
| Met | Phe | Lys | Leu | Leu | Gly | Leu | Thr | Leu | Leu | Met | Ala | Met | Val | Val | Leu |
| 1 | | | | 5 | | | | | 10 | | | | | 15 | |
| Gly | Arg | Pro | Glu | Pro | Pro | Val | Asn | Ser | Tyr | Leu | Pro | Pro | Ser | Asp | Ser |
| | | | 20 | | | | | 25 | | | | | 30 | | |
| Tyr | Gly | Ala | Pro | Gly | Gln | Ser | Gly | Pro | Gly | Gly | Arg | Pro | Ser | Asp | Ser |
| | | | 35 | | | | | 40 | | | | | 45 | | |
| Tyr | Gly | Ala | Pro | Gly | Gly | Gly | Asn | Gly | Gly | Arg | Pro | Ser | Asp | Ser | Tyr |
| | | | 50 | | | | | 55 | | | | | 60 | | |
| Gly | Ala | Pro | Gly | Gln | Gly | Gln | Gly | Gln | Gly | Gln | Gly | Gln | Gly | Gly | Tyr |
| 65 | | | | | 70 | | | | | 75 | | | | | 80 |
| Ala | Gly | Lys | Pro | Ser | Asp | Thr | Tyr | Gly | Ala | Pro | Gly | Gly | Asn | Gly | |
| | | | | 85 | | | | | 90 | | | | | 95 | |
| Asn | Gly | Gly | Arg | Pro | Ser | Ser | Ser | Tyr | Gly | Ala | Pro | Gly | Gly | Asn | |
| | | | | 100 | | | | | 105 | | | | | 110 | |
| Gly | Gly | Arg | Pro | Ser | Asp | Thr | Tyr | Gly | Ala | Pro | Gly | Gly | Asn | Gly | |
| | | | | 115 | | | | | 120 | | | | | 125 | |
| Gly | Arg | Pro | Ser | Asp | Thr | Tyr | Gly | Ala | Pro | Gly | Gly | Gly | Asn | Gly | |
| | | | 130 | | | | | 135 | | | | | 140 | | |
| Asn | Gly | Gly | Arg | Pro | Ser | Ser | Tyr | Gly | Ala | Pro | Gly | Gln | Gly | Gln | |
| 145 | | | | | 150 | | | | | 155 | | | | | 160 |
| Gly | Asn | Gly | Asn | Gly | Gly | Arg | Ser | Ser | Ser | Tyr | Gly | Ala | Pro | Gly | |
| | | | | 165 | | | | | 170 | | | | | 175 | |
| Gly | Gly | Asn | Gly | Gly | Arg | Pro | Ser | Asp | Thr | Tyr | Gly | Ala | Pro | Gly | Gly |
| | | | 180 | | | | | 185 | | | | | 190 | | |
| Gly | Asn | Gly | Gly | Arg | Pro | Ser | Asp | Thr | Tyr | Gly | Ala | Pro | Gly | Gly | Gly |
| | | | 195 | | | | | 200 | | | | | 205 | | |
| Asn | Asn | Gly | Gly | Arg | Pro | Ser | Ser | Ser | Tyr | Gly | Ala | Pro | Gly | Gly | Gly |
| | | | 210 | | | | | 215 | | | | | 220 | | |
| Asn | Gly | Gly | Arg | Pro | Ser | Asp | Thr | Tyr | Gly | Ala | Pro | Gly | Gly | Gly | Asn |
| 225 | | | | | 230 | | | | | 235 | | | | | 240 |
| Gly | Asn | Gly | Ser | Gly | Gly | Arg | Pro | Ser | Ser | Tyr | Gly | Ala | Pro | Gly | |
| | | | | 245 | | | | | 250 | | | | | 255 | |
| Gln | Gly | Gln | Gly | Gly | Phe | Gly | Arg | Pro | Ser | Asp | Ser | Tyr | Gly | Ala | |
| | | | | 260 | | | | | 265 | | | | | 270 | |
| Pro | Gly | Gln | Asn | Gln | Lys | Pro | Ser | Asp | Ser | Tyr | Gly | Ala | Pro | Gly | Ser |
| | | | | 275 | | | | | 280 | | | | | 285 | |
| Gly | Asn | Gly | Asn | Gly | Gly | Arg | Pro | Ser | Ser | Ser | Tyr | Gly | Ala | Pro | Gly |
| | | | | 290 | | | | | 295 | | | | | 300 | |
| Ser | Gly | Pro | Gly | Gly | Arg | Pro | Ser | Asp | Ser | Tyr | Gly | Pro | Pro | Ala | Ser |
| 305 | | | | | 310 | | | | | 315 | | | | | 320 |
| Gly | Ser | Gly | Ala | Gly | Gly | Ala | Gly | Gly | Ser | Gly | Pro | Gly | Gly | Ala | Asp |
| | | | | 325 | | | | | 330 | | | | | 335 | |
| Tyr | Asp | Asn | Asp | Ile | Val | Glu | Tyr | Glu | Ala | Asp | Gln | Gln | Gly | Tyr | Arg |
| | | | | 340 | | | | | 345 | | | | | 350 | |
| Pro | Gln | Ile | Arg | Tyr | Glu | Gly | Asp | Ala | Asn | Asp | Gly | Ser | Gly | Pro | Ser |
| | | | | 355 | | | | | 360 | | | | | 365 | |
| Gly | Pro | Gly | Gly | Pro | Gly | Gly | Gln | Asn | Leu | Gly | Ala | Asp | Gly | Tyr | Ser |
| | | | | 370 | | | | | 375 | | | | | 380 | |

```
Ser Gly Arg Pro Gly Asn Gly Asn Gly Asn Gly Gly Tyr Ser
385                 390                 395                 400

Gly Gly Arg Pro Gly Gln Asp Leu Gly Pro Ser Gly Tyr Ser Gly
            405                 410                 415

Gly Arg Pro Gly Gly Gln Asp Leu Gly Ala Gly Gly Tyr Ser Asn Gly
        420                 425                 430

Lys Pro Gly Gly Gln Asp Leu Gly Pro Gly Gly Tyr Ser Gly Gly Arg
    435                 440                 445

Pro Gly Gly Gln Asp Leu Gly Arg Asp Gly Tyr Ser Gly Gly Arg Pro
450                 455                 460

Gly Gly Gln Asp Leu Gly Ala Ser Gly Tyr Ser Asn Gly Arg Pro Gly
465                 470                 475                 480

Gly Asn Gly Asn Gly Gly Ser Asp Gly Gly Arg Val Ile Ile Gly Gly
                485                 490                 495

Arg Val Ile Gly Gly Gln Asp Gly Gly Asp Gln Gly Tyr Ser Gly Gly
            500                 505                 510

Arg Pro Gly Gly Gln Asp Leu Gly Arg Asp Gly Tyr Ser Ser Gly Arg
        515                 520                 525

Pro Gly Gly Arg Pro Gly Gly Asn Gly Gln Asp Ser Gln Asp Gly Gln
530                 535                 540

Gly Tyr Ser Ser Gly Arg Pro Gly Gln Gly Gly Arg Asn Gly Phe Gly
545                 550                 555                 560

Pro Gly Gly Gln Asn Gly Asp Asn Asp Gly Ser Gly Tyr Arg Tyr
                565                 570                 575

<210> SEQ ID NO 32
<211> LENGTH: 623
<212> TYPE: PRT
<213> ORGANISM: Drosophila sechellia

<400> SEQUENCE: 32

Met Phe Lys Leu Leu Gly Leu Thr Leu Leu Met Ala Met Val Val Leu
1               5                   10                  15

Gly Arg Pro Glu Pro Pro Val Asn Ser Tyr Leu Pro Pro Ser Asp Ser
            20                  25                  30

Tyr Gly Ala Pro Gly Gln Ser Gly Ala Gly Gly Arg Pro Ser Asp Thr
        35                  40                  45

Tyr Gly Ala Pro Gly Gly Gly Asn Gly Gly Arg Pro Ser Asp Ser Tyr
    50                  55                  60

Gly Ala Pro Gly Gln Gln Gly Gln Gly Gln Gly Gln Gly Gln Gly Tyr
65                  70                  75                  80

Gly Gly Lys Pro Ser Asp Ser Tyr Gly Ala Pro Gly Gly Gly Asn Gly
                85                  90                  95

Asn Gly Gly Arg Pro Ser Ser Ser Tyr Gly Ala Pro Gly Gly Gly Asn
            100                 105                 110

Gly Gly Arg Pro Ser Asp Thr Tyr Gly Ala Pro Gly Gly Gly Asn Gly
        115                 120                 125

Gly Arg Pro Ser Asp Thr Tyr Gly Ala Pro Gly Gly Gly Gly Asn Gly
    130                 135                 140

Asn Gly Gly Arg Pro Ser Ser Ser Tyr Gly Ala Pro Gly Gln Gly Gln
145                 150                 155                 160

Gly Asn Gly Asn Gly Gly Arg Pro Ser Ser Tyr Gly Ala Pro Gly
                165                 170                 175

Gly Gly Asn Gly Gly Arg Pro Ser Asp Thr Tyr Gly Ala Pro Gly Gly
            180                 185                 190
```

-continued

```
Gly Asn Gly Gly Arg Pro Ser Asp Thr Tyr Gly Ala Pro Gly Gly Gly
        195                 200                 205

Asn Asn Gly Gly Arg Pro Ser Ser Tyr Gly Ala Pro Gly Gly Gly
    210                 215                 220

Asn Gly Gly Arg Pro Ser Asp Thr Tyr Gly Ala Pro Gly Gly Asn
225                 230                 235                 240

Gly Asn Gly Ser Gly Gly Arg Pro Ser Ser Tyr Gly Ala Pro Ala
            245                 250                 255

Gln Gly Gln Gly Gly Phe Gly Gly Arg Pro Ser Asp Ser Tyr Gly Ala
                260                 265                 270

Pro Gly Gln Asn Gln Lys Pro Ser Asp Ser Tyr Gly Ala Pro Gly Ser
        275                 280                 285

Gly Asn Gly Ser Ala Gly Arg Pro Ser Ser Tyr Gly Ala Pro Gly
    290                 295                 300

Ser Gly Pro Gly Gly Arg Pro Ser Asp Ser Tyr Gly Pro Pro Ala Ser
305                 310                 315                 320

Gly Ser Gly Ala Gly Ala Gly Gly Ser Gly Pro Gly Gly Ala Asp
            325                 330                 335

Tyr Asp Asn Asp Glu Pro Ala Lys Tyr Glu Phe Asn Tyr Gln Val Glu
        340                 345                 350

Asp Ala Pro Ser Gly Leu Ser Phe Gly His Ser Glu Met Arg Asp Gly
        355                 360                 365

Asp Phe Thr Thr Gly Gln Tyr Asn Val Leu Leu Pro Asp Gly Arg Lys
    370                 375                 380

Gln Ile Val Glu Tyr Glu Ala Asp Gln Gly Tyr Arg Pro Gln Ile
385                 390                 395                 400

Arg Tyr Glu Gly Asp Ala Asn Asp Gly Ser Gly Pro Ser Gly Pro Ser
                405                 410                 415

Gly Pro Gly Gly Pro Gly Gly Gln Asn Leu Gly Ala Asp Gly Tyr Ser
            420                 425                 430

Ser Gly Arg Pro Gly Asn Gly Asn Gly Asn Gly Tyr Ser
        435                 440                 445

Ser Gly Arg Pro Gly Gly Gln Asp Leu Gly Pro Ser Gly Tyr Ser Gly
        450                 455                 460

Gly Arg Pro Gly Gly Gln Asp Leu Gly Ala Gly Gly Tyr Ser Asn Val
465                 470                 475                 480

Lys Pro Gly Gly Gln Asp Leu Gly Pro Gly Gly Tyr Ser Gly Arg
            485                 490                 495

Pro Gly Gly Gln Asp Leu Gly Arg Asp Gly Tyr Ser Gly Arg Pro
        500                 505                 510

Gly Gly Gln Asp Leu Gly Ala Gly Ala Tyr Ser Asn Gly Arg Pro Gly
        515                 520                 525

Gly Asn Gly Asn Gly Gly Ser Asp Gly Gly Arg Val Ile Ile Gly Gly
    530                 535                 540

Arg Val Ile Gly Gly Gln Asp Gly Gly Asp Gln Gly Tyr Ser Gly Gly
545                 550                 555                 560

Arg Pro Gly Gly Gln Asp Leu Gly Arg Asp Gly Tyr Ser Ser Gly Arg
            565                 570                 575

Pro Gly Gly Arg Pro Gly Gly Asn Gly Gln Asp Ser Gln Asp Gly Gln
        580                 585                 590

Gly Tyr Ser Ser Gly Arg Pro Gly Gln Gly Gly Arg Asn Gly Phe Gly
    595                 600                 605

Pro Gly Gly Gln Asn Gly Asp Asn Asp Gly Ser Gly Tyr Arg Tyr
610                 615                 620
```

<210> SEQ ID NO 33
<211> LENGTH: 619
<212> TYPE: PRT
<213> ORGANISM: Drosophila erecta

<400> SEQUENCE: 33

```
Met Phe Lys Leu Leu Gly Leu Thr Leu Leu Met Ala Met Val Val Leu
1               5                   10                  15

Gly Arg Pro Glu Pro Pro Val Asn Ser Tyr Leu Pro Pro Ser Asp Ser
            20                  25                  30

Tyr Gly Ala Pro Gly Gln Ser Gly Pro Gly Arg Pro Ser Asp Ser
        35                  40                  45

Tyr Gly Ala Pro Gly Gly Asn Gly Gly Arg Pro Ser Asp Ser Tyr
    50                  55                  60

Gly Ala Pro Gly Leu Gly Gln Gly Gln Gly Gln Gly Gln Gly
65                  70                  75                  80

Gly Phe Gly Gly Lys Pro Ser Asp Ser Tyr Gly Ala Pro Gly Ala Gly
                85                  90                  95

Asn Gly Asn Gly Gly Arg Pro Ser Ser Tyr Gly Ala Pro Gly Ala
                100                 105                 110

Gly Asn Gly Gly Arg Pro Ser Asp Thr Tyr Gly Ala Pro Gly Gly Gly
                115                 120                 125

Ser Gly Gly Arg Pro Ser Asp Thr Tyr Gly Ala Pro Gly Gly Gly Asn
    130                 135                 140

Gly Asn Gly Asn Gly Gly Arg Pro Ser Ser Tyr Gly Ala Pro Gly
145                 150                 155                 160

Gln Gly Gln Gly Asn Gly Asn Ser Gly Arg Pro Ser Ser Ser Tyr Gly
                165                 170                 175

Ala Pro Gly Ala Gly Asn Gly Gly Arg Pro Ser Asp Thr Tyr Gly Ala
                180                 185                 190

Pro Gly Gly Gly Asn Gly Gly Arg Pro Ser Ser Ser Tyr Gly Ala Pro
                195                 200                 205

Gly Ala Gly Asn Gly Gly Asn Gly Gly Arg Pro Ser Asp Thr Tyr Gly
    210                 215                 220

Ala Pro Gly Gly Asn Gly Asn Gly Asn Gly Asn Gly Asn Gly Ser
225                 230                 235                 240

Gly Gly Arg Pro Ser Ser Ser Tyr Gly Ala Pro Gly Gln Gly Gln Gly
                245                 250                 255

Gly Phe Gly Gly Arg Pro Ser Asp Ser Tyr Gly Ala Pro Gly Gln Asn
                260                 265                 270

Gln Lys Pro Ser Asp Ser Tyr Gly Ala Pro Gly Ser Gly Ser Gly Ser
            275                 280                 285

Gly Asn Gly Asn Gly Gly Arg Pro Ser Ser Tyr Gly Ala Pro Gly
    290                 295                 300

Ser Gly Pro Gly Gly Arg Pro Ser Asp Ser Tyr Gly Pro Pro Ala Ser
305                 310                 315                 320

Gly Ser Gly Ala Gly Gly Ala Gly Gly Ser Gly Pro Gly Gly Ala Asp
                325                 330                 335

Tyr Asp Asn Asp Glu Pro Ala Lys Tyr Glu Phe Asn Tyr Gln Val Glu
                340                 345                 350

Asp Ala Pro Ser Gly Leu Ser Phe Gly His Ser Glu Met Arg Asp Gly
            355                 360                 365

Asp Phe Thr Thr Gly Gln Tyr Asn Val Leu Leu Pro Asp Gly Arg Lys
        370                 375                 380
```

```
Gln Ile Val Glu Tyr Glu Ala Asp Gln Gly Tyr Arg Pro Gln Ile
385                 390                 395                 400

Arg Tyr Glu Gly Asp Ala Asn Asp Gly Ser Gly Pro Ser Gly Pro Gly
            405                 410                 415

Gly Gln Asn Leu Gly Ala Asp Gly Tyr Ser Ser Gly Arg Pro Gly Asn
            420                 425                 430

Gly Asn Gly Asn Gly Asn Gly Gly Tyr Ser Gly Arg Pro Gly Gly
            435                 440                 445

Gln Asp Leu Gly Pro Ser Gly Tyr Ser Gly Gly Arg Pro Gly Gly Gln
450                 455                 460

Asp Leu Gly Ala Gly Gly Tyr Ser Asn Gly Arg Pro Gly Gly Gln Asp
465                 470                 475                 480

Leu Gly Pro Ser Gly Tyr Ser Gly Gly Arg Pro Gly Gly Gln Asp Leu
            485                 490                 495

Gly Pro Ser Gly Tyr Ser Gly Gly Arg Pro Gly Gly Gln Asp Leu Gly
            500                 505                 510

Ala Gly Gly Tyr Ser Asn Gly Arg Pro Gly Gly Asn Gly Asn Gly Asn
            515                 520                 525

Gly Gly Ala Asp Gly Gly Arg Val Ile Ile Gly Gly Arg Val Ile Gly
530                 535                 540

Gly Gln Asp Gly Gly Asp Gln Gly Tyr Ser Gly Gly Arg Pro Gly Gly
545                 550                 555                 560

Gln Asp Leu Gly Arg Asp Gly Tyr Ser Ser Gly Arg Pro Gly Gly Arg
            565                 570                 575

Pro Gly Ala Asn Gly Gln Asp Asn Gln Asp Gly Gln Gly Tyr Ser Ser
            580                 585                 590

Gly Arg Ser Gly Lys Gly Gly Arg Asn Ser Phe Gly Pro Gly Gly Gln
            595                 600                 605

Asn Gly Asp Asn Asp Gly Ser Gly Tyr Arg Tyr
            610                 615

<210> SEQ ID NO 34
<211> LENGTH: 609
<212> TYPE: PRT
<213> ORGANISM: Drosophila simulans

<400> SEQUENCE: 34

Met Phe Lys Leu Leu Gly Leu Thr Leu Leu Met Ala Met Val Val Leu
1               5                   10                  15

Gly Arg Pro Glu Pro Pro Val Asn Ser Tyr Leu Pro Pro Ser Asp Ser
            20                  25                  30

Tyr Gly Ala Pro Gly Gln Ser Gly Val Pro Ala Gly Arg Pro Ser Asp
        35                  40                  45

Ser Tyr Gly Ala Pro Gly Gln Gly Gln Gly Gln Gly Gln Gly
    50                  55                  60

Gly Tyr Gly Gly Lys Pro Ser Asp Ser Tyr Gly Ala Pro Gly Gly Gly
65                  70                  75                  80

Asn Gly Asn Gly Gly Arg Pro Ser Ser Tyr Gly Ala Pro Gly Gly
                85                  90                  95

Gly Asn Gly Gly Arg Pro Ser Asp Thr Tyr Gly Ala Pro Gly Gly Gly
            100                 105                 110

Asn Gly Gly Arg Pro Ser Asp Thr Tyr Gly Ala Pro Gly Gly Gly Gly
        115                 120                 125

Asn Gly Asn Gly Gly Arg Pro Ser Ser Tyr Gly Ala Pro Gly Gln
    130                 135                 140
```

```
Gly Gln Gly Asn Gly Asn Gly Arg Pro Ser Ser Tyr Gly Ala
145                 150                 155                 160

Pro Gly Gly Gly Asn Gly Gly Arg Pro Ser Asp Thr Tyr Gly Ala Pro
                165                 170                 175

Gly Gly Gly Asn Gly Gly Arg Pro Ser Asp Thr Tyr Gly Ala Pro Gly
            180                 185                 190

Gly Gly Asn Asn Gly Gly Arg Pro Ser Ser Ser Tyr Gly Ala Pro Gly
            195                 200                 205

Gly Gly Asn Gly Gly Arg Pro Ser Asp Thr Tyr Gly Ala Pro Gly Gly
        210                 215                 220

Gly Asn Gly Asn Gly Ser Gly Arg Pro Ser Ser Ser Tyr Gly Ala
225                 230                 235                 240

Pro Gly Gln Gly Gln Gly Gly Phe Gly Gly Arg Pro Ser Asp Ser Tyr
                245                 250                 255

Gly Ala Pro Gly Gln Asn Gln Lys Pro Ser Asp Ser Tyr Gly Ala Pro
            260                 265                 270

Gly Ser Gly Asn Gly Ser Gly Gly Arg Pro Ser Ser Ser Tyr Gly Ala
        275                 280                 285

Pro Gly Ser Gly Pro Gly Gly Arg Pro Ser Asp Ser Tyr Gly Pro Pro
        290                 295                 300

Ala Ser Gly Ser Gly Ala Gly Gly Ala Gly Gly Ser Gly Pro Gly Gly
305                 310                 315                 320

Ala Asp Tyr Asp Asn Asp Glu Pro Ala Lys Tyr Glu Phe Asn Tyr Gln
                325                 330                 335

Val Glu Asp Ala Pro Ser Gly Leu Ser Phe Gly His Ser Glu Met Arg
                340                 345                 350

Asp Gly Asp Phe Thr Thr Gly Gln Tyr Asn Val Leu Leu Pro Asp Gly
            355                 360                 365

Arg Lys Gln Ile Val Glu Tyr Glu Ala Asp Gln Gln Gly Tyr Arg Pro
370                 375                 380

Gln Ile Arg Tyr Glu Gly Asp Ala Asn Asp Gly Ser Gly Pro Ser Gly
385                 390                 395                 400

Pro Ser Gly Pro Gly Gly Pro Gly Gly Gln Asn Leu Gly Ala Asp Gly
                405                 410                 415

Tyr Ser Ser Gly Arg Pro Gly Asn Gly Asn Gly Asn Gly Asn Gly Gly
                420                 425                 430

Tyr Ser Gly Gly Arg Pro Gly Gly Gln Asp Leu Gly Pro Ser Gly Tyr
            435                 440                 445

Ser Gly Gly Arg Pro Gly Gly Gln Asp Leu Gly Ala Gly Gly Tyr Ser
    450                 455                 460

Asn Gly Lys Pro Gly Gly Gln Asp Leu Gly Pro Gly Tyr Ser Gly
465                 470                 475                 480

Gly Arg Pro Gly Gly Gln Asp Leu Gly Arg Asp Gly Tyr Ser Gly Gly
                485                 490                 495

Arg Pro Gly Gly Gln Asp Leu Gly Ala Gly Gly Tyr Ser Asn Gly Arg
            500                 505                 510

Pro Gly Gly Asn Gly Asn Gly Ser Asp Gly Gly Arg Val Ile Ile
        515                 520                 525

Gly Gly Arg Val Ile Gly Gly Gln Asp Gly Gly Asp Gln Gly Tyr Ser
        530                 535                 540

Gly Gly Arg Pro Gly Gly Gln Asp Leu Gly Arg Asp Gly Tyr Ser Ser
545                 550                 555                 560

Gly Arg Pro Gly Gly Arg Pro Gly Gly Asn Gly Gln Asp Ser Gln Asp
```

```
                565                 570                 575
Gly Gln Gly Tyr Ser Ser Gly Arg Pro Gly Gln Gly Gly Arg Asn Gly
            580                 585                 590

Phe Gly Pro Gly Gly Gln Asn Gly Asp Asn Asp Gly Ser Gly Tyr Arg
        595                 600                 605

Tyr

<210> SEQ ID NO 35
<211> LENGTH: 622
<212> TYPE: PRT
<213> ORGANISM: Drosophila yakuba

<400> SEQUENCE: 35

Met Phe Lys Leu Leu Gly Leu Thr Leu Leu Met Ala Met Val Val Leu
1               5                   10                  15

Gly Arg Pro Glu Pro Pro Val Asn Ser Tyr Leu Pro Pro Ser Asp Ser
            20                  25                  30

Tyr Gly Ala Pro Gly Gln Ser Gly Pro Gly Gly Arg Pro Ser Asp Ala
        35                  40                  45

Tyr Gly Ala Pro Gly Gly Asn Gly Gly Arg Pro Ser Asp Ser Tyr
    50                  55                  60

Gly Ala Pro Gly Val Gly Gln Gly Gln Gly Gln Gly Gln Gly Gln Gly
65                  70                  75                  80

Gly Phe Gly Gly Lys Pro Ser Asp Ser Tyr Gly Ala Pro Gly Gly Gly
                85                  90                  95

Asn Gly Asn Gly Gly Arg Pro Ser Ser Tyr Gly Ala Pro Gly Gly
            100                 105                 110

Gly Asn Gly Gly Arg Pro Ser Asp Thr Tyr Gly Ala Pro Gly Gly Gly
        115                 120                 125

Ser Gly Gly Arg Pro Ser Asp Ser Tyr Gly Ala Pro Gly Gly Gly Asn
    130                 135                 140

Gly Asn Ser Gly Arg Pro Ser Ser Tyr Gly Ala Pro Gly Gln Gly
145                 150                 155                 160

Gln Gly Asn Gly Asn Gly Gly Arg Pro Ser Gly Ser Tyr Gly Ala Pro
                165                 170                 175

Gly Gly Gly Asn Gly Gly Arg Pro Ser Asp Thr Tyr Gly Ala Pro Gly
            180                 185                 190

Gly Gly Asn Gly Gly Arg Pro Ser Ser Tyr Gly Ala Pro Gly Gly
        195                 200                 205

Gly Asn Gly Asn Gly Gly Arg Pro Ser Asp Ser Tyr Gly Ala Pro Gly
    210                 215                 220

Gly Gly Asn Gly Asn Gly Asn Gly Ser Gly Gly Arg Pro Ser Ser Ser
225                 230                 235                 240

Tyr Gly Ala Pro Gly Gln Gly Gln Gly Gly Phe Gly Gly Arg Pro Ser
                245                 250                 255

Asp Ser Tyr Gly Ala Pro Gly Gln Asn Gln Lys Pro Ser Asp Thr Tyr
            260                 265                 270

Gly Ala Pro Gly Asn Gly Asn Gly Asn Gly Asn Gly Gly Arg Pro Ser
        275                 280                 285

Ser Ser Tyr Gly Ala Pro Gly Thr Gly Pro Gly Gly Arg Pro Ser Asp
    290                 295                 300

Ser Tyr Gly Pro Pro Ala Ser Gly Ser Gly Ala Gly Gly Ala Gly Gly
305                 310                 315                 320

Gly Ser Gly Pro Gly Gly Ala Asp Tyr Asp Asn Asp Glu Pro Ala Lys
                325                 330                 335
```

```
Tyr Glu Phe Asn Tyr Gln Val Glu Asp Ala Pro Ser Gly Leu Ser Phe
            340                 345                 350

Gly His Ser Glu Met Arg Asp Gly Asp Phe Thr Thr Gly Gln Tyr Asn
        355                 360                 365

Val Leu Leu Pro Asp Gly Arg Lys Gln Ile Val Glu Tyr Glu Ala Asp
370                 375                 380

Gln Gln Gly Tyr Arg Pro Gln Ile Arg Tyr Glu Gly Asp Ala Asn Asp
385                 390                 395                 400

Gly Ser Gly Pro Ser Gly Pro Ser Gly Pro Gly Gly Ala Gly Gly Pro
                405                 410                 415

Gly Gly Gln Asn Leu Gly Ala Asp Gly Tyr Ser Ser Gly Arg Pro Gly
                420                 425                 430

Asn Gly Asn Gly Asn Gly Gly Tyr Pro Gly Gly Arg Pro Gly
                435                 440                 445

Gly Gln Asp Leu Gly Pro Ser Gly Tyr Ser Gly Gly Arg Pro Gly Gly
                450                 455                 460

Gln Asp Leu Gly Pro Gly Gly Tyr Ser Asn Gly Arg Pro Gly Gly Gln
465                 470                 475                 480

Asp Leu Gly Pro Ser Gly Tyr Ser Gly Gly Arg Pro Gly Gly Gln Asp
                485                 490                 495

Leu Gly Pro Asn Gly Tyr Ser Gly Gly Arg Pro Gly Gly Gln Asp Leu
                500                 505                 510

Gly Pro Gly Gly Tyr Ser Asn Gly Arg Pro Gly Gly Asn Gly Asn Gly
                515                 520                 525

Asn Gly Asn Gly Gly Ser Asp Gly Gly Arg Val Ile Ile Gly Gly Arg
530                 535                 540

Val Ile Gly Gly Gln Asp Gly Asp Gln Gly Tyr Ser Gly Gly Arg
545                 550                 555                 560

Pro Gly Gly Gln Asp Leu Gly Arg Asp Gly Tyr Ser Gly Gly Arg Pro
                565                 570                 575

Gly Gly Arg Pro Gly Ala Asn Gly Gln Asp Asn Gln Asp Gly Gln Gly
                580                 585                 590

Tyr Ser Gly Arg Pro Gly Gln Gly Gly Arg Asn Gly Phe Gly Pro
                595                 600                 605

Gly Gly Gln Asn Gly Asp Asn Asp Gly Ser Gly Tyr Arg Tyr
                610                 615                 620

<210> SEQ ID NO 36
<211> LENGTH: 621
<212> TYPE: PRT
<213> ORGANISM: Drosophila pseudoobscura

<400> SEQUENCE: 36

Met Phe Lys Leu Leu Gly Leu Thr Leu Leu Cys Thr Ala Val Leu Ala
1               5                   10                  15

Arg Pro Glu Pro Pro Val Asn Ser Tyr Leu Pro Ser Asp Ser Tyr
            20                  25                  30

Gly Ala Pro Gly Gln Ser Gly Pro Gly Ala Gln Gly Gly Gly Pro Gly
        35                  40                  45

Gly Arg Pro Thr Asp Ser Tyr Gly Pro Pro Gly Leu Gly Gln Gly Gln
    50                  55                  60

Gly Gln Gly Gln Gly Gln Ala Gln Gly Gly Phe Gly Gly Lys Pro Ser
65                  70                  75                  80

Asp Ser Tyr Gly Ala Pro Gly Val Gly Gly Asn Gly Asn Gly Gly Gly
            85                  90                  95
```

```
Arg Pro Ser Ser Ser Tyr Gly Ala Pro Gly Asn Ala Asn Gly Gly Gly
                100                 105                 110

Arg Pro Ser Ser Ser Tyr Gly Ala Pro Gly Gln Gly Gln Gly Gln Gly
                115                 120                 125

Gly Arg Pro Ser Asp Ser Tyr Gly Ala Pro Gly Ala Ser Gly Asn Gly
        130                 135                 140

Asn Gly Asn Gly Gly Arg Pro Ser Ser Tyr Gly Ala Pro Gly
145                 150                 155                 160

Gln Gly Gln Gly Gly Arg Pro Ser Asp Ser Tyr Gly Ala Pro Gly Ala
                165                 170                 175

Ser Gly Asn Gly Asn Gly Asn Gly Gly Arg Pro Ser Ser Ser Tyr
                180                 185                 190

Gly Ala Pro Gly Gln Gly Gln Gly Gly Arg Pro Ser Asp Ser Tyr Gly
                195                 200                 205

Ala Pro Gly Ala Ser Gly Asn Gly Asn Gly Asn Gly Gly Ser Arg Pro
        210                 215                 220

Ser Ser Asn Tyr Gly Ala Pro Gly Gln Gly Gln Gly Gly Arg Pro Ser
225                 230                 235                 240

Asp Ser Tyr Gly Ala Pro Gly Ala Ser Gly Asn Gly Asn Gly Asn Gly
                245                 250                 255

Gly Gly Arg Pro Ser Ser Tyr Gly Ala Pro Gly Ala Gly Ser Gly
                260                 265                 270

Gly Arg Pro Ser Asp Ser Tyr Gly Pro Pro Ala Ser Gly Ala Gly Ala
        275                 280                 285

Gly Gly Gly Ser Gly Gly Pro Gly Ser Gly Ala Asp Tyr Asp Asn
        290                 295                 300

Asp Glu Pro Ala Lys Tyr Glu Phe Asn Tyr Gln Val Glu Asp Ala Pro
305                 310                 315                 320

Ser Gly Leu Ser Phe Gly His Ser Glu Met Arg Asp Gly Asp Phe Thr
                325                 330                 335

Thr Gly Gln Tyr Asn Val Leu Leu Pro Asp Gly Arg Lys Gln Ile Val
                340                 345                 350

Glu Tyr Glu Ala Asp Gln Gln Gly Tyr Arg Pro Gln Ile Arg Tyr Glu
                355                 360                 365

Gly Glu Ala Asn Asp Gly Gly Ala Ser Gly Pro Gly Gly Gln Asn Leu
                370                 375                 380

Gly Ala Asp Gly Tyr Ser Ser Gly Arg Pro Gly Gly Asn Gly Asn Gly
385                 390                 395                 400

Gln Asn Gly Tyr Ser Gly Gly Arg Pro Gly Gly Gln Asp Leu Gly Arg
                405                 410                 415

Asp Gly Tyr Ser Gly Gly Arg Pro Gly Gly Gln Asp Leu Gly Gln Asn
                420                 425                 430

Gly Tyr Ser Gly Gly Arg Pro Gly Gly Gln Asp Leu Gly Ala Ser Gly
                435                 440                 445

Tyr Ser Gly Gly Arg Pro Gly Gly Gln Asp Leu Gly Gln Asn Gly Tyr
        450                 455                 460

Ser Gly Gly Arg Pro Gly Gly Gln Asp Leu Gly Ala Gly Gly Tyr Ser
465                 470                 475                 480

Gly Gly Arg Pro Gly Gly Gln Asp Leu Gly Gln Asn Gly Tyr Ser Ser
                485                 490                 495

Gly Arg Pro Gly Gly Asn Gly Gly Asn Ala Gly Ser Asp Gly Gly Arg
                500                 505                 510

Val Ile Ile Ala Gly Arg Val Thr Gly Pro Asp Gly Ser Asp Gln Gly
```

```
                515                 520                 525
Gln Gly Phe Ser Gly Gly Arg Pro Gly Gly Asn Ser Asn Gly Gly Arg
            530                 535                 540

Gln Ile Ser Gly Gln Asp Leu Gly Arg Asp Gly Tyr Ser Gly Gly Arg
545                 550                 555                 560

Pro Gly Gly Gln Asp Leu Gly Ala Gly Gly Tyr Ser Gly Gly Arg Pro
                565                 570                 575

Gly Gly Gln Asp Leu Gly Gln Asn Gly Tyr Ser Ser Gly Lys Pro Gln
            580                 585                 590

Gly Gln Gly Gln Gly Gln Gly Gln Gly Arg Asn Gly Phe Gly Pro Gly
                595                 600                 605

Gly Gln Asn Gly Asp Asn Asp Gly Ser Gly Tyr Arg Tyr
            610                 615                 620

<210> SEQ ID NO 37
<211> LENGTH: 621
<212> TYPE: PRT
<213> ORGANISM: Drosophila persimilis

<400> SEQUENCE: 37

Met Phe Lys Leu Leu Gly Leu Thr Leu Leu Cys Thr Ala Val Leu Ala
1               5                   10                  15

Arg Pro Glu Pro Pro Val Asn Ser Tyr Leu Pro Pro Ser Asp Ser Tyr
                20                  25                  30

Gly Ala Pro Gly Gln Ser Gly Pro Gly Ala Gln Gly Gly Gly Pro Gly
            35                  40                  45

Gly Arg Pro Thr Asp Ser Tyr Gly Pro Pro Gly Leu Gly Gln Gly Gln
        50                  55                  60

Gly Gln Gly Gln Gly Gln Gly Gln Ala Gln Gly Gly Phe Gly Gly Lys
65                  70                  75                  80

Pro Ser Asp Ser Tyr Gly Ala Pro Gly Val Gly Gly Asn Gly Asn Gly
                85                  90                  95

Gly Gly Arg Pro Ser Ser Ser Tyr Gly Ala Pro Gly Asn Ala Asn Gly
            100                 105                 110

Gly Gly Arg Pro Ser Ser Ser Tyr Gly Ala Pro Gly Gln Gly Gln Gly
        115                 120                 125

Gln Gly Gly Arg Pro Ser Asp Ser Tyr Gly Ala Pro Gly Ala Ser Gly
    130                 135                 140

Asn Gly Asn Gly Asn Gly Gly Arg Pro Ser Ser Tyr Gly Ala
145                 150                 155                 160

Pro Gly Gln Gly Gln Gly Gly Arg Pro Ser Asp Ser Tyr Gly Ala Pro
                165                 170                 175

Gly Ala Ser Gly Asn Gly Asn Gly Asn Gly Gly Arg Pro Ser Ser
            180                 185                 190

Ser Tyr Gly Ala Pro Gly Gln Gly Gln Gly Gly Arg Pro Ser Asp Ser
        195                 200                 205

Tyr Gly Ala Pro Gly Ala Ser Gly Asn Gly Asn Gly Asn Gly Gly Ser
    210                 215                 220

Arg Pro Ser Ser Asn Tyr Gly Ala Pro Gly Gln Gly Gln Gly Gly Arg
225                 230                 235                 240

Pro Ser Asp Ser Tyr Gly Ala Pro Gly Ala Ser Gly Asn Gly Asn Gly
                245                 250                 255

Asn Gly Gly Gly Arg Pro Ser Ser Tyr Gly Ala Pro Gly Ala Gly
            260                 265                 270

Ser Gly Gly Arg Pro Ser Asp Ser Tyr Gly Pro Pro Ala Ser Gly Ala
```

```
                275                 280                 285
Gly Ala Gly Gly Gly Ser Gly Pro Gly Gly Ser Gly Ala Asp Tyr
        290                 295                 300
Asp Asn Asp Glu Pro Ala Lys Tyr Glu Phe Asn Tyr Gln Val Glu Asp
305                 310                 315                 320
Ala Pro Ser Gly Leu Ser Phe Gly His Ser Glu Met Arg Asp Gly Asp
                325                 330                 335
Phe Thr Thr Gly Gln Tyr Asn Val Leu Leu Pro Asp Gly Arg Lys Gln
            340                 345                 350
Ile Val Glu Tyr Glu Ala Asp Gln Gln Gly Tyr Arg Pro Gln Ile Arg
            355                 360                 365
Tyr Glu Gly Glu Ala Asn Asp Gly Ala Ser Gly Pro Gly Gly Gln
    370                 375                 380
Asn Leu Gly Ala Asp Gly Tyr Ser Ser Gly Arg Pro Gly Gly Asn Gly
385                 390                 395                 400
Asn Gly Gln Asn Gly Tyr Ser Gly Gly Arg Pro Gly Gln Asp Leu
                405                 410                 415
Gly Arg Asp Gly Tyr Ser Gly Gly Arg Pro Gly Gly Gln Asp Leu Gly
            420                 425                 430
Gln Asn Gly Tyr Ser Gly Gly Arg Pro Gly Gly Gln Asp Leu Gly Ala
        435                 440                 445
Ser Gly Tyr Ser Gly Gly Arg Pro Gly Gly Gln Asp Leu Gly Gln Asn
450                 455                 460
Gly Tyr Ser Gly Gly Arg Pro Gly Gly Gln Asp Leu Gly Ala Gly Gly
465                 470                 475                 480
Tyr Ser Gly Gly Arg Pro Gly Gly Gln Asp Leu Gly Gln Asn Gly Tyr
                485                 490                 495
Ser Ser Gly Arg Pro Gly Gly Asn Gly Gly Asn Ala Gly Ser Asp Gly
            500                 505                 510
Gly Arg Val Ile Ile Ala Gly Arg Val Thr Gly Pro Asp Gly Ser Asp
            515                 520                 525
Gln Gly Gln Gly Phe Ser Gly Arg Pro Gly Gly Asn Ser Asn Gly
    530                 535                 540
Gly Arg Gln Ile Gly Gly Gln Asp Leu Gly Arg Asp Gly Tyr Ser Gly
545                 550                 555                 560
Gly Arg Pro Gly Gly Gln Asp Leu Gly Ala Gly Tyr Ser Gly Gly
                565                 570                 575
Arg Pro Gly Gly Gln Asp Leu Gly Gln Asn Gly Tyr Ser Ser Gly Lys
            580                 585                 590
Pro Gln Gly Gln Gly Gln Gly Arg Asn Gly Phe Gly Pro Gly
    595                 600                 605
Gly Gln Asn Gly Asp Asn Asp Gly Ser Gly Tyr Arg Tyr
    610                 615                 620

<210> SEQ ID NO 38
<211> LENGTH: 589
<212> TYPE: PRT
<213> ORGANISM: Drosophila mojavensis

<400> SEQUENCE: 38

Met Phe Lys Leu Phe Gly Ile Met Leu Leu Thr Ala Thr Val Leu Ala
1               5                   10                  15
Arg Pro Glu Pro Pro Val Asn Ser Tyr Leu Pro Pro Ser Pro Gly Asp
            20                  25                  30
Ser Tyr Gly Ala Pro Gly Gln Gly Gln Gly Gln Gly Gln Gly Gly Phe
```

```
                35                  40                  45
Gly Gly Arg Pro Ser Asp Ser Tyr Gly Ala Pro Gly Ala Gly Asn Gly
 50                  55                  60

Asn Gly Gly Gly Arg Pro Ser Ser Ser Tyr Gly Ala Pro Gly Gln Gly
 65                  70                  75                  80

Gln Gly Arg Pro Ser Asp Ser Tyr Gly Ala Pro Gly Ala Gly Asn Gly
                 85                  90                  95

Asn Gly Gly Arg Pro Ser Ser Ser Tyr Gly Ala Pro Gly Gln Gly
            100                 105                 110

Gln Gly Gly Leu Gly Gly Arg Pro Ser Ser Ser Tyr Gly Ala Pro Gly
            115                 120                 125

Ser Gly Asn Gly Asn Gly Asn Gly Arg Pro Ser Ser Ser Tyr Gly Ala
            130                 135                 140

Pro Gly Gln Gly Gln Gly Gly Lys Pro Ser Asp Ser Tyr Gly Ala Pro
145                 150                 155                 160

Gly Leu Gly Asn Gly Asn Gly Asn Gly Asn Gly Arg Pro Ser Ser Ser
                165                 170                 175

Tyr Gly Ala Pro Gly Gln Gly Gln Gly Ser Phe Gly Gly Lys Pro Ser
                180                 185                 190

Asp Thr Tyr Gly Ala Pro Gly Ala Gly Asn Ala Asn Gly Asn Gly Arg
                195                 200                 205

Pro Ser Ser Ser Tyr Gly Ala Pro Gly Gln Gly Gln Gly Gly Phe Gly
            210                 215                 220

Gly Lys Pro Ser Asp Ser Tyr Gly Ala Pro Gly Ala Gly Asn Gly Asn
225                 230                 235                 240

Gly Gly Gly Arg Pro Ser Ser Ser Tyr Gly Ala Pro Gly Gln Gly Gln
                245                 250                 255

Gly Gln Gly Gly Phe Gly Gly Arg Pro Ser Asp Ser Tyr Gly Pro Pro
                260                 265                 270

Ala Ser Gly Ala Gly Ser Ala Gly Ala Gly Pro Gly Gly Ala Gly
            275                 280                 285

Gly Asp Tyr Asp Asn Asp Glu Pro Ala Lys Tyr Glu Phe Asn Tyr Gln
 290                 295                 300

Val Glu Asp Pro Pro Ser Gly Leu Ser Phe Gly His Ser Glu Met Arg
305                 310                 315                 320

Asp Gly Asp Phe Thr Thr Gly Gln Tyr Asn Val Leu Leu Pro Asp Gly
                325                 330                 335

Arg Lys Gln Ile Val Glu Tyr Glu Ala Asp Gln Gln Gly Tyr Arg Pro
                340                 345                 350

Gln Ile Arg Tyr Glu Gly Asp Ala Asn Gly Ala Gly Gly Ala Gly
                355                 360                 365

Gly Pro Gly Gly Gln Asp Leu Gly Gln Asn Gly Tyr Ser Ser Gly Arg
            370                 375                 380

Pro Gly Gly Gln Asp Leu Gly Gly Gly Tyr Ser Gly Gly Arg Pro
385                 390                 395                 400

Gly Gly Gln Asp Leu Gly Gln Asn Gly Tyr Ser Gly Gly Arg Pro Gly
                405                 410                 415

Gly Gln Asp Leu Gly Gln Asn Gly Tyr Ser Gly Gly Arg Pro Gly Gly
            420                 425                 430

Gln Asp Leu Gly Gln Asn Gly Tyr Ser Gly Gly Arg Pro Gly Gly Gln
            435                 440                 445

Asp Leu Gly Gln Asn Gly Tyr Ser Ser Gly Arg Pro Gly Gly Gln Asp
450                 455                 460
```

```
Leu Gly Gln Asn Gly Tyr Ser Gly Gly Arg Pro Gly Gly Gln Asp Leu
465                 470                 475                 480

Gly Gln Asn Gly Tyr Ser Gly Gly Arg Pro Gly Gly Gln Asp Leu Gly
            485                 490                 495

Gln Asn Gly Tyr Ser Ser Gly Arg Pro Gly Gly Asn Gly Gly Ser Asp
        500                 505                 510

Gly Gly Arg Val Ile Ile Gly Gly Arg Val Ile Gly Gln Asp Ala Gly
            515                 520                 525

Asp Gly Gln Gly Tyr Ser Ser Gly Arg Pro Asn Gly Gln Asp Gly Gly
        530                 535                 540

Phe Gly Gln Asp Asn Val Asp Gly Arg Gly Tyr Ser Ser Gly Lys Pro
545                 550                 555                 560

Gly Gln Gly Arg Asn Gly Asn Gly Asn Gly Ser Ser Phe Gly Pro Gly
            565                 570                 575

Gly Gln Asn Gly Asp Asn Asp Gly Ser Gly Tyr Arg Tyr
        580                 585

<210> SEQ ID NO 39
<211> LENGTH: 633
<212> TYPE: PRT
<213> ORGANISM: Drosophila virilis

<400> SEQUENCE: 39

Met Phe Lys Leu Phe Gly Leu Thr Leu Leu Thr Ala Ala Val Leu
1               5                   10                  15

Ala Arg Pro Glu Pro Pro Val Asn Ser Tyr Leu Pro Pro Ser Pro Gly
            20                  25                  30

Asp Ser Tyr Gly Ala Pro Gly Gln Gly Gln Gly Gln Gly Gln Gly Gly
        35                  40                  45

Phe Gly Gly Lys Pro Ser Asp Ser Tyr Gly Ala Pro Gly Ala Gly Asn
    50                  55                  60

Gly Asn Gly Asn Gly Arg Pro Ser Ser Ser Tyr Gly Ala Pro Gly Gln
65                  70                  75                  80

Gly Gln Gly Gln Gly Gly Phe Gly Gly Lys Pro Ser Asp Ser Tyr Gly
            85                  90                  95

Ala Pro Gly Ala Gly Asn Gly Asn Gly Asn Gly Arg Pro Ser Ser Ser
            100                 105                 110

Tyr Gly Ala Pro Gly Gln Gly Gln Gly Gln Gly Gly Phe Gly Gly Arg
        115                 120                 125

Pro Ser Ser Ser Tyr Gly Ala Pro Gly Gln Gly Gln Gly Gly Phe Gly
        130                 135                 140

Gly Lys Pro Ser Asp Thr Tyr Gly Ala Pro Gly Ala Gly Asn Gly Asn
145                 150                 155                 160

Gly Arg Pro Ser Ser Ser Tyr Gly Ala Pro Gly Gln Gly Gln Gly Gly
            165                 170                 175

Ile Gly Gly Lys Pro Ser Asp Ser Tyr Gly Ala Pro Gly Ala Gly Asn
            180                 185                 190

Gly Asn Gly Asn Gly Arg Pro Ser Ser Ser Tyr Gly Ala Pro Gly Gln
        195                 200                 205

Gly Gln Gly Gly Phe Gly Gly Lys Pro Ser Asp Thr Tyr Gly Ala Pro
    210                 215                 220

Gly Ala Gly Asn Gly Asn Gly Arg Pro Ser Ser Ser Tyr Gly Ala Pro
225                 230                 235                 240

Gly Gln Gly Gln Gly Gly Phe Gly Gly Lys Pro Ser Asp Thr Tyr Gly
            245                 250                 255
```

```
Ala Pro Gly Ala Gly Asn Gly Asn Gly Asn Gly Arg Pro Ser Ser Ser
            260                 265                 270

Tyr Gly Ala Pro Gly Gln Gly Gln Gly Gly Phe Gly Gly Lys Pro Ser
        275                 280                 285

Asp Thr Tyr Gly Ala Pro Gly Ala Gly Asn Gly Asn Gly Arg Pro Ser
    290                 295                 300

Ser Ser Tyr Gly Ala Pro Gly Gln Gly Gln Gly Gln Gly Gly Phe Gly
305                 310                 315                 320

Gly Lys Pro Ser Asp Ser Tyr Gly Pro Pro Ala Ser Gly Ala Gly Ala
                325                 330                 335

Gly Gly Ala Gly Gly Pro Gly Ala Gly Gly Gly Asp Tyr Asp Asn
            340                 345                 350

Asp Glu Pro Ala Lys Tyr Glu Phe Asn Tyr Gln Val Glu Asp Ala Pro
        355                 360                 365

Ser Gly Leu Ser Phe Gly His Ser Glu Met Arg Asp Gly Asp Phe Thr
    370                 375                 380

Thr Gly Gln Tyr Asn Val Leu Leu Pro Asp Gly Arg Lys Gln Ile Val
385                 390                 395                 400

Glu Tyr Glu Ala Asp Gln Gln Gly Tyr Arg Pro Gln Val Arg Tyr Glu
                405                 410                 415

Gly Asp Ala Asn Gly Asn Gly Gly Pro Gly Gly Ala Gly Gly Pro Gly
            420                 425                 430

Gly Gln Asp Leu Gly Gln Asn Gly Tyr Ser Ser Gly Arg Pro Gly Gly
        435                 440                 445

Gln Asp Leu Gly Gln Gly Gly Tyr Ser Asn Gly Arg Pro Gly Gly Gln
    450                 455                 460

Asp Leu Gly Gln Asn Gly Tyr Ser Gly Gly Arg Pro Gly Gly Gln Asp
465                 470                 475                 480

Leu Gly Gln Asn Gly Tyr Ser Gly Gly Arg Pro Gly Gly Gln Asp Leu
                485                 490                 495

Gly Gln Asn Gly Tyr Ser Gly Gly Arg Pro Gly Gly Gln Asp Leu Gly
            500                 505                 510

Gln Asn Gly Tyr Ser Gly Gly Arg Pro Gly Gly Gln Asp Leu Gly Gln
        515                 520                 525

Asn Gly Tyr Ser Gly Gly Arg Pro Gly Gly Gln Asp Leu Gly Gln Asn
    530                 535                 540

Gly Tyr Ser Gly Gly Arg Pro Gly Gly Asn Gly Gly Ser Asp Gly Gly
545                 550                 555                 560

Arg Val Ile Ile Gly Gly Arg Val Ile Gly Gln Asp Gly Gly Asp Gly
                565                 570                 575

Gln Gly Tyr Ser Ser Gly Arg Pro Asn Gly Gln Asp Gly Gly Phe Gly
            580                 585                 590

Gln Asp Asn Thr Asp Gly Arg Gly Tyr Ser Ser Gly Lys Pro Gly Gln
        595                 600                 605

Gly Arg Asn Gly Asn Gly Asn Ser Phe Gly Pro Gly Gly Gln Asn Gly
    610                 615                 620

Asp Asn Asp Gly Ser Gly Tyr Arg Tyr
625                 630

<210> SEQ ID NO 40
<211> LENGTH: 836
<212> TYPE: PRT
<213> ORGANISM: Drosophila grimshawi

<400> SEQUENCE: 40
```

```
Met Ser Ser Ser Tyr Ala Val Leu Phe Gly Val Val Ala Ala Val Phe
1               5                   10                  15
Ile Val Val Val Ser Pro Pro Asp Val Ala Ala Lys Arg Glu Ala
            20              25                  30
Pro Leu Asn Asn Ala Tyr Leu Pro Pro Ser Ser Gly Ser Arg Pro Ser
        35                  40                  45
Ser Lys Tyr Gly Ala Pro Pro Ser Ser Tyr Leu Pro Pro Ala Ser
    50              55                  60
Gly Pro Ala Pro Ser Phe Asn Ser Arg Pro Ala Pro Ser Ser Ser Tyr
65              70                  75                  80
Ser Ala Pro Gly Ala Ser Ser Gly Gly Pro Tyr Pro Ala Ser Asn His
                85                  90                  95
His Lys Pro Ser Ser Ser Tyr Gly Pro Pro Ser Arg Pro Ala Pro Ala
            100                 105                 110
Pro Ser Ser Ser Tyr Gly Ala Pro Pro Ser Arg Pro Ser Gln Ser Tyr
        115                 120                 125
Gly Pro Pro Pro Arg Lys His His Ser Ser Arg Arg Pro Ser Ser
    130                 135                 140
Ser Tyr Gly Pro Pro Lys Ser Ser Ala Pro Ser Ser Tyr Gly Ala
145                 150                 155                 160
Pro Ala Pro Pro Ala Pro Pro Ser Ser Lys Tyr Gly Pro Pro Lys Ser
                165                 170                 175
Pro Ser Ser Ser Tyr Gly Ala Pro Ser Arg Pro Ser Ser Tyr Gly
        180                 185                 190
Ala Pro Ser Val Asn Ser Phe Val Pro Leu Pro Ser Ala Pro Ser Thr
    195                 200                 205
Asn Tyr Gly Ala Pro Ser Lys Thr Gln Val Leu Gly Ser Ser Gly Tyr
210                 215                 220
Thr Ser Gly Pro Gly Ala Pro Ser Ala Pro Ser Ser Tyr Gly Ala
225                 230                 235                 240
Pro Ser Ser Gly Ser Ser Ser Phe His Pro Ile Ser Pro Pro Ser Ser
                245                 250                 255
Lys Tyr Gly Ala Pro Ser Gly Ser Ser Ser Ser Ser Ser Phe
        260                 265                 270
Ser Thr His Pro Ser Phe Ser Ser Pro Ser Ser Ser Tyr Ser Ala Pro
    275                 280                 285
Ser Pro Ser Ala Asn Ser Gly Gly Ser Tyr Pro Ala Ala Pro Ser Ser
    290                 295                 300
Ser Tyr Gly Ala Pro Lys Gly Ser Ser Gly Gly Pro Tyr Pro
305                 310                 315                 320
Ala Ala Pro Ser Ser Ser Tyr Gly Ala Pro Ile Ser Lys Pro Ser Ser
                325                 330                 335
Ser Tyr Ser Ala Pro Ser Pro Gly Ala Ser Gly Gly Pro Tyr Pro
        340                 345                 350
Ala Ala Pro Ser Ser Ser Tyr Gly Ala Pro Ser Ala Pro Ser Ser
    355                 360                 365
Ser Tyr Ser Ala Pro Ser His Gly Ser Asn Ser Gly Gly Pro Tyr Pro
    370                 375                 380
Ala Ala Pro Ser Ser Ser Tyr Gly Ala Pro Lys Arg Ala Pro Ser Ser
385                 390                 395                 400
Ser Tyr Ser Ala Pro Ser Pro Gly Ala Ser Gly Gly Pro Tyr Pro
                405                 410                 415
Ala Ala Pro Ser Ser Ser Tyr Gly Ala Pro Ser Ser Ala Pro Ser Ser
                420                 425                 430
```

```
Ser Tyr Ser Ala Pro Ser His Gly Ser Asn Ser Gly Gly Pro Tyr Pro
            435                 440                 445

Ala Ala Pro Ser Ser Ser Tyr Gly Ala Pro Lys Arg Ala Pro Ser Ser
        450                 455                 460

Ser Tyr Ser Ala Pro Ser Gly Ala Ser Ser Gly Gly Pro Tyr Pro
465                 470                 475                 480

Ala Ala Pro Ser Ser Ser Tyr Gly Ala Pro Ser Thr Gly Pro Ser Ser
        485                 490                 495

Ser Tyr Ser Ala Pro Ser His Glu Ala Ser Ser Gly Pro Tyr Pro
            500                 505                 510

Ala Ala Pro Ser Ser Ser Tyr Gly Ala Pro Ser Ala Pro Ala Pro Ser
        515                 520                 525

Ser Ser Tyr Ser Ala Pro Ser His Gly Ser Ser Ser Gly Gly Pro Tyr
            530                 535                 540

Pro Ser Ala Pro Ser Ser Tyr Gly Ala Pro Ser Ser Gly Pro Ser
545                 550                 555                 560

Ser Ser Tyr Ser Ala Pro Ser Leu Gly Ala Ser Ser Gly Gly Pro Tyr
                565                 570                 575

Pro Ala Ala Pro Ser Ser Tyr Gly Ala Pro Ser Ala Pro Ala Pro
                580                 585                 590

Ser Ser Ser Tyr Ser Ala Pro Ser His Gly Ser Asn Ser Gly Gly Pro
            595                 600                 605

Tyr Pro Ala Ala Pro Ser Ser Tyr Gly Ala Pro Ser Ser Gly Pro
        610                 615                 620

Ser Ser Ser Tyr Ser Ala Pro Ser His Gly Ser Ser Ser Gly Gly Pro
625                 630                 635                 640

Tyr Pro Ala Ala Pro Ser Ser Tyr Gly Ala Pro Ser Ser Gly Pro
                645                 650                 655

Ser Ser Ser Tyr Ser Ala Pro Ser His Gly Ser Ser Ser Gly Gly Pro
                660                 665                 670

Tyr Pro Ser Ala Pro Ser Ser Tyr Gly Ala Pro Ser Thr Gly Pro
        675                 680                 685

Ser Ser Ser Tyr Ser Ala Pro Ala Pro Ala Ala Pro Ser Ser Ser Tyr
            690                 695                 700

Gly Ala Pro Pro Ser Ser Ser Tyr Ser Ala Pro Ser Gly Gly Gly Ser
705                 710                 715                 720

Ser Gly Gly Pro Tyr Pro Ala Ala Pro Pro Ser Ser Tyr Gly Ala
                725                 730                 735

Pro Ser Ser Ser His Ser Ser Gly Ser Phe Ser Ser His Gly Gly Ser
            740                 745                 750

Ser Phe Gly Ser Ser Phe Ala Ser Ser Ala Ser Ser Ser Ser Ser
        755                 760                 765

Ser Gly Gly Gly Phe Ser Thr Gly Pro Leu Ser Ser Tyr Ser Ala Pro
    770                 775                 780

Ala Ala Pro Ser Ser Tyr Gly Ala Pro Ser Glu Pro Ser Ser Ser
785                 790                 795                 800

Tyr Gly Ala Pro Ser Gln Asp Ser Gly Tyr Ser Tyr Ser Ala Pro Ser
                805                 810                 815

Gln Val Pro Glu Thr Ile Gln Gln Gly Tyr Ser Ser Asn Gly Gly Tyr
            820                 825                 830

Thr Tyr Arg Lys
            835
```

<210> SEQ ID NO 41
<211> LENGTH: 605
<212> TYPE: PRT
<213> ORGANISM: Drosophila grimshawi

<400> SEQUENCE: 41

```
Met Phe Lys Leu Phe Gly Leu Met Leu Leu Leu Thr Thr Ala Val Leu
1               5                   10                  15

Ala Arg Pro Glu Pro Pro Val Asn Thr Tyr Leu Pro Pro Thr Pro Gly
            20                  25                  30

Asp Ser Tyr Gly Ala Pro Gly Gln Gly Gln Gly Ala Gln Gly Gly
        35                  40                  45

Arg Pro Ser Ser Ser Tyr Gly Ala Pro Gly Gln Gly Gln Gly Gln Gly
    50                  55                  60

Gln Pro Gly Phe Gly Gly Lys Pro Ser Asp Ser Tyr Gly Ala Pro Ala
65                  70                  75                  80

Ala Gly Asn Gly Asn Gly Asn Gly Asn Gly Arg Pro Ser Ser Ser Tyr
                85                  90                  95

Gly Ala Pro Gly Gln Ser Gln Gly Gln Asn Gly Phe Gly Gly Arg Pro
            100                 105                 110

Ser Ser Ser Tyr Gly Ala Pro Gly Gln Gly Ala Ala Gly Asn Gly Asn
        115                 120                 125

Gly Asn Gly Asn Gly Arg Pro Ser Ser Ser Tyr Gly Ala Pro Gly Gln
    130                 135                 140

Gly Gln Gly Gln Ala Gly Arg Pro Ser Asp Ser Tyr Gly Ala Pro Ala
145                 150                 155                 160

Gly Gly Asn Gly Asn Gly Asn Gly Asn Gly Arg Pro Ser Ser Ser Tyr
                165                 170                 175

Gly Ala Pro Gly Gln Gly Gln Gly Gln Gly Gly Phe Gly Gly Ala Ser
            180                 185                 190

Gly Ala Gly Asn Gly Asn Gly Asn Val Arg Pro Ser Ser Ser Tyr Gly
    195                 200                 205

Ala Pro Gly Gln Gly Gln Gly Gly Arg Pro Ser Asp Ser Tyr Gly Ala
210                 215                 220

Pro Gly Ala Gly Asn Gly Asn Gly Arg Pro Ser Ser Ser Tyr Gly Ala
225                 230                 235                 240

Pro Gly Gln Ala Gln Gly Gly Phe Gly Gly Lys Pro Ser Asp Ser Tyr
                245                 250                 255

Gly Ala Pro Gly Ala Gly Ala Pro Gly Gln Gly Gln Gly Thr Gly Gly
            260                 265                 270

Phe Gly Gly Lys Pro Ser Asp Ser Tyr Gly Pro Pro Ala Ser Gly
    275                 280                 285

Ala Gly Ala Gly Gly Pro Gly Gly Ala Gly Ala Gly Gly Asp
290                 295                 300

Tyr Asn Asn Asp Glu Pro Ala Lys Tyr Glu Phe Asn Tyr Gln Val Glu
305                 310                 315                 320

Asp Ala Pro Ser Gly Leu Ser Phe Gly His Ser Glu Met Arg Asp Gly
                325                 330                 335

Asp Phe Thr Thr Gly Gln Tyr Asn Val Leu Leu Pro Asp Gly Arg Lys
            340                 345                 350

Gln Ile Val Glu Tyr Glu Ala Asp Gln Gln Gly Tyr Arg Pro Gln Ile
    355                 360                 365

Arg Tyr Glu Gly Asp Ala Asn Gly Ala Gly Ala Gly Gly Ala Gly
370                 375                 380

Gly Ala Gly Gly Gln Asp Leu Gly Gln Ala Gly Tyr Ser Ser Gly Arg
```

```
                385                 390                 395                 400
Pro Gly Gly Gln Asp Leu Gly Gln Asn Gly Tyr Ser Gly Gly Arg Pro
                    405                 410                 415
Gly Gly Gln Asp Leu Gly Gln Asn Gly Tyr Ser Ser Gly Arg Pro Gly
            420                 425                 430
Gly Gln Asn Gly Tyr Ser Gly Gly Arg Pro Gly Gly Gln Asp Ala Ala
        435                 440                 445
Gln Gly Gly Tyr Ser Gly Gly Arg Pro Gly Gly Gln Asp Leu Gly Gln
    450                 455                 460
Asn Gly Tyr Ser Gly Gly Arg Pro Gly Gly Gln Asp Leu Gly Gln Asn
465                 470                 475                 480
Gly Tyr Ser Gly Gly Arg Pro Gly Gly Gln Asp Leu Gly Gln Asn Gly
                485                 490                 495
Tyr Ser Gly Gly Arg Pro Gly Gly Gln Asp Leu Gly Pro Asn Gly Tyr
            500                 505                 510
Ser Ser Gly Arg Pro Gly Gly Asn Gly Asn Asp Asn Gly Asn Gly Gly
        515                 520                 525
Ser Asp Gly Gly Arg Val Ile Ile Arg Gly Arg Val Thr Gly Gln Asp
    530                 535                 540
Gly Gly Asp Gly Gln Gly Tyr Ser Gly Gly Arg Pro Ser Gly Gln Asn
545                 550                 555                 560
Gly Gly Asn Gly Gln Asp Asn Ile Asp Gly Arg Gly Tyr Ser Ser Gly
                565                 570                 575
Arg Pro Gly Gln Gly Gln Gly Gln Gly Arg Asn Gly Phe Gly Pro Gly
            580                 585                 590
Gly Gln Asn Gly Asp Asn Asp Gly Ser Gly Tyr Arg Tyr
        595                 600                 605

<210> SEQ ID NO 42
<211> LENGTH: 605
<212> TYPE: PRT
<213> ORGANISM: Drosophila willistoni

<400> SEQUENCE: 42

Met Phe Lys Leu Leu Gly Leu Met Leu Leu Val Thr Ala Val Leu Ala
1               5                   10                  15
Arg Pro Glu Pro Pro Val Asn Ser Tyr Leu Pro Pro Ser Asp Ser Tyr
                20                  25                  30
Gly Ala Pro Asp Ala Asn Gly Gly Gly Ser Gly Gly Arg Pro Ser
            35                  40                  45
Asp Ser Tyr Gly Ala Pro Gly Asn Gly Asn Gly Asn Asn Gly Gly Gly
    50                  55                  60
Arg Pro Ser Ser Ser Tyr Gly Ala Pro Gly Gln Gly Gly Gln Gly Gln
65                  70                  75                  80
Gly Gly Phe Gly Gly Arg Pro Ser Asp Ser Tyr Gly Ala Pro Gly Asn
                85                  90                  95
Gly Asn Asn Gly Gly Gly Arg Pro Ser Ser Ser Tyr Gly Ala Pro Gly
            100                 105                 110
Gln Gly Gly Pro Gly Gly Gly Leu Gly Gly Lys Pro Ser Asp Thr Tyr
        115                 120                 125
Gly Ala Pro Gly Asn Gly Asn Asn Gly Gly Arg Pro Ser Ser Ser
    130                 135                 140
Tyr Gly Ala Pro Gly Gln Gly Gly Gln Gly Gln Gly Gly Ile Gly Gly
145                 150                 155                 160
Arg Pro Ser Asp Ser Tyr Gly Ala Pro Gly Asn Gly Asn Asn Gly Gly
```

-continued

```
                165                 170                 175
Gly Arg Pro Ser Ser Ser Tyr Gly Ala Pro Gly Gln Gly Gly Pro Gly
                180                 185                 190
Gly Lys Pro Ser Asp Thr Tyr Gly Ala Pro Gly Asn Gly Asn Asn Gly
                195                 200                 205
Gly Gly Arg Pro Ser Ser Ser Tyr Gly Ala Pro Gly Gln Gly Gly Gln
                210                 215                 220
Gly Gln Gly Gly Phe Gly Gly Arg Pro Ser Asp Ser Tyr Gly Ala Pro
225                 230                 235                 240
Gly Asn Gly Asn Gly Gly Arg Pro Ser Ser Tyr Gly Ala Pro
                245                 250                 255
Gly Gln Gly Gly Gln Gly Gly Leu Gly Gly Lys Pro Ser Asp Thr
                260                 265                 270
Tyr Gly Ala Pro Gly Asn Gly Asn Asn Gly Gly Arg Pro Ser Ser
            275                 280                 285
Ser Tyr Gly Ala Pro Gly Gln Gly Gly Gln Gly Gly Phe Gly
        290                 295                 300
Gly Arg Pro Ser Asp Ser Tyr Gly Pro Pro Ala Ser Gly Ala Gly Ala
305                 310                 315                 320
Gly Gly Gly Ala Gly Gly Asn Gly Asn Gly Ala Asp Tyr Asp Asn Asp
                325                 330                 335
Glu Pro Ala Lys Tyr Glu Phe Asn Tyr Gln Val Glu Asp Ala Pro Ser
                340                 345                 350
Gly Leu Ser Phe Gly His Ser Glu Met Arg Asp Gly Asp Phe Thr Thr
                355                 360                 365
Gly Gln Tyr Asn Val Leu Leu Pro Asp Gly Arg Lys Gln Ile Val Glu
                370                 375                 380
Tyr Glu Ala Asp Gln Gln Gly Tyr Arg Pro Gln Ile Arg Tyr Glu Gly
385                 390                 395                 400
Asp Ala Asn Asp Gly Ser Gly Ser Gly Ser Thr Gly Pro Gly Gly
                405                 410                 415
Gln Ser Leu Gly Ala Asp Gly Tyr Ser Ser Gly Arg Pro Gly Asn Gly
                420                 425                 430
Asn Gly Gly Gly Tyr Ser Gly Gly Arg Pro Gly Gly Gln Asp Leu
            435                 440                 445
Gly Gln Asn Gly Tyr Ser Ser Gly Arg Pro Gly Gly Asn Gly Asn Gly
                450                 455                 460
Asn Gly Asp Gly Gly Tyr Pro Gly Gly Arg Pro Gly Gly Gln Asp Leu
465                 470                 475                 480
Gly Gln Gly Gly Tyr Ser Ser Gly Arg Pro Gly Ser Asn Gly Asn Gly
                485                 490                 495
Asn Gly Gly Asp Gly Gly Arg Val Ile Ile Gly Gly Arg Val Ile Gly
                500                 505                 510
Gln Asp Asn Asn Asp Gly Gln Gly Tyr Ser Gly Arg Pro Gly Gly
            515                 520                 525
Gln Gly Gln Asp Phe Gly Ala Gly Gly Tyr Ser Ser Gly Arg Pro Gly
        530                 535                 540
Gly Gln Gly Gln Asp Leu Asn Gly Gln Asn Gly Tyr Ser Ser Gly Arg
545                 550                 555                 560
Pro Gly Gly Arg Ser Asn Asp Gln Asp Asn Asp Gly Gln Gly Tyr Ser
                565                 570                 575
Ser Gly Lys Pro Gly Gln Gly Arg Asn Gly Asn Gly Phe Gly Pro Gly
                580                 585                 590
```

-continued

Gly Gln Asn Gly Asp Asn Asp Gly Ser Gly Tyr Arg Tyr
            595                 600                 605

<210> SEQ ID NO 43
<211> LENGTH: 587
<212> TYPE: PRT
<213> ORGANISM: Drosophila ananassae

<400> SEQUENCE: 43

Met Phe Lys Leu Leu Gly Leu Thr Leu Leu Met Ala Val Met Val Leu
1               5                   10                  15

Gly Arg Pro Glu Pro Pro Val Asn Ser Tyr Leu Pro Pro Ser Asp Ser
            20                  25                  30

Tyr Gly Ala Pro Gly Gln Ser Gly Pro Gly Gly Arg Pro Ser Asp Ser
        35                  40                  45

Tyr Gly Ala Pro Gly Gly Ser Gly Gly Arg Pro Ser Asp Ser Tyr
    50                  55                  60

Gly Ala Pro Gly Leu Gly Gly Gln Gly Gly Phe Gly Gly Lys
65                  70                  75                  80

Pro Ser Asp Ser Tyr Gly Ala Pro Gly Asn Gly Asn Gly Asn
                85                  90                  95

Gly Asn Gly Gly Arg Pro Ser Ser Ser Tyr Gly Ala Pro Gly Leu Gly
                100                 105                 110

Gly Gly Gln Gly Gly Gly Phe Gly Gly Lys Pro Ser Asp Ser Tyr Gly
            115                 120                 125

Ala Pro Gly Ser Gly Asn Gly Asn Gly Gly Arg Pro Ser Ser Ser Tyr
        130                 135                 140

Gly Ala Pro Gly Gln Gly Gln Gly Gly Tyr Ser Asn Gly Gly Asn Gly
145                 150                 155                 160

Asn Gly Asn Gly Asn Gly Gly Arg Pro Ser Ser Thr Tyr Gly Ala Pro
                165                 170                 175

Gly Gln Gly Arg Pro Ser Asp Thr Tyr Gly Ala Pro Gly Gln Gly Gly
            180                 185                 190

Asn Gly Gly Arg Pro Ser Asp Ser Tyr Gly Ala Pro Gly Gln Gly Gly
        195                 200                 205

Asn Gly Gly Arg Pro Ser Asp Ser Tyr Gly Ala Pro Gly Gln Gly Gly
    210                 215                 220

Asn Gly Gly Arg Pro Ser Ser Ser Tyr Gly Ala Pro Gly Gln Gly Gln
225                 230                 235                 240

Gly Gly Gln Gly Gly Phe Gly Gly Arg Pro Ser Asp Thr Tyr Gly Ala
                245                 250                 255

Pro Gly Gln Asn Gly Asn Gly Arg Pro Ser Ser Ser Tyr Gly Ala
            260                 265                 270

Pro Gly Ser Gly Pro Gly Gly Arg Pro Ser Asp Ser Tyr Gly Pro Pro
        275                 280                 285

Ala Ser Gly Ala Gly Ala Gly Gly Ala Gly Gly Ser Gly Pro Gly Leu
    290                 295                 300

Pro Gly Gly Gly Gly Ala Asp Tyr Asp Asn Asp Glu Pro Ala Lys Tyr
305                 310                 315                 320

Glu Phe Asn Tyr Gln Val Glu Asp Ala Pro Ser Gly Leu Ser Phe Gly
                325                 330                 335

His Ser Glu Met Arg Asp Gly Asp Phe Thr Thr Gly Gln Tyr Asn Val
            340                 345                 350

Leu Leu Pro Asp Gly Arg Lys Gln Ile Val Glu Tyr Glu Ala Asp Gln
        355                 360                 365

-continued

```
Gln Gly Tyr Arg Pro Gln Ile Arg Tyr Glu Gly Asp Ala Asn Asp Gly
    370                 375                 380

Ser Gly Ala Ser Gly Pro Gly Gly Gln Asn Leu Gly Pro Asp Gly Tyr
385                 390                 395                 400

Ser Asn Gly Arg Pro Gly Asn Gly Asn Gly Asn Gly Asn Gly Asn Gly
                405                 410                 415

Asn Gly Gly Tyr Ser Gly Gly Arg Pro Gly Gly Gln Asp Leu Gly Pro
            420                 425                 430

Gly Gly Tyr Ser Asn Gly Arg Pro Gly Gly Gln Asp Phe Gly Pro Ser
        435                 440                 445

Gly Tyr Ser Gly Gly Arg Pro Gly Gly Gln Asp Leu Gly Ala Gly Gly
    450                 455                 460

Tyr Ser Asn Gly Arg Pro Gly Gly Gln Asp Phe Gly Pro Gly Gly Tyr
465                 470                 475                 480

Ser Ser Gly Arg Pro Gly Gly Asn Gly Asn Gly Asn Gly Asn Gly Asn
                485                 490                 495

Gly Asn Gly Asn Gly Asp Gly Arg Val Ile Ile Gly Gly Arg Val Ile
            500                 505                 510

Gly Gly Gln Asp Gly Gly Asp Gln Gly Tyr Ser Gly Gly Arg Pro Gly
        515                 520                 525

Gly Gln Asp Leu Gly Arg Asp Gly Tyr Ser Ser Gly Arg Pro Gly Gly
    530                 535                 540

Gly Arg Ser Asn Gly Gln Asp Asn Gln Asp Gly Gln Gly Tyr Ser Ser
545                 550                 555                 560

Gly Lys Pro Gly Gly Gln Gly Arg Asn Gly Phe Gly Pro Gly Gly Gln
                565                 570                 575

Asn Gly Asp Asn Asp Gly Ser Gly Tyr Arg Tyr
            580                 585

<210> SEQ ID NO 44
<211> LENGTH: 805
<212> TYPE: PRT
<213> ORGANISM: Culex quinquefasciatus

<400> SEQUENCE: 44

Met Arg Met His His Lys Leu Thr Ala Leu Ala Val Leu Cys Cys Ala
1               5                   10                  15

Leu Gly Pro Ala Phe Ala Ala Ser Val Thr Lys Arg Glu Ala Pro Leu
            20                  25                  30

Pro Gly Gly Ser Tyr Leu Pro Pro Ser Asn Gly Gly Ala Gly Gly
        35                  40                  45

Tyr Pro Ala Ala Gly Pro Pro Ser Gly Ser Tyr Gly Pro Pro Ser Asn
50                  55                  60

Gly Asn Gly Asn Gly Asn Gly Ala Gly Gly Tyr Pro Ser Ala Pro Ser
65                  70                  75                  80

Gln Gln Tyr Gly Ala Pro Ala Gly Gly Ala Pro Ser Gln Gln Tyr Gly
            85                  90                  95

Ala Pro Ser Asn Gly Asn Gly Gly Ala Gly Gly Tyr Pro Ser Ala Pro
                100                 105                 110

Ser Gln Gln Tyr Gly Ala Pro Asn Gly Asn Gly Asn Gly Gly Phe Gly
            115                 120                 125

Gly Arg Pro Gln Ala Pro Ser Gln Gln Tyr Gly Ala Pro Ser Asn Gly
        130                 135                 140

Asn Gly Gly Ala Arg Pro Ser Gln Gln Tyr Gly Ala Pro Asn Gly Gly
145                 150                 155                 160
```

```
Asn Gly Asn Gly Arg Pro Gln Thr Pro Ser Ser Gln Tyr Gly Ala Pro
            165                 170                 175

Ser Gly Gly Ala Pro Ser Ser Gln Tyr Gly Ala Pro Ser Gly Gly Ala
            180                 185                 190

Pro Ser Gln Gln Tyr Gly Ala Pro Asn Gly Gly Asn Gly Asn Gly Arg
            195                 200                 205

Pro Gln Thr Pro Ser Ser Gln Tyr Gly Ala Pro Ser Gly Gly Ala Pro
            210                 215                 220

Ser Gln Gln Tyr Gly Ala Pro Asn Gly Gly Asn Gly Asn Gly Arg Pro
225                 230                 235                 240

Gln Thr Pro Ser Ser Gln Tyr Gly Ala Pro Ser Gly Gly Ala Pro Ser
            245                 250                 255

Ser Gln Tyr Gly Ala Pro Ser Gly Gly Ala Pro Ser Ser Gln Tyr Gly
            260                 265                 270

Ala Pro Ala Gly Gly Ala Pro Ser Ser Gln Tyr Gly Ala Pro Ala Gly
            275                 280                 285

Gly Ala Pro Ser Ser Gln Tyr Gly Ala Pro Ala Gly Gly Ala Pro Ser
            290                 295                 300

Ser Gln Tyr Gly Ala Pro Ala Gly Gly Ala Pro Ser Ser Gln Tyr Gly
305                 310                 315                 320

Ala Pro Ala Gly Gly Ala Pro Ser Ser Gln Tyr Gly Ala Pro Ser Ser
            325                 330                 335

Gln Tyr Gly Ala Pro Ala Gly Gly Ala Pro Ser Ser Gln Tyr Gly Ala
            340                 345                 350

Pro Ala Gly Gly Ala Pro Ser Ser Gln Tyr Gly Ala Pro Ser Gly Gly
            355                 360                 365

Ala Pro Ser Ser Gln Tyr Gly Ala Pro Ser Gly Gly Ala Pro Ser Ser
            370                 375                 380

Gln Tyr Gly Ala Pro Ala Gly Gly Ala Pro Ser Ser Gln Tyr Gly Ala
385                 390                 395                 400

Pro Ser Gly Gly Ala Pro Ser Ser His Met Ala Leu His Leu Val Val
            405                 410                 415

Pro His Leu Ser Asn Thr Val Pro Arg Lys Thr Asp Ser Arg Val Lys
            420                 425                 430

Asp His Gln Pro Leu Ala Thr Glu Ser Gln Leu Asp His Leu Thr Glu
            435                 440                 445

Thr Asp Leu Glu Asp Ala His Arg Ala Ser Met Val Pro Gln Pro Pro
            450                 455                 460

Glu Glu Thr Glu Thr Glu Val Ala His Arg Ala Ser Thr Val Pro Gln
465                 470                 475                 480

Leu Arg Glu Glu Thr Glu Thr Val Asp Thr Ala Thr Val Met Val Asp
            485                 490                 495

Ala Leu Gln Ala Ser Met Val Pro Gln Leu Gln Glu Ala Thr Ala Thr
            500                 505                 510

Val Asp Ala Leu Gln Ala Ser Met Val Pro Gln Leu Gln Val Val Thr
            515                 520                 525

Ala Thr Val Asp Ala His Gln Ala Asn Thr Val Pro Gln Leu Gln Val
            530                 535                 540

Glu Thr Glu Thr Asp Ala Gln Ala Ser Arg Thr Glu Pro Gln Val Pro
545                 550                 555                 560

Val Leu Leu Leu Pro Asn Met Ala Leu Leu Leu Leu Arg Leu Ser
            565                 570                 575

Met Val Pro Gln Leu Gln Val Val Thr Glu Met Val Asp Ala His Gln
            580                 585                 590
```

```
Ala Asn Thr Val Pro Gln Leu Gln Val Glu Thr Glu Thr Asp Ala Gln
            595                 600                 605

Ala Ser Arg Thr Glu Leu Gln Val Pro Val Leu Leu Leu Pro Asn Met
        610                 615                 620

Ala Leu Leu Leu Leu Leu Arg Leu Ser Met Val Pro Gln Leu Gln Val
625                 630                 635                 640

Val Thr Glu Thr Val Asp Ala His Gln Ala Asn Thr Val Pro Gln Leu
                645                 650                 655

Gln Val Glu Thr Glu Thr Asp Ala Gln Ala Ser Arg Thr Ala Pro Gln
                660                 665                 670

Val Pro Val Leu Leu Leu Pro Asn Met Ala Leu Leu Leu Leu Pro Arg
            675                 680                 685

Leu Ser Thr Val Leu Leu Arg Leu His Arg Arg Asn Met Val Pro Arg
        690                 695                 700

Ala Thr Val Thr Ala Thr Ala Ala Pro Glu Thr Ala Thr Arg
705                 710                 715                 720

Arg Ala Arg Ser Pro Pro Ala Ala Ser Arg Pro Thr Val Glu Ala Ala
                725                 730                 735

Ala Ala Pro Asp Thr Ala Arg Ala Asp Pro Thr Val Asp His Pro Ser
            740                 745                 750

Arg Pro Pro Ser Leu Ser His Thr Leu Lys Ala Glu Ala Thr Thr Thr
        755                 760                 765

Lys Leu Gly Leu Arg Thr Lys Pro Gln Thr Leu Leu Arg Thr Ile Asn
            770                 775                 780

Gly Ile Pro Arg Thr Ala Ser His Ala Pro Gln Met Asn Met Cys Leu
785                 790                 795                 800

Lys Thr Cys Met Ile
            805

<210> SEQ ID NO 45
<211> LENGTH: 567
<212> TYPE: PRT
<213> ORGANISM: Tribolium castaneum

<400> SEQUENCE: 45

Met Asp Lys His Phe Leu Val Leu Val Leu Thr Trp Ser Ala Phe Val
1               5                   10                  15

Arg Ala Glu Pro Pro Val Asn Ser Tyr Leu Pro Pro Ser Gln Asn Gly
            20                  25                  30

Gly Pro Ser Ser Thr Tyr Gly Pro Pro Gly Phe Gln Pro Gly Thr Pro
        35                  40                  45

Leu Gly Gly Gly Asn Gly His Pro Pro Ser Gln Gly Gly Asn
    50                  55                  60

Gly Gly Phe Gly Gly Arg His Pro Asp Ser Asp Gln Arg Pro Gly Thr
65              70                  75                  80

Ser Tyr Leu Pro Pro Gly Gln Asn Gly Gly Ala Gly Arg Pro Gly Val
                85                  90                  95

Thr Tyr Gly Pro Pro Gly Gln Gly Gly Gln Asn Gly Gly Pro
            100                 105                 110

Ser Ser Thr Tyr Gly Pro Pro Gly Gln Gly Gly Asn Gly Phe Gly Gly
        115                 120                 125

Gly Gln Asn Gly Gly Arg Leu Ser Ser Thr Tyr Gly Pro Pro Gly Gln
    130                 135                 140

Gly Gly Asn Gly Phe Gly Gly Gly Gln Asn Gly Gly Arg Pro Ser Ser
145                 150                 155                 160
```

```
Thr Tyr Gly Pro Pro Gly Gln Gly Gly Asn Gly Phe Gly Gly Gln
            165                 170                 175

Asn Gly Gly Arg Pro Ser Ser Thr Tyr Gly Pro Pro Gly Gln Gly Gly
            180                 185                 190

Asn Gly Phe Gly Gly Gln Asn Gly Gly Arg Pro Ser Ser Thr Tyr
            195                 200                 205

Gly Pro Pro Gly Gln Gly Gly Asn Gly Phe Gly Gly Gln Asn Gly
    210                 215                 220

Gly Arg Pro Ser Ser Thr Tyr Gly Pro Pro Gly Gln Gly Gly Asn Gly
225                 230                 235                 240

Phe Gly Gly Gln Asn Gly Gly Arg Pro Ser Ser Thr Tyr Gly Pro
                245                 250                 255

Pro Gly Gln Gly Gly Asn Gly Phe Gly Gly Gln Asn Gly Gly Lys
                260                 265                 270

Pro Ser Ser Thr Tyr Gly Pro Pro Gly Gln Gly Gly Asn Gly Phe Gly
        275                 280                 285

Gly Gly Gln Asn Gly Gly Arg Pro Ser Ser Thr Tyr Gly Pro Pro Gly
        290                 295                 300

Gln Gly Gly Asn Gly Asn Gly Gly His Asn Gly Gln Arg Pro Gly
305                 310                 315                 320

Gly Ser Tyr Leu Pro Pro Ser Gln Gly Gly Asn Gly Gly Tyr Pro Ser
                325                 330                 335

Gly Gly Pro Gly Gly Tyr Pro Ser Gly Gly Pro Gly Asn Gly Gly
            340                 345                 350

Tyr Gly Gly Glu Glu Glu Ser Thr Glu Pro Ala Lys Tyr Glu Phe Glu
            355                 360                 365

Tyr Gln Val Asp Asp Glu His Asn Thr His Phe Gly His Gln Glu
    370                 375                 380

Ser Arg Asp Gly Asp Lys Ala Thr Gly Glu Tyr Asn Val Leu Leu Pro
385                 390                 395                 400

Asp Gly Arg Lys Gln Val Val Gln Tyr Glu Ala Asp Ser Glu Gly Tyr
                405                 410                 415

Lys Pro Lys Ile Ser Tyr Glu Gly Gly Asn Gly Asn Gly Gly Tyr Pro
                420                 425                 430

Ser Gly Gly Pro Gly Gly Ala Gly Asn Gly Gly Tyr Pro Ser Gly Gly
            435                 440                 445

Pro Gln Gly Gly Asn Gly Gly Tyr Pro Ser Gly Gly Pro Gln Gly Gly
            450                 455                 460

Asn Gly Gly Tyr Pro Ser Gly Gly Pro Gln Gly Gly Asn Gly Gly Tyr
465                 470                 475                 480

Pro Ser Gly Gly Pro Gln Gly Gly Asn Gly Gly Tyr Pro Ser Gly Gly
                485                 490                 495

Pro Gln Gly Gly Asn Gly Gly Tyr Pro Ser Gly Gly Pro Gln Gly Gly
            500                 505                 510

Asn Gly Gly Tyr Pro Ser Gly Gly Pro Gln Gly Gly Asn Gly Gly Tyr
        515                 520                 525

Pro Ser Gly Gly Pro Gln Gly Gly Asn Gly Gly Tyr Thr Ser Gly Gly
        530                 535                 540

Pro Gln Gly Gly Asn Gly Gly Tyr Pro Ser Gly Gly Pro Gln Gly Gly
545                 550                 555                 560

Asn Gly Gly Ser Gly Pro Tyr
            565
```

-continued

```
<210> SEQ ID NO 46
<211> LENGTH: 467
<212> TYPE: PRT
<213> ORGANISM: Tribolium castaneum

<400> SEQUENCE: 46
```

| | | | | | | | | | | | | | | | |
|---|---|---|---|---|---|---|---|---|---|---|---|---|---|---|---|
| Met | Ser | Ser | Phe | Lys | Leu | Val | Ser | Cys | Thr | Leu | Ala | Leu | Cys | Cys | Leu |
| 1 | | | | 5 | | | | | 10 | | | | | 15 | |
| Leu | Asn | Gly | Ser | Leu | Gly | Gly | Gln | Leu | Thr | Lys | Arg | Asp | Ala | Pro | Leu |
| | | | 20 | | | | | 25 | | | | | 30 | | |
| Ser | Gly | Gly | Tyr | Pro | Ser | Gly | Gly | Pro | Ala | Asn | Ser | Tyr | Leu | Pro | Pro |
| | | 35 | | | | | 40 | | | | | 45 | | | |
| Gly | Gly | Ala | Ser | Gln | Pro | Ser | Gly | Asn | Tyr | Gly | Ala | Pro | Ser | Gly | Gly |
| 50 | | | | | 55 | | | | | 60 | | | | | |
| Phe | Gly | Gly | Lys | Ser | Gly | Gly | Phe | Gly | Gly | Ser | Gly | Gly | Phe | Gly | Gly |
| 65 | | | | | 70 | | | | | 75 | | | | | 80 |
| Ala | Pro | Ser | Gln | Ser | Tyr | Gly | Ala | Pro | Ser | Gly | Gly | Phe | Gly | Gly | Ser |
| | | | | 85 | | | | | 90 | | | | | 95 | |
| Ser | Ser | Phe | Gly | Lys | Ser | Gly | Gly | Phe | Gly | Gly | Ala | Pro | Ser | Gln | Ser |
| | | | 100 | | | | | 105 | | | | | 110 | | |
| Tyr | Gly | Ala | Pro | Ser | Gly | Gly | Phe | Gly | Gly | Ser | Ser | Ser | Phe | Gly | Lys |
| | | | 115 | | | | | 120 | | | | | 125 | | |
| Ser | Ser | Gly | Gly | Phe | Gly | Gly | Ala | Pro | Ser | Gln | Ser | Tyr | Gly | Ala | Pro |
| 130 | | | | | 135 | | | | | 140 | | | | | |
| Ser | Gly | Gly | Phe | Gly | Gly | Ser | Ser | Ser | Phe | Gly | Lys | Ser | Gly | Gly | Phe |
| 145 | | | | | 150 | | | | | 155 | | | | | 160 |
| Gly | Gly | Ala | Pro | Ser | Gln | Ser | Tyr | Gly | Ala | Pro | Ser | Gly | Gly | Phe | Gly |
| | | | | 165 | | | | | 170 | | | | | 175 | |
| Gly | Ser | Ser | Ser | Phe | Gly | Lys | Ser | Gly | Gly | Phe | Gly | Gly | Ala | Pro | Ser |
| | | | 180 | | | | | 185 | | | | | 190 | | |
| Gln | Ser | Tyr | Gly | Ala | Pro | Ser | Gly | Gly | Phe | Gly | Gly | Lys | Ser | Ser | Ser |
| | | | 195 | | | | | 200 | | | | | 205 | | |
| Phe | Ser | Ser | Ala | Pro | Ser | Gln | Ser | Tyr | Gly | Ala | Pro | Ser | Gly | Gly | Phe |
| 210 | | | | | 215 | | | | | 220 | | | | | |
| Gly | Gly | Lys | Ser | Gly | Gly | Phe | Gly | Gly | Ala | Pro | Ser | Gln | Ser | Tyr | Gly |
| 225 | | | | | 230 | | | | | 235 | | | | | 240 |
| Ala | Pro | Ser | Gly | Gly | Phe | Gly | Gly | Lys | Ser | Gly | Gly | Phe | Gly | Gly | Ala |
| | | | | 245 | | | | | 250 | | | | | 255 | |
| Pro | Ser | Gln | Ser | Tyr | Gly | Ala | Pro | Ser | Gly | Gly | Phe | Gly | Gly | Ser | Ser |
| | | | 260 | | | | | 265 | | | | | 270 | | |
| Ser | Phe | Gly | Lys | Ser | Gly | Gly | Phe | Gly | Gly | Ala | Pro | Ser | Gln | Ser | Tyr |
| | | | 275 | | | | | 280 | | | | | 285 | | |
| Gly | Ala | Pro | Ser | Gly | Gly | Phe | Gly | Gly | Ser | Ser | Ser | Phe | Gly | Lys | Ser |
| | | | | 290 | | | | | 295 | | | | | 300 | |
| Ser | Gly | Phe | Gly | His | Gly | Ser | Gly | Ala | Pro | Ser | Gln | Ser | Tyr | Gly | Ala |
| 305 | | | | | 310 | | | | | 315 | | | | | 320 |
| Pro | Ser | Arg | Ser | Gln | Pro | Gln | Ser | Asn | Tyr | Leu | Pro | Pro | Ser | Thr | Ser |
| | | | 325 | | | | | 330 | | | | | 335 | | |
| Tyr | Gly | Thr | Pro | Val | Ser | Ser | Ala | Lys | Ser | Ser | Gly | Ser | Phe | Gly | Gly |
| | | | 340 | | | | | 345 | | | | | 350 | | |
| Ala | Pro | Ser | Gln | Ser | Tyr | Gly | Ala | Pro | Ser | Gln | Ser | His | Ala | Pro | Ser |
| | | | 355 | | | | | 360 | | | | | 365 | | |
| Gln | Ser | Tyr | Gly | Ala | Pro | Ser | Arg | Ser | Phe | Ser | Gln | Ala | Pro | Ser | Gln |
| | | | 370 | | | | | 375 | | | | | 380 | | |
| Ser | Tyr | Gly | Ala | Pro | Ser | Gln | Gly | His | Ala | Pro | Ala | Pro | Gln | Gln | Ser |

-continued

```
            385                 390                 395                 400
Tyr Ser Ala Pro Ser Gln Ser Tyr Gly Ala Pro Ser Gly Gly Phe Gly
                405                 410                 415

Gly Gly His Gly Gly Phe Gly Gly Gln Gly Gln Gly Phe Gly Gly Gly
            420                 425                 430

Arg Ser Gln Pro Ser Gln Ser Tyr Gly Ala Pro Ala Pro Ser Gln Ser
            435                 440                 445

Tyr Gly Ala Pro Ser Ala Gly Gly Gln Gln Tyr Ala Ser Asn Gly Gly
            450                 455                 460

Tyr Ser Tyr
465

<210> SEQ ID NO 47
<211> LENGTH: 492
<212> TYPE: PRT
<213> ORGANISM: Apis mellifera

<400> SEQUENCE: 47

Met Tyr Pro Tyr Leu Asn Gln His Pro Thr Leu Pro Pro Val Phe
1               5                   10                  15

Ser Thr Ser Ser Pro Ile Ala Gln Thr Phe Cys Ile Gln Asp Met Ser
                20                  25                  30

Val Cys Thr His Trp Thr Phe Arg Ser Ser His Pro Phe Lys Phe Arg
            35                  40                  45

Ser Phe Arg Leu Gln Ile Gly Leu Ala Val Phe Val Leu Ala Leu Thr
        50                  55                  60

Leu Val Arg Ser Glu Pro Pro Val Asn Ser Tyr Leu Pro Pro Ser Gly
65                  70                  75                  80

Asn Gly Asn Gly Gly Gly Gly Gly Ser Ser Asn Val Tyr Gly Pro
                85                  90                  95

Pro Gly Phe Asp Gly Gln Asn Gly Ile Gly Glu Gly Asp Asn Gly Arg
            100                 105                 110

Asn Gly Ile Ser Asn Ser Tyr Gly Val Pro Thr Gly Gly Asn Gly Tyr
        115                 120                 125

Asn Gly Asp Ser Ser Gly Asn Gly Arg Pro Gly Thr Asn Gly Gly Arg
    130                 135                 140

Asn Gly Asn Gly Asn Gly Arg Gly Asn Gly Tyr Gly Gly Gly Gln Pro
145                 150                 155                 160

Ser Asn Ser Tyr Gly Pro Pro Ser Asn Gly His Gly Gly Asn Gly Ala
                165                 170                 175

Gly Arg Pro Ser Ser Tyr Gly Ala Pro Gly Gly Gly Asn Gly Phe
            180                 185                 190

Ala Gly Gly Ser Asn Gly Lys Asn Gly Phe Gly Gly Pro Ser Ser
        195                 200                 205

Ser Tyr Gly Pro Pro Glu Asn Gly Asn Gly Phe Asn Gly Gly Asn Gly
    210                 215                 220

Gly Pro Ser Gly Leu Tyr Gly Pro Pro Gly Arg Asn Gly Gly Asn Gly
225                 230                 235                 240

Gly Asn Gly Gly Asn Gly Gly Arg Pro Ser Gly Ser Tyr Gly Thr Pro
                245                 250                 255

Glu Arg Asn Gly Gly Arg Leu Gly Gly Leu Tyr Gly Ala Pro Gly Arg
            260                 265                 270

Asn Gly Asn Asn Gly Gly Asn Gly Tyr Pro Ser Gly Gly Leu Asn Gly
        275                 280                 285

Gly Asn Gly Gly Tyr Pro Ser Gly Gly Pro Gly Asn Gly Gly Ala Asn
```

```
                    290                 295                 300
Gly Gly Tyr Pro Ser Gly Gly Ser Asn Gly Asp Asn Gly Gly Tyr Pro
305                 310                 315                 320

Ser Gly Gly Pro Asn Gly Asn Gly Asn Gly Asn Gly Gly Tyr Gly Gln
                    325                 330                 335

Asp Glu Asn Asn Glu Pro Ala Lys Tyr Glu Phe Ser Tyr Glu Val Lys
                340                 345                 350

Asp Glu Gln Ser Gly Ala Asp Tyr Gly His Thr Glu Ser Arg Asp Gly
                355                 360                 365

Asp Arg Ala Gln Gly Glu Phe Asn Val Leu Leu Pro Asp Gly Arg Lys
370                 375                 380

Gln Ile Val Glu Tyr Glu Ala Asp Gln Asp Gly Phe Lys Pro Gln Ile
385                 390                 395                 400

Arg Tyr Glu Gly Glu Ala Asn Ser Gln Gly Tyr Ser Gly Pro
                        405                 410                 415

Gly Gly Asn Gly Gly Asp Asn Gly Tyr Pro Ser Gly Gly Pro Gly Gly
                420                 425                 430

Asn Gly Tyr Ser Ser Gly Arg Pro Asn Gly Gly Ser Asp Phe Ser Asp
                435                 440                 445

Gly Gly Tyr Pro Ser Thr Arg Pro Gly Gly Glu Asn Gly Tyr Arg
450                 455                 460

Asn Gly Asn Asn Gly Asn Gly Asn Gly Tyr Pro Ser Gly Asn
465                 470                 475                 480

Gly Gly Asp Ala Ala Ala Asn Gly Gly Tyr Gln Tyr
                485                 490

<210> SEQ ID NO 48
<211> LENGTH: 344
<212> TYPE: PRT
<213> ORGANISM: Apis mellifera

<400> SEQUENCE: 48

Met Arg Pro Gly Lys Ser Trp Ala Pro Leu Ala Ala Thr Val Leu Ala
1               5                   10                  15

Thr Ala Leu Leu Leu Gln Pro Ile His Ala Asp Ala Pro Ile Ser Gly
                20                  25                  30

Ser Tyr Leu Pro Pro Ser Thr Ser Tyr Gly Thr Pro Asn Leu Gly Gly
                35                  40                  45

Gly Gly Pro Ser Ser Thr Tyr Gly Ala Pro Ser Gly Gly Gly Gly
            50                  55                  60

Arg Pro Ser Ser Ser Tyr Gly Ala Pro Ser Ser Thr Tyr Gly Ala Pro
65                  70                  75                  80

Ser Ser Thr Tyr Gly Ala Pro Ser Asn Gly Gly Arg Pro Ser Ser
                        85                  90                  95

Thr Tyr Gly Ala Pro Ser Asn Gly Gly Arg Pro Ser Ser Ser Tyr
                100                 105                 110

Gly Ala Pro Ser Ser Ser Tyr Gly Ala Pro Ser Ser Thr Tyr Gly Ala
                115                 120                 125

Pro Ser Asn Gly Gly Gly Arg Pro Ser Ser Tyr Gly Ala Pro Ser
            130                 135                 140

Phe Gly Gly Gly Gly Gly Phe Gly Gly Gly Asn Gly Leu Ser Thr Ser
145                 150                 155                 160

Tyr Gly Ala Pro Ser Arg Gly Gly Gly Gly Gly Ser Ile Ser
                        165                 170                 175

Ser Ser Tyr Gly Ala Pro Thr Gly Gly Gly Gly Gly Pro Ser Thr
```

```
            180             185             190
Thr Tyr Gly Ala Pro Asn Gly Gly Asn Gly Tyr Ser Arg Pro Ser
            195             200             205
Ser Thr Tyr Gly Thr Pro Ser Thr Gly Gly Ser Phe Gly Gly Ser
        210             215             220
Gly Gly Tyr Ser Gly Gly Gly Gly Tyr Ser Gly Gly Asn Gly
225             230             235             240
Tyr Ser Gly Gly Gly Gly Gly Tyr Ser Gly Asn Gly Gly
                245             250             255
Tyr Ser Gly Gly Gly Asn Gly Gly Tyr Ser Gly Gly Asn Gly Gly
            260             265             270
Gly Tyr Ser Gly Gly Gly Gly Gly Tyr Ser Gly Gly Gly Gly
            275             280             285
Gly Tyr Ser Gly Gly Gly Asn Gly Tyr Ser Gly Gly Gly Gly Gly
        290             295             300
Tyr Ser Gly Gly Asn Gly Gly Tyr Ser Gly Gly Asn Gly Gly Tyr Ser
305             310             315             320
Gly Gly Gly Gly Tyr Ser Gly Gly Gly Gly Gly Gln Ser Tyr
                325             330             335
Ala Ser Asn Gly Gly Tyr Gln Tyr
            340

<210> SEQ ID NO 49
<211> LENGTH: 752
<212> TYPE: PRT
<213> ORGANISM: Nasonia vitripennis

<400> SEQUENCE: 49

Met Glu Lys Val Ile Cys Leu Ile Ala Val Leu Thr Leu Cys Ala Ala
1               5                   10                  15
Arg Pro Glu Pro Pro Val Asn Ser Tyr Leu Pro Pro Gly Gln Gly Gly
            20                  25                  30
Gly Phe Gly Gly Gly Arg Pro Ser Gly Ala Ser Pro Ser Asp Gln Tyr
        35                  40                  45
Gly Pro Pro Asp Phe Gln Gly Ala Gly Gly Arg Gly Gly Gln Ala Ala
    50                  55                  60
Gly Gly Asn Phe Gly Gly Gly Asn Gly Phe Gly Gly Ala Pro Ser
65                  70                  75                  80
Ser Ser Tyr Gly Pro Pro Gly Phe Gly Ser Asn Glu Pro Asn Lys Phe
                85                  90                  95
Ser Gly Ala Gly Gly Gly Ala Gly Arg Pro Gln Asp Ser Tyr Gly
            100                 105                 110
Pro Pro Ala Gly Gly Asn Gly Phe Ala Gly Ser Ala Gly Ala Gly Asn
        115                 120                 125
Ser Gly Arg Pro Gly Gly Ala Ala Gly Gly Arg Pro Ser Asp Ser
    130                 135                 140
Tyr Gly Pro Pro Gln Gly Gly Ser Gly Phe Gly Gly Asn Ala
145                 150                 155                 160
Gly Arg Pro Ser Asp Ser Tyr Gly Pro Pro Ser Ala Gly Gly Gly
                165                 170                 175
Phe Gly Gly Ser Pro Gly Gly Phe Gly Gly Ser Pro Gly
            180                 185                 190
Gly Gly Phe Gly Gly Gly Asn Gln Gly Ala Pro Gln Ser Ser Tyr Gly
        195                 200                 205
Pro Pro Ala Ser Gly Phe Gly Gly Gln Gly Gly Ala Gly Gln Gly Arg
```

-continued

```
                210                 215                 220
Pro Ser Asp Ser Tyr Gly Pro Gly Gly Ser Gly Gly Arg Pro
225                 230                 235                 240

Ser Gln Gly Gly Asn Gly Phe Gly Gly Asn Ala Gly Arg Pro Ser
                245                 250                 255

Asp Ser Tyr Gly Pro Pro Ala Ala Gly Gly Gly Phe Gly Gly Asn
                260                 265                 270

Ala Gly Gly Asn Gly Gly Asn Gly Phe Gly Gly Arg Pro Ser
                275                 280                 285

Gly Ser Pro Gly Gly Phe Gly Gly Gln Gly Gly Gly Arg Pro Ser
290                 295                 300

Asp Ser Tyr Leu Pro Pro Ser Gly Ser Gly Phe Gly Gly Asn
305                 310                 315                 320

Gly Arg Gln Pro Gly Gly Phe Gly Gln Gln Gly Gly Asn Gly Ala Gly
                325                 330                 335

Gln Gln Asn Gly Gly Gly Ala Gly Arg Pro Ser Ser Ser Tyr Gly
                340                 345                 350

Pro Pro Ser Asn Gly Asn Gly Gly Phe Ser Gly Gln Asn Gly Gly
                355                 360                 365

Arg Gly Ser Pro Ser Ser Gly Gly Phe Gly Gly Ala Gly Gly Ser
                370                 375                 380

Pro Ser Ser Ser Tyr Gly Pro Pro Ala Gly Gly Ser Gly Phe Gly Asn
385                 390                 395                 400

Asn Gly Gly Ala Gly Gly Arg Pro Ser Ser Ser Tyr Gly Pro Pro Ser
                405                 410                 415

Ser Gly Gln Gly Gly Gln Gly Gly Arg Pro Ser Ser Ser Tyr Gly Pro
                420                 425                 430

Pro Ser Asn Gly Asn Gly Gly Phe Gly Gly Asn Gly Gly Arg Pro
                435                 440                 445

Ser Ser Asn Gly Tyr Pro Gln Gly Gln Gly Asn Gly Asn Gly Phe
                450                 455                 460

Gly Gly Gln Gly Gly Asn Gly Arg Pro Ser Ser Ser Tyr Gly Pro
465                 470                 475                 480

Pro Gly Gly Asp Ser Gly Tyr Pro Ser Gly Gly Pro Ser Asp Ser Tyr
                485                 490                 495

Gly Pro Pro Pro Ser Gly Ala Val Asn Gly Asn Gly Asn Gly Tyr Ser
                500                 505                 510

Ser Gly Gly Pro Gly Gly Asn Gly Leu Asp Glu Gly Asn Asp Glu Pro
                515                 520                 525

Ala Lys Tyr Glu Phe Ser Tyr Glu Val Lys Asp Asp Gln Ser Gly Ser
                530                 535                 540

Asn Phe Gly His Thr Glu Met Arg Asp Gly Asp Arg Ala Gln Gly Glu
545                 550                 555                 560

Phe Asn Val Leu Leu Pro Asp Gly Arg Lys Gln Ile Val Glu Tyr Glu
                565                 570                 575

Ala Asp Gln Asp Gly Phe Lys Pro Gln Ile Arg Tyr Glu Gly Glu Ala
                580                 585                 590

Asn Thr Gly Ala Gly Gly Ala Gly Gly Tyr Pro Ser Gly Gly Gly Gly
                595                 600                 605

Asp Ser Gly Tyr Pro Ser Gly Pro Ser Gly Ala Gly Gly Asn Ala Gly
                610                 615                 620

Tyr Pro Ser Gly Gly Gly Gly Gly Ala Gly Gly Phe Gly Gly Asn Gly
625                 630                 635                 640
```

```
Gly Gly Ser Asn Gly Tyr Pro Ser Gly Gly Pro Ser Gly Gly Gln Gly
            645                 650                 655

Gln Phe Gly Gly Gln Gln Gly Gly Asn Gly Gly Tyr Pro Ser Gly Pro
        660                 665                 670

Gln Gly Gly Ser Gly Phe Gly Gly Ser Gln Gly Ser Gly Ser Gly
    675                 680                 685

Gly Tyr Pro Ser Gly Gly Pro Gly Gly Asn Gly Gly Asn Asn Phe
    690                 695                 700

Gly Gly Gly Asn Ala Gly Tyr Pro Ser Gly Gly Pro Ser Gly Gly Asn
705                 710                 715                 720

Gly Phe Asn Gln Gly Gln Asn Gln Gly Gly Ser Gly Gly Tyr
            725                 730                 735

Pro Ser Gly Ser Gly Gly Asp Ala Ala Ala Asn Gly Gly Tyr Gln Tyr
            740                 745                 750

<210> SEQ ID NO 50
<211> LENGTH: 545
<212> TYPE: PRT
<213> ORGANISM: Camponotus floridanus

<400> SEQUENCE: 50

Met Thr Arg Ser Glu Pro Pro Val Asn Ser Tyr Leu Pro Ser Arg Thr
1               5                   10                  15

Gly Ile Ser Gly Ala Asn Asp Gly Gln Ala Asp Leu Ser Thr Gln Tyr
            20                  25                  30

Gly Thr Pro Asp Phe Gly Asn Gly Asn Ala Asn Arg Asn Gly Gly
        35                  40                  45

Ala Thr Ser Phe Ser Gly Pro Gly Gly Asn Gly Ala Gly Asn Gly Pro
50                  55                  60

Ser Lys Leu Tyr Asp Ala Pro Ile Gly Gly Asn Ala Arg Val Asn Gly
65              70                  75                  80

Leu Gly Gln Ser Arg Arg Asn Gly Phe Gly Asn Gly Gln Ser Ser Ser
            85                  90                  95

Tyr Ser Ala Ser Ser Phe Gly Asp Phe Ser Glu Thr Gly Gly Asn Val
            100                 105                 110

Arg Pro Ser Ser Ser Tyr Gly Val Pro Ile Ala Asn Gly Asn Asn Gly
        115                 120                 125

Asp Gly Phe Arg Asn Gly Asp Asn Gly Asp Lys Pro Ser Ile Asn Tyr
    130                 135                 140

Gly Val Pro Gly Ile Asn Gly Asn Gly Asp Arg Asn Arg Gly Asn
145                 150                 155                 160

Gly Glu Arg Pro Ser Thr Asn Tyr Gly Ala Pro Gly Ala Asn Gly Asn
            165                 170                 175

His Gly Gly Ser Gly Asn Asn Asn Gly Arg Pro Ser Thr
        180                 185                 190

Ser Tyr Gly Val Pro Ala Asn Gly Asn Thr Asn Gly Lys Asn His Phe
    195                 200                 205

Asn Gly Gly Ser Asn Gly Asn Gly Gly Lys Leu Ser Ser Asn Tyr Glu
210                 215                 220

Ser Pro Asn Val Pro Lys Ile Asn Gly Phe Gly Thr Asn Gly Gly Leu
225                 230                 235                 240

Ser Ser Ser Tyr Gly Pro Pro Asp Arg Asn Gly His Gly Asn Asn Gly
            245                 250                 255

Tyr Pro Ser Glu Ser Pro Thr Arg Asn Gly Glu Gly Phe Arg Asn Gly
            260                 265                 270
```

-continued

```
Gly Ala Asn Gly Tyr Pro Ser Gly Gly Thr Asn Gly His Val Gly
        275                 280                 285
Asn Phe Glu Asn Gly Gly Ser Phe Lys Asn Glu Gly Arg Gly Asn
        290                 295                 300
Gly Gly Tyr Asn Asp Asn Ala Gln Glu Ser Thr Glu Pro Ala Lys
305                 310                 315                 320
Tyr Glu Phe Ser Tyr Glu Val Lys Asp Glu Gln Ser Gly Ser Asn Tyr
                325                 330                 335
Gly His Lys Glu Thr Arg Asn Gly Asp His Ala Gln Gly Glu Phe Asn
                340                 345                 350
Val Leu Leu Pro Asp Gly Arg Lys Gln Ile Val Glu Tyr Glu Ala Asp
                355                 360                 365
Gln Asp Gly Phe Lys Pro Gln Ile Arg Tyr Glu Gly Glu Ala Asn Thr
        370                 375                 380
Gly Gly Gly Tyr Ser Ser Gly Gly Pro Asn Gly Asn Asn Asp Gly Tyr
385                 390                 395                 400
Ser Ser Gly Arg Pro Asp Ser Lys Ser Gly Phe Ala Asp Asn Ser
                405                 410                 415
Gly Phe Asn Gly Gly Thr Asn Gly Tyr Pro Asn Gly Ser Pro Gly
        420                 425                 430
Glu Gly Lys Pro Asn Gly Phe Asn Gly Gly Asn Gly Tyr Gln Ser
                435                 440                 445
Gly Lys Ser Ala Gly Gln Ser Phe Ser Arg Asp Asn Asp Asn Leu
450                 455                 460
Asn Gly Asn Ile Gly Gly Tyr Phe Ser Asn Ala Pro Ser Asn His Ile
465                 470                 475                 480
Gly Asp Asn Ala Asp Ile Gly Asn Asn Arg Gln Asn Ala Gly Pro Val
                485                 490                 495
Leu Gly Val Thr Asp Leu Pro Glu Arg Val Ala Pro Gly Ser Arg Val
                500                 505                 510
Cys Pro Thr Arg Thr Arg Lys Asp Lys Thr Asp Thr Arg Lys Phe Tyr
                515                 520                 525
Cys Asp Leu Leu Ala His Leu Gln Gly Ser Lys Glu Ile Gln Val Ser
530                 535                 540
Arg
545
```

<210> SEQ ID NO 51
<211> LENGTH: 4
<212> TYPE: PRT
<213> ORGANISM: Artificial Sequence
<220> FEATURE:
<223> OTHER INFORMATION: Resilin-like polypeptide

<400> SEQUENCE: 51

Tyr Gly Ala Pro
1

<210> SEQ ID NO 52
<211> LENGTH: 11
<212> TYPE: PRT
<213> ORGANISM: Artificial Sequence
<220> FEATURE:
<223> OTHER INFORMATION: Resilin-like polypeptide

<400> SEQUENCE: 52

Ala Gln Thr Pro Ser Ser Gln Tyr Gly Ala Pro
1               5                   10

```
<210> SEQ ID NO 53
<211> LENGTH: 15
<212> TYPE: PRT
<213> ORGANISM: Artificial Sequence
<220> FEATURE:
<223> OTHER INFORMATION: Resilin-like polypeptide

<400> SEQUENCE: 53

Gly Gly Arg Pro Ser Asp Ser Tyr Gly Ala Pro Gly Gly Gly Asn
1               5                   10                  15

<210> SEQ ID NO 54
<211> LENGTH: 13
<212> TYPE: PRT
<213> ORGANISM: Artificial Sequence
<220> FEATURE:
<223> OTHER INFORMATION: Resilin-like polypeptide

<400> SEQUENCE: 54

Gly Tyr Ser Gly Gly Arg Pro Gly Gly Gln Asp Leu Gly
1               5                   10

<210> SEQ ID NO 55
<211> LENGTH: 5
<212> TYPE: PRT
<213> ORGANISM: Artificial Sequence
<220> FEATURE:
<223> OTHER INFORMATION: Resilin-like polypeptide

<400> SEQUENCE: 55

Pro Gly Gly Gly Asn
1               5

<210> SEQ ID NO 56
<211> LENGTH: 9
<212> TYPE: PRT
<213> ORGANISM: Artificial Sequence
<220> FEATURE:
<223> OTHER INFORMATION: Resilin-like polypeptide

<400> SEQUENCE: 56

Pro Gly Gly Gly Asn Gly Gly Arg Pro
1               5

<210> SEQ ID NO 57
<211> LENGTH: 15
<212> TYPE: PRT
<213> ORGANISM: Artificial Sequence
<220> FEATURE:
<223> OTHER INFORMATION: Resilin-like polypeptide

<400> SEQUENCE: 57

Ser Asp Thr Tyr Gly Ala Pro Gly Gly Gly Asn Gly Gly Arg Pro
1               5                   10                  15

<210> SEQ ID NO 58
<211> LENGTH: 24
<212> TYPE: PRT
<213> ORGANISM: Artificial Sequence
<220> FEATURE:
<223> OTHER INFORMATION: Resilin-like polypeptide

<400> SEQUENCE: 58

Pro Gly Gly Gly Asn Gly Gly Arg Pro Ser Asp Thr Tyr Gly Ala Pro
1               5                   10                  15

Gly Gly Gly Asn Gly Gly Arg Pro
            20
```

-continued

```
<210> SEQ ID NO 59
<211> LENGTH: 62
<212> TYPE: PRT
<213> ORGANISM: Artificial Sequence
<220> FEATURE:
<223> OTHER INFORMATION: Resilin-like polypeptide

<400> SEQUENCE: 59

Ser Met Ser Asp Thr Tyr Gly Ala Pro Gly Gly Asn Gly Gly Arg
1               5                   10                  15

Pro Ser Asp Thr Tyr Gly Ala Pro Gly Gly Gly Asn Gly Gly Arg Pro
            20                  25                  30

Ser Asp Thr Tyr Gly Ala Pro Gly Gly Gly Asn Gly Gly Arg Pro Ser
        35                  40                  45

Asp Thr Tyr Gly Ala Pro Gly Gly Gly Asn Gly Gly Arg Pro
    50                  55                  60

<210> SEQ ID NO 60
<211> LENGTH: 50
<212> TYPE: PRT
<213> ORGANISM: Artificial Sequence
<220> FEATURE:
<223> OTHER INFORMATION: Resilin-like polypeptide

<400> SEQUENCE: 60

Pro Gly Gly Gly Asn Pro Gly Gly Gly Asn Pro Gly Gly Gly Asn Pro
1               5                   10                  15

Gly Gly Gly Asn Pro Gly Gly Gly Asn Pro Gly Gly Gly Asn Pro Gly
            20                  25                  30

Gly Gly Asn Pro Gly Gly Gly Asn Pro Gly Gly Gly Asn Pro Gly Gly
        35                  40                  45

Gly Asn
    50

<210> SEQ ID NO 61
<211> LENGTH: 272
<212> TYPE: PRT
<213> ORGANISM: Artificial Sequence
<220> FEATURE:
<223> OTHER INFORMATION: Resilin-like polypeptide

<400> SEQUENCE: 61

Gly Gly Gly Asp Gln Lys Gly Gly Arg Pro Ser Asp Ser Phe Gly Ala
1               5                   10                  15

Pro Gly Gly Gly Asn Gly Gly Arg Pro Ser Asp Ser Phe Gly Ala Pro
            20                  25                  30

Gly Gly Gly Asn Gly Gly Arg Pro Ser Asp Ser Phe Gly Ala Pro Gly
        35                  40                  45

Gly Gly Asn Gly Gly Lys Gly Gly Arg Pro Ser Asp Ser Phe Gly Ala
    50                  55                  60

Pro Gly Gly Gly Asn Gly Gly Arg Pro Ser Asp Ser Phe Gly Ala Pro
65                  70                  75                  80

Gly Gly Gly Asn Gly Gly Arg Pro Ser Asp Ser Phe Gly Ala Pro Gly
            85                  90                  95

Gly Gly Asn Gly Gly Lys Gly Gly Arg Gly Asp Ser Pro Ala Glu
        100                 105                 110

Asp Leu Gly Asp Gln Lys Gly Gly Arg Pro Ser Asp Ser Phe Gly Ala
    115                 120                 125

Pro Gly Gly Gly Asn Gly Gly Arg Pro Ser Asp Ser Phe Gly Ala Pro
```

```
            130                 135                 140
Gly Gly Gly Asn Gly Gly Arg Pro Ser Asp Ser Phe Gly Ala Pro Gly
145                 150                 155                 160

Gly Gly Asn Gly Gly Lys Gly Gly Arg Pro Ser Asp Ser Phe Gly Ala
                165                 170                 175

Pro Gly Gly Gly Asn Gly Gly Arg Pro Ser Asp Ser Phe Gly Ala Pro
            180                 185                 190

Gly Gly Gly Asn Gly Gly Arg Pro Ser Asp Ser Phe Gly Ala Pro Gly
            195                 200                 205

Gly Gly Asn Gly Gly Lys Gly Gly Arg Gly Asp Ser Pro Ala Glu
        210                 215                 220

Asp Leu Gly Pro Gln Gly Ile Trp Gly Gln Gly Arg Gly Gly Cys
225                 230                 235                 240

Lys Ala Ala Lys Arg Pro Lys Ala Ala Lys Asp Lys Gln Thr Lys Gly
                245                 250                 255

Glu Asp Leu Gly Asp Pro Met Ala Ser Met Thr Gly Gly Gln Gln Met
            260                 265                 270
```

<210> SEQ ID NO 62
<211> LENGTH: 570
<212> TYPE: PRT
<213> ORGANISM: Homo sapiens

<400> SEQUENCE: 62

```
Met Ala Gly Leu Thr Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
        50                  55                  60

Pro Val Pro Gly Gly Leu Ala Gly Ala Gly Leu Gly Ala Gly Val Gly
65                  70                  75                  80

Gly Ala Phe Ala Gly Ile Pro Gly Val Gly Pro Phe Gly Gly Pro Gln
                85                  90                  95

Pro Gly Val Pro Leu Gly Tyr Pro Ile Lys Ala Pro Lys Leu Pro Gly
            100                 105                 110

Tyr Gly Pro Gly Gly Val Ala Gly Ala Ala Gly Lys Ala Gly Tyr Pro
        115                 120                 125

Thr Gly Thr Gly Val Gly Pro Gln Ala Ala Ala Ala Ala Ala Ala Lys
    130                 135                 140

Ala Ala Ala Lys Phe Gly Ala Gly Ala Ala Gly Val Leu Pro Gly Val
145                 150                 155                 160

Gly Gly Ala Gly Val Pro Gly Val Pro Gly Ala Ile Pro Gly Ile Gly
                165                 170                 175

Gly Ile Ala Gly Val Gly Thr Pro Ala Ala Ala Ala Ala Ala Ala Ala
            180                 185                 190

Ala Ala Lys Ala Ala Lys Tyr Gly Ala Ala Ala Gly Leu Val Pro Gly
        195                 200                 205

Gly Pro Gly Phe Gly Pro Gly Val Val Gly Val Pro Gly Ala Gly Val
    210                 215                 220

Pro Gly Val Gly Val Pro Gly Ala Gly Ile Pro Val Val Pro Gly Ala
225                 230                 235                 240

Gly Ile Pro Gly Ala Ala Val Pro Gly Val Val Ser Pro Glu Ala Ala
```

```
                245                 250                 255
Ala Lys Ala Ala Lys Ala Ala Lys Tyr Gly Ala Arg Pro Gly Val
                260                 265                 270

Gly Val Gly Gly Ile Pro Thr Tyr Gly Val Gly Ala Gly Phe Pro
            275                 280                 285

Gly Phe Gly Val Gly Val Gly Ile Pro Gly Val Ala Gly Val Pro
        290                 295                 300

Gly Val Gly Gly Val Pro Gly Val Gly Val Pro Gly Val Gly Ile
305                 310                 315                 320

Ser Pro Glu Ala Gln Ala Ala Ala Ala Lys Ala Ala Lys Tyr Gly
                325                 330                 335

Leu Val Pro Gly Val Gly Val Ala Pro Gly Val Gly Val Ala Pro Gly
                340                 345                 350

Val Gly Val Ala Pro Gly Val Gly Leu Ala Pro Gly Val Gly Val Ala
            355                 360                 365

Pro Gly Val Gly Val Ala Pro Gly Val Gly Val Ala Pro Gly Ile Gly
        370                 375                 380

Pro Gly Gly Val Ala Ala Ala Lys Ser Ala Ala Lys Val Ala Ala
385                 390                 395                 400

Lys Ala Gln Leu Arg Ala Ala Ala Gly Leu Gly Ala Gly Ile Pro Gly
                405                 410                 415

Leu Gly Val Gly Val Gly Val Pro Gly Leu Gly Val Gly Ala Gly Val
            420                 425                 430

Pro Gly Leu Gly Val Gly Ala Gly Val Pro Gly Phe Gly Ala Val Pro
        435                 440                 445

Gly Ala Leu Ala Ala Ala Lys Ala Ala Lys Tyr Gly Ala Ala Val Pro
450                 455                 460

Gly Val Leu Gly Gly Leu Gly Ala Leu Gly Gly Val Gly Ile Pro Gly
465                 470                 475                 480

Gly Val Val Gly Ala Gly Pro Ala Ala Ala Ala Ala Ala Ala Lys Ala
                485                 490                 495

Ala Ala Lys Ala Ala Gln Phe Gly Leu Val Gly Ala Ala Gly Leu Gly
                500                 505                 510

Gly Leu Gly Val Gly Gly Leu Gly Val Pro Gly Val Gly Gly Leu Gly
            515                 520                 525

Gly Ile Pro Pro Ala Ala Ala Ala Lys Ala Ala Lys Tyr Gly Val Ala
        530                 535                 540

Ala Arg Pro Gly Phe Gly Leu Ser Pro Ile Phe Pro Gly Gly Ala Cys
545                 550                 555                 560

Leu Gly Lys Ala Cys Gly Arg Lys Arg Lys
                565                 570

<210> SEQ ID NO 63
<211> LENGTH: 705
<212> TYPE: PRT
<213> ORGANISM: Homo sapiens

<400> SEQUENCE: 63

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
```

```
                 50                  55                  60
Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
                    100                 105                 110

Gly Gly Val Pro Gly Val Gly Leu Gly Val Ser Ala Gly Ala Val
            115                 120                 125

Val Pro Gln Pro Gly Ala Gly Val Lys Pro Gly Lys Val Pro Gly Val
130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Ala Phe Ala Gly Ile Pro Gly Val
            180                 185                 190

Gly Pro Phe Gly Gly Pro Gln Pro Gly Val Pro Leu Gly Tyr Pro Ile
                195                 200                 205

Lys Ala Pro Lys Leu Pro Gly Gly Tyr Gly Leu Pro Tyr Thr Thr Gly
210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                    245                 250                 255

Ala Ala Ala Ala Lys Ala Ala Lys Phe Gly Ala Gly Ala Ala Gly
                260                 265                 270

Val Leu Pro Gly Val Gly Gly Ala Gly Val Pro Gly Val Pro Gly Ala
        275                 280                 285

Ile Pro Gly Ile Gly Gly Ile Ala Gly Val Gly Thr Pro Ala Ala Ala
    290                 295                 300

Ala Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
            355                 360                 365

Ser Pro Glu Ala Ala Ala Lys Ala Ala Ala Lys Ala Ala Lys Tyr Gly
370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                    405                 410                 415

Val Ala Gly Val Pro Gly Val Gly Val Pro Gly Val Gly Gly Val
            420                 425                 430

Pro Gly Val Gly Ile Ser Pro Glu Ala Gln Ala Ala Ala Ala Ala Lys
                435                 440                 445

Ala Ala Lys Tyr Gly Leu Val Pro Gly Val Gly Val Ala Pro Gly Val
        450                 455                 460

Gly Val Ala Pro Gly Val Gly Val Ala Pro Gly Val Gly Leu Ala Pro
465                 470                 475                 480
```

-continued

```
Gly Val Gly Val Ala Pro Gly Val Gly Val Ala Pro Gly Val Gly Val
            485                 490                 495

Ala Pro Gly Ile Gly Pro Gly Val Ala Ala Ala Lys Ser Ala
            500                 505                 510

Ala Lys Val Ala Ala Lys Ala Gln Leu Arg Ala Ala Gly Leu Gly
            515                 520                 525

Ala Gly Ile Pro Gly Leu Gly Val Gly Val Pro Gly Leu Gly
            530                 535                 540

Val Gly Ala Gly Val Pro Gly Leu Gly Val Gly Ala Gly Val Pro Gly
545                 550                 555                 560

Phe Gly Ala Val Pro Gly Ala Leu Ala Ala Lys Ala Ala Lys Tyr
            565                 570                 575

Gly Ala Ala Val Pro Gly Val Leu Gly Gly Leu Gly Ala Leu Gly Gly
            580                 585                 590

Val Gly Ile Pro Gly Gly Val Val Gly Ala Gly Pro Ala Ala Ala Ala
            595                 600                 605

Ala Ala Ala Lys Ala Ala Ala Lys Ala Ala Gln Phe Gly Leu Val Gly
            610                 615                 620

Ala Ala Gly Leu Gly Gly Leu Gly Val Gly Gly Leu Gly Val Pro Gly
625                 630                 635                 640

Val Gly Gly Leu Gly Gly Ile Pro Pro Ala Ala Ala Lys Ala Ala
            645                 650                 655

Lys Tyr Gly Ala Ala Gly Leu Gly Gly Val Leu Gly Gly Ala Gly Gln
            660                 665                 670

Phe Pro Leu Gly Gly Val Ala Ala Arg Pro Gly Phe Gly Leu Ser Pro
            675                 680                 685

Ile Phe Pro Gly Gly Ala Cys Leu Gly Lys Ala Cys Gly Arg Lys Arg
            690                 695                 700

Lys
705

<210> SEQ ID NO 64
<211> LENGTH: 730
<212> TYPE: PRT
<213> ORGANISM: Homo sapiens

<400> SEQUENCE: 64

Met Ala Gly Leu Thr Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
            50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
            85                  90                  95

Ala Asp Ala Ala Ala Ala Tyr Lys Ala Ala Lys Ala Gly Ala Gly Leu
            100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Gly Lys Val Pro Gly Val
            130                 135                 140
```

```
Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
        195                 200                 205

Lys Ala Pro Lys Leu Pro Gly Gly Tyr Gly Leu Pro Tyr Thr Thr Gly
    210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Ala Gly
            260                 265                 270

Val Leu Pro Gly Val Gly Gly Ala Gly Val Pro Gly Val Pro Gly Ala
        275                 280                 285

Ile Pro Gly Ile Gly Gly Ile Ala Gly Val Gly Thr Pro Ala Ala Ala
    290                 295                 300

Ala Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
        355                 360                 365

Ser Pro Glu Ala Ala Ala Lys Ala Ala Ala Lys Ala Ala Lys Tyr Gly
    370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Gly Val Gly Gly Val Pro Gly Val Gly Gly Val
            420                 425                 430

Pro Gly Val Gly Ile Ser Pro Glu Ala Gln Ala Ala Ala Ala Ala Lys
        435                 440                 445

Ala Ala Lys Tyr Gly Val Gly Thr Pro Ala Ala Ala Ala Ala Lys Ala
    450                 455                 460

Ala Ala Lys Ala Ala Gln Phe Ala Leu Leu Asn Leu Ala Gly Leu Val
465                 470                 475                 480

Pro Gly Val Gly Val Ala Pro Gly Val Gly Val Ala Pro Gly Val Gly
                485                 490                 495

Val Ala Pro Gly Val Gly Leu Ala Pro Gly Val Gly Val Ala Pro Gly
            500                 505                 510

Val Gly Val Ala Pro Gly Val Gly Val Ala Pro Gly Ile Gly Pro Gly
        515                 520                 525

Gly Val Ala Ala Ala Lys Ser Ala Ala Lys Val Ala Ala Lys Ala
    530                 535                 540

Gln Leu Arg Ala Ala Gly Leu Gly Ala Gly Ile Pro Gly Leu Gly
545                 550                 555                 560

Val Gly Val Gly Val Pro Gly Leu Gly Val Gly Ala Gly Val Pro Gly
                565                 570                 575
```

```
Leu Gly Val Gly Ala Gly Val Pro Gly Phe Gly Ala Val Pro Gly Ala
            580                 585                 590

Leu Ala Ala Ala Lys Ala Ala Lys Tyr Gly Ala Ala Val Pro Gly Val
            595                 600                 605

Leu Gly Gly Leu Gly Ala Leu Gly Gly Val Gly Ile Pro Gly Gly Val
610                 615                 620

Val Gly Ala Gly Pro Ala Ala Ala Ala Ala Ala Lys Ala Ala Ala
625                 630                 635                 640

Lys Ala Ala Gln Phe Gly Leu Val Gly Ala Ala Gly Leu Gly Gly Leu
                645                 650                 655

Gly Val Gly Gly Leu Gly Val Pro Gly Val Gly Gly Leu Gly Gly Ile
            660                 665                 670

Pro Pro Ala Ala Ala Ala Lys Ala Ala Lys Tyr Gly Ala Ala Gly Leu
            675                 680                 685

Gly Gly Val Leu Gly Gly Ala Gly Gln Phe Pro Leu Gly Gly Val Ala
            690                 695                 700

Ala Arg Pro Gly Phe Gly Leu Ser Pro Ile Phe Pro Gly Gly Ala Cys
705                 710                 715                 720

Leu Gly Lys Ala Cys Gly Arg Lys Arg Lys
                725                 730

<210> SEQ ID NO 65
<211> LENGTH: 692
<212> TYPE: PRT
<213> ORGANISM: Homo sapiens

<400> SEQUENCE: 65

Met Ala Gly Leu Thr Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
        50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
            100                 105                 110

Gly Gly Val Pro Gly Val Gly Gly Leu Gly Val Ser Ala Ala Pro Ser
            115                 120                 125

Val Pro Gly Ala Val Pro Gln Pro Gly Ala Gly Val Lys Pro Gly
        130                 135                 140

Lys Val Pro Gly Val Gly Leu Pro Gly Val Tyr Pro Gly Gly Val Leu
145                 150                 155                 160

Pro Gly Ala Arg Phe Pro Gly Val Gly Val Leu Pro Gly Val Pro Thr
                165                 170                 175

Gly Ala Gly Val Lys Pro Lys Ala Pro Gly Val Gly Gly Ala Phe Ala
            180                 185                 190

Gly Ile Pro Gly Val Gly Pro Phe Gly Gly Pro Gln Pro Gly Val Pro
            195                 200                 205

Leu Gly Tyr Pro Ile Lys Ala Pro Lys Leu Pro Gly Gly Tyr Gly Leu
        210                 215                 220
```

```
Pro Tyr Thr Thr Gly Lys Leu Pro Tyr Gly Tyr Gly Pro Gly Gly Val
225                 230                 235                 240

Ala Gly Ala Ala Gly Lys Ala Gly Tyr Pro Thr Gly Thr Gly Val Gly
                245                 250                 255

Pro Gln Ala Ala Ala Ala Ala Ala Lys Ala Ala Lys Phe Gly
        260                 265                 270

Ala Gly Ala Ala Gly Val Leu Pro Gly Val Gly Gly Ala Gly Val Pro
            275                 280                 285

Gly Val Pro Gly Ala Ile Pro Gly Ile Gly Gly Ile Ala Val Gly
        290                 295                 300

Thr Pro Ala Ala Ala Ala Ala Ala Ala Ala Lys Ala Ala Lys
305                 310                 315                 320

Tyr Gly Ala Ala Ala Gly Leu Val Pro Gly Pro Gly Phe Gly Pro
                325                 330                 335

Gly Val Val Gly Val Pro Gly Ala Gly Val Pro Gly Val Gly Val Pro
                340                 345                 350

Gly Ala Gly Ile Pro Val Val Pro Gly Ala Gly Ile Pro Gly Ala Ala
                355                 360                 365

Val Pro Gly Val Val Ser Pro Glu Ala Ala Ala Lys Ala Ala Ala Lys
370                 375                 380

Ala Ala Lys Tyr Gly Ala Arg Pro Gly Val Gly Val Gly Gly Ile Pro
385                 390                 395                 400

Thr Tyr Gly Val Gly Ala Gly Gly Phe Pro Gly Phe Gly Val Gly Val
                405                 410                 415

Gly Gly Ile Pro Gly Val Ala Gly Val Pro Gly Val Gly Gly Val Pro
                420                 425                 430

Gly Val Gly Gly Val Pro Gly Val Gly Ile Ser Pro Glu Ala Gln Ala
                435                 440                 445

Ala Ala Ala Ala Lys Ala Ala Lys Tyr Gly Leu Val Pro Gly Val Gly
                450                 455                 460

Val Ala Pro Gly Val Gly Val Ala Pro Gly Val Gly Val Ala Pro Gly
465                 470                 475                 480

Val Gly Leu Ala Pro Gly Val Gly Val Ala Pro Gly Val Gly Val Ala
                485                 490                 495

Pro Gly Val Gly Val Ala Pro Gly Ile Gly Pro Gly Gly Val Ala Ala
                500                 505                 510

Ala Ala Lys Ser Ala Ala Lys Val Ala Ala Lys Ala Gln Leu Arg Ala
                515                 520                 525

Ala Ala Gly Leu Gly Ala Gly Ile Pro Gly Leu Gly Val Gly Val Gly
                530                 535                 540

Val Pro Gly Leu Gly Val Gly Ala Gly Val Pro Gly Leu Gly Val Gly
545                 550                 555                 560

Ala Gly Val Pro Gly Phe Gly Ala Val Pro Gly Ala Leu Ala Ala Ala
                565                 570                 575

Lys Ala Ala Lys Tyr Gly Ala Ala Val Pro Gly Val Leu Gly Gly Leu
                580                 585                 590

Gly Ala Leu Gly Gly Val Gly Ile Pro Gly Gly Val Val Gly Ala Gly
            595                 600                 605

Pro Ala Ala Ala Ala Ala Ala Lys Ala Ala Ala Lys Ala Ala Gln
    610                 615                 620

Phe Gly Leu Val Gly Ala Ala Gly Leu Gly Gly Leu Gly Val Gly Gly
625                 630                 635                 640

Leu Gly Val Pro Gly Val Gly Gly Leu Gly Gly Ile Pro Pro Ala Ala
```

```
                       645                 650                 655
Ala Ala Lys Ala Ala Lys Tyr Gly Val Ala Ala Arg Pro Gly Phe Gly
            660                 665                 670

Leu Ser Pro Ile Phe Pro Gly Gly Ala Cys Leu Gly Lys Ala Cys Gly
            675                 680                 685

Arg Lys Arg Lys
            690

<210> SEQ ID NO 66
<211> LENGTH: 700
<212> TYPE: PRT
<213> ORGANISM: Homo sapiens

<400> SEQUENCE: 66

Met Ala Gly Leu Thr Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Ala Leu Gly Pro
            35                  40                  45

Gly Gly Lys Pro Leu Lys Pro Val Pro Gly Gly Leu Ala Gly Ala Gly
            50                  55                  60

Leu Gly Ala Gly Leu Gly Ala Phe Pro Ala Val Thr Phe Pro Gly Ala
65                  70                  75                  80

Leu Val Pro Gly Gly Val Ala Asp Ala Ala Ala Ala Tyr Lys Ala Ala
                85                  90                  95

Lys Ala Gly Ala Gly Leu Gly Val Pro Gly Val Gly Gly Leu Gly
            100                 105                 110

Val Ser Ala Ala Pro Ser Val Pro Gly Ala Val Pro Gln Pro Gly
            115                 120                 125

Ala Gly Val Lys Pro Gly Lys Val Pro Gly Val Gly Leu Pro Gly Val
            130                 135                 140

Tyr Pro Gly Gly Val Leu Pro Gly Ala Arg Phe Pro Gly Val Gly Val
145                 150                 155                 160

Leu Pro Gly Val Pro Thr Gly Ala Gly Val Lys Pro Lys Ala Pro Gly
                165                 170                 175

Val Gly Gly Ala Phe Ala Gly Ile Pro Gly Val Gly Pro Phe Gly Gly
            180                 185                 190

Pro Gln Pro Gly Val Pro Leu Gly Tyr Pro Ile Lys Ala Pro Lys Leu
            195                 200                 205

Pro Gly Gly Tyr Gly Leu Pro Tyr Thr Thr Gly Lys Leu Pro Tyr Gly
            210                 215                 220

Tyr Gly Pro Gly Gly Val Ala Gly Ala Ala Gly Lys Ala Gly Tyr Pro
225                 230                 235                 240

Thr Gly Thr Gly Val Gly Pro Gln Ala Ala Ala Ala Ala Ala Lys
            245                 250                 255

Ala Ala Ala Lys Phe Gly Ala Gly Ala Ala Gly Val Leu Pro Gly Val
            260                 265                 270

Gly Gly Ala Gly Val Pro Gly Val Pro Gly Ala Ile Pro Gly Ile Gly
            275                 280                 285

Gly Ile Ala Gly Val Gly Thr Pro Ala Ala Ala Ala Ala Ala Ala
            290                 295                 300

Ala Ala Lys Ala Ala Lys Tyr Gly Ala Ala Ala Gly Leu Val Pro Gly
305                 310                 315                 320

Gly Pro Gly Phe Gly Pro Gly Val Val Gly Val Pro Gly Ala Gly Val
```

```
                       325                 330                 335
Pro Gly Val Gly Val Pro Gly Ala Gly Ile Pro Val Pro Gly Ala
                340                 345                 350
Gly Ile Pro Gly Ala Ala Val Pro Gly Val Val Ser Pro Glu Ala Ala
                355                 360                 365
Ala Lys Ala Ala Ala Lys Ala Ala Lys Tyr Gly Ala Arg Pro Gly Val
                370                 375                 380
Gly Val Gly Gly Ile Pro Thr Tyr Gly Val Gly Ala Gly Gly Phe Pro
385                 390                 395                 400
Gly Phe Gly Val Gly Val Gly Gly Ile Pro Gly Val Ala Gly Val Pro
                405                 410                 415
Gly Val Gly Gly Val Pro Gly Val Gly Val Pro Gly Val Gly Ile
                420                 425                 430
Ser Pro Glu Ala Gln Ala Ala Ala Ala Ala Lys Ala Ala Lys Tyr Gly
                435                 440                 445
Leu Val Pro Gly Val Gly Val Ala Pro Gly Val Gly Val Ala Pro Gly
                450                 455                 460
Val Gly Val Ala Pro Gly Val Gly Leu Ala Pro Gly Val Gly Val Ala
465                 470                 475                 480
Pro Gly Val Gly Val Ala Pro Gly Val Gly Val Ala Pro Gly Ile Gly
                485                 490                 495
Pro Gly Gly Val Ala Ala Ala Ala Lys Ser Ala Ala Lys Val Ala Ala
                500                 505                 510
Lys Ala Gln Leu Arg Ala Ala Ala Gly Leu Gly Ala Gly Ile Pro Gly
                515                 520                 525
Leu Gly Val Gly Val Gly Val Pro Gly Leu Gly Val Gly Ala Gly Val
                530                 535                 540
Pro Gly Leu Gly Val Gly Ala Gly Val Pro Gly Phe Gly Ala Val Pro
545                 550                 555                 560
Gly Ala Leu Ala Ala Ala Lys Ala Ala Lys Tyr Gly Ala Ala Val Pro
                565                 570                 575
Gly Val Leu Gly Gly Leu Gly Ala Leu Gly Gly Val Gly Ile Pro Gly
                580                 585                 590
Gly Val Val Gly Ala Gly Pro Ala Ala Ala Ala Ala Ala Lys Ala
                595                 600                 605
Ala Ala Lys Ala Ala Gln Phe Gly Leu Val Gly Ala Ala Gly Leu Gly
                610                 615                 620
Gly Leu Gly Val Gly Gly Leu Gly Val Pro Gly Val Gly Gly Leu Gly
625                 630                 635                 640
Gly Ile Pro Pro Ala Ala Ala Lys Ala Ala Lys Tyr Gly Ala Ala
                645                 650                 655
Gly Leu Gly Gly Val Leu Gly Gly Ala Gly Gln Phe Pro Leu Gly Gly
                660                 665                 670
Val Ala Ala Arg Pro Gly Phe Gly Leu Ser Pro Ile Phe Pro Gly Gly
                675                 680                 685
Ala Cys Leu Gly Lys Ala Cys Gly Arg Lys Arg Lys
                690                 695                 700

<210> SEQ ID NO 67
<211> LENGTH: 381
<212> TYPE: PRT
<213> ORGANISM: Homo sapiens

<400> SEQUENCE: 67

Met Ala Gly Leu Thr Ala Ala Ala Pro Arg Pro Gly Val Leu Leu Leu
```

```
                1               5                  10                15
Leu Leu Ser Ile Leu His Pro Ser Arg Pro Gly Gly Val Pro Gly Ala
                20                  25                  30

Ile Pro Gly Gly Val Pro Gly Val Phe Tyr Pro Gly Ala Gly Leu
            35                  40                  45

Gly Ala Leu Gly Gly Ala Leu Gly Pro Gly Gly Lys Pro Leu Lys
        50                  55                  60

Pro Val Pro Gly Gly Leu Ala Gly Ala Gly Leu Ala Gly Leu Gly
65                  70                  75                  80

Ala Phe Pro Ala Val Thr Phe Pro Gly Ala Leu Val Pro Gly Val
                85                  90                  95

Ala Asp Ala Ala Ala Ala Tyr Lys Ala Ala Lys Ala Gly Ala Gly Leu
                    100                 105                 110

Gly Gly Val Pro Gly Val Gly Leu Gly Val Ser Ala Gly Ala Val
            115                 120                 125

Val Pro Gln Pro Gly Ala Gly Val Lys Pro Gly Lys Val Pro Gly Val
            130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Ala Phe Ala Gly Ile Pro Gly Val
            180                 185                 190

Gly Pro Phe Gly Gly Pro Gln Pro Gly Val Pro Leu Gly Tyr Pro Ile
                195                 200                 205

Lys Ala Pro Lys Leu Pro Gly Gly Tyr Gly Leu Pro Tyr Thr Thr Gly
210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Gly
            260                 265                 270

Val Leu Pro Gly Val Gly Gly Ala Gly Val Pro Gly Val Pro Gly Ala
    275                 280                 285

Ile Pro Gly Ile Gly Gly Ile Ala Gly Val Gly Thr Pro Ala Ala Ala
            290                 295                 300

Ala Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Leu Val Leu
                325                 330                 335

Val Phe Leu Asp Leu Glu Leu Val Leu Val Phe Leu Ala Ser Gly Gln
                340                 345                 350

Tyr Leu Glu Pro Trp Leu Pro Leu Lys Gln Pro Asn Met Glu Gln Gln
                355                 360                 365

Cys Leu Gly Ser Leu Glu Gly Ser Gly Leu Ser Val Glu
            370                 375                 380

<210> SEQ ID NO 68
<211> LENGTH: 711
<212> TYPE: PRT
<213> ORGANISM: Homo sapiens

<400> SEQUENCE: 68

Met Ala Gly Leu Thr Ala Ala Ala Pro Arg Pro Gly Val Leu Leu Leu
```

-continued

```
1               5                   10                  15
Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
                35                  40                  45

Gly Ala Leu Gly Gly Ala Leu Gly Pro Gly Gly Lys Pro Leu Lys
    50                  55                  60

Pro Val Pro Gly Gly Leu Ala Gly Ala Gly Leu Ala Gly Leu Gly
65                  70                  75                  80

Ala Phe Pro Ala Val Thr Phe Pro Gly Ala Leu Val Pro Gly Val
                85                  90                  95

Ala Asp Ala Ala Ala Tyr Lys Ala Ala Lys Ala Gly Ala Gly Leu
                100                 105                 110

Gly Gly Val Pro Gly Val Gly Leu Gly Val Ser Ala Ala Pro Ser
            115                 120                 125

Val Pro Gly Ala Val Pro Gln Pro Gly Ala Gly Val Lys Pro Gly
            130                 135                 140

Lys Val Pro Gly Val Gly Leu Pro Gly Val Tyr Pro Gly Gly Val Leu
145                 150                 155                 160

Pro Gly Ala Arg Phe Pro Gly Val Gly Val Leu Pro Gly Val Pro Thr
                165                 170                 175

Gly Ala Gly Val Lys Pro Lys Ala Pro Gly Val Gly Ala Phe Ala
                180                 185                 190

Gly Ile Pro Gly Val Gly Pro Phe Gly Gly Pro Gln Pro Gly Val Pro
            195                 200                 205

Leu Gly Tyr Pro Ile Lys Ala Pro Lys Leu Pro Gly Gly Tyr Gly Leu
    210                 215                 220

Pro Tyr Thr Thr Gly Lys Leu Pro Tyr Gly Tyr Gly Pro Gly Gly Val
225                 230                 235                 240

Ala Gly Ala Ala Gly Lys Ala Gly Tyr Pro Thr Gly Thr Gly Val Gly
                245                 250                 255

Pro Gln Ala Ala Ala Ala Ala Ala Lys Ala Ala Ala Lys Phe Gly
                260                 265                 270

Ala Gly Ala Ala Gly Val Leu Pro Gly Val Gly Gly Ala Gly Val Pro
    275                 280                 285

Gly Val Pro Gly Ala Ile Pro Gly Ile Gly Gly Ile Ala Gly Val Gly
            290                 295                 300

Thr Pro Ala Ala Ala Ala Ala Ala Ala Ala Lys Ala Ala Lys
305                 310                 315                 320

Tyr Gly Ala Ala Ala Gly Leu Val Pro Gly Gly Pro Gly Phe Gly Pro
                325                 330                 335

Gly Val Val Gly Val Pro Gly Ala Gly Val Pro Gly Val Gly Val Pro
            340                 345                 350

Gly Ala Gly Ile Pro Val Val Pro Gly Ala Gly Ile Pro Gly Ala Ala
            355                 360                 365

Val Pro Gly Val Val Ser Pro Glu Ala Ala Ala Lys Ala Ala Ala Lys
    370                 375                 380

Ala Ala Lys Tyr Gly Ala Arg Pro Gly Val Gly Val Gly Gly Ile Pro
385                 390                 395                 400

Thr Tyr Gly Val Gly Ala Gly Gly Phe Pro Gly Phe Gly Val Gly Val
                405                 410                 415

Gly Gly Ile Pro Gly Val Ala Gly Val Pro Gly Val Gly Val Pro
            420                 425                 430
```

```
Gly Val Gly Gly Val Pro Gly Val Gly Ile Ser Pro Glu Ala Gln Ala
            435                 440                 445

Ala Ala Ala Ala Lys Ala Ala Lys Tyr Gly Val Gly Thr Pro Ala Ala
    450                 455                 460

Ala Ala Ala Lys Ala Ala Ala Lys Ala Ala Gln Phe Gly Leu Val Pro
465                 470                 475                 480

Gly Val Gly Val Ala Pro Gly Val Gly Val Ala Pro Gly Val Gly Val
                485                 490                 495

Ala Pro Gly Val Gly Leu Ala Pro Gly Val Gly Val Ala Pro Gly Val
            500                 505                 510

Gly Val Ala Pro Gly Val Gly Val Ala Pro Gly Ile Gly Pro Gly Gly
            515                 520                 525

Val Ala Ala Ala Lys Ser Ala Ala Lys Val Ala Ala Lys Ala Gln
    530                 535                 540

Leu Arg Ala Ala Ala Gly Leu Gly Ala Gly Ile Pro Gly Leu Gly Val
545                 550                 555                 560

Gly Val Gly Val Pro Gly Leu Gly Val Gly Ala Gly Val Pro Gly Leu
                565                 570                 575

Gly Val Gly Ala Gly Val Pro Gly Phe Gly Ala Val Pro Gly Ala Leu
                580                 585                 590

Ala Ala Ala Lys Ala Ala Lys Tyr Gly Ala Ala Val Pro Gly Val Leu
            595                 600                 605

Gly Gly Leu Gly Ala Leu Gly Gly Val Gly Ile Pro Gly Gly Val Val
            610                 615                 620

Gly Ala Gly Pro Ala Ala Ala Ala Ala Ala Lys Ala Ala Ala Lys
625                 630                 635                 640

Ala Ala Gln Phe Gly Leu Val Gly Ala Ala Gly Leu Gly Gly Leu Gly
                645                 650                 655

Val Gly Gly Leu Gly Val Pro Gly Val Gly Gly Leu Gly Gly Ile Pro
                660                 665                 670

Pro Ala Ala Ala Ala Lys Ala Ala Lys Tyr Gly Val Ala Ala Arg Pro
                675                 680                 685

Gly Phe Gly Leu Ser Pro Ile Phe Pro Gly Gly Ala Cys Leu Gly Lys
            690                 695                 700

Ala Cys Gly Arg Lys Arg Lys
705                 710

<210> SEQ ID NO 69
<211> LENGTH: 643
<212> TYPE: PRT
<213> ORGANISM: Homo sapiens

<400> SEQUENCE: 69

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
        35                  40                  45

Gly Ala Leu Gly Gly Gly Ala Leu Gly Pro Gly Gly Lys Pro Leu Lys
    50                  55                  60

Pro Gly Leu Gly Ala Phe Pro Ala Val Thr Phe Pro Gly Ala Leu Val
65                  70                  75                  80

Pro Gly Gly Val Ala Asp Ala Ala Ala Tyr Lys Ala Ala Lys Ala
                85                  90                  95
```

-continued

```
Gly Ala Gly Leu Gly Gly Val Pro Gly Val Gly Leu Gly Val Ser
            100                 105                 110
Ala Gly Ala Val Val Pro Gln Pro Gly Ala Gly Val Lys Pro Gly Lys
        115                 120                 125
Val Pro Gly Val Gly Leu Pro Gly Val Tyr Pro Gly Gly Val Leu Pro
130                 135                 140
Gly Ala Arg Phe Pro Gly Val Gly Val Leu Pro Gly Val Pro Thr Gly
145                 150                 155                 160
Ala Gly Val Lys Pro Lys Ala Pro Gly Val Gly Pro Phe Gly Gly Pro
                165                 170                 175
Gln Pro Gly Val Pro Leu Gly Tyr Pro Ile Lys Ala Pro Lys Leu Pro
            180                 185                 190
Gly Tyr Gly Pro Gly Gly Val Ala Gly Ala Ala Gly Lys Ala Gly Tyr
        195                 200                 205
Pro Thr Gly Thr Gly Val Gly Pro Gln Ala Ala Ala Ala Ala Ala Ala
210                 215                 220
Lys Ala Ala Ala Lys Phe Gly Ala Gly Ala Ala Gly Val Leu Pro Gly
225                 230                 235                 240
Val Gly Gly Ala Gly Val Pro Gly Val Pro Gly Ala Ile Pro Gly Ile
                245                 250                 255
Gly Gly Ile Ala Gly Val Gly Thr Pro Ala Ala Ala Ala Ala Ala Ala
            260                 265                 270
Ala Ala Ala Lys Ala Ala Lys Tyr Gly Ala Ala Ala Gly Leu Val Pro
        275                 280                 285
Gly Gly Pro Gly Phe Gly Pro Gly Val Val Gly Val Pro Gly Ala Gly
290                 295                 300
Val Pro Gly Val Gly Val Pro Gly Ala Gly Ile Pro Val Val Pro Gly
305                 310                 315                 320
Ala Gly Ile Pro Gly Ala Ala Val Pro Gly Val Val Ser Pro Glu Ala
                325                 330                 335
Ala Ala Lys Ala Ala Ala Lys Ala Ala Lys Tyr Gly Ala Arg Pro Gly
            340                 345                 350
Val Gly Val Gly Gly Ile Pro Thr Tyr Gly Val Gly Ala Gly Gly Phe
        355                 360                 365
Pro Gly Phe Gly Val Gly Val Gly Ala Glu Ala Gln Ala Ala Ala Ala
370                 375                 380
Ala Lys Ala Ala Lys Tyr Gly Leu Val Pro Gly Val Gly Val Ala Pro
385                 390                 395                 400
Gly Val Gly Val Ala Pro Gly Val Gly Val Ala Pro Gly Val Gly Leu
                405                 410                 415
Ala Pro Gly Val Gly Val Ala Pro Gly Val Gly Val Ala Pro Gly Val
            420                 425                 430
Gly Val Ala Pro Gly Ile Gly Pro Gly Gly Val Ala Ala Ala Ala Lys
        435                 440                 445
Ser Ala Ala Lys Val Ala Ala Lys Ala Gln Leu Arg Ala Ala Ala Gly
450                 455                 460
Leu Gly Ala Gly Ile Pro Gly Leu Gly Val Gly Val Gly Val Pro Gly
465                 470                 475                 480
Leu Gly Val Gly Ala Gly Val Pro Gly Leu Gly Val Gly Ala Gly Val
                485                 490                 495
Pro Gly Phe Gly Ala Val Pro Gly Ala Leu Ala Ala Ala Lys Ala Ala
            500                 505                 510
Lys Tyr Gly Ala Ala Val Pro Gly Val Leu Gly Gly Leu Gly Ala Leu
        515                 520                 525
```

```
Gly Gly Val Gly Ile Pro Gly Val Val Gly Ala Gly Pro Ala Ala
            530             535             540

Ala Ala Ala Ala Ala Lys Ala Ala Lys Ala Ala Gln Phe Gly Leu
545             550             555             560

Val Gly Ala Ala Gly Leu Gly Gly Leu Gly Val Gly Gly Leu Gly Val
            565             570             575

Pro Gly Val Gly Gly Leu Gly Gly Ile Pro Ala Ala Ala Ala Lys
            580             585             590

Ala Ala Lys Tyr Gly Ala Ala Gly Leu Gly Gly Val Leu Gly Gly Ala
            595             600             605

Gly Gln Phe Pro Leu Gly Gly Val Ala Ala Arg Pro Gly Phe Gly Leu
610             615             620

Ser Pro Ile Phe Pro Gly Gly Ala Cys Leu Gly Lys Ala Cys Gly Arg
625             630             635             640

Lys Arg Lys

<210> SEQ ID NO 70
<211> LENGTH: 658
<212> TYPE: PRT
<213> ORGANISM: Homo sapiens

<400> SEQUENCE: 70

Met Ala Gly Leu Thr Ala Ala Pro Arg Pro Gly Val Leu Leu Leu
1               5               10              15

Leu Leu Ser Ile Leu His Pro Ser Arg Pro Gly Gly Val Pro Gly Ala
            20              25              30

Ile Pro Gly Gly Val Pro Gly Gly Val Phe Tyr Pro Gly Ala Gly Leu
            35              40              45

Gly Ala Leu Gly Gly Gly Ala Leu Gly Pro Gly Gly Lys Pro Leu Lys
            50              55              60

Pro Val Pro Gly Gly Leu Ala Gly Ala Gly Leu Gly Ala Gly Leu Gly
65              70              75              80

Ala Phe Pro Ala Val Thr Phe Pro Gly Ala Leu Val Pro Gly Gly Val
                85              90              95

Ala Asp Ala Ala Ala Ala Tyr Lys Ala Ala Lys Ala Gly Ala Gly Leu
            100             105             110

Gly Gly Val Pro Gly Val Gly Gly Leu Gly Val Ser Ala Gly Ala Val
            115             120             125

Val Pro Gln Pro Gly Ala Gly Val Lys Pro Gly Lys Val Pro Gly Val
130             135             140

Gly Leu Pro Gly Val Tyr Pro Gly Gly Val Leu Pro Gly Ala Arg Phe
145             150             155             160

Pro Gly Val Gly Val Leu Pro Gly Val Pro Thr Gly Ala Gly Val Lys
            165             170             175

Pro Lys Ala Pro Gly Val Gly Ala Phe Ala Gly Ile Pro Gly Val
            180             185             190

Gly Pro Phe Gly Gly Pro Gln Pro Gly Val Pro Leu Gly Tyr Pro Ile
            195             200             205

Lys Ala Pro Lys Leu Pro Gly Tyr Gly Pro Gly Gly Val Ala Gly Ala
210             215             220

Ala Gly Lys Ala Gly Tyr Pro Thr Gly Thr Gly Val Gly Pro Gln Ala
225             230             235             240

Ala Ala Ala Ala Ala Lys Ala Ala Lys Phe Gly Ala Gly Ala
            245             250             255
```

```
Ala Gly Val Leu Pro Gly Val Gly Ala Gly Val Pro Gly Val Pro
            260                 265                 270

Gly Ala Ile Pro Gly Ile Gly Ile Ala Gly Val Gly Thr Pro Ala
            275                 280                 285

Ala Ala Ala Ala Ala Ala Ala Ala Lys Ala Ala Lys Tyr Gly Ala
        290                 295                 300

Ala Ala Gly Leu Val Pro Gly Pro Gly Phe Gly Pro Gly Val Val
305                 310                 315                 320

Gly Val Pro Gly Ala Gly Val Pro Gly Val Gly Val Pro Gly Ala Gly
                325                 330                 335

Ile Pro Val Val Pro Gly Ala Gly Ile Pro Gly Ala Ala Val Pro Gly
            340                 345                 350

Val Val Ser Pro Glu Ala Ala Lys Ala Ala Lys Ala Ala Lys
            355                 360                 365

Tyr Gly Ala Arg Pro Gly Val Gly Val Gly Gly Ile Pro Thr Tyr Gly
            370                 375                 380

Val Gly Ala Gly Gly Phe Pro Gly Phe Gly Val Gly Val Gly Gly Ile
385                 390                 395                 400

Pro Gly Val Ala Gly Val Pro Gly Val Gly Val Pro Gly Val Gly
                405                 410                 415

Gly Val Pro Gly Val Gly Ile Ser Pro Glu Ala Gln Ala Ala Ala
            420                 425                 430

Ala Lys Ala Ala Lys Tyr Gly Leu Val Pro Gly Val Gly Val Ala Pro
        435                 440                 445

Gly Val Gly Val Ala Pro Gly Val Gly Val Ala Pro Gly Val Gly Leu
        450                 455                 460

Ala Pro Gly Val Gly Val Ala Pro Gly Val Gly Val Ala Pro Gly Val
465                 470                 475                 480

Gly Val Ala Pro Gly Ile Gly Pro Gly Val Ala Gly Ala Ala Ala
                485                 490                 495

Gly Leu Gly Ala Gly Ile Pro Gly Leu Gly Val Gly Val Gly Val Pro
            500                 505                 510

Gly Leu Gly Val Gly Ala Gly Val Pro Gly Leu Gly Val Gly Ala Gly
            515                 520                 525

Val Pro Gly Phe Gly Ala Val Pro Gly Ala Leu Ala Ala Ala Lys Ala
            530                 535                 540

Ala Lys Tyr Gly Ala Ala Val Pro Gly Val Leu Gly Gly Leu Gly Ala
545                 550                 555                 560

Leu Gly Gly Val Gly Ile Pro Gly Gly Val Val Gly Ala Gly Pro Ala
                565                 570                 575

Ala Ala Ala Ala Ala Ala Lys Ala Ala Ala Lys Ala Ala Gln Phe Gly
            580                 585                 590

Leu Val Gly Ala Ala Gly Leu Gly Gly Leu Gly Val Gly Gly Leu Gly
            595                 600                 605

Val Pro Gly Val Gly Gly Leu Gly Ile Pro Pro Ala Ala Ala Ala
            610                 615                 620

Lys Ala Ala Lys Tyr Gly Val Ala Ala Arg Pro Gly Phe Gly Leu Ser
625                 630                 635                 640

Pro Ile Phe Pro Gly Gly Ala Cys Leu Gly Lys Ala Cys Gly Arg Lys
                645                 650                 655

Arg Lys

<210> SEQ ID NO 71
<211> LENGTH: 724
```

```
<212> TYPE: PRT
<213> ORGANISM: Homo sapiens

<400> SEQUENCE: 71

Met Ala Gly Leu Thr Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
        35                  40                  45

Gly Ala Leu Gly Gly Gly Ala Leu Gly Pro Gly Gly Lys Pro Leu Lys
    50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
            100                 105                 110

Gly Gly Val Pro Gly Val Gly Gly Leu Gly Val Ser Ala Gly Ala Val
        115                 120                 125

Val Pro Gln Pro Gly Ala Gly Val Lys Pro Gly Lys Val Pro Gly Val
130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
        195                 200                 205

Lys Ala Pro Lys Leu Pro Gly Gly Tyr Gly Leu Pro Tyr Thr Thr Gly
    210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Ala Lys Phe Gly Ala Gly Ala Ala Gly
            260                 265                 270

Val Leu Pro Gly Val Gly Gly Ala Gly Val Pro Gly Val Pro Gly Ala
        275                 280                 285

Ile Pro Gly Ile Gly Gly Ile Ala Gly Val Gly Thr Pro Ala Ala Ala
    290                 295                 300

Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
        355                 360                 365

Ser Pro Glu Ala Ala Ala Lys Ala Ala Ala Lys Ala Ala Lys Tyr Gly
    370                 375                 380

Ala Arg Pro Gly Val Gly Val Gly Gly Ile Pro Thr Tyr Gly Val Gly
385                 390                 395                 400
```

```
Ala Gly Gly Phe Pro Gly Phe Gly Val Gly Val Gly Ile Pro Gly
            405                 410                 415

Val Ala Gly Val Pro Gly Val Gly Val Pro Gly Val Gly Gly Val
            420                 425                 430

Pro Gly Val Gly Ile Ser Pro Glu Ala Gln Ala Ala Ala Ala Lys
            435                 440                 445

Ala Ala Lys Tyr Gly Val Gly Thr Pro Ala Ala Ala Ala Lys Ala
            450                 455                 460

Ala Ala Lys Ala Ala Gln Phe Gly Leu Val Pro Gly Val Gly Val Ala
465                 470                 475                 480

Pro Gly Val Gly Val Ala Pro Gly Val Gly Val Ala Pro Gly Val Gly
            485                 490                 495

Leu Ala Pro Gly Val Gly Val Ala Pro Gly Val Gly Val Ala Pro Gly
            500                 505                 510

Val Gly Val Ala Pro Gly Ile Gly Pro Gly Gly Val Ala Ala Ala
            515                 520                 525

Lys Ser Ala Ala Lys Val Ala Ala Lys Ala Gln Leu Arg Ala Ala
            530                 535                 540

Gly Leu Gly Ala Gly Ile Pro Gly Leu Gly Val Gly Val Gly Val Pro
545                 550                 555                 560

Gly Leu Gly Val Gly Ala Gly Val Pro Gly Leu Gly Val Gly Ala Gly
            565                 570                 575

Val Pro Gly Phe Gly Ala Val Pro Gly Ala Leu Ala Ala Ala Lys Ala
            580                 585                 590

Ala Lys Tyr Gly Ala Ala Val Pro Gly Val Leu Gly Gly Leu Gly Ala
            595                 600                 605

Leu Gly Gly Val Gly Ile Pro Gly Gly Val Val Gly Ala Gly Pro Ala
            610                 615                 620

Ala Ala Ala Ala Ala Lys Ala Ala Ala Lys Ala Ala Gln Phe Gly
625                 630                 635                 640

Leu Val Gly Ala Ala Gly Leu Gly Gly Leu Gly Val Gly Gly Leu Gly
                645                 650                 655

Val Pro Gly Val Gly Gly Leu Gly Gly Ile Pro Pro Ala Ala Ala
            660                 665                 670

Lys Ala Ala Lys Tyr Gly Ala Ala Gly Leu Gly Gly Val Leu Gly Gly
            675                 680                 685

Ala Gly Gln Phe Pro Leu Gly Gly Val Ala Ala Arg Pro Gly Phe Gly
            690                 695                 700

Leu Ser Pro Ile Phe Pro Gly Gly Ala Cys Leu Gly Lys Ala Cys Gly
705                 710                 715                 720

Arg Lys Arg Lys

<210> SEQ ID NO 72
<211> LENGTH: 677
<212> TYPE: PRT
<213> ORGANISM: Homo sapiens

<400> SEQUENCE: 72

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Ala Leu Gly Pro
            35                  40                  45

Gly Gly Lys Pro Leu Lys Pro Val Pro Gly Gly Leu Ala Gly Ala Gly
```

-continued

```
                50                  55                  60
Leu Gly Ala Gly Leu Gly Ala Phe Pro Ala Val Thr Phe Pro Gly Ala
 65                  70                  75                  80
Leu Val Pro Gly Gly Val Ala Asp Ala Ala Ala Tyr Lys Ala Ala
                 85                  90                  95
Lys Ala Gly Ala Gly Leu Gly Val Pro Gly Val Gly Gly Leu Gly
                100                 105                 110
Val Ser Ala Gly Ala Val Pro Gln Pro Gly Ala Gly Val Lys Pro
                115                 120                 125
Gly Lys Val Pro Gly Val Gly Leu Pro Gly Val Tyr Pro Gly Gly Val
130                 135                 140
Leu Pro Gly Ala Arg Phe Pro Gly Val Gly Val Leu Pro Gly Val Pro
145                 150                 155                 160
Thr Gly Ala Gly Val Lys Pro Lys Ala Pro Gly Val Gly Gly Ala Phe
                165                 170                 175
Ala Gly Ile Pro Gly Val Gly Pro Phe Gly Gly Pro Gln Pro Gly Val
                180                 185                 190
Pro Leu Gly Tyr Pro Ile Lys Ala Pro Lys Leu Pro Gly Gly Tyr Gly
                195                 200                 205
Leu Pro Tyr Thr Thr Gly Lys Leu Pro Tyr Gly Tyr Gly Pro Gly Gly
210                 215                 220
Val Ala Gly Ala Ala Gly Lys Ala Gly Tyr Pro Thr Gly Thr Gly Val
225                 230                 235                 240
Gly Pro Gln Ala Ala Ala Ala Ala Ala Lys Ala Ala Ala Lys Phe
                245                 250                 255
Gly Ala Gly Ala Ala Gly Val Leu Pro Gly Val Gly Gly Ala Gly Val
                260                 265                 270
Pro Gly Val Pro Gly Ala Ile Pro Gly Ile Gly Gly Ile Ala Gly Val
                275                 280                 285
Gly Thr Pro Ala Ala Ala Ala Ala Ala Ala Ala Lys Ala Ala
                290                 295                 300
Lys Tyr Gly Ala Ala Ala Gly Leu Val Pro Gly Gly Pro Gly Phe Gly
305                 310                 315                 320
Pro Gly Val Val Gly Val Pro Gly Ala Gly Val Pro Gly Val Gly Val
                325                 330                 335
Pro Gly Ala Gly Ile Pro Val Val Pro Gly Ala Gly Ile Pro Gly Ala
                340                 345                 350
Ala Val Pro Gly Val Val Ser Pro Glu Ala Ala Ala Lys Ala Ala Ala
                355                 360                 365
Lys Ala Ala Lys Tyr Gly Ala Arg Pro Gly Val Gly Val Gly Gly Ile
                370                 375                 380
Pro Thr Tyr Gly Val Gly Ala Gly Gly Phe Pro Gly Phe Gly Val Gly
385                 390                 395                 400
Val Gly Gly Ile Pro Gly Val Ala Gly Val Pro Gly Val Gly Gly Val
                405                 410                 415
Pro Gly Val Gly Gly Val Pro Gly Val Gly Ile Ser Pro Glu Ala Gln
                420                 425                 430
Ala Ala Ala Ala Ala Lys Ala Ala Lys Tyr Gly Leu Val Pro Gly Val
                435                 440                 445
Gly Val Ala Pro Gly Val Gly Val Ala Pro Gly Val Gly Val Ala Pro
                450                 455                 460
Gly Val Gly Leu Ala Pro Gly Val Gly Val Ala Pro Gly Val Gly Val
465                 470                 475                 480
```

```
Ala Pro Gly Val Gly Val Ala Gly Ile Gly Pro Gly Gly Val Ala
            485                 490                 495

Ala Ala Ala Lys Ser Ala Ala Lys Val Ala Ala Lys Ala Gln Leu Arg
            500                 505                 510

Ala Ala Ala Gly Leu Gly Ala Gly Ile Pro Gly Leu Gly Val Gly Val
            515                 520                 525

Gly Val Pro Gly Leu Gly Val Gly Ala Gly Val Pro Gly Leu Gly Val
            530                 535                 540

Gly Ala Gly Val Pro Gly Phe Gly Ala Val Pro Gly Ala Leu Ala Ala
545                 550                 555                 560

Ala Lys Ala Ala Lys Tyr Gly Ala Ala Val Pro Gly Val Leu Gly Gly
            565                 570                 575

Leu Gly Ala Leu Gly Gly Val Gly Ile Pro Gly Gly Val Val Gly Ala
            580                 585                 590

Gly Pro Ala Ala Ala Ala Ala Ala Lys Ala Ala Ala Lys Ala Ala
            595                 600                 605

Gln Phe Gly Leu Val Gly Ala Ala Gly Leu Gly Gly Leu Gly Val Gly
            610                 615                 620

Gly Leu Gly Val Pro Gly Val Gly Gly Leu Gly Gly Ile Pro Pro Ala
625                 630                 635                 640

Ala Ala Ala Lys Ala Ala Lys Tyr Gly Val Ala Ala Arg Pro Gly Phe
            645                 650                 655

Gly Leu Ser Pro Ile Phe Pro Gly Gly Ala Cys Leu Gly Lys Ala Cys
            660                 665                 670

Gly Arg Lys Arg Lys
            675

<210> SEQ ID NO 73
<211> LENGTH: 617
<212> TYPE: PRT
<213> ORGANISM: Homo sapiens

<400> SEQUENCE: 73

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu Gly Pro
            35                  40                  45

Gly Gly Lys Pro Leu Lys Pro Val Pro Gly Gly Leu Ala Gly Ala Gly
            50                  55                  60

Leu Gly Ala Gly Leu Gly Ala Phe Pro Ala Val Thr Phe Pro Gly Ala
65                  70                  75                  80

Leu Val Pro Gly Gly Val Ala Asp Ala Ala Ala Ala Tyr Lys Ala Ala
            85                  90                  95

Lys Ala Gly Ala Gly Leu Gly Gly Val Pro Gly Val Gly Gly Leu Gly
            100                 105                 110

Val Ser Ala Gly Ala Val Val Pro Gln Pro Gly Ala Gly Val Lys Pro
            115                 120                 125

Gly Lys Val Pro Gly Val Gly Leu Pro Gly Val Tyr Pro Gly Gly Val
            130                 135                 140

Leu Pro Gly Val Gly Pro Phe Gly Gly Pro Gln Pro Gly Val Pro Leu
145                 150                 155                 160

Gly Tyr Pro Ile Lys Ala Pro Lys Leu Pro Gly Gly Tyr Gly Leu Pro
            165                 170                 175
```

```
Tyr Thr Thr Gly Lys Leu Pro Tyr Gly Tyr Gly Pro Gly Gly Val Ala
            180                 185                 190

Gly Ala Ala Gly Lys Ala Gly Tyr Pro Thr Gly Thr Gly Val Gly Pro
            195                 200                 205

Gln Ala Ala Ala Ala Ala Ala Lys Ala Ala Ala Lys Phe Gly Ala
210                 215                 220

Gly Ala Ala Gly Val Leu Pro Gly Val Gly Ala Gly Val Pro Gly
225                 230                 235                 240

Val Pro Gly Ala Ile Pro Gly Ile Gly Ile Ala Gly Val Gly Thr
                245                 250                 255

Pro Ala Ala Ala Ala Ala Ala Ala Ala Lys Ala Ala Lys Tyr
            260                 265                 270

Gly Ala Ala Ala Gly Leu Val Pro Gly Gly Pro Gly Phe Gly Pro Gly
            275                 280                 285

Val Val Gly Val Pro Gly Ala Gly Val Pro Gly Val Gly Val Pro Gly
            290                 295                 300

Ala Gly Ile Pro Val Val Pro Gly Ala Gly Ile Pro Gly Ala Ala Val
305                 310                 315                 320

Pro Gly Val Val Ser Pro Glu Ala Ala Lys Ala Ala Ala Lys Ala
                325                 330                 335

Ala Lys Tyr Gly Ala Arg Pro Gly Val Gly Val Gly Gly Ile Pro Thr
            340                 345                 350

Tyr Gly Val Gly Ala Gly Gly Phe Pro Gly Phe Gly Val Gly Val Gly
            355                 360                 365

Ala Glu Ala Gln Ala Ala Ala Ala Ala Lys Ala Ala Lys Tyr Gly Leu
            370                 375                 380

Val Pro Gly Val Gly Val Ala Pro Gly Val Gly Val Ala Pro Gly Val
385                 390                 395                 400

Gly Val Ala Pro Gly Val Gly Leu Ala Pro Gly Val Gly Val Ala Pro
                405                 410                 415

Gly Val Gly Val Ala Pro Gly Val Gly Val Ala Pro Gly Ile Gly Pro
            420                 425                 430

Gly Gly Val Ala Ala Ala Lys Ser Ala Ala Lys Val Ala Ala Lys
            435                 440                 445

Ala Gln Leu Arg Ala Ala Gly Leu Gly Ala Gly Ile Pro Gly Leu
450                 455                 460

Gly Val Gly Val Gly Val Pro Gly Leu Gly Val Gly Ala Gly Val Pro
465                 470                 475                 480

Gly Leu Gly Val Gly Ala Gly Val Pro Gly Phe Gly Ala Val Pro Gly
                485                 490                 495

Ala Leu Ala Ala Ala Lys Ala Ala Lys Tyr Gly Ala Ala Val Pro Gly
            500                 505                 510

Val Leu Gly Gly Leu Gly Ala Leu Gly Gly Val Gly Ile Pro Gly Gly
            515                 520                 525

Val Val Gly Ala Gly Pro Ala Ala Ala Ala Ala Ala Lys Ala Ala
            530                 535                 540

Ala Lys Ala Ala Gln Phe Gly Leu Val Gly Ala Ala Gly Leu Gly Gly
545                 550                 555                 560

Leu Gly Val Gly Gly Leu Gly Val Pro Gly Val Gly Gly Leu Gly Gly
                565                 570                 575

Ile Pro Pro Ala Ala Ala Ala Lys Ala Ala Lys Tyr Gly Val Ala Ala
            580                 585                 590

Arg Pro Gly Phe Gly Leu Ser Pro Ile Phe Pro Gly Gly Ala Cys Leu
            595                 600                 605
```

```
Gly Lys Ala Cys Gly Arg Lys Arg Lys
    610             615

<210> SEQ ID NO 74
<211> LENGTH: 747
<212> TYPE: PRT
<213> ORGANISM: Bos taurus

<400> SEQUENCE: 74

Met Arg Ser Leu Thr Ala Ala Arg Arg Pro Glu Val Leu Leu Leu
1               5                   10                  15

Leu Leu Cys Ile Leu Gln Pro Ser Gln Pro Gly Gly Val Pro Gly Ala
            20                  25                  30

Val Pro Gly Gly Val Pro Gly Gly Val Phe Phe Pro Gly Ala Gly Leu
        35                  40                  45

Gly Gly Leu Gly Val Gly Gly Leu Gly Pro Gly Val Lys Pro Ala Lys
    50                  55                  60

Pro Gly Val Gly Gly Leu Val Gly Pro Gly Leu Gly Ala Glu Gly Ser
65                  70                  75                  80

Ala Leu Pro Gly Ala Phe Pro Gly Gly Phe Phe Gly Ala Gly Gly Gly
                85                  90                  95

Ala Ala Gly Ala Ala Ala Ala Tyr Lys Ala Ala Lys Ala Gly Ala
                100                 105                 110

Ala Gly Leu Gly Val Gly Gly Ile Gly Gly Val Gly Leu Gly Val
            115                 120                 125

Ser Thr Gly Ala Val Val Pro Gln Leu Gly Ala Gly Val Gly Ala Gly
    130                 135                 140

Val Lys Pro Gly Lys Val Pro Gly Val Gly Leu Pro Gly Val Tyr Pro
145                 150                 155                 160

Gly Gly Val Leu Pro Gly Ala Gly Ala Arg Phe Pro Gly Ile Gly Val
                165                 170                 175

Leu Pro Gly Val Pro Thr Gly Ala Gly Val Lys Pro Lys Ala Gln Val
            180                 185                 190

Gly Ala Gly Ala Phe Ala Gly Ile Pro Gly Val Gly Pro Phe Gly Gly
        195                 200                 205

Gln Gln Pro Gly Leu Pro Leu Gly Tyr Pro Ile Lys Ala Pro Lys Leu
    210                 215                 220

Pro Ala Gly Tyr Gly Leu Pro Tyr Lys Thr Gly Lys Leu Pro Tyr Gly
225                 230                 235                 240

Phe Gly Pro Gly Gly Val Ala Gly Ser Ala Gly Lys Ala Gly Tyr Pro
                245                 250                 255

Thr Gly Thr Gly Val Gly Pro Gln Ala Ala Ala Ala Ala Lys Ala
            260                 265                 270

Ala Ala Lys Leu Gly Ala Gly Gly Ala Gly Val Leu Pro Gly Val Gly
        275                 280                 285

Val Gly Gly Pro Gly Ile Pro Gly Ala Pro Gly Ala Ile Pro Gly Ile
    290                 295                 300

Gly Gly Ile Ala Gly Val Gly Ala Pro Asp Ala Ala Ala Ala Ala
305                 310                 315                 320

Ala Ala Ala Lys Ala Ala Lys Phe Gly Ala Ala Gly Leu Pro Gly
                325                 330                 335

Val Gly Val Pro Gly Val Gly Val Pro Gly Val Gly Val Pro Gly Val
            340                 345                 350

Gly Val Pro Gly Val Gly Val Pro Gly Val Gly Val Pro Gly Val Gly
        355                 360                 365
```

```
Val Pro Gly Val Gly Val Pro Gly Val Gly Val Pro Gly Val Gly Val
        370                 375                 380

Pro Gly Val Gly Val Pro Gly Ala Leu Ser Pro Ala Ala Thr Ala Lys
385                 390                 395                 400

Ala Ala Ala Lys Ala Ala Lys Phe Gly Ala Arg Gly Ala Val Gly Ile
            405                 410                 415

Gly Gly Ile Pro Thr Phe Gly Leu Gly Pro Gly Gly Phe Pro Gly Ile
            420                 425                 430

Gly Asp Ala Ala Ala Pro Ala Ala Ala Ala Lys Ala Ala Lys
            435                 440                 445

Ile Gly Ala Gly Gly Val Gly Ala Leu Gly Gly Val Val Pro Gly Ala
        450                 455                 460

Pro Gly Ala Ile Pro Gly Leu Pro Gly Val Gly Val Pro Gly Val
465                 470                 475                 480

Gly Ile Pro Ala Ala Ala Ala Lys Ala Ala Lys Ala Ala Gln
            485                 490                 495

Phe Gly Leu Gly Pro Gly Val Gly Val Ala Pro Gly Val Gly Val Val
            500                 505                 510

Pro Gly Val Gly Val Val Pro Gly Val Gly Val Ala Pro Gly Ile Gly
        515                 520                 525

Leu Gly Pro Gly Gly Val Ile Gly Ala Gly Val Pro Ala Ala Ala Lys
530                 535                 540

Ser Ala Ala Lys Ala Ala Ala Lys Ala Gln Phe Arg Ala Ala Ala Gly
545                 550                 555                 560

Leu Pro Ala Gly Val Pro Gly Leu Gly Val Gly Ala Gly Val Pro Gly
            565                 570                 575

Leu Gly Val Gly Ala Gly Val Pro Gly Leu Gly Val Gly Ala Gly Val
            580                 585                 590

Pro Gly Pro Gly Ala Val Pro Gly Thr Leu Ala Ala Ala Lys Ala Ala
            595                 600                 605

Lys Phe Gly Pro Gly Gly Val Gly Ala Leu Gly Gly Val Gly Asp Leu
610                 615                 620

Gly Gly Ala Gly Ile Pro Gly Gly Val Ala Gly Val Val Pro Ala Ala
625                 630                 635                 640

Ala Ala Ala Ala Lys Ala Ala Lys Ala Ala Gln Phe Gly Leu Gly
            645                 650                 655

Gly Val Gly Gly Leu Gly Val Gly Gly Leu Gly Ala Val Pro Gly Ala
            660                 665                 670

Val Gly Leu Gly Gly Val Ser Pro Ala Ala Ala Lys Ala Ala Lys
        675                 680                 685

Phe Gly Ala Ala Gly Leu Gly Gly Val Leu Gly Ala Gly Gln Pro Phe
        690                 695                 700

Pro Ile Gly Gly Gly Ala Gly Gly Leu Gly Val Gly Gly Lys Pro Pro
705                 710                 715                 720

Lys Pro Phe Gly Gly Ala Leu Gly Ala Leu Gly Phe Pro Gly Gly Ala
            725                 730                 735

Cys Leu Gly Lys Ser Cys Gly Arg Lys Arg Lys
            740                 745
```

<210> SEQ ID NO 75
<211> LENGTH: 733
<212> TYPE: PRT
<213> ORGANISM: Bos taurus

<400> SEQUENCE: 75

```
Met Arg Ser Leu Thr Ala Ala Arg Arg Pro Glu Val Leu Leu Leu
1               5                   10                  15

Leu Leu Cys Ile Leu Gln Pro Ser Gln Pro Gly Gly Val Pro Gly Ala
            20              25                  30

Val Pro Gly Gly Val Pro Gly Val Phe Phe Pro Gly Ala Gly Leu
        35              40                  45

Gly Gly Leu Gly Val Gly Gly Leu Gly Pro Gly Val Lys Pro Ala Lys
        50              55                  60

Pro Gly Val Gly Leu Val Gly Pro Gly Leu Gly Ala Glu Gly Ser
65              70              75                  80

Ala Leu Pro Gly Ala Phe Pro Gly Gly Phe Gly Ala Gly Gly
                85              90                  95

Ala Ala Gly Ala Ala Ala Ala Tyr Lys Ala Ala Lys Ala Gly Ala
            100             105                 110

Ala Gly Leu Gly Val Gly Gly Ile Gly Gly Val Gly Gly Leu Gly Val
        115             120                 125

Ser Thr Gly Ala Val Val Pro Gln Leu Gly Ala Gly Val Gly Ala Gly
    130             135                 140

Val Lys Pro Gly Lys Val Pro Gly Val Gly Leu Pro Gly Val Tyr Pro
145             150             155                 160

Gly Gly Val Leu Pro Gly Ala Gly Ala Arg Phe Pro Gly Ile Gly Val
            165             170                 175

Leu Pro Gly Val Pro Thr Gly Ala Gly Val Lys Pro Lys Ala Gln Val
        180             185                 190

Gly Ala Gly Ala Phe Ala Gly Ile Pro Gly Val Gly Pro Phe Gly Gly
    195             200             205

Gln Gln Pro Gly Leu Pro Leu Gly Tyr Pro Ile Lys Ala Pro Lys Leu
    210             215                 220

Pro Gly Phe Gly Pro Gly Gly Val Ala Gly Ser Ala Gly Lys Ala Gly
225             230             235                 240

Tyr Pro Thr Gly Thr Gly Val Gly Pro Gln Ala Ala Ala Ala Ala
            245             250                 255

Lys Ala Ala Ala Lys Leu Gly Ala Gly Gly Ala Gly Val Leu Pro Gly
            260             265                 270

Val Gly Val Gly Gly Pro Gly Ile Pro Gly Ala Pro Gly Ala Ile Pro
    275             280                 285

Gly Ile Gly Gly Ile Ala Gly Val Ala Pro Asp Ala Ala Ala
        290             295             300

Ala Ala Ala Ala Ala Lys Ala Ala Lys Phe Gly Ala Ala Gly Gly Leu
305             310             315                 320

Pro Gly Val Gly Val Pro Gly Val Gly Val Pro Gly Val Gly Val Pro
            325             330                 335

Gly Val Gly Val Pro Gly Val Gly Val Pro Gly Val Gly Val Pro Gly
        340             345                 350

Val Gly Val Pro Gly Val Gly Val Pro Gly Val Gly Val Pro Gly Val
    355             360                 365

Gly Val Pro Gly Val Gly Val Pro Gly Ala Leu Ser Pro Ala Ala Thr
        370             375             380

Ala Lys Ala Ala Lys Ala Lys Phe Gly Ala Arg Gly Ala Val
385             390             395                 400

Gly Ile Gly Gly Ile Pro Thr Phe Gly Leu Gly Pro Gly Gly Phe Pro
        405             410                 415

Gly Ile Gly Asp Ala Ala Ala Ala Pro Ala Ala Ala Ala Ala Lys Ala
```

```
                    420                 425                 430
Ala Lys Ile Gly Ala Gly Val Gly Ala Leu Gly Gly Val Val Pro
                435                 440                 445
Gly Ala Pro Gly Ala Ile Pro Gly Leu Pro Gly Val Gly Gly Val Pro
            450                 455                 460
Gly Val Gly Ile Pro Ala Ala Ala Ala Lys Ala Ala Lys Ala
465                 470                 475                 480
Ala Gln Phe Gly Leu Gly Pro Gly Val Gly Val Ala Pro Gly Val Gly
                485                 490                 495
Val Val Pro Gly Val Gly Val Pro Gly Val Gly Val Ala Pro Gly
                500                 505                 510
Ile Gly Leu Gly Pro Gly Gly Val Ile Gly Ala Gly Val Pro Ala Ala
                515                 520                 525
Ala Lys Ser Ala Ala Lys Ala Ala Ala Lys Ala Gln Phe Arg Ala Ala
                530                 535                 540
Ala Gly Leu Pro Ala Gly Val Pro Gly Leu Gly Val Gly Ala Gly Val
545                 550                 555                 560
Pro Gly Leu Gly Val Gly Ala Gly Val Pro Gly Leu Gly Val Gly Ala
                565                 570                 575
Gly Val Pro Gly Pro Gly Ala Val Pro Gly Thr Leu Ala Ala Ala Lys
                580                 585                 590
Ala Ala Lys Phe Gly Pro Gly Gly Val Gly Ala Leu Gly Gly Val Gly
                595                 600                 605
Asp Leu Gly Gly Ala Gly Ile Pro Gly Gly Val Ala Gly Val Val Pro
                610                 615                 620
Ala Ala Ala Ala Ala Ala Lys Ala Ala Ala Lys Ala Ala Gln Phe Gly
625                 630                 635                 640
Leu Gly Gly Val Gly Gly Leu Gly Val Gly Leu Gly Ala Val Pro
                645                 650                 655
Gly Ala Val Gly Leu Gly Val Ser Pro Ala Ala Ala Lys Ala
                660                 665                 670
Ala Lys Phe Gly Ala Ala Gly Leu Gly Gly Val Leu Gly Ala Gly Gln
                675                 680                 685
Pro Phe Pro Ile Gly Gly Gly Ala Gly Gly Leu Gly Val Gly Gly Lys
                690                 695                 700
Pro Pro Lys Pro Phe Gly Gly Ala Leu Gly Ala Leu Gly Phe Pro Gly
705                 710                 715                 720
Gly Ala Cys Leu Gly Lys Ser Cys Gly Arg Lys Arg Lys
                725                 730

<210> SEQ ID NO 76
<211> LENGTH: 713
<212> TYPE: PRT
<213> ORGANISM: Bos taurus

<400> SEQUENCE: 76

Met Arg Ser Leu Thr Ala Ala Ala Arg Arg Pro Glu Val Leu Leu Leu
1               5                   10                  15
Leu Leu Cys Ile Leu Gln Pro Ser Gln Pro Gly Gly Val Pro Gly Ala
                20                  25                  30
Val Pro Gly Gly Val Pro Gly Gly Val Phe Phe Pro Gly Ala Gly Leu
            35                  40                  45
Gly Gly Leu Gly Val Gly Gly Leu Gly Pro Gly Val Lys Pro Ala Lys
        50                  55                  60
Pro Gly Val Gly Gly Leu Val Gly Pro Gly Leu Gly Ala Glu Gly Ser
```

-continued

```
               65                  70                  75                  80
Ala Leu Pro Gly Ala Phe Pro Gly Gly Phe Gly Ala Gly Gly
                    85                  90                  95

Ala Ala Gly Ala Ala Ala Ala Tyr Lys Ala Ala Lys Ala Gly Ala
                    100                 105                 110

Ala Gly Leu Gly Val Gly Gly Ile Gly Gly Val Gly Gly Leu Gly Val
                    115                 120                 125

Ser Thr Gly Ala Val Val Pro Gln Leu Gly Ala Gly Val Gly Ala Gly
                    130                 135                 140

Val Lys Pro Gly Lys Val Pro Gly Val Gly Leu Pro Gly Val Tyr Pro
145                 150                 155                 160

Gly Gly Val Leu Pro Gly Ala Gly Ala Arg Phe Pro Gly Ile Gly Val
                    165                 170                 175

Leu Pro Gly Val Pro Thr Gly Ala Gly Val Lys Pro Lys Ala Gln Val
                    180                 185                 190

Gly Ala Gly Ala Phe Ala Gly Ile Pro Gly Val Gly Pro Phe Gly Gly
                    195                 200                 205

Gln Gln Pro Gly Leu Pro Leu Gly Tyr Pro Ile Lys Ala Pro Lys Leu
         210                 215                 220

Pro Gly Val Gly Pro Gln Ala Ala Ala Ala Ala Lys Ala Ala Ala
225                 230                 235                 240

Lys Leu Gly Ala Gly Ala Gly Val Leu Pro Gly Val Gly Val
                    245                 250                 255

Gly Pro Gly Ile Pro Gly Ala Pro Gly Ala Ile Pro Gly Ile Gly Gly
                    260                 265                 270

Ile Ala Gly Val Gly Ala Pro Asp Ala Ala Ala Ala Ala Ala Ala
                    275                 280                 285

Ala Lys Ala Ala Lys Phe Gly Ala Ala Gly Leu Pro Gly Val Gly
         290                 295                 300

Val Pro Gly Val Gly Val Pro Gly Val Gly Val Pro Gly Val Gly Val
305                 310                 315                 320

Pro Gly Val Gly Val Pro Gly Val Gly Val Pro Gly Val Gly Val Pro
                    325                 330                 335

Gly Val Gly Val Pro Gly Val Gly Val Pro Gly Val Gly Val Pro Gly
                    340                 345                 350

Val Gly Val Pro Gly Ala Leu Ser Pro Ala Ala Thr Ala Lys Ala Ala
                    355                 360                 365

Ala Lys Ala Ala Lys Phe Gly Ala Arg Gly Ala Val Gly Ile Gly Gly
         370                 375                 380

Ile Pro Thr Phe Gly Leu Gly Pro Gly Gly Phe Pro Gly Ile Gly Asp
385                 390                 395                 400

Ala Ala Ala Ala Pro Ala Ala Ala Ala Lys Ala Ala Lys Ile Gly
                    405                 410                 415

Ala Gly Gly Val Gly Ala Leu Gly Gly Val Pro Gly Ala Pro Gly
                    420                 425                 430

Ala Ile Pro Gly Leu Pro Gly Val Gly Val Pro Gly Val Gly Ile
                    435                 440                 445

Pro Ala Ala Ala Ala Lys Ala Ala Lys Ala Ala Gln Phe Gly
         450                 455                 460

Leu Gly Pro Gly Val Gly Val Ala Pro Gly Val Gly Val Pro Gly
465                 470                 475                 480

Val Gly Val Val Pro Gly Val Gly Val Ala Pro Gly Ile Gly Leu Gly
                    485                 490                 495
```

```
Pro Gly Gly Val Ile Gly Ala Gly Val Pro Ala Ala Lys Ser Ala
            500                 505                 510

Ala Lys Ala Ala Ala Lys Ala Gln Phe Arg Ala Ala Ala Gly Leu Pro
        515                 520                 525

Ala Gly Val Pro Gly Leu Gly Val Gly Ala Gly Val Pro Gly Leu Gly
    530                 535                 540

Val Gly Ala Gly Val Pro Gly Leu Gly Val Gly Ala Gly Val Pro Gly
545                 550                 555                 560

Pro Gly Ala Val Pro Gly Thr Leu Ala Ala Ala Lys Ala Ala Lys Phe
                565                 570                 575

Gly Pro Gly Gly Val Gly Ala Leu Gly Gly Val Gly Asp Leu Gly Gly
            580                 585                 590

Ala Gly Ile Pro Gly Gly Val Ala Gly Val Val Pro Ala Ala Ala Ala
        595                 600                 605

Ala Ala Lys Ala Ala Ala Lys Ala Ala Gln Phe Gly Leu Gly Gly Val
    610                 615                 620

Gly Gly Leu Gly Val Gly Gly Leu Gly Ala Val Pro Gly Ala Val Gly
625                 630                 635                 640

Leu Gly Gly Val Ser Pro Ala Ala Ala Lys Ala Ala Lys Phe Gly
                645                 650                 655

Ala Ala Gly Leu Gly Gly Val Leu Gly Ala Gly Gln Pro Phe Pro Ile
            660                 665                 670

Gly Gly Gly Ala Gly Gly Leu Gly Val Gly Gly Lys Pro Pro Lys Pro
        675                 680                 685

Phe Gly Gly Ala Leu Gly Ala Leu Gly Phe Pro Gly Gly Ala Cys Leu
    690                 695                 700

Gly Lys Ser Cys Gly Arg Lys Arg Lys
705                 710

<210> SEQ ID NO 77
<211> LENGTH: 860
<212> TYPE: PRT
<213> ORGANISM: Mus musculus

<400> SEQUENCE: 77

Met Ala Gly Leu Thr Ala Val Val Pro Gln Pro Gly Val Leu Leu Ile
1               5                   10                  15

Leu Leu Leu Asn Leu Leu His Pro Ala Gln Pro Gly Gly Val Pro Gly
            20                  25                  30

Ala Val Pro Gly Gly Leu Pro Gly Gly Val Pro Gly Gly Val Tyr Tyr
        35                  40                  45

Pro Gly Ala Gly Ile Gly Gly Leu Gly Gly Gly Gly Ala Leu Gly
    50                  55                  60

Pro Gly Gly Lys Pro Pro Lys Pro Gly Ala Gly Leu Leu Gly Thr Phe
65                  70                  75                  80

Gly Ala Gly Pro Gly Gly Leu Gly Gly Ala Gly Pro Gly Ala Gly Leu
                85                  90                  95

Gly Ala Phe Pro Ala Gly Thr Phe Pro Gly Ala Gly Ala Leu Val Pro
            100                 105                 110

Gly Gly Ala Ala Gly Ala Ala Ala Ala Tyr Lys Ala Ala Ala Lys Ala
        115                 120                 125

Gly Ala Gly Leu Gly Gly Val Gly Gly Val Pro Gly Val Gly Val
    130                 135                 140

Gly Gly Val Pro Gly Gly Val Gly Val Gly Gly Val Pro Gly Gly Val
145                 150                 155                 160
```

```
Gly Val Gly Gly Val Pro Gly Val Gly Ile Gly Ile Gly
            165                 170                 175
Gly Leu Gly Val Ser Thr Gly Ala Val Pro Gln Val Gly Ala Gly
            180                 185                 190
Ile Gly Ala Gly Gly Lys Pro Gly Lys Val Pro Gly Val Gly Leu Pro
            195                 200                 205
Gly Val Tyr Pro Gly Gly Val Leu Pro Gly Thr Gly Ala Arg Phe Pro
            210                 215                 220
Gly Val Gly Val Leu Pro Gly Val Pro Thr Gly Thr Gly Val Lys Ala
225                 230                 235                 240
Lys Ala Pro Gly Gly Gly Ala Phe Ala Gly Ile Pro Gly Val Gly
            245                 250                 255
Pro Phe Gly Gly Gln Gln Pro Gly Val Pro Leu Gly Tyr Pro Ile Lys
            260                 265                 270
Ala Pro Lys Leu Pro Gly Gly Tyr Gly Leu Pro Tyr Thr Asn Gly Lys
            275                 280                 285
Leu Pro Tyr Gly Val Ala Gly Ala Gly Lys Ala Gly Tyr Pro Thr
            290                 295                 300
Gly Thr Gly Val Gly Ser Gln Ala Ala Ala Ala Ala Lys Ala Ala
305                 310                 315                 320
Lys Tyr Gly Ala Gly Ala Gly Val Leu Pro Gly Val Gly Gly
            325                 330                 335
Gly Ile Pro Gly Gly Ala Gly Ala Ile Pro Gly Ile Gly Ile Ala
            340                 345                 350
Gly Ala Gly Thr Pro Ala Ala Ala Ala Ala Lys Ala Ala Lys
            355                 360                 365
Ala Ala Lys Tyr Gly Ala Gly Gly Leu Val Pro Gly Gly Pro Gly
370                 375                 380
Val Arg Leu Pro Gly Ala Gly Ile Pro Gly Val Gly Ile Pro Gly
385                 390                 395                 400
Val Gly Gly Ile Pro Gly Val Gly Gly Pro Gly Ile Gly Pro Gly
            405                 410                 415
Ile Val Gly Gly Pro Gly Ala Val Ser Pro Ala Ala Ala Lys Ala
            420                 425                 430
Ala Ala Lys Ala Ala Lys Tyr Gly Ala Arg Gly Gly Val Gly Ile Pro
            435                 440                 445
Thr Tyr Gly Val Gly Ala Gly Gly Phe Pro Gly Tyr Gly Val Gly Ala
            450                 455                 460
Gly Ala Gly Leu Gly Gly Ala Ser Pro Ala Ala Ala Ala Ala
465                 470                 475                 480
Lys Ala Ala Lys Tyr Gly Ala Gly Gly Ala Gly Ala Leu Gly Gly Leu
            485                 490                 495
Val Pro Gly Ala Val Pro Gly Ala Leu Pro Gly Ala Val Pro Ala Val
            500                 505                 510
Pro Gly Ala Gly Gly Val Pro Gly Ala Gly Thr Pro Ala Ala Ala
            515                 520                 525
Ala Ala Ala Ala Lys Ala Ala Lys Ala Gly Leu Gly Pro Gly
            530                 535                 540
Val Gly Val Pro Gly Gly Val Gly Val Gly Gly Ile Pro Gly Gly
545                 550                 555                 560
Val Gly Val Gly Gly Val Pro Gly Gly Val Gly Pro Gly Gly Val Thr
            565                 570                 575
Gly Ile Gly Ala Gly Pro Gly Gly Leu Gly Gly Ala Gly Ser Pro Ala
            580                 585                 590
```

Ala Ala Lys Ser Ala Ala Lys Ala Ala Lys Ala Gln Tyr Arg Ala
            595                 600                 605

Ala Ala Gly Leu Gly Ala Gly Val Pro Gly Phe Gly Ala Gly Ala Gly
    610                 615                 620

Val Pro Gly Phe Gly Ala Gly Ala Gly Val Pro Gly Phe Gly Ala Gly
625                 630                 635                 640

Ala Gly Val Pro Gly Phe Gly Ala Gly Ala Gly Val Pro Gly Phe Gly
            645                 650                 655

Ala Gly Ala Val Pro Gly Ser Leu Ala Ala Ser Lys Ala Ala Lys Tyr
        660                 665                 670

Gly Ala Ala Gly Gly Leu Gly Gly Pro Gly Gly Leu Gly Gly Pro Gly
    675                 680                 685

Gly Leu Gly Gly Pro Gly Gly Leu Gly Gly Ala Gly Val Pro Gly Arg
    690                 695                 700

Val Ala Gly Ala Ala Pro Pro Ala Ala Ala Ala Ala Ala Lys Ala
705                 710                 715                 720

Ala Ala Lys Ala Ala Gln Tyr Gly Leu Gly Gly Ala Gly Gly Leu Gly
            725                 730                 735

Ala Gly Gly Leu Gly Ala Gly Gly Leu Gly Ala Gly Gly Leu Gly Ala
        740                 745                 750

Gly Gly Leu Gly Ala Gly Leu Gly Ala Gly Leu Gly Ala
    755                 760                 765

Gly Leu Gly Ala Gly Gly Val Ser Pro Ala Ala Ala Lys Ala
    770                 775                 780

Ala Lys Tyr Gly Ala Ala Gly Leu Gly Gly Val Leu Gly Ala Arg Pro
785                 790                 795                 800

Phe Pro Gly Gly Gly Val Ala Ala Arg Pro Gly Phe Gly Leu Ser Pro
            805                 810                 815

Ile Tyr Pro Gly Gly Gly Ala Gly Gly Leu Gly Val Gly Gly Lys Pro
        820                 825                 830

Pro Lys Pro Tyr Gly Gly Ala Leu Gly Ala Leu Gly Tyr Gln Gly Gly
        835                 840                 845

Gly Cys Phe Gly Lys Ser Cys Gly Arg Lys Arg Lys
    850                 855                 860

<210> SEQ ID NO 78
<211> LENGTH: 466
<212> TYPE: PRT
<213> ORGANISM: Mus musculus

<400> SEQUENCE: 78

Met Ala Gly Leu Thr Ala Val Val Pro Gln Pro Gly Val Leu Leu Ile
1               5                   10                  15

Leu Leu Leu Asn Leu Leu His Pro Ala Gln Pro Gly Gly Val Pro Gly
            20                  25                  30

Ala Val Pro Gly Gly Leu Pro Gly Gly Val Pro Gly Gly Val Tyr Tyr
        35                  40                  45

Pro Gly Ala Gly Ile Gly Leu Gly Gly Gly Gly Ala Leu Gly
    50                  55                  60

Pro Gly Gly Lys Pro Lys Pro Gly Ala Gly Leu Leu Gly Thr Phe
65                  70                  75                  80

Gly Ala Gly Pro Gly Gly Leu Gly Gly Ala Gly Pro Gly Ala Gly Leu
            85                  90                  95

Gly Ala Phe Pro Ala Gly Thr Phe Pro Gly Ala Gly Ala Leu Val Pro
        100                 105                 110

Gly Gly Ala Ala Gly Ala Ala Ala Tyr Lys Ala Ala Lys Ala
            115                 120                 125
Gly Ala Gly Leu Gly Gly Val Gly Gly Val Pro Gly Val Gly Val
        130                 135                 140
Gly Gly Val Pro Gly Val Gly Val Gly Gly Val Pro Gly Gly Val
145                 150                 155                 160
Gly Val Gly Gly Val Pro Gly Gly Val Gly Ile Gly Gly Ile Gly
                165                 170                 175
Gly Leu Gly Val Ser Thr Gly Ala Val Pro Gln Val Gly Ala Gly
                180                 185                 190
Ile Gly Ala Gly Gly Lys Pro Gly Lys Val Pro Gly Val Gly Leu Pro
        195                 200                 205
Gly Val Tyr Pro Gly Gly Val Leu Pro Gly Thr Gly Ala Arg Phe Pro
    210                 215                 220
Gly Val Gly Val Leu Pro Gly Val Pro Thr Gly Thr Gly Val Lys Ala
225                 230                 235                 240
Lys Ala Pro Gly Gly Gly Ala Phe Ala Gly Ile Pro Gly Val Gly
                245                 250                 255
Pro Phe Gly Gly Gln Gln Pro Gly Val Pro Leu Gly Tyr Pro Ile Lys
                260                 265                 270
Ala Pro Lys Leu Pro Gly Gly Tyr Gly Leu Pro Tyr Thr Asn Gly Lys
        275                 280                 285
Leu Pro Tyr Gly Val Ala Gly Ala Gly Lys Ala Gly Tyr Pro Thr
    290                 295                 300
Gly Thr Gly Val Gly Ser Gln Ala Ala Ala Ala Ala Lys Ala Ala
305                 310                 315                 320
Lys Tyr Gly Ala Gly Gly Ala Gly Val Leu Pro Gly Val Gly Gly Gly
                325                 330                 335
Gly Ile Pro Gly Gly Ala Gly Ala Ile Pro Gly Ile Gly Gly Ile Ala
                340                 345                 350
Gly Ala Gly Thr Pro Ala Ala Ala Ala Ala Lys Ala Ala Ala Lys
        355                 360                 365
Ala Ala Lys Tyr Gly Ala Ala Gly Gly Leu Val Pro Gly Gly Pro Gly
        370                 375                 380
Val Arg Leu Pro Gly Ala Gly Ile Pro Gly Val Gly Gly Ile Pro Gly
385                 390                 395                 400
Val Gly Gly Ile Pro Gly Val Gly Gly Pro Gly Ile Gly Gly Pro Gly
                405                 410                 415
Ile Val Gly Gly Pro Gly Ala Val Ser Pro Ala Ala Ala Lys Ala
                420                 425                 430
Ala Ala Lys Ala Ala Lys Tyr Gly Ala Arg Gly Gly Val Ala Thr His
        435                 440                 445
Pro Pro Thr His Pro Ser Ile His Pro Ser Ile His Pro Ser Ile Leu
    450                 455                 460
Thr Ala
465

<210> SEQ ID NO 79
<211> LENGTH: 375
<212> TYPE: PRT
<213> ORGANISM: Mus musculus

<400> SEQUENCE: 79

Glu Ser Arg Gln Val Leu Trp Cys Pro Lys Ser Glu Leu Ala Ser Glu
1               5                   10                  15

Leu Glu Glu Ser Leu Gly Lys Phe Leu Val Leu Val Phe Gln Val Tyr
            20                  25                  30

Thr Gln Ala Glu Cys Ser Gln Glu Gln Leu Gly Ser Leu Val Trp
        35                  40                  45

Gly Cys Ser Leu Glu Phe Pro Leu Ala Gln Glu Ser Lys Pro Arg Leu
 50                  55                  60

Gln Val Phe Gly Val Gly Ile Pro Gly Val Gly Val Gly Gly
 65                  70                  75                  80

Val Pro Gly Gly Val Gly Pro Gly Val Thr Gly Ile Gly Ala Gly
                    85                  90                  95

Pro Gly Gly Leu Gly Gly Ala Gly Ser Pro Ala Ala Ala Lys Ser Ala
                100                 105                 110

Ala Lys Ala Ala Lys Ala Gln Tyr Arg Ala Ala Ala Gly Leu Gly
            115                 120                 125

Ala Gly Val Pro Gly Phe Gly Ala Gly Ala Gly Val Pro Gly Phe Gly
            130                 135                 140

Ala Gly Ala Gly Val Pro Gly Phe Gly Ala Gly Ala Gly Val Pro Gly
145                 150                 155                 160

Phe Gly Ala Gly Ala Gly Val Pro Gly Phe Gly Ala Gly Ala Val Pro
                165                 170                 175

Gly Ser Leu Ala Ala Ser Lys Ala Ala Lys Tyr Gly Ala Ala Gly Gly
                180                 185                 190

Leu Gly Gly Pro Gly Gly Leu Gly Pro Gly Gly Leu Gly Gly Pro
            195                 200                 205

Gly Gly Leu Gly Gly Ala Gly Val Pro Gly Arg Val Ala Gly Ala Ala
            210                 215                 220

Pro Pro Ala Ala Ala Ala Ala Ala Lys Ala Ala Ala Lys Ala Ala
225                 230                 235                 240

Gln Tyr Gly Leu Gly Gly Ala Gly Gly Leu Gly Ala Gly Gly Leu Gly
                245                 250                 255

Ala Gly Gly Leu Gly Ala Gly Gly Leu Gly Ala Gly Gly Leu Gly Ala
            260                 265                 270

Gly Gly Leu Gly Ala Gly Gly Leu Gly Ala Gly Gly Leu Gly Ala Gly
            275                 280                 285

Gly Gly Val Ser Pro Ala Ala Ala Ala Lys Ala Ala Lys Tyr Gly Ala
            290                 295                 300

Ala Gly Leu Gly Gly Val Leu Gly Ala Arg Pro Phe Pro Gly Gly Gly
305                 310                 315                 320

Val Ala Ala Arg Pro Gly Phe Gly Leu Ser Pro Ile Tyr Pro Gly Gly
                325                 330                 335

Gly Ala Gly Gly Leu Gly Val Gly Lys Pro Pro Lys Pro Tyr Gly
            340                 345                 350

Gly Ala Leu Gly Ala Leu Gly Tyr Gln Gly Gly Cys Phe Gly Lys
            355                 360                 365

Ser Cys Gly Arg Lys Arg Lys
    370                 375

<210> SEQ ID NO 80
<211> LENGTH: 683
<212> TYPE: PRT
<213> ORGANISM: Rattus norvegicus

<400> SEQUENCE: 80

Met Ala Gly Leu Thr Ala Ala Val Pro Gln Pro Gly Val Leu Leu Ile
1               5                   10                  15

```
Leu Leu Leu Asn Leu Leu His Pro Ala Gln Pro Gly Gly Val Pro Gly
                20                  25                  30
Ala Val Pro Gly Gly Val Pro Gly Gly Leu Pro Gly Gly Val Pro Gly
            35                  40                  45
Gly Val Tyr Tyr Pro Gly Ala Gly Ile Gly Gly Leu Gly Gly Gly
        50                  55                  60
Ala Leu Gly Pro Gly Gly Lys Pro Pro Lys Pro Gly Ala Gly Leu Leu
65                  70                  75                  80
Gly Ala Phe Gly Ala Gly Pro Gly Leu Gly Gly Ala Gly Pro Gly
                85                  90                  95
Ala Gly Leu Ser Tyr Ala Ser Arg Pro Gly Gly Val Leu Val Pro Gly
                100                 105                 110
Gly Gly Ala Gly Ala Ala Ala Tyr Lys Ala Ala Lys Ala Gly
            115                 120                 125
Ala Gly Leu Gly Gly Ile Gly Gly Val Pro Gly Gly Val Gly Val Gly
            130                 135                 140
Gly Val Pro Gly Ala Val Gly Gly Val Pro Gly Ala Val Gly
145                 150                 155                 160
Gly Ile Gly Gly Ile Gly Gly Leu Gly Val Ser Thr Gly Ala Val Val
                165                 170                 175
Pro Gln Leu Gly Ala Gly Val Gly Ala Gly Gly Lys Pro Gly Lys Val
            180                 185                 190
Pro Gly Val Gly Leu Pro Gly Val Tyr Pro Gly Gly Val Leu Pro Gly
            195                 200                 205
Thr Gly Ala Arg Phe Pro Gly Val Gly Val Leu Pro Gly Val Pro Thr
            210                 215                 220
Gly Thr Gly Val Lys Ala Lys Val Pro Gly Gly Gly Gly Ala Phe
225                 230                 235                 240
Ser Gly Ile Pro Gly Val Gly Pro Phe Gly Gly Gln Gln Pro Gly Val
                245                 250                 255
Pro Leu Gly Tyr Pro Ile Lys Ala Pro Lys Leu Pro Gly Gly Tyr Gly
            260                 265                 270
Leu Pro Tyr Thr Asn Gly Lys Leu Pro Tyr Gly Val Ala Gly Ala Gly
            275                 280                 285
Gly Lys Ala Gly Tyr Pro Thr Gly Thr Gly Val Gly Ser Gln Ala Ala
            290                 295                 300
Val Ala Ala Ala Lys Ala Ala Lys Tyr Gly Ala Gly Gly Gly Val
305                 310                 315                 320
Leu Pro Gly Val Gly Gly Gly Ile Pro Gly Gly Ala Gly Ala Ile
                325                 330                 335
Pro Gly Ile Gly Gly Ile Thr Gly Ala Gly Thr Pro Ala Ala Ala
            340                 345                 350
Ala Ala Lys Ala Ala Ala Lys Ala Ala Lys Tyr Gly Ala Val Ser Pro
            355                 360                 365
Ala Ala Ala Ala Lys Ala Ala Lys Ala Ala Lys Tyr Gly Ala Arg
            370                 375                 380
Gly Gly Val Gly Ile Pro Thr Tyr Gly Val Gly Ala Gly Gly Phe Pro
385                 390                 395                 400
Gly Tyr Gly Val Gly Ala Gly Ala Gly Leu Gly Gly Ala Ser Gln Ala
                405                 410                 415
Ala Ala Ala Ala Ala Ala Lys Ala Ala Lys Tyr Gly Ala Gly Gly
            420                 425                 430
Ala Gly Thr Leu Gly Gly Leu Val Pro Gly Ala Val Pro Gly Ala Leu
```

```
                435                 440                 445
Pro Gly Ala Val Pro Gly Ala Leu Pro Gly Ala Val Pro Gly Ala Leu
        450                 455                 460
Pro Gly Ala Val Pro Gly Val Pro Gly Thr Gly Val Pro Gly Ala
465                 470                 475                 480
Gly Thr Pro Ala Ala Ala Ala Ala Ala Ala Lys Ala Ala
                485                 490                 495
Lys Ala Gly Gln Tyr Gly Leu Gly Pro Gly Val Gly Val Pro Gly
                500                 505                 510
Gly Val Gly Val Gly Gly Leu Pro Gly Gly Val Gly Pro Gly Gly Val
            515                 520                 525
Thr Gly Ile Gly Thr Gly Pro Gly Thr Gly Leu Val Pro Gly Asp Leu
        530                 535                 540
Gly Gly Ala Gly Thr Pro Ala Ala Ala Lys Ser Ala Ala Lys Ala Ala
545                 550                 555                 560
Ala Lys Ala Gln Tyr Ile Pro Gly Ser Leu Ala Ala Ser Lys Ala Ala
                565                 570                 575
Lys Tyr Gly Gly Ala Pro Ala Ala Ala Ala Ala Lys Ala Ala Ala
                580                 585                 590
Lys Ala Ala Gln Tyr Gly Val Ser Pro Ala Ala Ala Lys Ala Ala
                595                 600                 605
Lys Tyr Gly Ala Ala Gly Leu Gly Gly Val Leu Gly Ala Arg Pro Phe
            610                 615                 620
Pro Gly Gly Gly Val Ala Ala Arg Pro Gly Phe Gly Leu Ser Pro Ile
625                 630                 635                 640
Tyr Pro Gly Gly Gly Ala Gly Gly Leu Gly Val Gly Gly Lys Pro Pro
                645                 650                 655
Lys Pro Tyr Gly Gly Ala Leu Gly Ala Leu Gly Tyr Gln Gly Gly
                660                 665                 670
Cys Phe Gly Lys Ser Cys Gly Arg Lys Arg Lys
                675                 680

<210> SEQ ID NO 81
<211> LENGTH: 633
<212> TYPE: PRT
<213> ORGANISM: Rattus norvegicus

<400> SEQUENCE: 81

Met Ala Gly Leu Thr Ala Ala Val Pro Gln Pro Gly Val Leu Leu Ile
1               5                  10                  15
Leu Leu Leu Asn Leu Leu His Pro Ala Gln Pro Gly Gly Val Pro Gly
            20                  25                  30
Ala Val Pro Gly Gly Val Pro Gly Gly Leu Pro Gly Val Pro Gly
        35                  40                  45
Gly Val Tyr Tyr Pro Gly Ala Gly Ile Gly Gly Leu Gly Gly Gly
        50                  55                  60
Ala Leu Gly Pro Gly Gly Lys Pro Pro Lys Pro Gly Ala Gly Leu Leu
65                  70                  75                  80
Gly Ala Phe Gly Ala Gly Pro Gly Leu Gly Gly Ala Gly Pro Gly
                85                  90                  95
Ala Gly Leu Ser Tyr Ala Ser Arg Pro Gly Val Leu Val Pro Gly
                100                 105                 110
Gly Gly Ala Gly Ala Ala Ala Ala Tyr Lys Ala Ala Ala Lys Ala Gly
            115                 120                 125
Ala Gly Leu Gly Gly Ile Gly Gly Val Pro Gly Gly Val Gly Val Gly
```

-continued

```
            130                 135                 140
Gly Val Pro Gly Ala Val Gly Val Gly Val Pro Gly Ala Val Gly
145                 150                 155                 160

Gly Ile Gly Gly Ile Gly Gly Leu Gly Val Ser Thr Gly Ala Val Val
                165                 170                 175

Pro Gln Leu Gly Ala Gly Val Gly Ala Gly Gly Lys Pro Gly Lys Val
                180                 185                 190

Pro Gly Val Gly Leu Pro Gly Val Tyr Pro Gly Val Leu Pro Gly
                195                 200                 205

Thr Gly Ala Arg Phe Pro Gly Val Gly Leu Pro Gly Val Pro Thr
    210                 215                 220

Gly Thr Gly Val Lys Ala Lys Val Pro Gly Gly Gly Gly Ala Phe
225                 230                 235                 240

Ser Gly Ile Pro Gly Val Pro Phe Gly Gln Gln Pro Gly Val
                245                 250                 255

Pro Leu Gly Tyr Pro Ile Lys Ala Pro Lys Leu Pro Gly Tyr Gly
                260                 265                 270

Leu Pro Tyr Thr Asn Gly Lys Leu Pro Tyr Gly Val Ala Gly Ala Gly
    275                 280                 285

Gly Lys Ala Gly Tyr Pro Thr Gly Thr Gly Val Gly Ser Gln Ala Ala
    290                 295                 300

Val Ala Ala Ala Lys Ala Lys Tyr Gly Ala Gly Gly Gly Gly Val
305                 310                 315                 320

Leu Pro Gly Val Gly Gly Gly Ile Pro Gly Gly Ala Gly Ala Ile
                325                 330                 335

Pro Gly Ile Gly Gly Ile Thr Gly Ala Gly Thr Pro Ala Ala Ala
                340                 345                 350

Ala Ala Lys Ala Ala Ala Lys Ala Ala Lys Tyr Gly Ala Val Ser Pro
            355                 360                 365

Ala Ala Ala Ala Lys Ala Ala Lys Ala Ala Lys Tyr Gly Ala Arg
            370                 375                 380

Gly Gly Val Gly Ile Pro Thr Tyr Gly Val Gly Ala Gly Gly Phe Pro
385                 390                 395                 400

Gly Tyr Gly Val Gly Ala Gly Ala Gly Leu Gly Gly Ala Ser Gln Ala
                405                 410                 415

Ala Ala Ala Ala Ala Ala Lys Ala Ala Lys Tyr Gly Ala Gly Thr
                420                 425                 430

Pro Ala Ala Ala Ala Ala Ala Ala Lys Ala Ala Ala Lys Ala
            435                 440                 445

Gly Gln Tyr Gly Leu Gly Pro Gly Val Gly Gly Val Pro Gly Gly Val
            450                 455                 460

Gly Val Gly Gly Leu Pro Gly Val Gly Pro Gly Gly Val Thr Gly
465                 470                 475                 480

Ile Gly Thr Gly Pro Gly Thr Gly Leu Val Pro Gly Asp Leu Gly Gly
                485                 490                 495

Ala Gly Thr Pro Ala Ala Ala Lys Ser Ala Lys Ala Ala Ala Lys
            500                 505                 510

Ala Gln Tyr Ile Pro Gly Ser Leu Ala Ala Ser Lys Ala Ala Lys Tyr
            515                 520                 525

Gly Gly Ala Pro Ala Ala Ala Ala Ala Lys Ala Ala Lys Ala
            530                 535                 540

Ala Gln Tyr Gly Val Ser Pro Ala Ala Ala Lys Ala Ala Lys Tyr
545                 550                 555                 560
```

-continued

```
Gly Ala Ala Gly Leu Gly Val Leu Gly Ala Arg Pro Phe Pro Gly
                565                 570                 575

Gly Gly Val Ala Ala Arg Pro Gly Phe Gly Leu Ser Pro Ile Tyr Pro
            580                 585                 590

Gly Gly Gly Ala Gly Gly Leu Gly Val Gly Gly Lys Pro Pro Lys Pro
            595                 600                 605

Tyr Gly Gly Ala Leu Gly Ala Leu Gly Tyr Gln Gly Gly Gly Cys Phe
    610                 615                 620

Gly Lys Ser Cys Gly Arg Lys Arg Lys
625                 630

<210> SEQ ID NO 82
<211> LENGTH: 406
<212> TYPE: PRT
<213> ORGANISM: Rattus norvegicus

<400> SEQUENCE: 82

Met Ala Gly Leu Thr Ala Ala Val Pro Gln Pro Gly Val Leu Leu Ile
1               5                   10                  15

Leu Leu Leu Asn Leu Leu His Pro Ala Gln Pro Gly Gly Val Pro Gly
                20                  25                  30

Ala Val Pro Gly Gly Val Pro Gly Gly Leu Pro Gly Gly Val Pro Gly
            35                  40                  45

Gly Val Tyr Tyr Pro Gly Ala Gly Ile Gly Gly Leu Gly Gly Gly
    50                  55                  60

Ala Leu Gly Pro Gly Gly Lys Pro Pro Lys Pro Gly Ala Gly Leu Leu
65                  70                  75                  80

Gly Ala Phe Gly Ala Gly Pro Gly Leu Gly Gly Ala Gly Pro Gly
                85                  90                  95

Ala Gly Leu Ser Tyr Ala Ser Arg Pro Gly Gly Val Leu Val Pro Gly
            100                 105                 110

Gly Gly Ala Gly Ala Ala Ala Tyr Lys Ala Ala Ala Lys Ala Gly
        115                 120                 125

Ala Gly Leu Gly Gly Ile Gly Gly Val Pro Gly Gly Val Gly Val Gly
        130                 135                 140

Gly Val Pro Gly Ala Val Gly Val Gly Gly Val Pro Gly Ala Val Gly
145                 150                 155                 160

Gly Ile Gly Gly Ile Gly Gly Leu Gly Val Ser Thr Gly Ala Val Val
                165                 170                 175

Pro Gln Leu Gly Ala Gly Val Gly Ala Gly Gly Lys Pro Gly Lys Val
            180                 185                 190

Pro Gly Val Gly Leu Pro Gly Val Tyr Pro Gly Gly Val Leu Pro Gly
        195                 200                 205

Thr Gly Ala Arg Phe Pro Gly Val Gly Val Leu Pro Gly Val Pro Thr
    210                 215                 220

Gly Thr Gly Val Lys Ala Lys Val Pro Gly Gly Gly Gly Ala Phe
225                 230                 235                 240

Ser Gly Ile Pro Gly Val Gly Pro Phe Gly Gly Gln Gln Pro Gly Val
                245                 250                 255

Pro Leu Gly Tyr Pro Ile Lys Ala Pro Lys Leu Pro Gly Gly Tyr Gly
            260                 265                 270

Leu Pro Tyr Thr Asn Gly Lys Leu Pro Tyr Gly Val Ala Gly Ala Gly
        275                 280                 285

Gly Lys Ala Gly Tyr Pro Thr Gly Thr Gly Val Gly Ser Gln Ala Ala
    290                 295                 300
```

```
Val Ala Ala Ala Lys Ala Ala Lys Tyr Gly Ala Gly Gly Gly Val
305                 310                 315                 320

Leu Pro Gly Val Gly Gly Gly Ile Pro Gly Ala Gly Ala Ala Ile
                325                 330                 335

Pro Gly Ile Gly Gly Ile Thr Gly Ala Gly Thr Pro Ala Ala Ala
                340                 345                 350

Ala Ala Lys Ala Ala Lys Ala Ala Lys Tyr Gly Ala Val Ser Pro
                355                 360                 365

Ala Ala Ala Lys Ala Ala Lys Ala Ala Lys Tyr Gly Ala Arg
                370                 375                 380

Ala Thr His Pro Arg Thr His Pro Ser Phe His Pro Ser Ser Ile His
385                 390                 395                 400

Pro Ser Val Arg Pro Ser
                405
```

<210> SEQ ID NO 83
<211> LENGTH: 5
<212> TYPE: PRT
<213> ORGANISM: Artificial Sequence
<220> FEATURE:
<223> OTHER INFORMATION: Elastin-like polypeptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 83

```
Val Pro Gly Xaa Gly
1               5
```

<210> SEQ ID NO 84
<211> LENGTH: 5
<212> TYPE: PRT
<213> ORGANISM: Artificial Seqeunce
<220> FEATURE:
<223> OTHER INFORMATION: Elastin-like polypeptide

<400> SEQUENCE: 84

```
Lys Gly Gly Val Gly
1               5
```

<210> SEQ ID NO 85
<211> LENGTH: 5
<212> TYPE: PRT
<213> ORGANISM: Artificial Seqeunce
<220> FEATURE:
<223> OTHER INFORMATION: Elastin-like polypeptide

<400> SEQUENCE: 85

```
Leu Gly Gly Val Gly
1               5
```

<210> SEQ ID NO 86
<211> LENGTH: 7
<212> TYPE: PRT
<213> ORGANISM: Artificial Sequence
<220> FEATURE:
<223> OTHER INFORMATION: Elastin-like polypeptide

<400> SEQUENCE: 86

```
Leu Gly Ala Gly Gly Ala Gly
1               5
```

<210> SEQ ID NO 87
<211> LENGTH: 9

```
<212> TYPE: PRT
<213> ORGANISM: Artificial Sequence
<220> FEATURE:
<223> OTHER INFORMATION: Elastin-like polypeptide

<400> SEQUENCE: 87

Leu Gly Ala Gly Gly Ala Gly Val Leu
1               5

<210> SEQ ID NO 88
<211> LENGTH: 5
<212> TYPE: PRT
<213> ORGANISM: Artificial Sequence
<220> FEATURE:
<223> OTHER INFORMATION: Leader peptide sequence

<400> SEQUENCE: 88

Ser Lys Gly Pro Gly
1               5

<210> SEQ ID NO 89
<211> LENGTH: 208
<212> TYPE: PRT
<213> ORGANISM: Artificial Sequence
<220> FEATURE:
<223> OTHER INFORMATION: Elastin-like polypeptide

<400> SEQUENCE: 89

Met Ser Lys Gly Pro Gly Val Gly Val Pro Gly Ile Gly Val Pro Gly
1               5                   10                  15

Ile Gly Val Pro Gly Glu Gly Val Pro Gly Ile Gly Val Pro Gly Val
            20                  25                  30

Gly Val Pro Gly Ile Gly Val Pro Gly Ile Gly Val Pro Gly Glu Gly
        35                  40                  45

Val Pro Gly Ile Gly Val Pro Gly Val Gly Val Pro Gly Ile Gly Val
    50                  55                  60

Pro Gly Ile Gly Val Pro Gly Glu Gly Val Pro Gly Ile Gly Val Pro
65                  70                  75                  80

Gly Val Gly Val Pro Gly Ile Gly Val Pro Gly Ile Gly Val Pro Gly
                85                  90                  95

Glu Gly Val Pro Gly Ile Gly Val Pro Gly Val Gly Val Pro Gly Ile
            100                 105                 110

Gly Val Pro Gly Ile Gly Val Pro Gly Glu Gly Val Pro Gly Ile Gly
        115                 120                 125

Val Pro Gly Val Gly Val Pro Gly Ile Gly Val Pro Gly Ile Gly Val
    130                 135                 140

Pro Gly Glu Gly Val Pro Gly Ile Gly Val Pro Gly Val Gly Val Pro
145                 150                 155                 160

Gly Ile Gly Val Pro Gly Ile Gly Val Pro Gly Glu Gly Val Pro Gly
                165                 170                 175

Ile Gly Val Pro Gly Val Gly Val Pro Gly Ile Gly Val Pro Gly Ile
            180                 185                 190

Gly Val Pro Gly Glu Gly Val Pro Gly Ile Gly Val Pro Gly Trp Pro
        195                 200                 205

<210> SEQ ID NO 90
<211> LENGTH: 808
<212> TYPE: PRT
<213> ORGANISM: Artificial Sequence
<220> FEATURE:
<223> OTHER INFORMATION: Elastin-like polypeptide
```

-continued

```
<400> SEQUENCE: 90

Met Ser Lys Gly Pro Gly Val Gly Val Pro Gly Ile Gly Val Pro Gly
1               5                   10                  15

Ile Gly Val Pro Gly Glu Gly Val Pro Gly Ile Gly Val Pro Gly Val
            20                  25                  30

Gly Val Pro Gly Ile Gly Val Pro Gly Ile Gly Val Pro Gly Glu Gly
        35                  40                  45

Val Pro Gly Ile Gly Val Pro Gly Val Gly Val Pro Gly Ile Gly Val
    50                  55                  60

Pro Gly Ile Gly Val Pro Gly Glu Gly Val Pro Gly Ile Gly Val Pro
65                  70                  75                  80

Gly Val Gly Val Pro Gly Ile Gly Val Pro Gly Ile Gly Val Pro Gly
                85                  90                  95

Glu Gly Val Pro Gly Ile Gly Val Pro Gly Val Gly Val Pro Gly Ile
            100                 105                 110

Gly Val Pro Gly Ile Gly Val Pro Gly Glu Gly Val Pro Gly Ile Gly
        115                 120                 125

Val Pro Gly Val Gly Val Pro Gly Ile Gly Val Pro Gly Ile Gly Val
    130                 135                 140

Pro Gly Glu Gly Val Pro Gly Ile Gly Val Pro Gly Val Gly Val Pro
145                 150                 155                 160

Gly Ile Gly Val Pro Gly Ile Gly Val Pro Gly Glu Gly Val Pro Gly
                165                 170                 175

Ile Gly Val Pro Gly Val Gly Val Pro Gly Ile Gly Val Pro Gly Ile
            180                 185                 190

Gly Val Pro Gly Glu Gly Val Pro Gly Ile Gly Val Pro Gly Val Gly
        195                 200                 205

Val Pro Gly Ile Gly Val Pro Gly Ile Gly Val Pro Gly Glu Gly Val
    210                 215                 220

Pro Gly Ile Gly Val Pro Gly Val Gly Val Pro Gly Ile Gly Val Pro
225                 230                 235                 240

Gly Ile Gly Val Pro Gly Glu Gly Val Pro Gly Ile Gly Val Pro Gly
                245                 250                 255

Val Gly Val Pro Gly Ile Gly Val Pro Gly Ile Gly Val Pro Gly Glu
            260                 265                 270

Gly Val Pro Gly Ile Gly Val Pro Gly Val Gly Val Pro Gly Ile Gly
        275                 280                 285

Val Pro Gly Ile Gly Val Pro Gly Glu Gly Val Pro Gly Ile Gly Val
    290                 295                 300

Pro Gly Val Gly Val Pro Gly Ile Gly Val Pro Gly Ile Gly Val Pro
305                 310                 315                 320

Gly Glu Gly Val Pro Gly Ile Gly Val Pro Gly Val Gly Val Pro Gly
                325                 330                 335

Ile Gly Val Pro Gly Ile Gly Val Pro Gly Glu Gly Val Pro Gly Ile
            340                 345                 350

Gly Val Pro Gly Val Gly Val Pro Gly Ile Gly Val Pro Gly Ile Gly
        355                 360                 365

Val Pro Gly Glu Gly Val Pro Gly Ile Gly Val Pro Gly Val Gly Val
    370                 375                 380

Pro Gly Ile Gly Val Pro Gly Ile Gly Val Pro Gly Glu Gly Val Pro
385                 390                 395                 400

Gly Ile Gly Val Pro Gly Val Gly Val Pro Gly Ile Gly Val Pro Gly
                405                 410                 415
```

Ile Gly Val Pro Gly Glu Val Pro Gly Ile Val Pro Gly Val
            420                 425                 430

Gly Val Pro Gly Ile Gly Val Pro Gly Ile Gly Val Pro Gly Glu Gly
            435                 440                 445

Val Pro Gly Ile Gly Val Pro Gly Val Gly Val Pro Gly Ile Gly Val
450                 455                 460

Pro Gly Ile Gly Val Pro Gly Glu Gly Val Pro Gly Ile Gly Val Pro
465                 470                 475                 480

Gly Val Gly Val Pro Gly Ile Gly Val Pro Gly Ile Gly Val Pro Gly
            485                 490                 495

Glu Gly Val Pro Gly Ile Gly Val Pro Gly Val Gly Val Pro Gly Ile
            500                 505                 510

Gly Val Pro Gly Ile Gly Val Pro Gly Glu Gly Val Pro Gly Ile Gly
            515                 520                 525

Val Pro Gly Val Gly Val Pro Gly Ile Gly Val Pro Gly Ile Gly Val
            530                 535                 540

Pro Gly Glu Gly Val Pro Gly Ile Gly Val Pro Gly Val Gly Val Pro
545                 550                 555                 560

Gly Ile Gly Val Pro Gly Ile Gly Val Pro Gly Glu Gly Val Pro Gly
            565                 570                 575

Ile Gly Val Pro Gly Val Gly Val Pro Gly Ile Gly Val Pro Gly Ile
            580                 585                 590

Gly Val Pro Gly Glu Gly Val Pro Gly Ile Gly Val Pro Gly Val Gly
            595                 600                 605

Val Pro Gly Ile Gly Val Pro Gly Ile Gly Val Pro Gly Glu Gly Val
            610                 615                 620

Pro Gly Ile Gly Val Pro Gly Val Gly Val Pro Gly Ile Gly Val Pro
625                 630                 635                 640

Gly Ile Gly Val Pro Gly Glu Gly Val Pro Gly Ile Gly Val Pro Gly
            645                 650                 655

Val Gly Val Pro Gly Ile Gly Val Pro Gly Ile Gly Val Pro Gly Glu
            660                 665                 670

Gly Val Pro Gly Ile Gly Val Pro Gly Val Gly Val Pro Gly Ile Gly
            675                 680                 685

Val Pro Gly Ile Gly Val Pro Gly Glu Gly Val Pro Gly Ile Gly Val
            690                 695                 700

Pro Gly Val Gly Val Pro Gly Ile Gly Val Pro Gly Ile Gly Val Pro
705                 710                 715                 720

Gly Glu Gly Val Pro Gly Ile Gly Val Pro Gly Val Gly Val Pro Gly
            725                 730                 735

Ile Gly Val Pro Gly Ile Gly Val Pro Gly Glu Gly Val Pro Gly Ile
            740                 745                 750

Gly Val Pro Gly Val Gly Val Pro Gly Ile Gly Val Pro Gly Ile Gly
            755                 760                 765

Val Pro Gly Glu Gly Val Pro Gly Ile Gly Val Pro Gly Val Gly Val
            770                 775                 780

Pro Gly Ile Gly Val Pro Gly Ile Gly Val Pro Gly Glu Gly Val Pro
785                 790                 795                 800

Gly Ile Gly Val Pro Gly Trp Pro
            805

<210> SEQ ID NO 91
<211> LENGTH: 547
<212> TYPE: PRT
<213> ORGANISM: Artificial Sequence -continued
<220> FEATURE:
<223> OTHER INFORMATION: Elastin-like polypeptide

<400> SEQUENCE: 91

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Gly Pro Val Pro Gly Gly Gly
                85                  90                  95

Val Pro Gly Val Gly Val Pro Gly Val Gly Val Pro Gly Gly Gly Val
            100                 105                 110

Pro Gly Ala Gly Val Pro Gly Val Gly Val Pro Gly Val Gly Val Pro
        115                 120                 125

Gly Val Gly Val Pro Gly Gly Val Pro Gly Ala Gly Val Pro Gly
    130                 135                 140

Gly Gly Val Pro Gly Gly Val Pro Gly Val Gly Val Pro Gly Gly
145                 150                 155                 160

Gly Val Pro Gly Ala Gly Val Pro Gly Val Gly Val Pro Gly Val Gly
            165                 170                 175

Val Pro Gly Val Gly Val Pro Gly Gly Val Pro Gly Ala Gly Val
        180                 185                 190

Pro Gly Gly Gly Val Pro Gly Val Gly Val Pro Gly Val Gly Val Pro
    195                 200                 205

Gly Gly Gly Val Pro Gly Ala Gly Val Pro Gly Val Gly Val Pro Gly
    210                 215                 220

Val Gly Val Pro Gly Val Gly Val Pro Gly Gly Gly Val Pro Gly Ala
225                 230                 235                 240

Gly Val Pro Gly Gly Gly Val Pro Gly Val Gly Val Pro Gly Val Gly
            245                 250                 255

Val Pro Gly Gly Gly Val Pro Gly Ala Gly Val Pro Gly Val Gly Val
        260                 265                 270

Pro Gly Val Gly Val Pro Gly Val Gly Val Pro Gly Gly Gly Val Pro
    275                 280                 285

Gly Ala Gly Val Pro Gly Gly Gly Val Pro Gly Val Gly Val Pro Gly
    290                 295                 300

Val Gly Val Pro Gly Gly Gly Val Pro Gly Ala Gly Val Pro Gly Val
305                 310                 315                 320

Gly Val Pro Gly Val Gly Val Pro Gly Val Gly Val Pro Gly Gly Gly
            325                 330                 335

Val Pro Gly Ala Gly Val Pro Gly Gly Gly Val Pro Gly Val Gly Val
        340                 345                 350

Pro Gly Val Gly Val Pro Gly Gly Gly Val Pro Gly Ala Gly Val Pro
    355                 360                 365

Gly Val Gly Val Pro Gly Val Gly Val Pro Gly Val Gly Val Pro Gly
    370                 375                 380

Gly Gly Val Pro Gly Ala Gly Val Pro Gly Gly Gly Val Pro Gly Val
385                 390                 395                 400

```
Gly Val Pro Gly Val Gly Pro Gly Gly Val Pro Gly Ala Gly
                405                 410                 415
Val Pro Gly Val Gly Val Pro Gly Val Gly Pro Gly Gly Val
            420                 425                 430
Pro Gly Gly Gly Val Pro Gly Ala Gly Val Pro Gly Gly Val Pro
        435                 440                 445
Gly Val Gly Val Pro Gly Val Gly Val Pro Gly Gly Val Pro Gly
    450                 455                 460
Ala Gly Val Pro Gly Val Gly Val Pro Gly Val Gly Val Pro Gly Val
465                 470                 475                 480
Gly Val Pro Gly Gly Val Pro Gly Ala Gly Val Pro Gly Gly
            485                 490                 495
Val Pro Gly Val Gly Val Pro Gly Val Gly Val Pro Gly Gly Gly Val
            500                 505                 510
Pro Gly Ala Gly Val Pro Gly Val Gly Val Pro Gly Val Gly Val Pro
        515                 520                 525
Gly Val Gly Val Pro Gly Gly Val Pro Gly Ala Gly Val Pro Gly
    530                 535                 540
Gly Gly Ala
545

<210> SEQ ID NO 92
<211> LENGTH: 262
<212> TYPE: PRT
<213> ORGANISM: Bombyx mori

<400> SEQUENCE: 92

Met Lys Pro Ile Phe Leu Val Leu Val Ala Thr Ser Ala Tyr Ala
1                   5                   10                  15

Ala Pro Ser Val Thr Ile Asn Gln Tyr Ser Asp Asn Glu Ile Pro Arg
            20                  25                  30

Asp Ile Asp Asp Gly Lys Ala Ser Ser Val Ile Ser Arg Arg Trp Asp
        35                  40                  45

Tyr Val Asp Asp Thr Asp Lys Ser Ile Ala Ile Leu Asn Val Gln Glu
    50                  55                  60

Ile Leu Lys Asp Met Ala Ser Gln Gly Asp Tyr Ala Ser Gln Ala Ser
65                  70                  75                  80

Ala Val Ala Gln Thr Ala Gly Ile Ile Ala His Leu Ser Ala Gly Ile
                85                  90                  95

Pro Gly Asp Ala Cys Ala Ala Ala Asn Val Ile Asn Ser Tyr Thr Asp
            100                 105                 110

Gly Val Arg Ser Gly Asn Phe Ala Gly Phe Arg Gln Ser Leu Gly Pro
        115                 120                 125

Phe Phe Gly His Val Gly Gln Asn Leu Asn Leu Ile Asn Gln Leu Val
    130                 135                 140

Ile Asn Pro Gly Gln Leu Arg Tyr Ser Val Gly Pro Ala Leu Gly Cys
145                 150                 155                 160

Ala Gly Gly Gly Arg Ile Tyr Asp Phe Glu Ala Ala Trp Asp Ala Ile
                165                 170                 175

Leu Ala Ser Ser Asp Ser Ser Phe Leu Asn Glu Glu Tyr Cys Ile Val
            180                 185                 190

Lys Arg Leu Tyr Asn Ser Arg Asn Ser Gln Ser Asn Asn Ile Ala Ala
        195                 200                 205

Tyr Ile Thr Ala His Leu Leu Pro Pro Val Ala Gln Val Phe His Gln
    210                 215                 220
```

-continued

```
Ser Ala Gly Ser Ile Thr Asp Leu Leu Arg Gly Val Gly Asn Gly Asn
225                 230                 235                 240

Asp Ala Thr Gly Leu Val Ala Asn Ala Gln Arg Tyr Ile Ala Gln Ala
            245                 250                 255

Ala Ser Gln Val His Val
        260

<210> SEQ ID NO 93
<211> LENGTH: 5263
<212> TYPE: PRT
<213> ORGANISM: Bombyx mori

<400> SEQUENCE: 93

Met Arg Val Lys Thr Phe Val Ile Leu Cys Cys Ala Leu Gln Tyr Val
1               5                   10                  15

Ala Tyr Thr Asn Ala Asn Ile Asn Asp Phe Asp Glu Asp Tyr Phe Gly
            20                  25                  30

Ser Asp Val Thr Val Gln Ser Ser Asn Thr Thr Asp Glu Ile Ile Arg
        35                  40                  45

Asp Ala Ser Gly Ala Val Ile Glu Glu Gln Ile Thr Thr Lys Lys Met
    50                  55                  60

Gln Arg Lys Asn Lys Asn His Gly Ile Leu Gly Lys Asn Glu Lys Met
65                  70                  75                  80

Ile Lys Thr Phe Val Ile Thr Thr Asp Ser Asp Gly Asn Glu Ser Ile
                85                  90                  95

Val Glu Glu Asp Val Leu Met Lys Thr Leu Ser Asp Gly Thr Val Ala
            100                 105                 110

Gln Ser Tyr Val Ala Ala Asp Ala Gly Ala Tyr Ser Gln Ser Gly Pro
        115                 120                 125

Tyr Val Ser Asn Ser Gly Tyr Ser Thr His Gln Gly Tyr Thr Ser Asp
    130                 135                 140

Phe Ser Thr Ser Ala Ala Val Gly Ala Gly Ala Gly Ala Gly Ala Ala
145                 150                 155                 160

Ala Gly Ser Gly Ala Gly Ala Gly Ala Gly Tyr Gly Ala Ala Ser Gly
                165                 170                 175

Ala Gly Ala Gly Ala Gly Ala Gly Ala Gly Ala Gly Tyr Gly Thr Gly
            180                 185                 190

Ala Gly Ala Gly Ala Gly Ala Gly Tyr Gly Ala Gly Ala Gly Ala Gly
        195                 200                 205

Ala Gly Ala Gly Tyr Gly Ala Gly Ala Gly Ala Gly Ala Gly Ala Gly
    210                 215                 220

Tyr Gly Ala Gly Ala Gly Ala Gly Ala Gly Tyr Gly Ala Gly Ala Gly
225                 230                 235                 240

Ala Gly Ala Gly Ala Gly Ala Gly Tyr Gly Ala Gly Ala Gly Ala Gly
                245                 250                 255

Ala Gly Ala Gly Tyr Gly Ala Ala Ser Gly Ala Gly Ala Gly Ala Gly
            260                 265                 270

Tyr Gly Gln Gly Val Gly Ser Gly Ala Ala Ser Gly Ala Gly Ala Gly
        275                 280                 285

Ala Gly Ala Gly Ser Ala Ala Gly Ser Gly Ala Gly Ala Gly Ala Gly
    290                 295                 300

Thr Gly Ala Gly Ala Gly Tyr Gly Ala Gly Ala Gly Ala Gly Ala Gly
305                 310                 315                 320

Ala Gly Tyr Gly Ala Ala Ser Gly Thr Gly Ala Gly Tyr Gly Ala Gly
                325                 330                 335
```

```
Ala Gly Ala Gly Tyr Gly Gly Ala Ser Gly Ala Gly Ala Gly
            340                 345                 350

Ala Gly Ala Gly Ala Gly Ala Gly Ala Gly Tyr Gly Thr Gly Ala Gly
            355                 360                 365

Tyr Gly Ala Gly Ala Gly Ala Gly Ala Gly Ala Gly Ala Gly
    370                 375                 380

Tyr Gly Ala Gly Ala Gly Ala Gly Tyr Gly Ala Gly Tyr Gly Val Gly
385                 390                 395                 400

Ala Gly Ala Gly Tyr Gly Ala Gly Tyr Gly Ala Gly Ala Gly Ser Gly
                405                 410                 415

Ala Ala Ser Gly Ala Gly Ser Gly Ala Gly Ala Gly Ser Gly Ala Gly
            420                 425                 430

Ala Gly Ser Gly Ala Gly Ala Gly Ser Gly Ala Gly Ala Gly Ser Gly
            435                 440                 445

Ala Gly Ala Gly Ser Gly Ala Gly Ala Gly Ser Gly Ala Gly Ala Gly
            450                 455                 460

Ser Gly Ala Gly Ala Gly Ser Gly Thr Gly Ala Gly Ser Gly Ala Gly
465                 470                 475                 480

Ala Gly Tyr Gly Ala Gly Ala Gly Ala Gly Tyr Gly Ala Gly Ala Gly
            485                 490                 495

Ser Gly Ala Ala Ser Gly Ala Gly Ala Gly Ser Gly Ala Gly Ala Gly
            500                 505                 510

Ser Gly Ala Gly Ala Gly Ser Gly Ala Gly Ala Gly Ser Gly Ala Gly
            515                 520                 525

Ala Gly Ser Gly Ala Gly Ala Gly Tyr Gly Ala Gly Ala Gly Ala Gly
            530                 535                 540

Tyr Gly Ala Gly Ala Gly Ala Gly Tyr Gly Ala Gly Ala Gly Val Gly
545                 550                 555                 560

Tyr Gly Ala Gly Ala Gly Ser Gly Ala Ala Ser Gly Ala Gly Ala Gly
            565                 570                 575

Ser Gly Ala Gly Ala Gly Ser Gly Ala Gly Ala Gly Ser Gly Ala Gly
            580                 585                 590

Ala Gly Ser Gly Ala Gly Ala Gly Ser Gly Ala Gly Ala Gly Ser Gly
            595                 600                 605

Ala Gly Ala Gly Ser Gly Ala Gly Ala Gly Ser Gly Ala Gly Ala Gly
            610                 615                 620

Ser Gly Ala Gly Val Gly Tyr Gly Ala Gly Val Gly Ala Gly Tyr Gly
625                 630                 635                 640

Ala Gly Tyr Gly Ala Gly Ala Gly Ala Gly Tyr Gly Ala Gly Ala Gly
            645                 650                 655

Ser Gly Ala Ala Ser Gly Ala Gly Ala Gly Ala Gly Ala Gly Ala Gly
            660                 665                 670

Thr Gly Ser Ser Gly Phe Gly Pro Tyr Val Ala Asn Gly Gly Tyr Ser
            675                 680                 685

Arg Ser Asp Gly Tyr Glu Tyr Ala Trp Ser Ser Asp Phe Gly Thr Gly
            690                 695                 700

Ser Gly Ala Gly Ala Gly Ser Gly Ala Gly Ala Gly Ser Gly Ala Gly
705                 710                 715                 720

Ala Gly Ser Gly Ala Gly Ala Gly Ser Gly Ala Gly Ala Gly Ser Gly
            725                 730                 735

Ala Gly Ala Gly Tyr Gly Ala Gly Val Gly Val Gly Tyr Gly Ala Gly
            740                 745                 750

Tyr Gly Ala Gly Ala Gly Ala Gly Tyr Gly Ala Gly Ala Gly Ser Gly
            755                 760                 765
```

-continued

```
Ala Ala Ser Gly Ala Gly Ala Gly Ser Gly Ala Gly Ala Gly Ser Gly
        770                 775                 780
Ala Gly Ala Gly Ser Gly Ala Gly Ala Gly Ser Gly Ala Gly Ala Gly
785                 790                 795                 800
Ser Gly Ala Gly Ala Gly Ser Gly Ala Gly Ala Gly Ser Gly Ala Gly
                805                 810                 815
Ala Gly Ser Gly Ala Gly Ala Gly Ser Gly Ala Gly Ala Gly Ser Gly
            820                 825                 830
Ala Gly Val Gly Ser Gly Ala Gly Ala Gly Ser Gly Ala Gly Ala Gly
        835                 840                 845
Val Gly Tyr Gly Ala Gly Ala Gly Val Gly Tyr Gly Ala Gly Ala Gly
    850                 855                 860
Ser Gly Ala Ala Ser Gly Ala Gly Ala Gly Ser Gly Ala Gly Ala Gly
865                 870                 875                 880
Ser Gly Ala Gly Ala Gly Ser Gly Ala Gly Ala Gly Ser Gly Ala Gly
                885                 890                 895
Ala Gly Ser Gly Ala Gly Ala Gly Ser Gly Ala Gly Ala Gly Ser Gly
            900                 905                 910
Ala Gly Ala Gly Ser Gly Ala Gly Ala Gly Ser Gly Ala Gly Val Gly
        915                 920                 925
Tyr Gly Ala Gly Val Gly Ala Gly Tyr Gly Ala Gly Tyr Gly Ala Gly
    930                 935                 940
Ala Gly Ala Gly Tyr Gly Ala Gly Ala Gly Ser Gly Ala Ala Ser Gly
945                 950                 955                 960
Ala Gly Ala Gly Ser Gly Ala Gly Ala Gly Ser Gly Ala Gly Ala Gly
                965                 970                 975
Ser Gly Ala Gly Ala Gly Ser Gly Ala Gly Ala Gly Ser Gly Ala Gly
            980                 985                 990
Ala Gly Ser Gly Ala Gly Ala Gly Ser Gly Ala Gly Ala Gly Ser Gly
        995                 1000                1005
Ala Gly Ala Gly Ser Gly Ala Gly Ala Gly Ser Gly Ala Gly Ala
    1010                1015                1020
Gly Ser Gly Ala Gly Ala Gly Tyr Gly Ala Gly Ala Gly Ala Gly
    1025                1030                1035
Tyr Gly Ala Gly Tyr Gly Ala Gly Ala Gly Ala Gly Tyr Gly Ala
    1040                1045                1050
Gly Ala Gly Ser Gly Ala Ala Ser Gly Ala Gly Ser Gly Ala Gly
    1055                1060                1065
Ala Gly Ser Gly Ala Gly Ala Gly Ala Gly Ser Gly Ala Gly Ala
    1070                1075                1080
Gly Ser Gly Ala Gly Ala Gly Ser Gly Ala Gly Ala Gly Ser Gly
    1085                1090                1095
Ala Gly Ala Gly Ser Gly Ala Gly Ala Gly Ser Gly Ala Gly Ala
    1100                1105                1110
Gly Tyr Gly Ala Gly Val Gly Ala Gly Tyr Gly Ala Gly Tyr Gly
    1115                1120                1125
Ala Gly Ala Gly Ala Gly Tyr Gly Ala Gly Ala Gly Ser Gly Ala
    1130                1135                1140
Ala Ser Gly Ala Gly Ala Gly Ser Gly Ala Gly Ala Gly Ser Gly
    1145                1150                1155
Ala Gly Ala Gly Ser Gly Ala Gly Ala Gly Ser Gly Ala Gly Ala
    1160                1165                1170
Gly Ser Gly Ala Gly Ala Gly Ser Gly Ala Gly Ala Gly Ser Gly
```

```
                1175                1180                1185

Ala Gly Val Gly Tyr Gly Ala Gly Tyr Gly Ala Gly Ala
    1190                1195                1200

Gly Tyr Gly Ala Gly Ala Gly Ser Gly Ala Ala Ser Gly Ala Gly
    1205                1210                1215

Ala Gly Ala Gly Ala Gly Ala Gly Thr Gly Ser Ser Gly Phe Gly
    1220                1225                1230

Pro Tyr Val Ala His Gly Gly Tyr Ser Gly Tyr Glu Tyr Ala Trp
    1235                1240                1245

Ser Ser Glu Ser Asp Phe Gly Thr Gly Ser Gly Ala Gly Ala Gly
    1250                1255                1260

Ser Gly Ala Gly Ala Gly Ser Gly Ala Gly Ala Gly Ser Gly Ala
    1265                1270                1275

Gly Ala Gly Ser Gly Ala Gly Tyr Gly Ala Gly Val Gly Ala Gly
    1280                1285                1290

Tyr Gly Ala Gly Tyr Gly Ala Gly Ala Gly Ala Gly Tyr Gly Ala
    1295                1300                1305

Gly Ala Gly Ser Gly Ala Gly Ser Gly Ala Gly Ala Gly Ser Gly
    1310                1315                1320

Ala Gly Ala Gly Ser Gly Ala Gly Ala Gly Ser Gly Ala Gly Ala
    1325                1330                1335

Gly Ser Gly Ala Gly Ala Gly Ser Gly Ala Gly Ala Gly Ser Gly
    1340                1345                1350

Ala Gly Ala Gly Ser Gly Ala Gly Ala Gly Ser Gly Ala Gly Ala
    1355                1360                1365

Gly Tyr Gly Ala Gly Tyr Gly Ala Gly Ala Gly Ala Gly Tyr Gly
    1370                1375                1380

Ala Gly Ala Gly Ser Gly Ala Gly Ser Gly Ala Gly Ala Gly Ser
    1385                1390                1395

Gly Ala Gly Ala Gly Ser Gly Ala Gly Ala Gly Ser Gly Ala Gly
    1400                1405                1410

Ala Gly Ser Gly Ala Gly Ala Gly Ser Gly Ala Gly Ala Gly Ser
    1415                1420                1425

Gly Ala Gly Ala Gly Ser Gly Ala Gly Ala Gly Tyr Gly Ala Gly
    1430                1435                1440

Val Gly Ala Gly Tyr Gly Ala Gly Tyr Gly Ala Gly Ala Gly Ala
    1445                1450                1455

Gly Tyr Gly Ala Gly Ala Gly Ser Gly Ala Gly Ser Gly Ala Gly
    1460                1465                1470

Ala Gly Ser Gly Ala Gly Ala Gly Ser Gly Ala Gly Ala Gly Ser
    1475                1480                1485

Gly Ala Gly Val Gly Ser Gly Ala Gly Ala Gly Ser Gly Ala Gly
    1490                1495                1500

Ala Gly Ser Gly Ala Gly Ala Gly Ser Gly Ala Gly Ala Gly Tyr
    1505                1510                1515

Gly Ala Gly Tyr Gly Ala Gly Ala Gly Ala Gly Tyr Gly Ala Gly
    1520                1525                1530

Ala Gly Ser Gly Ala Gly Ser Gly Ala Gly Ala Gly Ser Gly Ala
    1535                1540                1545

Gly Ala Gly Ser Gly Ala Gly Ala Gly Ser Gly Ala Gly Ala Gly
    1550                1555                1560

Ser Gly Ala Gly Ala Gly Ser Gly Ala Gly Ala Gly Ser Gly Ala
    1565                1570                1575
```

-continued

Gly Ala Gly Ser Gly Ala Gly Val Gly Tyr Gly Ala Gly Val Gly
1580                1585                1590

Ala Gly Tyr Gly Ala Gly Tyr Gly Ala Gly Ala Gly Ala Gly Tyr
1595                1600                1605

Gly Ala Gly Ala Gly Ser Gly Ala Ala Ser Gly Ala Gly Ala Gly
1610                1615                1620

Ala Gly Ala Gly Ala Gly Thr Gly Ser Ser Gly Phe Gly Pro Tyr
1625                1630                1635

Val Ala Asn Gly Gly Tyr Ser Gly Tyr Glu Tyr Ala Trp Ser Ser
1640                1645                1650

Glu Ser Asp Phe Gly Thr Gly Ser Gly Ala Gly Ala Gly Ser Gly
1655                1660                1665

Ala Gly Ala Gly Ser Gly Ala Gly Ala Gly Ser Gly Ala Gly Ala
1670                1675                1680

Gly Ser Gly Ala Gly Ala Gly Tyr Gly Ala Gly Tyr Gly Ala Gly
1685                1690                1695

Ala Gly Ala Gly Tyr Gly Ala Gly Ala Gly Ser Gly Ala Gly Ser
1700                1705                1710

Gly Ala Gly Ala Gly Ser Gly Ala Gly Ala Gly Ser Gly Ala Gly
1715                1720                1725

Ala Gly Ser Gly Ala Gly Ala Gly Ser Gly Ala Gly Ala Gly Ser
1730                1735                1740

Gly Ala Gly Ala Gly Ser Gly Ala Gly Ala Gly Ser Gly Ala Gly
1745                1750                1755

Ser Gly Ser Gly Ala Gly Ala Gly Ser Gly Ala Gly Ala Gly Ser
1760                1765                1770

Gly Ala Gly Ala Gly Tyr Gly Ala Gly Val Gly Ala Gly Tyr Gly
1775                1780                1785

Val Gly Tyr Gly Ala Gly Ala Gly Ala Gly Tyr Gly Ala Gly Ala
1790                1795                1800

Gly Ser Gly Ala Ala Ser Gly Ala Gly Ala Gly Ala Gly Ala Gly
1805                1810                1815

Ala Gly Thr Gly Ser Ser Gly Phe Gly Pro Tyr Val Ala His Gly
1820                1825                1830

Gly Tyr Ser Gly Tyr Glu Tyr Ala Trp Ser Ser Glu Ser Asp Phe
1835                1840                1845

Gly Thr Gly Ser Gly Ala Gly Ala Gly Ser Gly Ala Gly Ala Gly
1850                1855                1860

Ser Gly Ala Gly Ala Gly Ser Gly Ala Gly Ala Gly Ser Gly Ala
1865                1870                1875

Gly Ala Gly Ser Gly Ala Gly Ala Gly Ser Gly Ala Gly Ala Gly
1880                1885                1890

Tyr Gly Ala Gly Val Gly Ala Gly Tyr Gly Ala Ala Tyr Gly Ala
1895                1900                1905

Gly Ala Gly Ala Gly Tyr Gly Ala Gly Ala Gly Ser Gly Ala Ala
1910                1915                1920

Ser Gly Ala Gly Ala Gly Ser Gly Ala Gly Ala Gly Ser Gly Ala
1925                1930                1935

Gly Ala Gly Ser Gly Ala Gly Ala Gly Ser Gly Ala Gly Ala Gly
1940                1945                1950

Ser Gly Ala Gly Ala Gly Ser Gly Ala Gly Ala Gly Ser Gly Ala
1955                1960                1965

Gly Ala Gly Ser Gly Ala Gly Ala Gly Ser Gly Ala Gly Ala Gly
1970                1975                1980

```
Ser Gly Ala Gly Ala Gly Tyr Gly Ala Gly Ala Gly Tyr
    1985            1990             1995

Gly Ala Gly Ala Gly Ser Gly Ala Gly Ser Ala Gly Ala Gly
    2000            2005             2010

Ser Gly Ala Gly Ala Gly Ser Gly Ala Gly Ala Gly Ser Gly Ala
    2015            2020             2025

Gly Ala Gly Ser Gly Ala Gly Ala Gly Ser Gly Ala Gly Ser Gly
    2030            2035             2040

Ser Gly Ala Gly Ala Gly Ser Gly Ala Gly Ala Gly Ser Gly Ala
    2045            2050             2055

Gly Ala Gly Tyr Gly Ala Gly Val Gly Ala Gly Tyr Gly Ala Gly
    2060            2065             2070

Tyr Gly Ala Gly Ala Gly Ala Gly Tyr Gly Ala Gly Ala Gly Ser
    2075            2080             2085

Gly Ala Gly Ser Gly Ala Gly Ala Gly Ser Gly Ala Gly Ala Gly
    2090            2095             2100

Tyr Gly Ala Gly Ala Gly Ala Gly Tyr Gly Ala Gly Tyr Gly Ala
    2105            2110             2115

Gly Ala Gly Ala Gly Tyr Gly Ala Gly Ala Gly Thr Gly Ala Gly
    2120            2125             2130

Ser Gly Ala Gly Ala Gly Ser Gly Ala Gly Ala Gly Ser Gly Ala
    2135            2140             2145

Gly Ala Gly Ser Gly Ala Gly Ala Gly Ser Gly Ala Gly Ala Gly
    2150            2155             2160

Ser Gly Ala Gly Ala Gly Ser Gly Ala Gly Ser Gly Ser Gly Ala
    2165            2170             2175

Gly Ala Gly Ser Gly Ala Gly Ala Gly Ser Gly Ala Gly Ala Gly
    2180            2185             2190

Ser Gly Ala Gly Ala Gly Ser Gly Ala Gly Ala Gly Ser Gly Ala
    2195            2200             2205

Gly Ala Gly Tyr Gly Ala Gly Ala Gly Ala Gly Tyr Gly Ala Gly
    2210            2215             2220

Tyr Gly Ala Gly Ala Gly Ala Gly Tyr Gly Ala Gly Ala Gly Ser
    2225            2230             2235

Gly Ala Gly Ser Gly Ala Gly Ala Gly Ser Gly Ala Gly Ala Gly
    2240            2245             2250

Ser Gly Ala Gly Ala Gly Ser Gly Ala Gly Ala Gly Tyr Gly Ala
    2255            2260             2265

Gly Tyr Gly Ala Gly Ala Gly Ser Gly Ala Ala Ser Gly Ala Gly
    2270            2275             2280

Ala Gly Ala Gly Ala Gly Ala Gly Thr Gly Ser Ser Gly Phe Gly
    2285            2290             2295

Pro Tyr Val Ala His Gly Gly Tyr Ser Gly Tyr Glu Tyr Ala Trp
    2300            2305             2310

Ser Ser Glu Ser Asp Phe Gly Thr Gly Ser Gly Ala Gly Ala Gly
    2315            2320             2325

Ser Gly Ala Gly Ala Gly Ala Gly Ala Gly Ala Gly Ser Gly Ala
    2330            2335             2340

Gly Ala Gly Tyr Gly Ala Gly Val Gly Ala Gly Tyr Gly Ala Gly
    2345            2350             2355

Tyr Gly Ala Gly Ala Gly Ala Gly Tyr Gly Ala Gly Ala Gly Ser
    2360            2365             2370

Gly Thr Gly Ser Gly Ala Gly Ala Gly Ser Gly Ala Gly Ala Gly
```

-continued

```
            2375                2380                2385

Tyr Gly Ala Gly Val Gly Ala Gly Tyr Gly Ala Gly Ala Gly Ser
            2390                2395                2400

Gly Ala Ala Phe Gly Ala Gly Ala Gly Ala Gly Ala Gly Ser Gly
            2405                2410                2415

Ala Gly Ala Gly Ser Gly Ala Gly Ala Gly Ser Gly Ala Gly Ala
            2420                2425                2430

Gly Ser Gly Ala Gly Ala Gly Ser Gly Ala Gly Ala Gly Tyr Gly
            2435                2440                2445

Ala Gly Tyr Gly Ala Gly Val Gly Ala Gly Tyr Gly Ala Gly Ala
            2450                2455                2460

Gly Ser Gly Ala Ala Ser Gly Ala Gly Ala Gly Ser Gly Ala Gly
            2465                2470                2475

Ala Gly Ser Gly Ala Gly Ala Gly Ser Gly Ala Gly Ala Gly Ser
            2480                2485                2490

Gly Ala Gly Ala Gly Ser Gly Ala Gly Ala Gly Tyr Gly Ala Gly
            2495                2500                2505

Val Gly Ala Gly Tyr Gly Ala Gly Tyr Gly Ala Gly Ala Gly Ala
            2510                2515                2520

Gly Tyr Gly Ala Gly Ala Gly Ser Gly Ala Ala Ser Gly Ala Gly
            2525                2530                2535

Ala Gly Ser Gly Ala Gly Ala Gly Ala Gly Ser Gly Ala Gly Ala
            2540                2545                2550

Gly Ser Gly Ala Gly Ala Gly Ser Gly Ala Gly Ala Gly Ser Gly
            2555                2560                2565

Ala Gly Ser Gly Ala Gly Ala Gly Ser Gly Ala Gly Ala Gly Ser
            2570                2575                2580

Gly Ala Gly Ala Gly Tyr Gly Ala Gly Ala Gly Ser Gly Ala Ala
            2585                2590                2595

Ser Gly Ala Gly Ala Gly Ala Gly Ala Gly Ala Gly Thr Gly Ser
            2600                2605                2610

Ser Gly Phe Gly Pro Tyr Val Ala Asn Gly Gly Tyr Ser Gly Tyr
            2615                2620                2625

Glu Tyr Ala Trp Ser Ser Glu Ser Asp Phe Gly Thr Gly Ser Gly
            2630                2635                2640

Ala Gly Ala Gly Ser Gly Ala Gly Ala Gly Ser Gly Ala Gly Ala
            2645                2650                2655

Gly Ser Gly Ala Gly Ala Gly Ser Gly Ala Gly Ala Gly Tyr Gly
            2660                2665                2670

Ala Gly Val Gly Ala Gly Tyr Gly Ala Gly Tyr Gly Ala Gly Ala
            2675                2680                2685

Gly Ala Gly Tyr Gly Ala Gly Ala Gly Ser Gly Ala Gly Ser Gly
            2690                2695                2700

Ala Gly Ala Gly Ser Gly Ala Gly Ala Gly Ser Gly Ala Gly Ala
            2705                2710                2715

Gly Ser Gly Ala Gly Ala Gly Ser Gly Ala Gly Ala Gly Ser Gly
            2720                2725                2730

Ala Gly Ala Gly Ser Gly Ala Gly Ala Gly Tyr Gly Ala Gly Ala
            2735                2740                2745

Gly Ser Gly Ala Ala Ser Gly Ala Gly Ala Gly Ser Gly Ala Gly
            2750                2755                2760

Ala Gly Ser Gly Ala Gly Ala Gly Ser Gly Ala Gly Ala Gly Ser
            2765                2770                2775
```

-continued

```
Gly Ala Gly Ala Gly Ser Gly Ala Gly Ala Ser Gly Ala Gly
            2780                2785                2790

Ala Gly Tyr Gly Ala Gly Val Gly Ala Gly Tyr Gly Val Gly Tyr
        2795                2800                2805

Gly Ala Gly Ala Gly Ala Gly Tyr Gly Ala Gly Ala Gly Ser Gly
            2810                2815                2820

Ala Gly Ser Gly Ala Gly Ala Gly Ser Gly Ala Gly Ala Gly Ser
        2825                2830                2835

Gly Ala Gly Ala Gly Ser Gly Ala Gly Ala Gly Ser Gly Ala Gly
            2840                2845                2850

Ser Gly Ala Gly Ala Gly Ser Gly Ala Gly Ala Gly Ser Gly Ala
        2855                2860                2865

Gly Ala Gly Ser Gly Ala Gly Ser Gly Ala Gly Ala Gly Ser Gly
            2870                2875                2880

Ala Gly Ala Gly Tyr Gly Val Gly Tyr Gly Ala Gly Ala Gly Ala
        2885                2890                2895

Gly Tyr Gly Ala Gly Ala Gly Ser Gly Ala Gly Ser Gly Ala Gly
    2900                2905                2910

Ala Gly Ser Gly Ala Gly Ala Gly Ser Gly Ala Gly Ala Gly Ser
        2915                2920                2925

Gly Ala Gly Ser Gly Ala Gly Ala Gly Ser Gly Ala Gly Ala Gly
            2930                2935                2940

Ser Gly Ala Gly Ala Gly Ser Gly Ala Gly Ala Gly Tyr Gly Ala
        2945                2950                2955

Gly Val Gly Ala Gly Tyr Gly Val Gly Tyr Gly Ala Gly Ala Gly
    2960                2965                2970

Ala Gly Tyr Gly Ala Gly Ala Gly Ser Gly Ala Gly Ser Gly Ala
        2975                2980                2985

Gly Ala Gly Ser Gly Ala Gly Ala Gly Ser Gly Ala Gly Ala Gly
            2990                2995                3000

Ser Gly Ala Gly Ala Gly Ser Gly Ala Gly Ala Gly Ser Gly Ala
        3005                3010                3015

Gly Ala Gly Ser Gly Ala Gly Ala Gly Ser Gly Ala Gly Ser Gly
            3020                3025                3030

Ala Gly Ala Gly Ser Gly Ala Gly Ala Gly Ser Gly Ala Gly Ala
        3035                3040                3045

Gly Ser Gly Ala Gly Ala Gly Ser Gly Ala Gly Ser Gly Ala Gly
    3050                3055                3060

Ala Gly Ser Gly Ala Gly Ala Gly Ser Gly Ala Gly Ala Gly Ser
        3065                3070                3075

Gly Ala Gly Ala Gly Tyr Gly Ala Gly Val Gly Ala Gly Tyr Gly
            3080                3085                3090

Val Gly Tyr Gly Ala Gly Val Gly Ala Gly Tyr Gly Ala Gly Ala
    3095                3100                3105

Gly Ser Gly Ala Ala Ser Gly Ala Gly Ala Gly Ser Gly Ala Gly
    3110                3115                3120

Ala Gly Ala Gly Ser Gly Ala Gly Ala Gly Ser Gly Ala Gly Ala
        3125                3130                3135

Gly Ser Gly Ala Gly Ala Gly Ser Gly Ala Gly Ala Gly Ser Gly
    3140                3145                3150

Ala Gly Ala Gly Ser Gly Ala Gly Ala Gly Tyr Gly Ala Gly Tyr
        3155                3160                3165

Gly Ala Gly Val Gly Ala Gly Tyr Gly Ala Gly Ala Gly Val Gly
            3170                3175                3180
```

Tyr Gly Ala Gly Ala Gly Gly Tyr Gly Ala Gly Ala Gly Ser
3185            3190                3195

Gly Ala Ala Ser Gly Ala Gly Ala Gly Ala Gly Ser Gly Ala Gly
3200            3205                3210

Ala Gly Thr Gly Ala Gly Ala Gly Ser Gly Ala Gly Ala Gly Tyr
3215            3220                3225

Gly Ala Gly Ala Gly Ser Gly Ala Ala Ser Gly Ala Gly Ala Gly
3230            3235                3240

Ala Gly Ala Gly Ala Gly Thr Gly Ser Ser Gly Phe Gly Pro Tyr
3245            3250                3255

Val Ala Asn Gly Gly Tyr Ser Gly Tyr Glu Tyr Ala Trp Ser Ser
3260            3265                3270

Glu Ser Asp Phe Gly Thr Gly Ser Gly Ala Gly Ala Gly Ser Gly
3275            3280                3285

Ala Gly Ala Gly Ser Gly Ala Gly Ala Gly Ser Gly Ala Gly Ala
3290            3295                3300

Gly Ser Gly Ala Gly Ala Gly Tyr Gly Ala Gly Val Gly Ala Gly
3305            3310                3315

Tyr Gly Ala Gly Ala Gly Ser Gly Ala Gly Ser Gly Ala Gly Ala
3320            3325                3330

Gly Ser Gly Ala Gly Ala Gly Ser Gly Ala Gly Ala Gly Ser Gly
3335            3340                3345

Ala Gly Ala Gly Ser Gly Ala Gly Ala Gly Tyr Gly Ala Gly Ala
3350            3355                3360

Gly Ser Gly Thr Gly Ser Gly Ala Gly Ala Gly Ser Gly Ala Gly
3365            3370                3375

Ala Gly Ser Gly Ala Gly Ala Gly Ser Gly Ala Gly Ala Gly Ser
3380            3385                3390

Gly Ala Gly Ala Gly Ser Gly Ala Gly Ala Gly Ser Gly Val Gly
3395            3400                3405

Ala Gly Tyr Gly Val Gly Tyr Gly Ala Gly Ala Gly Ala Gly Tyr
3410            3415                3420

Gly Val Gly Tyr Gly Ala Gly Ala Gly Ala Gly Tyr Gly Ala Gly
3425            3430                3435

Ala Gly Ser Gly Thr Gly Ser Gly Ala Gly Ala Gly Ser Gly Ala
3440            3445                3450

Gly Ala Gly Ser Gly Ala Gly Ala Gly Ser Gly Ala Gly Ala Gly
3455            3460                3465

Ser Gly Ala Gly Ala Gly Ser Gly Ala Gly Ala Gly Ser Gly Ala
3470            3475                3480

Gly Ala Gly Tyr Gly Ala Gly Val Gly Ala Gly Tyr Gly Val Gly
3485            3490                3495

Tyr Gly Ala Gly Ala Gly Ala Gly Tyr Gly Ala Gly Ala Gly Ser
3500            3505                3510

Gly Ala Gly Ser Gly Ala Gly Ala Gly Ser Gly Ala Gly Ala Gly
3515            3520                3525

Ser Gly Ala Gly Ala Gly Ser Gly Ala Gly Ala Gly Ser Gly Ala
3530            3535                3540

Gly Ser Gly Ala Gly Ala Gly Ser Gly Ala Gly Ala Gly Ser Gly
3545            3550                3555

Ala Gly Ala Gly Ser Gly Ala Gly Ser Gly Ala Gly Ala Gly Ser
3560            3565                3570

Gly Ala Gly Ala Gly Tyr Gly Val Gly Tyr Gly Ala Gly Ala Gly

-continued

Ala Gly Tyr Gly Ala Gly Ala Gly Ser Gly Ala Gly Ser Gly Ala
                3575                3580                3585

Gly Ala Gly Ser Gly Ala Gly Ala Gly Ser Gly Ala Gly Ala Gly
3590                3595                3600

Ser Gly Ala Gly Ser Gly Ala Gly Ala Gly Ser Gly Ala Gly Ala
3605                3610                3615

Gly Ser Gly Ala Gly Ala Gly Ser Gly Ala Gly Ala Gly Tyr Gly
3620                3625                3630

Ala Gly Val Gly Ala Gly Tyr Gly Val Gly Tyr Gly Ala Gly Ala
3635                3640                3645

Gly Ala Gly Tyr Gly Ala Gly Ala Gly Ser Gly Ala Gly Ser Gly
3650                3655                3660

Ala Gly Ala Gly Ser Gly Ala Gly Ala Gly Ser Gly Ala Gly Ala
3665                3670                3675

Gly Ser Gly Ala Gly Ala Gly Ser Gly Ala Gly Ala Gly Ser Gly
3680                3685                3690

Ala Gly Ala Gly Ser Gly Ala Gly Ala Gly Ser Gly Ala Gly Ser
3695                3700                3705

Gly Ala Gly Ala Gly Ser Gly Ala Gly Ala Gly Ser Gly Ala Gly
3710                3715                3720

Ala Gly Ser Gly Ala Gly Ala Gly Tyr Gly Ala Gly Val Gly Ala
3725                3730                3735

Gly Tyr Gly Val Gly Tyr Gly Ala Gly Ala Gly Ala Gly Tyr Gly
3740                3745                3750

Ala Gly Ala Gly Ser Gly Ala Ala Ser Gly Ala Gly Ala Gly Ala
3755                3760                3765

Gly Ala Gly Ala Gly Thr Gly Ser Ser Gly Phe Gly Pro Tyr Val
3770                3775                3780

Ala Asn Gly Gly Tyr Ser Gly Tyr Glu Tyr Ala Trp Ser Ser Glu
3785                3790                3795

Ser Asp Phe Gly Thr Gly Ser Gly Ala Gly Ala Gly Ser Gly Ala
3800                3805                3810

Gly Ala Gly Ser Gly Ala Gly Ala Gly Tyr Gly Ala Gly Tyr Gly
3815                3820                3825

Ala Gly Val Gly Ala Gly Tyr Gly Ala Gly Ala Gly Val Gly Tyr
3830                3835                3840

Gly Ala Gly Ala Gly Ala Gly Tyr Gly Ala Gly Ala Gly Ser Gly
3845                3850                3855

Ala Ala Ser Gly Ala Gly Ala Gly Ala Gly Ala Gly Ala Gly Ser
3860                3865                3870

Gly Ala Gly Ala Gly Ser Gly Ala Gly Ala Gly Ala Gly Ser Gly
3875                3880                3885

Ala Gly Ala Gly Tyr Gly Ala Gly Tyr Gly Ile Gly Val Gly Ala
3890                3895                3900

Gly Tyr Gly Ala Gly Ala Gly Val Gly Tyr Gly Ala Gly Ala Gly
3905                3910                3915

Ala Gly Tyr Gly Ala Gly Ala Gly Ser Gly Ala Ala Ser Gly Ala
3920                3925                3930

Gly Ala Gly Ser Gly Ala Gly Ala Gly Ser Gly Ala Gly Ala Gly
3935                3940                3945

Ser Gly Ala Gly Ala Gly Ser Gly Ala Gly Ala Gly Ser Gly Ala
3950                3955                3960
                3965                3970                3975

```
Gly Ala Gly Ser Gly Ala Gly Ala Gly Tyr Gly Ala Gly Tyr Gly
        3980            3985            3990

Ala Gly Val Gly Ala Gly Tyr Gly Ala Gly Ala Gly Val Gly Tyr
    3995            4000            4005

Gly Ala Gly Ala Gly Ala Gly Tyr Gly Ala Gly Ala Gly Ser Gly
        4010            4015            4020

Ala Ala Ser Gly Ala Gly Ala Gly Ala Gly Ala Gly Ala Gly Ala
        4025            4030            4035

Gly Ser Gly Ala Gly Ala Gly Ser Gly Ala Gly Ala Gly Ser Gly
        4040            4045            4050

Ala Gly Ala Gly Ser Gly Ala Gly Ala Gly Ser Gly Ala Gly Ala
        4055            4060            4065

Gly Ser Gly Ala Gly Ala Gly Ser Gly Ala Gly Ala Gly Ser Gly
        4070            4075            4080

Ala Gly Ala Gly Ser Gly Ala Gly Ala Gly Tyr Gly Ala Gly Val
        4085            4090            4095

Gly Ala Gly Tyr Gly Ala Gly Tyr Gly Ala Gly Ala Gly Tyr
        4100            4105            4110

Gly Ala Gly Ala Gly Ser Gly Ala Ala Ser Gly Ala Gly Ala Gly
        4115            4120            4125

Ser Gly Ala Gly Ala Gly Ser Gly Ala Gly Ala Gly Ser Gly Ala
        4130            4135            4140

Gly Ala Gly Ser Gly Ala Gly Ala Ser Gly Ala Gly Ala Gly Ala Gly
        4145            4150            4155

Tyr Gly Ala Gly Ala Gly Ser Gly Ala Ala Ser Gly Ala Gly Ala
        4160            4165            4170

Gly Ala Gly Ala Gly Ala Gly Thr Gly Ser Ser Gly Phe Gly Pro
        4175            4180            4185

Tyr Val Asn Gly Gly Tyr Ser Gly Tyr Glu Tyr Ala Trp Ser Ser
        4190            4195            4200

Glu Ser Asp Phe Gly Thr Gly Ser Gly Ala Gly Ala Gly Ser Gly
        4205            4210            4215

Ala Gly Ala Gly Ser Gly Ala Gly Ala Gly Tyr Gly Ala Gly Val
        4220            4225            4230

Gly Ala Gly Tyr Gly Ala Gly Tyr Gly Ala Gly Ala Gly Ala Gly
        4235            4240            4245

Tyr Gly Ala Gly Ala Gly Ser Gly Ala Ala Ser Gly Ala Gly Ala
        4250            4255            4260

Gly Ser Gly Ala Gly Ala Gly Ser Gly Ala Gly Ala Gly Ser Gly
        4265            4270            4275

Ala Gly Ala Gly Ser Gly Ala Gly Ser Gly Ala Gly Ala Gly Ser
        4280            4285            4290

Gly Ala Gly Ala Gly Ser Gly Ala Gly Ala Gly Ser Gly Ala Gly
        4295            4300            4305

Ala Gly Ser Gly Ala Gly Ala Gly Ser Gly Ala Gly Ala Gly Tyr
        4310            4315            4320

Gly Ala Gly Val Gly Ala Gly Tyr Gly Ala Gly Tyr Gly Ala Gly
        4325            4330            4335

Ala Gly Ala Gly Tyr Gly Ala Gly Ala Gly Ser Gly Ala Ala Ser
        4340            4345            4350

Gly Ala Gly Ala Gly Ser Gly Ala Gly Ala Gly Ala Gly Ser Gly
        4355            4360            4365

Ala Gly Ala Gly Ser Gly Ala Gly Ala Gly Ser Gly Ala Gly Ala
        4370            4375            4380
```

```
Gly Ser Gly Ala Gly Ala Gly Ser Gly Ala Gly Ser Gly
    4385                4390                4395

Ala Gly Ser Gly Ala Gly Ala Gly Ser Gly Ala Gly Ala Gly Tyr
    4400                4405                4410

Gly Ala Gly Tyr Gly Ala Gly Val Gly Ala Gly Tyr Gly Ala Gly
    4415                4420                4425

Ala Gly Val Gly Tyr Gly Ala Gly Ala Gly Ala Gly Tyr Gly Ala
    4430                4435                4440

Gly Ala Gly Ser Gly Ala Ala Ser Gly Ala Gly Ala Gly Ser Gly
    4445                4450                4455

Ser Gly Ala Gly Ser Gly Ala Gly Ala Gly Ser Gly Ala Gly Ala
    4460                4465                4470

Gly Ser Gly Ala Gly Ala Gly Ala Gly Ser Gly Ala Gly Ala Gly
    4475                4480                4485

Ser Gly Ala Gly Ala Gly Ser Gly Ala Gly Ala Gly Tyr Gly Ala
    4490                4495                4500

Gly Tyr Gly Ala Gly Ala Gly Ser Gly Ala Ala Ser Gly Ala Gly
    4505                4510                4515

Ala Gly Ala Gly Ala Gly Ala Gly Thr Gly Ser Ser Gly Phe Gly
    4520                4525                4530

Pro Tyr Val Ala Asn Gly Gly Tyr Ser Gly Tyr Glu Tyr Ala Trp
    4535                4540                4545

Ser Ser Glu Ser Asp Phe Gly Thr Gly Ser Gly Ala Gly Ala Gly
    4550                4555                4560

Ser Gly Ala Gly Ala Gly Ser Gly Ala Gly Ala Gly Tyr Gly Ala
    4565                4570                4575

Gly Val Gly Ala Gly Tyr Gly Ala Gly Tyr Gly Ala Gly Ala Gly
    4580                4585                4590

Ala Gly Tyr Gly Ala Gly Ala Gly Ser Gly Ala Gly Ser Gly Ala
    4595                4600                4605

Gly Ala Gly Ser Gly Ala Gly Ala Gly Ser Gly Ala Gly Ala Gly
    4610                4615                4620

Ser Gly Ala Gly Ala Gly Ser Gly Ala Gly Ala Gly Ser Gly Ala
    4625                4630                4635

Gly Ala Gly Ser Gly Ala Gly Ala Gly Ser Gly Ala Gly Ala Gly
    4640                4645                4650

Tyr Gly Ala Gly Tyr Gly Ala Gly Ala Gly Ala Gly Tyr Gly Ala
    4655                4660                4665

Gly Ala Gly Val Gly Tyr Gly Ala Gly Ala Gly Ala Gly Tyr Gly
    4670                4675                4680

Ala Gly Ala Gly Ser Gly Ala Gly Ser Gly Ala Gly Ala Gly Ser
    4685                4690                4695

Gly Ser Gly Ala Gly Ala Gly Ser Gly Ser Gly Ala Gly Ser Gly
    4700                4705                4710

Ala Gly Ala Gly Ser Gly Ala Gly Ala Gly Ser Gly Ala Gly Ala
    4715                4720                4725

Gly Ser Gly Ala Gly Ala Gly Ser Gly Ala Gly Ala Gly Ser Gly
    4730                4735                4740

Ala Gly Ala Gly Ser Gly Ala Gly Ala Gly Tyr Gly Ala Gly Tyr
    4745                4750                4755

Gly Ile Gly Val Gly Ala Gly Tyr Gly Ala Gly Ala Gly Val Gly
    4760                4765                4770

Tyr Gly Ala Gly Ala Gly Ala Gly Tyr Gly Ala Gly Ala Gly Ser
```

-continued

```
            4775                4780                4785
Gly Ala  Ala Ser Gly Ala  Gly Ala Gly Ser  Gly Ala Gly
            4790                4795                4800
Ser Gly  Ala Gly Ala Gly  Ser Gly Ala Gly  Ser Gly Ala
            4805                4810                4815
Gly Ala  Gly Ser Gly Ala  Gly Ala Gly Ser  Gly Ala Gly
            4820                4825                4830
Ser Gly  Ala Gly Ala Gly  Ser Gly Ala Gly  Ser Gly Ala
            4835                4840                4845
Gly Ala  Gly Tyr Gly Ala  Gly Ala Gly Val  Gly Tyr Gly Ala Gly
            4850                4855                4860
Ala Gly  Ser Gly Ala Ala  Ser Gly Ala Gly  Ala Gly Ser Gly Ala
            4865                4870                4875
Gly Ala  Gly Ser Gly Ala  Gly Ala Gly Ser  Gly Ala Gly Ala Gly
            4880                4885                4890
Ser Gly  Ala Gly Ala Gly  Ser Gly Ala Gly  Ala Gly Ser Gly Ala
            4895                4900                4905
Gly Ala  Gly Ser Gly Ala  Gly Ser Gly Ala  Gly Ala Gly Ser Gly
            4910                4915                4920
Ala Gly  Ala Gly Tyr Gly Ala  Gly Tyr Gly Ala Gly  Val Gly Ala
            4925                4930                4935
Gly Tyr  Gly Ala Gly Ala Gly  Tyr Gly Ala Gly  Tyr Gly Val Gly
            4940                4945                4950
Ala Gly  Ala Gly Tyr Gly Ala  Gly Ala Gly Ser Gly  Ala Gly Ser
            4955                4960                4965
Gly Ala  Gly Ala Gly Ser Gly  Ala Gly Ala Gly Ser  Gly Ala Gly
            4970                4975                4980
Ala Gly  Ser Gly Ala Gly Ala  Gly Ser Gly Ala Gly  Ala Gly Ser
            4985                4990                4995
Gly Ala  Gly Ser Gly Ala Gly  Ala Gly Tyr Gly Ala  Gly Ala Gly
            5000                5005                5010
Ala Gly  Tyr Gly Ala Gly Ala  Gly Ala Gly Tyr Gly  Ala Gly Ala
            5015                5020                5025
Gly Ser  Gly Ala Ala Ser Gly  Ala Gly Ala Gly Ala  Gly Ala Gly
            5030                5035                5040
Ser Gly  Ala Gly Ala Gly Ser  Gly Ala Gly Ala Gly  Ser Gly Ala
            5045                5050                5055
Gly Ser  Gly Ala Gly Ala Gly  Ser Gly Ala Gly Ala  Gly Tyr Gly
            5060                5065                5070
Ala Gly  Ala Gly Ser Gly Ala  Ala Ser Gly Ala Gly  Ala Gly Ser
            5075                5080                5085
Gly Ala  Gly Ala Gly Ala Gly  Ala Gly Ala Gly Ala  Gly Ser Gly
            5090                5095                5100
Ala Gly  Ala Gly Ser Gly Ala  Gly Ala Gly Tyr Gly  Ala Gly Ala
            5105                5110                5115
Gly Ser  Gly Ala Ala Ser Gly  Ala Gly Ala Gly Ala  Gly Ala Gly
            5120                5125                5130
Thr Gly  Ser Ser Gly Phe Gly  Pro Tyr Val Ala Asn  Gly Gly Tyr
            5135                5140                5145
Ser Arg  Arg Glu Gly Tyr Glu  Tyr Ala Trp Ser Ser  Lys Ser Asp
            5150                5155                5160
Phe Glu  Thr Gly Ser Gly Ala  Ala Ser Gly Ala Gly  Ala Gly Ala
            5165                5170                5175
```

```
Gly Ser Gly Ala Gly Ala Gly Ser Gly Ala Gly Ser Gly
        5180                5185                5190

Ala Gly Ala Gly Ser Gly Ala Gly Ala Gly Ser Val Ser Tyr
        5195                5200                5205

Gly Ala Gly Arg Gly Tyr Gln Gly Ala Gly Ser Ala Ala Ser
        5210                5215                5220

Ser Val Ser Ser Ala Ser Ser Arg Ser Tyr Asp Tyr Ser Arg Arg
        5225                5230                5235

Asn Val Arg Lys Asn Cys Gly Ile Pro Arg Arg Gln Leu Val Val
        5240                5245                5250

Lys Phe Arg Ala Leu Pro Cys Val Asn Cys
        5255                5260

<210> SEQ ID NO 94
<211> LENGTH: 220
<212> TYPE: PRT
<213> ORGANISM: Bombyx mori

<400> SEQUENCE: 94

Met Leu Ala Arg Cys Leu Ala Val Ala Val Ala Val Leu Ala Ser
  1               5                  10                  15

Ala Gly Pro Pro Ser Pro Ile Tyr Arg Pro Cys Tyr Leu Asp Asp Tyr
                 20                  25                  30

Lys Cys Ile Ser Asp His Leu Ala Asn Ser Lys Cys Ile Pro Gly
             35                  40                  45

Arg Gly Gln Ile Pro Ser Gln Tyr Glu Ile Pro Val Phe Gln Phe Glu
         50                  55                  60

Ile Pro Tyr Phe Asn Ala Thr Tyr Val Asp His Asn Leu Ile Thr Arg
 65                  70                  75                  80

Asn His Asp Gln Cys Arg Val Ser Glu Phe Tyr Asp Asn Val Arg Thr
                 85                  90                  95

Leu Lys Thr Val Leu Thr Val Asp Cys Pro Trp Leu Asn Phe Glu Ser
                100                 105                 110

Asn Arg Thr Leu Ala Gln His Met Ser Phe Lys Glu Asp Val Val Leu
            115                 120                 125

Ser Phe Tyr Ile Asn Gly Ser Tyr Pro Leu Ile Arg Leu Thr Thr Val
        130                 135                 140

Phe Asp Lys Gly Asn Asn Phe Asp Leu Cys Ser Ala Phe Thr Phe Ala
145                 150                 155                 160

Asp Leu Ala Gly Gly Leu Pro Ile Phe His Ile Asn Pro Asn Asp Gln
                165                 170                 175

Arg Thr Ala Gln Trp Leu Ser Lys Asp Leu Thr Leu Leu His Ile Tyr
            180                 185                 190

Glu Arg Glu His Ile Phe Gly Lys Arg Asn Trp Leu Ala Arg Ser Phe
        195                 200                 205

Ile Ser Arg Thr Leu Cys Asp Phe Gly Cys Gln His
    210                 215                 220

<210> SEQ ID NO 95
<211> LENGTH: 6
<212> TYPE: PRT
<213> ORGANISM: Artificial Sequence
<220> FEATURE:
<223> OTHER INFORMATION: Fibroin-like polypeptide

<400> SEQUENCE: 95

Gly Ala Gly Ala Gly Ser
  1               5
```

<210> SEQ ID NO 96
<211> LENGTH: 5
<212> TYPE: PRT
<213> ORGANISM: Artificial Sequence
<220> FEATURE:
<223> OTHER INFORMATION: Fibroin-like polypeptide

<400> SEQUENCE: 96

Gly Ala Ala Gly Tyr
1               5

<210> SEQ ID NO 97
<211> LENGTH: 9
<212> TYPE: PRT
<213> ORGANISM: Artificial Sequence
<220> FEATURE:
<223> OTHER INFORMATION: Fibroin-like polypeptide

<400> SEQUENCE: 97

Ala Gly Ala Gly Ala Gly Pro Glu Gly
1               5

<210> SEQ ID NO 98
<211> LENGTH: 8
<212> TYPE: PRT
<213> ORGANISM: Artificial Sequence
<220> FEATURE:
<223> OTHER INFORMATION: Fibroin-like polypeptide

<400> SEQUENCE: 98

Ala Gly Ala Gly Ala Gly Glu Gly
1               5

<210> SEQ ID NO 99
<211> LENGTH: 59
<212> TYPE: PRT
<213> ORGANISM: Artificial Sequence
<220> FEATURE:
<223> OTHER INFORMATION: Fibroin-like polypeptide

<400> SEQUENCE: 99

Gly Ala Gly Ala Gly Ser Gly Ala Ala Gly Gly Ala Gly Ala Gly Ser
1               5                   10                  15

Gly Ala Gly Ala Gly Ser Gly Ala Ala Gly Ser Gly Ala Gly Ala
            20                  25                  30

Gly Ser Gly Ala Gly Ala Gly Ser Gly Ala Gly Ala Gly Ser Gly Ala
        35                  40                  45

Gly Ala Gly Ser Gly Ala Gly Ala Gly Ser Tyr
    50                  55

<210> SEQ ID NO 100
<211> LENGTH: 13
<212> TYPE: PRT
<213> ORGANISM: Artificial Sequence
<220> FEATURE:
<223> OTHER INFORMATION: Fibroin-like polypeptide

<400> SEQUENCE: 100

Tyr Gly Gly Leu Gly Ser Gln Gly Ala Gly Arg Gly Gly
1               5                   10

<210> SEQ ID NO 101
<211> LENGTH: 878
<212> TYPE: PRT
<213> ORGANISM: Artificial Sequence

```
<220> FEATURE:
<223> OTHER INFORMATION: Silk-elastin-like polypeptide (SELP)

<400> SEQUENCE: 101

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Val Gly Val Pro
        35                  40                  45

Gly Val Gly Val Pro Gly Val Gly Val Pro Gly Val Gly Val Pro Gly
    50                  55                  60

Lys Gly Val Pro Gly Val Gly Val Pro Gly Val Gly Val Pro Gly Val
65                  70                  75                  80

Gly Val Pro Gly Ala Gly Ala Gly Ser Gly Ala Gly Ala Gly Ser Gly
            85                  90                  95

Ala Gly Ala Gly Ser Gly Ala Gly Ala Gly Ser Gly Val Gly Val Pro
            100                 105                 110

Gly Val Gly Val Pro Gly Val Gly Val Pro Gly Val Gly Val Pro Gly
        115                 120                 125

Lys Gly Val Pro Gly Val Gly Val Pro Gly Val Gly Val Pro Gly Val
            130                 135                 140

Gly Val Pro Gly Ala Gly Ala Gly Ser Gly Ala Gly Ala Gly Ser Gly
145                 150                 155                 160

Ala Gly Ala Gly Ser Gly Ala Gly Ala Gly Ser Gly Val Gly Val Pro
            165                 170                 175

Gly Val Gly Val Pro Gly Val Gly Val Pro Gly Val Gly Val Pro Gly
        180                 185                 190

Lys Gly Val Pro Gly Val Gly Val Pro Gly Val Gly Val Pro Gly Val
            195                 200                 205

Gly Val Pro Gly Ala Gly Ala Gly Ser Gly Ala Gly Ala Gly Ser Gly
        210                 215                 220

Ala Gly Ala Gly Ser Gly Ala Gly Ala Gly Ser Gly Val Gly Val Pro
225                 230                 235                 240

Gly Val Gly Val Pro Gly Val Gly Val Pro Gly Val Gly Val Pro Gly
            245                 250                 255

Lys Gly Val Pro Gly Val Gly Val Pro Gly Val Gly Val Pro Gly Val
        260                 265                 270

Gly Val Pro Gly Ala Gly Ala Gly Ser Gly Ala Gly Ala Gly Ser Gly
            275                 280                 285

Ala Gly Ala Gly Ser Gly Ala Gly Ala Gly Ser Gly Val Gly Val Pro
        290                 295                 300

Gly Val Gly Val Pro Gly Val Gly Val Pro Gly Val Gly Val Pro Gly
305                 310                 315                 320

Lys Gly Val Pro Gly Val Gly Val Pro Gly Val Gly Val Pro Gly Val
            325                 330                 335

Gly Val Pro Gly Ala Gly Ala Gly Ser Gly Ala Gly Ala Gly Ser Gly
        340                 345                 350

Ala Gly Ala Gly Ser Gly Ala Gly Ala Gly Ser Gly Val Gly Val Pro
            355                 360                 365

Gly Val Gly Val Pro Gly Val Gly Val Pro Gly Val Gly Val Pro Gly
        370                 375                 380

Lys Gly Val Pro Gly Val Gly Val Pro Gly Val Gly Val Pro Gly Val
385                 390                 395                 400
```

-continued

Gly Val Pro Gly Ala Gly Ala Gly Ser Gly Ala Gly Ser Gly
            405                 410                 415

Ala Gly Ala Gly Ser Gly Ala Gly Ala Gly Ser Gly Val Gly Val Pro
            420                 425                 430

Gly Val Gly Val Pro Gly Val Gly Val Pro Gly Val Gly Val Pro Gly
            435                 440                 445

Lys Gly Val Pro Gly Val Gly Val Pro Gly Val Gly Val Pro Gly Val
            450                 455                 460

Gly Val Pro Gly Ala Gly Ala Gly Ser Gly Ala Gly Ala Gly Ser Gly
465                 470                 475                 480

Ala Gly Ala Gly Ser Gly Ala Gly Ala Gly Ser Gly Val Gly Val Pro
            485                 490                 495

Gly Val Gly Val Pro Gly Val Gly Val Pro Gly Val Gly Val Pro Gly
            500                 505                 510

Lys Gly Val Pro Gly Val Gly Val Pro Gly Val Gly Val Pro Gly Val
            515                 520                 525

Gly Val Pro Gly Ala Gly Ala Gly Ser Gly Ala Gly Ala Gly Ser Gly
            530                 535                 540

Ala Gly Ala Gly Ser Gly Ala Gly Ala Gly Ser Gly Val Gly Val Pro
545                 550                 555                 560

Gly Val Gly Val Pro Gly Val Gly Val Pro Gly Val Gly Val Pro Gly
            565                 570                 575

Lys Gly Val Pro Gly Val Gly Val Pro Gly Val Gly Val Pro Gly Val
            580                 585                 590

Gly Val Pro Gly Ala Gly Ala Gly Ser Gly Ala Gly Ala Gly Ser Gly
            595                 600                 605

Ala Gly Ala Gly Ser Gly Ala Gly Ala Gly Ser Gly Val Gly Val Pro
            610                 615                 620

Gly Val Gly Val Pro Gly Val Gly Val Pro Gly Val Gly Val Pro Gly
625                 630                 635                 640

Lys Gly Val Pro Gly Val Gly Val Pro Gly Val Gly Val Pro Gly Val
            645                 650                 655

Gly Val Pro Gly Ala Gly Ala Gly Ser Gly Ala Gly Ala Gly Ser Gly
            660                 665                 670

Ala Gly Ala Gly Ser Gly Ala Gly Ala Gly Ser Gly Val Gly Val Pro
            675                 680                 685

Gly Val Gly Val Pro Gly Val Gly Val Pro Gly Val Gly Val Pro Gly
            690                 695                 700

Lys Gly Val Pro Gly Val Gly Val Pro Gly Val Gly Val Pro Gly Val
705                 710                 715                 720

Gly Val Pro Gly Ala Gly Ala Gly Ser Gly Ala Gly Ala Gly Ser Gly
            725                 730                 735

Ala Gly Ala Gly Ser Gly Ala Gly Ala Gly Ser Gly Val Gly Val Pro
            740                 745                 750

Gly Val Gly Val Pro Gly Val Gly Val Pro Gly Val Gly Val Pro Gly
            755                 760                 765

Lys Gly Val Pro Gly Val Gly Val Pro Gly Val Gly Val Pro Gly Val
            770                 775                 780

Gly Val Pro Gly Ala Gly Ala Gly Ser Gly Ala Gly Ala Gly Ser Gly
785                 790                 795                 800

Ala Gly Ala Gly Ser Gly Ala Gly Ala Gly Ser Gly Val Gly Val Pro
            805                 810                 815

Gly Val Gly Val Pro Gly Val Gly Val Pro Gly Val Gly Val Pro Gly
            820                 825                 830

```
Lys Gly Val Pro Gly Val Gly Val Pro Gly Val Gly Val
        835                 840                 845

Gly Val Pro Gly Ala Gly Ala Gly Ser Gly Ala Gly Ala Gly Ser Gly
        850                 855                 860

Ala Gly Ala Met Asp Pro Gly Arg Tyr Gln Asp Leu Arg Ser
865                 870                 875

<210> SEQ ID NO 102
<211> LENGTH: 670
<212> TYPE: PRT
<213> ORGANISM: Artificial Sequence
<220> FEATURE:
<223> OTHER INFORMATION: Silk-elastin-like polypeptide (SELP)

<400> SEQUENCE: 102

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Val Gly Val Pro
        35                  40                  45

Gly Val Gly Val Pro Gly Val Gly Val Pro Gly Val Gly Val Pro Gly
    50                  55                  60

Lys Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
                85                  90                  95

Val Pro Gly Val Gly Val Pro Gly Val Gly Val Pro Gly Val Gly Val
            100                 105                 110

Pro Gly Val Gly Val Pro Gly Val Gly Val Pro Gly Ala Gly Ala Gly
        115                 120                 125

Ser Gly Ala Gly Ala Gly Ser Gly Ala Gly Ala Gly Ser Gly Ala Gly
    130                 135                 140

Ala Gly Ser Gly Val Gly Val Pro Gly Val Gly Val Pro Gly Val Gly
145                 150                 155                 160

Val Pro Gly Val Gly Val Pro Gly Lys Gly Val Pro Gly Val Gly Val
                165                 170                 175

Pro Gly Val Gly Val Pro Gly Val Gly Val Pro Gly Val Gly Val Pro
            180                 185                 190

Gly Val Gly Val Pro Gly Val Gly Val Pro Gly Val Gly Val Pro Gly
        195                 200                 205

Val Gly Val Pro Gly Val Gly Val Pro Gly Val Gly Val Pro Gly Val
    210                 215                 220

Gly Val Pro Gly Ala Gly Ala Gly Ser Gly Ala Gly Ala Gly Ser Gly
225                 230                 235                 240

Ala Gly Ala Gly Ser Gly Ala Gly Ala Gly Ser Gly Val Gly Val Pro
                245                 250                 255

Gly Val Gly Val Pro Gly Val Gly Val Pro Gly Val Gly Val Pro Gly
            260                 265                 270

Lys Gly Val Pro Gly Val Gly Val Pro Gly Val Gly Val Pro Gly Val
        275                 280                 285

Gly Val Pro Gly Val Gly Val Pro Gly Val Gly Val Pro Gly Val Gly
    290                 295                 300

Val Pro Gly Val Gly Val Pro Gly Val Gly Val Pro Gly Val Gly Val
305                 310                 315                 320
```

```
Pro Gly Val Gly Val Pro Gly Val Gly Val Pro Gly Ala Gly Ala Gly
            325                 330                 335
Ser Gly Ala Gly Ala Gly Ser Gly Ala Gly Ala Gly Ser Gly Ala Gly
            340                 345                 350
Ala Gly Ser Gly Val Gly Val Pro Gly Val Gly Val Pro Gly Val Gly
            355                 360                 365
Val Pro Gly Val Gly Val Pro Gly Lys Gly Val Pro Gly Val Gly Val
            370                 375                 380
Pro Gly Val Gly Val Pro Gly Val Gly Val Pro Gly Val Gly Val Pro
385                 390                 395                 400
Gly Val Gly Val Pro Gly Val Gly Val Pro Gly Val Gly Val Pro Gly
            405                 410                 415
Val Gly Val Pro Gly Val Gly Val Pro Gly Val Gly Val Pro Gly Val
            420                 425                 430
Gly Val Pro Gly Ala Gly Ala Gly Ser Gly Ala Gly Ala Gly Ser Gly
            435                 440                 445
Ala Gly Ala Gly Ser Gly Ala Gly Ala Gly Ser Gly Val Gly Val Pro
            450                 455                 460
Gly Val Gly Val Pro Gly Val Gly Val Pro Gly Val Gly Val Pro Gly
465                 470                 475                 480
Lys Gly Val Pro Gly Val Gly Val Pro Gly Val Gly Val Pro Gly Val
            485                 490                 495
Gly Val Pro Gly Val Gly Val Pro Gly Val Gly Val Pro Gly Val Gly
            500                 505                 510
Val Pro Gly Val Gly Val Pro Gly Val Gly Val Pro Gly Val Gly Val
            515                 520                 525
Pro Gly Val Gly Val Pro Gly Val Gly Val Pro Gly Ala Gly Ala Gly
            530                 535                 540
Ser Gly Ala Gly Ala Gly Ser Gly Ala Gly Ala Gly Ser Gly Ala Gly
545                 550                 555                 560
Ala Gly Ser Gly Val Gly Val Pro Gly Val Gly Val Pro Gly Val Gly
            565                 570                 575
Val Pro Gly Val Gly Val Pro Gly Lys Gly Val Pro Gly Val Gly Val
            580                 585                 590
Pro Gly Val Gly Val Pro Gly Val Gly Val Pro Gly Val Gly Val Pro
            595                 600                 605
Gly Val Gly Val Pro Gly Val Gly Val Pro Gly Val Gly Val Pro Gly
            610                 615                 620
Val Gly Val Pro Gly Val Gly Val Pro Gly Val Gly Val Pro Gly Val
625                 630                 635                 640
Gly Val Pro Gly Ala Gly Ala Gly Ser Gly Ala Gly Ala Gly Ser Gly
            645                 650                 655
Ala Gly Ala Met Asp Pro Gly Arg Tyr Gln Asp Leu Arg Ser
            660                 665                 670

<210> SEQ ID NO 103
<211> LENGTH: 878
<212> TYPE: PRT
<213> ORGANISM: Artificial Sequence
<220> FEATURE:
<223> OTHER INFORMATION: Silk-elastin-like polypeptide (SELP)

<400> SEQUENCE: 103

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
```

-continued

```
                    20                  25                  30
Met Gly Ala Gly Ser Gly Ala Gly Ala Gly Ser Gly Val Gly Val Pro
                35                  40                  45
Gly Val Gly Val Pro Gly Val Gly Val Pro Gly Val Gly Val Pro Gly
            50                  55                  60
Lys Gly Val Pro Gly Val Gly Val Pro Gly Val Gly Val Pro Gly Val
65                  70                  75                  80
Gly Val Pro Gly Val Gly Val Pro Gly Val Gly Val Pro Gly Val Gly
                85                  90                  95
Val Pro Gly Val Gly Val Pro Gly Val Gly Val Pro Gly Val Gly Val
            100                 105                 110
Pro Gly Val Gly Val Pro Gly Val Gly Val Pro Gly Ala Gly Ala Gly
        115                 120                 125
Ser Gly Ala Gly Ala Gly Ser Gly Ala Gly Ala Gly Ser Gly Ala Gly
    130                 135                 140
Ala Gly Ser Gly Val Gly Val Pro Gly Val Gly Val Pro Gly Val Gly
145                 150                 155                 160
Val Pro Gly Val Gly Val Pro Gly Lys Gly Val Pro Gly Val Gly Val
                165                 170                 175
Pro Gly Val Gly Val Pro Gly Val Gly Val Pro Gly Val Gly Val Pro
            180                 185                 190
Gly Val Gly Val Pro Gly Val Gly Val Pro Gly Val Gly Val Pro Gly
        195                 200                 205
Val Gly Val Pro Gly Val Gly Val Pro Gly Val Gly Val Pro Gly Val
    210                 215                 220
Gly Val Pro Gly Ala Gly Ala Gly Ser Gly Ala Gly Ala Gly Ser Gly
225                 230                 235                 240
Ala Gly Ala Gly Ser Gly Ala Gly Ala Gly Ser Gly Val Gly Val Pro
                245                 250                 255
Gly Val Gly Val Pro Gly Val Gly Val Pro Gly Val Gly Val Pro Gly
            260                 265                 270
Lys Gly Val Pro Gly Val Gly Val Pro Gly Val Gly Val Pro Gly Val
        275                 280                 285
Gly Val Pro Gly Val Gly Val Pro Gly Val Gly Val Pro Gly Val Gly
    290                 295                 300
Val Pro Gly Val Gly Val Pro Gly Val Gly Val Pro Gly Val Gly Val
305                 310                 315                 320
Pro Gly Val Gly Val Pro Gly Val Gly Val Pro Gly Ala Gly Ala Gly
                325                 330                 335
Ser Gly Ala Gly Ala Gly Ser Gly Ala Gly Ala Gly Ser Gly Ala Gly
            340                 345                 350
Ala Gly Ser Gly Val Gly Val Pro Gly Val Gly Val Pro Gly Val Gly
        355                 360                 365
Val Pro Gly Val Gly Val Pro Gly Lys Gly Val Pro Gly Val Gly Val
    370                 375                 380
Pro Gly Val Gly Val Pro Gly Val Gly Val Pro Gly Val Gly Val Pro
385                 390                 395                 400
Gly Val Gly Val Pro Gly Val Gly Val Pro Gly Val Gly Val Pro Gly
                405                 410                 415
Val Gly Val Pro Gly Val Gly Val Pro Gly Val Gly Val Pro Gly Val
            420                 425                 430
Gly Val Pro Gly Ala Gly Ala Gly Ser Gly Ala Gly Ala Gly Ser Gly
        435                 440                 445
```

```
Ala Gly Ala Gly Ser Gly Ala Gly Ala Gly Ser Gly Val Gly Val Pro
            450                 455                 460
Gly Val Gly Val Pro Gly Val Gly Val Pro Gly Val Gly Val Pro Gly
465                 470                 475                 480
Lys Gly Val Pro Gly Val Gly Val Pro Gly Val Gly Val Pro Gly Val
                485                 490                 495
Gly Val Pro Gly Val Gly Val Pro Gly Val Gly Val Pro Gly Val Gly
            500                 505                 510
Val Pro Gly Val Gly Val Pro Gly Val Gly Val Pro Gly Val Gly Val
        515                 520                 525
Pro Gly Val Gly Val Pro Gly Val Gly Val Pro Gly Ala Gly Ala Gly
    530                 535                 540
Ser Gly Ala Gly Ala Gly Ser Gly Ala Gly Ala Gly Ser Gly Ala Gly
545                 550                 555                 560
Ala Gly Ser Gly Val Gly Val Pro Gly Val Gly Val Pro Gly Val Gly
                565                 570                 575
Val Pro Gly Val Gly Val Pro Gly Lys Gly Val Pro Gly Val Gly Val
        580                 585                 590
Pro Gly Val Gly Val Pro Gly Val Gly Val Pro Gly Val Gly Val Pro
    595                 600                 605
Gly Val Gly Val Pro Gly Val Gly Val Pro Gly Val Gly Val Pro Gly
610                 615                 620
Val Gly Val Pro Gly Val Gly Val Pro Gly Val Gly Val Pro Gly Val
625                 630                 635                 640
Gly Val Pro Gly Ala Gly Ala Gly Ser Gly Ala Gly Ala Gly Ser Gly
                645                 650                 655
Ala Gly Ala Gly Ser Gly Ala Gly Ala Gly Ser Gly Val Gly Val Pro
            660                 665                 670
Gly Val Gly Val Pro Gly Val Gly Val Pro Gly Val Gly Val Pro Gly
            675                 680                 685
Lys Gly Val Pro Gly Val Gly Val Pro Gly Val Gly Val Pro Gly Val
        690                 695                 700
Gly Val Pro Gly Val Gly Val Pro Gly Val Gly Val Pro Gly Val Gly
705                 710                 715                 720
Val Pro Gly Val Gly Val Pro Gly Val Gly Val Pro Gly Val Gly Val
            725                 730                 735
Pro Gly Val Gly Val Pro Gly Val Gly Val Pro Gly Ala Gly Ala Gly
                740                 745                 750
Ser Gly Ala Gly Ala Gly Ser Gly Ala Gly Ala Gly Ser Gly Ala Gly
            755                 760                 765
Ala Gly Ser Gly Val Gly Val Pro Gly Val Gly Val Pro Gly Val Gly
            770                 775                 780
Val Pro Gly Val Gly Val Pro Gly Lys Gly Val Pro Gly Val Gly Val
785                 790                 795                 800
Pro Gly Val Gly Val Pro Gly Val Gly Val Pro Gly Val Gly Val Pro
                805                 810                 815
Gly Val Gly Val Pro Gly Val Gly Val Pro Gly Val Gly Val Pro Gly
            820                 825                 830
Val Gly Val Pro Gly Val Gly Val Pro Gly Val Gly Val Pro Gly Val
        835                 840                 845
Gly Val Pro Gly Ala Gly Ala Gly Ser Gly Ala Gly Ala Gly Ser Gly
    850                 855                 860
Ala Gly Ala Met Asp Pro Gly Arg Tyr Gln Asp Leu Arg Ser
865                 870                 875
```

<210> SEQ ID NO 104
<211> LENGTH: 1086
<212> TYPE: PRT
<213> ORGANISM: Artificial Sequence
<220> FEATURE:
<223> OTHER INFORMATION: Silk-elastin-like polypeptide (SELP)

<400> SEQUENCE: 104

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Val Gly Val Pro
        35                  40                  45

Gly Val Gly Val Pro Gly Val Gly Val Pro Gly Val Gly Val Pro Gly
    50                  55                  60

Lys Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
                85                  90                  95

Val Pro Gly Val Gly Val Pro Gly Val Gly Val Pro Gly Val Gly Val
            100                 105                 110

Pro Gly Val Gly Val Pro Gly Val Gly Val Pro Gly Ala Gly Ala Gly
        115                 120                 125

Ser Gly Ala Gly Ala Gly Ser Gly Ala Gly Ala Gly Ser Gly Ala Gly
    130                 135                 140

Ala Gly Ser Gly Val Gly Val Pro Gly Val Gly Val Pro Gly Val Gly
145                 150                 155                 160

Val Pro Gly Val Gly Val Pro Gly Lys Gly Val Pro Gly Val Gly Val
                165                 170                 175

Pro Gly Val Gly Val Pro Gly Val Gly Val Pro Gly Val Gly Val Pro
            180                 185                 190

Gly Val Gly Val Pro Gly Val Gly Val Pro Gly Val Gly Val Pro Gly
        195                 200                 205

Val Gly Val Pro Gly Val Gly Val Pro Gly Val Gly Val Pro Gly Val
    210                 215                 220

Gly Val Pro Gly Ala Gly Ala Gly Ser Gly Ala Gly Ala Gly Ser Gly
225                 230                 235                 240

Ala Gly Ala Gly Ser Gly Ala Gly Ala Gly Ser Gly Val Gly Val Pro
                245                 250                 255

Gly Val Gly Val Pro Gly Val Gly Val Pro Gly Val Gly Val Pro Gly
            260                 265                 270

Lys Gly Val Pro Gly Val Gly Val Pro Gly Val Gly Val Pro Gly Val
        275                 280                 285

Gly Val Pro Gly Val Gly Val Pro Gly Val Gly Val Pro Gly Val Gly
    290                 295                 300

Val Pro Gly Val Gly Val Pro Gly Val Gly Val Pro Gly Val Gly Val
305                 310                 315                 320

Pro Gly Val Gly Val Pro Gly Val Gly Val Pro Gly Ala Gly Ala Gly
                325                 330                 335

Ser Gly Ala Gly Ala Gly Ser Gly Ala Gly Ala Gly Ser Gly Ala Gly
            340                 345                 350

Ala Gly Ser Gly Val Gly Val Pro Gly Val Gly Val Pro Gly Val Gly
        355                 360                 365
```

-continued

```
Val Pro Gly Val Gly Val Pro Gly Lys Gly Val Pro Gly Val Gly Val
    370                 375                 380
Pro Gly Val Gly Val Pro Gly Val Gly Val Pro Gly Val Gly Val Pro
385                 390                 395                 400
Gly Val Gly Val Pro Gly Val Gly Val Pro Gly Val Gly Val Pro Gly
                405                 410                 415
Val Gly Val Pro Gly Val Gly Val Pro Gly Val Gly Val Pro Gly Val
            420                 425                 430
Gly Val Pro Gly Ala Gly Ala Gly Ser Gly Ala Gly Ala Gly Ser Gly
        435                 440                 445
Ala Gly Ala Gly Ser Gly Ala Gly Ala Gly Ser Gly Val Gly Val Pro
    450                 455                 460
Gly Val Gly Val Pro Gly Val Gly Val Pro Gly Val Gly Val Pro Gly
465                 470                 475                 480
Lys Gly Val Pro Gly Val Gly Val Pro Gly Val Gly Val Pro Gly Val
                485                 490                 495
Gly Val Pro Gly Val Gly Val Pro Gly Val Gly Val Pro Gly Val Gly
            500                 505                 510
Val Pro Gly Val Gly Val Pro Gly Val Gly Val Pro Gly Val Gly Val
        515                 520                 525
Pro Gly Val Gly Val Pro Gly Val Gly Val Pro Gly Ala Gly Ala Gly
    530                 535                 540
Ser Gly Ala Gly Ala Gly Ser Gly Ala Gly Ala Gly Ser Gly Ala Gly
545                 550                 555                 560
Ala Gly Ser Gly Val Gly Val Pro Gly Val Gly Val Pro Gly Val Gly
                565                 570                 575
Val Pro Gly Val Gly Val Pro Gly Lys Gly Val Pro Gly Val Gly Val
            580                 585                 590
Pro Gly Val Gly Val Pro Gly Val Gly Val Pro Gly Val Gly Val Pro
        595                 600                 605
Gly Val Gly Val Pro Gly Val Gly Val Pro Gly Val Gly Val Pro Gly
    610                 615                 620
Val Gly Val Pro Gly Val Gly Val Pro Gly Val Gly Val Pro Gly Val
625                 630                 635                 640
Gly Val Pro Gly Ala Gly Ala Gly Ser Gly Ala Gly Ala Gly Ser Gly
                645                 650                 655
Ala Gly Ala Gly Ser Gly Ala Gly Ala Gly Ser Gly Val Gly Val Pro
            660                 665                 670
Gly Val Gly Val Pro Gly Val Gly Val Pro Gly Val Gly Val Pro Gly
        675                 680                 685
Lys Gly Val Pro Gly Val Gly Val Pro Gly Val Gly Val Pro Gly Val
    690                 695                 700
Gly Val Pro Gly Val Gly Val Pro Gly Val Gly Val Pro Gly Val Gly
705                 710                 715                 720
Val Pro Gly Val Gly Val Pro Gly Val Gly Val Pro Gly Val Gly Val
                725                 730                 735
Pro Gly Val Gly Val Pro Gly Val Gly Val Pro Gly Ala Gly Ala Gly
            740                 745                 750
Ser Gly Ala Gly Ala Gly Ser Gly Ala Gly Ala Gly Ser Gly Ala Gly
        755                 760                 765
Ala Gly Ser Gly Val Gly Val Pro Gly Val Gly Val Pro Gly Val Gly
    770                 775                 780
Val Pro Gly Val Gly Val Pro Gly Lys Gly Val Pro Gly Val Gly Val
785                 790                 795                 800
```

Pro Gly Val Gly Val Pro Gly Val Gly Val Pro Gly Val Gly Val Pro
            805                 810                 815
Gly Val Gly Val Pro Gly Val Gly Val Pro Gly Val Gly Val Pro Gly
            820                 825                 830
Val Gly Val Pro Gly Val Gly Val Pro Gly Val Gly Val Pro Gly Val
            835                 840                 845
Gly Val Pro Gly Ala Gly Ala Gly Ser Gly Ala Gly Ala Gly Ser Gly
            850                 855                 860
Ala Gly Ala Gly Ser Gly Ala Gly Ala Gly Ser Gly Val Gly Val Pro
865                 870                 875                 880
Gly Val Gly Val Pro Gly Val Gly Val Pro Gly Val Gly Val Pro Gly
            885                 890                 895
Lys Gly Val Pro Gly Val Gly Val Pro Gly Val Gly Val Pro Gly Val
            900                 905                 910
Gly Val Pro Gly Val Gly Val Pro Gly Val Gly Val Pro Gly Val Gly
            915                 920                 925
Val Pro Gly Val Gly Val Pro Gly Val Gly Val Pro Gly Val Gly Val
            930                 935                 940
Pro Gly Val Gly Val Pro Gly Val Gly Val Pro Gly Ala Gly Ala Gly
945                 950                 955                 960
Ser Gly Ala Gly Ala Gly Ser Gly Ala Gly Ala Gly Ser Gly Ala Gly
            965                 970                 975
Ala Gly Ser Gly Val Gly Val Pro Gly Val Gly Val Pro Gly Val Gly
            980                 985                 990
Val Pro Gly Val Gly Val Pro Gly Lys Gly Val Pro Gly Val Gly Val
            995                 1000                1005
Pro Gly Val Gly Val Pro Gly Val Gly Val Pro Gly Val Gly Val
            1010                1015                1020
Pro Gly Val Gly Val Pro Gly Val Gly Val Pro Gly Val Gly Val
            1025                1030                1035
Pro Gly Val Gly Val Pro Gly Val Gly Val Pro Gly Val Gly Val
            1040                1045                1050
Pro Gly Val Gly Val Pro Gly Ala Gly Ala Gly Ser Gly Ala Gly
            1055                1060                1065
Ala Gly Ser Gly Ala Gly Ala Met Asp Pro Gly Arg Tyr Gln Asp
            1070                1075                1080
Leu Arg Ser
    1085

<210> SEQ ID NO 105
<211> LENGTH: 10
<212> TYPE: PRT
<213> ORGANISM: Artificial Sequence
<220> FEATURE:
<223> OTHER INFORMATION: Abductin-like polypeptide
<220> FEATURE:
<221> NAME/KEY: misc_feature
<222> LOCATION: (10)..(10)
<223> OTHER INFORMATION: Xaa can be any naturally occurring amino acid

<400> SEQUENCE: 105

Gly Gly Phe Gly Gly Met Gly Gly Gly Xaa
1               5                   10

<210> SEQ ID NO 106
<211> LENGTH: 136
<212> TYPE: PRT
<213> ORGANISM: Argopecten irradians

<400> SEQUENCE: 106

Met Asn Ala Tyr Ile Cys Leu Ala Ala Cys Leu Ile Ala Ala Val Ser
1               5                   10                  15

Ala Ala Gly Tyr Gly Gly Gly Ala Gly Ser Met Gly Gly Thr Gly Gly
            20                  25                  30

Met Gly Gly Gly Met Asn Ala Gly Gly Phe Gly Gly Met Gly Gly Gly
        35                  40                  45

Met Gly Gly Gly Lys Gly Gly Phe Gly Gly Ile Gly Phe Gly Gly
    50                  55                  60

Met Gly Gly Gly Met Gly Gly Gly Pro Gly Gly Phe Gly Gly Met Gly
65                  70                  75                  80

Gly Phe Gly Gly Met Gly Gly Gly Lys Gly Gly Phe Gly Gly Met Gly
                85                  90                  95

Ser Gly Met Gly Gly Phe Gly Gly Met Gly Gly Gly Asn Ala Gly Phe
            100                 105                 110

Gly Gly Met Gly Gly Gly Asn Ala Gly Phe Gly Gly Met Gly Gly Gln
            115                 120                 125

Gly Gly Phe Gly Gly Lys Gly Tyr
        130                 135

<210> SEQ ID NO 107
<211> LENGTH: 132
<212> TYPE: PRT
<213> ORGANISM: Argopecten irradians

<400> SEQUENCE: 107

Met Asn Ala Tyr Ile Cys Leu Ala Ala Cys Leu Ile Ala Val Val Ser
1               5                   10                  15

Ala Ala Gly Tyr Gly Gly Gly Ala Gly Ser Met Gly Gly Thr Gly Gly
            20                  25                  30

Met Gly Gly Gly Met Asn Ala Gly Gly Phe Gly Gly Ile Gly Gly Gly
        35                  40                  45

Met Gly Gly Gly Lys Gly Gly Phe Gly Gly Met Gly Gly Gly Pro Gly
    50                  55                  60

Gly Phe Gly Gly Ile Gly Gly Ser Gly Gly Phe Gly Gly Met Gly
65                  70                  75                  80

Gly Phe Gly Gly Met Gly Gly Gly Lys Gly Gly Phe Gly Gly Met Gly
                85                  90                  95

Ser Ser Met Gly Gly Phe Gly Gly Met Gly Gly Gly Asn Ala Gly Phe
            100                 105                 110

Gly Gly Met Gly Gly Gln Ser Gly Met Gly Gly Gln Ser Gly Phe Gly
            115                 120                 125

Gly Lys Gly Tyr
    130

<210> SEQ ID NO 108
<211> LENGTH: 131
<212> TYPE: PRT
<213> ORGANISM: Argopecten irradians

<400> SEQUENCE: 108

Met Asn Ala Tyr Ile Cys Leu Ala Ala Cys Leu Ile Ala Ala Val Ser
1               5                   10                  15

Ala Ala Gly Tyr Gly Gly Gly Ala Gly Ser Met Gly Gly Thr Gly Gly
            20                  25                  30

Met Gly Gly Gly Met Asn Ala Gly Gly Phe Gly Gly Met Gly Gly Met

-continued

```
                35                  40                  45
Gly Gly Gly Lys Gly Gly Phe Gly Gly Ile Gly Phe Gly Gly
         50                  55                  60
Met Gly Gly Pro Gly Gly Phe Gly Met Gly Gly Phe Gly Gly
 65                  70                  75                  80
Met Ala Ala Lys Gly Gly Phe Gly Met Gly Ser Gly Met Gly Gly
                 85                  90                  95
Phe Gly Gly Met Gly Gly Asn Ala Gly Phe Gly Met Gly Gly
                100                 105                 110
Gly Asn Ala Gly Phe Gly Gly Met Gly Gly Gln Gly Gly Phe Gly Gly
                115                 120                 125
Lys Gly Tyr
        130

<210> SEQ ID NO 109
<211> LENGTH: 126
<212> TYPE: PRT
<213> ORGANISM: Argopecten irradians

<400> SEQUENCE: 109

Met Asn Ala Tyr Ile Cys Leu Ser Ala Cys Leu Ile Ala Ala Val Ser
  1               5                  10                  15
Ala Ala Gly Tyr Gly Gly Gly Ala Gly Ser Met Gly Gly Thr Gly Gly
                 20                  25                  30
Met Gly Gly Gly Met Asn Ala Gly Phe Gly Gly Met Gly Gly Gly
                 35                  40                  45
Met Gly Gly Gly Lys Gly Gly Phe Gly Gly Met Gly Gly Phe Gly Gly
         50                  55                  60
Met Gly Gly Gly Met Gly Gly Gly Pro Gly Gly Phe Gly Gly Met Gly
 65                  70                  75                  80
Gly Phe Gly Gly Met Gly Gly Gly Lys Gly Gly Phe Gly Gly Met Gly
                 85                  90                  95
Ser Gly Met Gly Gly Phe Gly Gly Met Gly Gly Gly Asn Ala Gly Phe
                100                 105                 110
Gly Gly Met Gly Gly Gln Gly Gly Phe Gly Gly Lys Gly Tyr
                115                 120                 125

<210> SEQ ID NO 110
<211> LENGTH: 290
<212> TYPE: PRT
<213> ORGANISM: Triticum aestivum

<400> SEQUENCE: 110

Met Val Arg Val Pro Val Pro Gln Leu Gln Pro Gln Asn Pro Ser Gln
  1               5                  10                  15
Gln Gln Pro Gln Glu Gln Val Pro Leu Val Gln Gln Gln Gln Phe Pro
                 20                  25                  30
Gly Gln Gln Gln Pro Phe Pro Pro Gln Gln Pro Tyr Pro Gln Pro Gln
                 35                  40                  45
Pro Phe Pro Ser Gln Gln Pro Tyr Leu Gln Leu Gln Pro Phe Pro Gln
         50                  55                  60
Pro Gln Leu Pro Tyr Pro Gln Pro Gln Leu Pro Tyr Pro Gln Pro Gln
 65                  70                  75                  80
Leu Pro Tyr Pro Gln Pro Gln Pro Phe Arg Pro Gln Gln Pro Tyr Pro
                 85                  90                  95
Gln Ser Gln Pro Gln Tyr Ser Gln Pro Gln Gln Pro Ile Ser Gln Gln
                100                 105                 110
```

```
Gln Gln Gln Gln Gln Gln Gln Gln Lys Gln Gln Gln Gln
            115                 120                 125

Gln Gln Gln Ile Leu Gln Gln Ile Leu Gln Gln Leu Ile Pro Cys
    130                 135                 140

Arg Asp Val Val Leu Gln His Ser Ile Ala Tyr Gly Ser Ser Gln
145                 150                 155                 160

Val Leu Gln Gln Ser Thr Tyr Gln Leu Val Gln Gln Leu Cys Cys Gln
                165                 170                 175

Gln Leu Trp Gln Ile Pro Glu Gln Ser Arg Cys Gln Ala Ile His Asn
            180                 185                 190

Val Val His Ala Ile Ile Leu His Gln Gln Gln Gln Gln Gln Gln
    195                 200                 205

Gln Gln Gln Gln Pro Leu Ser Gln Val Ser Phe Gln Gln Pro Gln Gln
    210                 215                 220

Gln Tyr Pro Ser Gly Gln Gly Ser Phe Gln Pro Ser Gln Gln Asn Pro
225                 230                 235                 240

Gln Ala Gln Gly Ser Val Gln Pro Gln Leu Pro Gln Phe Glu Glu
                245                 250                 255

Ile Arg Asn Leu Ala Leu Glu Thr Leu Pro Ala Met Cys Asn Val Tyr
            260                 265                 270

Ile Pro Pro Tyr Cys Thr Ile Ala Pro Val Gly Ile Phe Gly Thr Asn
    275                 280                 285

Tyr Arg
    290

<210> SEQ ID NO 111
<211> LENGTH: 288
<212> TYPE: PRT
<213> ORGANISM: Triticum aestivum

<400> SEQUENCE: 111

Met Lys Thr Phe Leu Ile Leu Ala Leu Leu Ala Ile Val Ala Thr Thr
1               5                   10                  15

Ala Thr Thr Ala Val Arg Val Pro Val Pro Gln Leu Gln Pro Gln Asn
                20                  25                  30

Pro Ser Gln Gln Gln Pro Gln Glu Gln Val Pro Leu Val Gln Gln Gln
            35                  40                  45

Gln Phe Leu Gly Gln Gln Gln Pro Phe Pro Gln Gln Pro Tyr Pro
    50                  55                  60

Gln Pro Gln Pro Phe Pro Ser Gln Gln Pro Tyr Leu Gln Leu Gln Pro
65                  70                  75                  80

Phe Pro Gln Pro Gln Leu Pro Tyr Ser Gln Pro Gln Pro Phe Arg Pro
                85                  90                  95

Gln Gln Pro Tyr Pro Gln Pro Gln Pro Gln Tyr Ser Gln Pro Gln Gln
            100                 105                 110

Pro Ile Ser Gln Gln Gln Gln Gln Gln Gln Gln Gln Gln Gln Gln
    115                 120                 125

Gln Gln Gln Gln Gln Gln Ile Leu Gln Gln Ile Leu Gln Gln Gln
    130                 135                 140

Leu Ile Pro Cys Met Asp Val Val Leu Gln Gln His Asn Ile Ala His
145                 150                 155                 160

Gly Arg Ser Gln Val Leu Gln Gln Ser Thr Tyr Gln Leu Leu Gln Glu
                165                 170                 175

Leu Cys Cys Gln His Leu Trp Gln Ile Pro Glu Gln Ser Gln Cys Gln
            180                 185                 190
```

Ala Ile His Lys Val His Ala Ile Ile Leu His Gln Gln Lys
195                 200                 205

Gln Gln Gln Pro Ser Ser Gln Val Ser Phe Gln Pro Leu Gln
210                 215                 220

Gln Tyr Pro Leu Gly Gln Gly Ser Phe Arg Pro Ser Gln Asn Pro
225                 230                 235                 240

Gln Ala Gln Gly Ser Val Gln Pro Gln Leu Pro Gln Phe Glu Glu
                245                 250                 255

Ile Arg Asn Leu Ala Leu Gln Thr Leu Pro Ala Met Cys Asn Val Tyr
            260                 265                 270

Ile Pro Pro Tyr Cys Thr Ile Thr Pro Phe Gly Ile Phe Gly Thr Asn
            275                 280                 285

<210> SEQ ID NO 112
<211> LENGTH: 278
<212> TYPE: PRT
<213> ORGANISM: Triticum aestivum

<400> SEQUENCE: 112

Met Val Arg Val Pro Val Pro Gln Leu Gln Pro Gln Asn Pro Ser Gln
1               5                   10                  15

Gln Gln Pro Gln Glu Gln Val Pro Leu Val Gln Gln Gln Gln Phe Leu
            20                  25                  30

Gly Gln Gln Gln Pro Phe Pro Pro Gln Gln Pro Tyr Pro Gln Pro Gln
        35                  40                  45

Pro Phe Pro Ser Gln Gln Pro Tyr Leu Gln Leu Gln Pro Phe Pro Gln
    50                  55                  60

Pro Gln Leu Ser Tyr Ser Gln Pro Gln Pro Phe Arg Pro Gln Gln Leu
65                  70                  75                  80

Tyr Pro Gln Pro Gln Pro Gln Tyr Ser Gln Pro Gln Gln Pro Ile Ser
                85                  90                  95

Gln Gln Gln Gln Gln Gln Gln Gln Gln Gln Gln Gln Gln Gln Gln
            100                 105                 110

Gln Gln Gln Gln Gln Gln Gln Glu Gln Gln Ile Leu Gln Gln Met
            115                 120                 125

Leu Gln Gln Gln Leu Ile Pro Cys Met Asp Val Val Leu Gln Gln His
130                 135                 140

Asn Ile Ala His Gly Arg Ser Gln Val Leu Gln Gln Ser Thr Tyr Gln
145                 150                 155                 160

Leu Leu Gln Glu Leu Cys Cys Gln His Leu Trp Gln Ile Leu Glu Gln
                165                 170                 175

Ser Gln Cys Gln Ala Ile His Asn Val Val His Ala Ile Ile Leu His
            180                 185                 190

Gln Gln Gln Lys Gln Gln Gln Pro Ser Ser Gln Val Ser Phe Gln
            195                 200                 205

Gln Pro Leu Gln Gln Tyr Pro Leu Gly Gln Gly Ser Phe Arg Pro Ser
210                 215                 220

Gln Gln Asn Pro Gln Ala Gln Gly Ser Val Gln Pro Gln Leu Pro
225                 230                 235                 240

Gln Phe Glu Glu Ile Arg Asn Leu Ala Leu Gln Thr Leu Pro Ala Met
                245                 250                 255

Cys Asn Val Tyr Ile Pro Pro Tyr Cys Thr Ile Ala Pro Phe Gly Ile
            260                 265                 270

Phe Gly Thr Asn Tyr Arg
            275

<210> SEQ ID NO 113
<211> LENGTH: 277
<212> TYPE: PRT
<213> ORGANISM: Triticum aestivum

<400> SEQUENCE: 113

Met Val Arg Val Pro Val Pro Gln Leu Gln Pro Gln Asn Pro Ser Gln
1               5                   10                  15

Gln His Pro Gln Glu Gln Val Pro Leu Val Gln Gln Gln Gln Phe Leu
            20                  25                  30

Gly Gln Gln Gln Ser Phe Pro Pro Gln Gln Pro Tyr Pro Gln Pro Gln
        35                  40                  45

Pro Phe Pro Ser Gln Gln Pro Tyr Leu Gln Leu Gln Pro Phe Pro Gln
    50                  55                  60

Pro Gln Leu Pro Tyr Leu Gln Pro Gln Pro Phe Arg Pro Gln Gln Pro
65                  70                  75                  80

Tyr Pro Gln Pro Gln Pro Gln Tyr Ser Gln Pro Gln Pro Ile Ser
                85                  90                  95

Gln Gln Gln Gln Gln Gln Gln Gln Gln Gln Gln Gln Gln Gln Gln
            100                 105                 110

Gln Gln Gln Gln Gln Gln Gln Gln Ile Leu Gln Gln Ile Leu
            115                 120                 125

Gln Gln Gln Leu Ile Pro Cys Met Asp Val Val Leu Gln Gln His Asn
130                 135                 140

Ile Ala His Gly Arg Ser Gln Val Leu Gln Gln Ser Thr Tyr Gln Leu
145                 150                 155                 160

Leu Gln Glu Leu Cys Cys Gln His Leu Trp Gln Ile Pro Glu Gln Ser
                165                 170                 175

Gln Cys Gln Ala Ile His Asn Val Val His Ala Ile Leu His Gln
            180                 185                 190

Gln Lys Gln Gln Gln Pro Ser Ser Gln Val Ser Phe Gln Gln
            195                 200                 205

Pro Leu Gln Gln Tyr Pro Leu Gly Gln Gly Ser Phe Arg Pro Ser Gln
    210                 215                 220

Gln Asn Pro Leu Ala Gln Gly Ser Val Gln Pro Gln Leu Pro Gln
225                 230                 235                 240

Phe Glu Glu Ile Arg Asn Leu Ala Leu Gln Thr Leu Pro Ala Met Cys
                245                 250                 255

Asn Val Tyr Ile Pro Pro Tyr Cys Thr Ile Val Pro Phe Gly Ile Phe
            260                 265                 270

Gly Thr Asn Tyr Arg
        275

<210> SEQ ID NO 114
<211> LENGTH: 276
<212> TYPE: PRT
<213> ORGANISM: Triticum aestivum

<400> SEQUENCE: 114

Met Val Arg Val Pro Val Pro Gln Leu Gln Pro Gln Asn Pro Ser Gln
1               5                   10                  15

Gln Gln Pro Gln Glu Gln Val Pro Leu Val Gln Gln Gln Gln Phe Leu
            20                  25                  30

Gly Gln Gln Gln Pro Phe Pro Gln Gln Pro Tyr Pro Gln Pro Gln
        35                  40                  45

```
Pro Phe Pro Ser Gln Gln Pro Tyr Leu Gln Leu Gln Pro Phe Pro Gln
 50                  55                  60

Pro Gln Leu Ser Tyr Ser Gln Pro Gln Phe Arg Pro Gln Gln Pro
 65                  70                  75                  80

Tyr Pro Gln Pro Gln Pro Gln Tyr Ser Gln Pro Gln Gln Pro Ile Ser
                 85                  90                  95

Gln Gln Gln Gln Gln Gln Gln Gln Gln Gln Gln Gln Gln Gln Gln
            100                 105                 110

Gln Gln Gln Gln Gln Glu Gln Gln Ile Leu Gln Gln Ile Leu Gln
            115                 120                 125

Gln Gln Leu Ile Pro Cys Met Asp Val Val Leu Gln Gln His Asn Ile
            130                 135                 140

Ala His Gly Arg Ser Gln Val Leu Gln Gln Ser Thr Tyr Gln Leu Leu
145                 150                 155                 160

Gln Glu Leu Cys Cys Gln His Leu Trp Gln Ile Pro Glu Gln Ser Gln
                165                 170                 175

Cys Gln Ala Ile His Asn Val Val His Ala Ile Ile Leu His Gln Gln
                180                 185                 190

Gln Lys Gln Gln Gln Pro Ser Ser Gln Val Ser Phe Gln Gln Pro
            195                 200                 205

Leu Gln Gln Tyr Pro Leu Gly Gln Gly Ser Phe Arg Pro Ser Gln Gln
210                 215                 220

Asn Pro Gln Ala Gln Gly Ser Val Gln Pro Gln Gln Leu Pro Gln Phe
225                 230                 235                 240

Glu Glu Ile Arg Asn Leu Ala Leu Gln Thr Leu Pro Ala Met Cys Asn
                245                 250                 255

Val Tyr Ile Pro Pro Tyr Cys Thr Met Ala Pro Phe Gly Ile Phe Gly
                260                 265                 270

Thr Asn Tyr Arg
        275

<210> SEQ ID NO 115
<211> LENGTH: 274
<212> TYPE: PRT
<213> ORGANISM: Triticum aestivum

<400> SEQUENCE: 115

Met Val Arg Val Thr Val Pro Gln Leu Gln Pro Gln Asn Pro Ser Gln
1               5                   10                  15

Gln Gln Pro Gln Glu Gln Val Pro Leu Val Gln Gln Gln Gln Phe Leu
            20                  25                  30

Gly Gln Gln Gln Pro Phe Pro Pro Gln Gln Pro Tyr Pro Gln Pro Gln
            35                  40                  45

Pro Phe Pro Ser Gln Gln Pro Tyr Leu Gln Leu Gln Pro Phe Pro Gln
 50                  55                  60

Pro Gln Leu Pro Tyr Ser Gln Pro Gln Pro Phe Arg Pro Gln Gln Pro
 65                  70                  75                  80

Tyr Pro Gln Pro Gln Pro Gln Tyr Ser Gln Pro Gln Gln Pro Ile Ser
                 85                  90                  95

Gln Gln Gln Gln Gln Gln Gln Gln Gln Gln Gln Gln Gln Gln Gln
            100                 105                 110

Gln Gln Gln Gln Gln Gln Ile Leu Gln Ile Leu Gln Gln Gln
            115                 120                 125

Leu Ile Pro Cys Met Asp Val Val Leu Gln Gln His Asn Ile Val His
            130                 135                 140
```

```
Gly Arg Ser Gln Val Leu Gln Gln Ser Thr Tyr Gln Leu Leu Gln Glu
145                 150                 155                 160

Leu Cys Cys Gln His Leu Trp Gln Ile Pro Glu Gln Ser Gln Cys Gln
                165                 170                 175

Ala Ile His Asn Val Val His Ala Ile Ile Leu His Gln Gln Gln Lys
            180                 185                 190

Gln Gln Gln Gln Pro Ser Ser Gln Val Ser Phe Gln Gln Pro Leu Gln
        195                 200                 205

Gln Tyr Pro Leu Gly Gln Gly Ser Phe Arg Pro Ser Gln Gln Asn Pro
210                 215                 220

Gln Ala Gln Gly Ser Val Gln Pro Gln Gln Leu Pro Gln Phe Glu Glu
225                 230                 235                 240

Ile Arg Asn Leu Ala Leu Gln Thr Leu Pro Ala Met Cys Asn Val Tyr
                245                 250                 255

Ile Pro Pro Tyr Cys Thr Ile Ala Pro Phe Gly Ile Phe Gly Thr Asn
                260                 265                 270

Tyr Arg

<210> SEQ ID NO 116
<211> LENGTH: 273
<212> TYPE: PRT
<213> ORGANISM: Triticum aestivum

<400> SEQUENCE: 116

Met Val Arg Val Pro Val Pro Gln Leu Gln Leu Gln Asn Pro Ser Gln
1               5                   10                  15

Gln Gln Pro Gln Glu Gln Val Pro Leu Val Gln Gln Gln Gln Phe Pro
            20                  25                  30

Gly Gln Gln Gln Pro Phe Pro Pro Gln Gln Pro Tyr Pro Gln Pro Gln
        35                  40                  45

Pro Phe Pro Ser Gln Gln Pro Tyr Leu Gln Leu Gln Pro Phe Pro Arg
    50                  55                  60

Pro Gln Leu Pro Tyr Pro Gln Pro Gln Pro Phe Arg Pro Gln Gln Pro
65                  70                  75                  80

Tyr Pro Gln Pro Gln Pro Gln Tyr Ser Gln Pro Gln Gln Pro Ile Ser
                85                  90                  95

Gln Gln Gln Gln Gln Gln Gln Gln Gln Gln Gln Gln Gln Gln Ile Leu
            100                 105                 110

Gln Gln Ile Leu Gln Gln Gln Leu Ile Pro Cys Arg Asp Val Val Leu
        115                 120                 125

Gln Gln His Asn Ile Ala His Gly Ser Ser Gln Val Leu Gln Glu Ser
130                 135                 140

Thr Tyr Gln Leu Val Gln Gln Leu Cys Cys Gln Gln Leu Trp Gln Ile
145                 150                 155                 160

Pro Glu Gln Ser Arg Cys Gln Ala Ile His Asn Val Val His Ala Ile
                165                 170                 175

Ile Leu His Gln Gln Gln His His His Gln Gln Gln Gln Gln Gln Gln
            180                 185                 190

Gln Gln Gln Pro Leu Ser Gln Val Ser Phe Gln Gln Pro Gln Gln Gln
        195                 200                 205

Tyr Pro Ser Gly Gln Gly Phe Phe Gln Pro Gln Gln Asn Pro Gln
210                 215                 220

Ala Gln Gly Ser Phe Gln Pro Gln Gln Leu Pro Gln Phe Glu Ala Ile
225                 230                 235                 240

Arg Asn Leu Ala Leu Gln Thr Leu Pro Ala Met Cys Asn Val Tyr Ile
```

-continued

```
                        245                 250                 255
Pro Pro Tyr Cys Thr Ile Ala Pro Phe Gly Ile Phe Gly Thr Asn Tyr
            260                 265                 270
Arg

<210> SEQ ID NO 117
<211> LENGTH: 270
<212> TYPE: PRT
<213> ORGANISM: Triticum aestivum

<400> SEQUENCE: 117

Met Val Arg Val Pro Met Pro Gln Leu Gln Pro Gln Asp Pro Ser Gln
1               5                   10                  15
Gln Gln Pro Gln Glu Gln Val Pro Leu Val Gln Gln Gln Gln Phe Leu
            20                  25                  30
Gly Gln Gln Gln Pro Phe Pro Gln Gln Pro Tyr Pro Gln Pro Gln
        35                  40                  45
Pro Phe Pro Ser Gln Gln Pro Tyr Leu Gln Leu Gln Pro Phe Pro Gln
    50                  55                  60
Pro Gln Leu Pro Tyr Ser Gln Pro Gln Pro Phe Arg Pro Gln Gln Pro
65                  70                  75                  80
Tyr Pro Gln Pro Gln Pro Gln Tyr Ser Gln Pro Gln Gln Pro Ile Ser
                85                  90                  95
Gln Gln Gln Gln Gln Gln Gln Gln Gln Gln Gln Gln Gln Gln Gln Gln
            100                 105                 110
Glu Gln Gln Ile Leu Gln Gln Ile Leu Gln Gln Gln Leu Ile Pro Cys
        115                 120                 125
Met Asp Val Val Leu Gln His Asn Leu Ala His Gly Arg Ser Gln
    130                 135                 140
Val Leu Gln Gln Ser Thr Tyr Gln Leu Leu Gln Glu Leu Cys Cys Gln
145                 150                 155                 160
His Leu Trp Gln Ile Pro Glu Gln Ser Gln Cys Gln Ala Ile His Asn
                165                 170                 175
Val Val His Ala Ile Ile Leu His Gln Gln Gln Lys Gln Gln Gln Gln
            180                 185                 190
Leu Ser Ser Gln Val Ser Phe Gln Gln Pro Gln Gln Gln Tyr Pro Leu
        195                 200                 205
Gly Gln Gly Ser Phe Arg Pro Ser Gln Gln Asn Ser Gln Ala Gln Gly
    210                 215                 220
Ser Val Gln Pro Gln Gln Leu Pro Gln Phe Glu Ile Arg Asn Leu
225                 230                 235                 240
Ala Leu Gln Thr Leu Pro Ala Met Cys Asn Val Tyr Ile Pro Pro Tyr
                245                 250                 255
Cys Thr Ile Ala Pro Phe Gly Ile Phe Gly Thr Asn Tyr Arg
            260                 265                 270

<210> SEQ ID NO 118
<211> LENGTH: 269
<212> TYPE: PRT
<213> ORGANISM: Triticum aestivum

<400> SEQUENCE: 118

Met Val Arg Val Pro Val Pro Gln Leu Gln Pro Gln Asn Pro Ser Gln
1               5                   10                  15
Gln Gln Pro Gln Glu Gln Val Pro Leu Val Gln Gln Gln Gln Phe Leu
            20                  25                  30
```

-continued

```
Gly Gln Gln Gln Pro Phe Pro Pro Gln Gln Pro Tyr Pro Gln Pro Gln
         35                  40                  45

Pro Phe Pro Ser Gln Leu Pro Tyr Leu Gln Leu Gln Pro Phe Pro Gln
 50                  55                  60

Pro Gln Leu Pro Tyr Ser Gln Pro Gln Pro Phe Arg Pro Gln Gln Pro
 65                  70                  75                  80

Tyr Pro Gln Pro Gln Pro Gln Tyr Ser Gln Pro Gln Gln Pro Ile Ser
                 85                  90                  95

Gln Gln Gln Gln Gln Gln Gln Gln Gln Gln Gln Gln Gln Gln Gln Gln
                100                 105                 110

Gln Gln Ile Leu Gln Gln Ile Leu Gln Gln Gln Leu Ile Pro Cys Met
            115                 120                 125

Asp Val Val Leu Gln Gln His Asn Ile Ala His Gly Arg Ser Gln Val
130                 135                 140

Leu Gln Gln Ser Thr Tyr Gln Leu Leu Gln Glu Leu Cys Cys Gln His
145                 150                 155                 160

Leu Trp Gln Ile Pro Glu Gln Ser Gln Cys Gln Ala Ile His Asn Val
                165                 170                 175

Val His Ala Ile Ile Leu His Gln Gln Lys Gln Gln Gln Gln Gln Pro
            180                 185                 190

Ser Ser Gln Val Ser Phe Gln Gln Pro Leu Gln Gln Tyr Pro Leu Gly
        195                 200                 205

Gln Gly Ser Phe Arg Pro Ser Gln Gln Asn Pro Gln Ala Gln Gly Ser
    210                 215                 220

Val Gln Pro Gln Gln Leu Pro Gln Phe Glu Glu Ile Arg Asn Leu Ala
225                 230                 235                 240

Leu Gln Thr Leu Pro Ala Met Cys Asn Val Tyr Ile Pro Pro Tyr Cys
                245                 250                 255

Thr Ile Ala Pro Phe Gly Ile Phe Gly Thr Asn Tyr Arg
            260                 265

<210> SEQ ID NO 119
<211> LENGTH: 265
<212> TYPE: PRT
<213> ORGANISM: Triticum aestivum

<400> SEQUENCE: 119

Met Val Arg Val Pro Val Pro Gln Leu Gln Pro Gln Asn Pro Ser Gln
1               5                   10                  15

Gln Gln Pro Gln Glu Gln Val Pro Leu Met Gln Gln Gln Gln Gln Phe
            20                  25                  30

Pro Gly Gln Gln Glu Gln Phe Pro Pro Gln Gln Pro Tyr Pro His Gln
         35                  40                  45

Gln Pro Phe Pro Ser Gln Gln Pro Tyr Pro Gln Pro Gln Pro Phe Pro
 50                  55                  60

Pro Gln Leu Pro Tyr Pro Gln Thr Gln Pro Phe Pro Pro Gln Gln Pro
 65                  70                  75                  80

Tyr Pro Gln Pro Gln Pro Gln Tyr Pro Gln Pro Gln Gln Pro Ile Ser
                 85                  90                  95

Gln Gln Gln Ala Gln Gln Gln Gln Gln Gln Gln Ile Leu Gln Gln Gln
                100                 105                 110

Ile Leu Gln Gln Gln Leu Ile Pro Cys Arg Asp Val Val Leu Gln Gln
            115                 120                 125

His Asn Ile Ala His Ala Ser Ser Gln Val Leu Gln Gln Ser Ser Tyr
130                 135                 140
```

```
Gln Gln Leu Gln Gln Leu Cys Cys Gln Gln Leu Phe Gln Ile Pro Glu
145                 150                 155                 160

Gln Ser Arg Cys Gln Ala Ile His Asn Val Val His Ala Ile Ile Leu
            165                 170                 175

His His His Gln Gln Gln Gln Gln Pro Ser Ser Gln Val Ser Tyr
        180                 185                 190

Gln Gln Pro Gln Glu Gln Tyr Pro Ser Gly Gln Gly Ser Phe Gln Ser
            195                 200                 205

Ser Gln Gln Asn Pro Gln Ala Gln Gly Ser Val Gln Pro Gln Gln Leu
        210                 215                 220

Pro Gln Phe Gln Glu Ile Arg Asn Leu Ala Leu Gln Thr Leu Pro Ala
225                 230                 235                 240

Met Cys Asn Val Tyr Ile Pro Pro Tyr Cys Ser Thr Thr Ile Ala Pro
            245                 250                 255

Phe Gly Ile Phe Gly Thr Asn Tyr Arg
        260                 265

<210> SEQ ID NO 120
<211> LENGTH: 337
<212> TYPE: PRT
<213> ORGANISM: Triticum aestivum

<400> SEQUENCE: 120

Met Lys Thr Leu Leu Ile Leu Thr Ile Ile Ala Val Ala Leu Thr Thr
1               5                   10                  15

Thr Thr Ala Asn Ile Gln Val Asp Pro Ser Gly Gln Val Gln Trp Pro
            20                  25                  30

Gln Gln Gln Gln Pro Phe Pro Gln Pro Gln Gln Pro Phe Ser Gln Gln
        35                  40                  45

Pro Gln Gln Ile Phe Pro Gln Pro Gln Gln Thr Phe Pro His Gln Pro
    50                  55                  60

Gln Gln Ala Phe Pro Gln Pro Gln Gln Thr Phe Pro His Gln Pro Gln
65                  70                  75                  80

Gln Gln Phe Pro Gln Pro Gln Gln Pro Gln Gln Pro Phe Pro Gln Gln
            85                  90                  95

Pro Gln Gln Gln Phe Pro Gln Pro Gln Gln Pro Gln Gln Pro Phe Pro
            100                 105                 110

Gln Gln Pro Gln Gln Phe Pro Gln Pro Gln Gln Pro Gln Gln Gln Pro
        115                 120                 125

Phe Pro Gln Pro Gln Gln Pro Gln Leu Pro Phe Pro Gln Gln Pro Gln
    130                 135                 140

Gln Pro Phe Pro Gln Pro Gln Gln Pro Gln Gln Pro Phe Pro Gln Leu
145                 150                 155                 160

Gln Gln Pro Gln Gln Pro Leu Pro Gln Pro Gln Gln Pro Gln Gln Pro
            165                 170                 175

Phe Pro Gln Gln Gln Pro Leu Ile Gln Pro Tyr Leu Gln Gln Gln
        180                 185                 190

Met Asn Pro Cys Lys Asn Tyr Leu Leu Gln Gln Cys Asn Pro Val Ser
            195                 200                 205

Leu Val Ser Ser Leu Val Ser Met Ile Leu Pro Arg Ser Asp Cys Lys
        210                 215                 220

Val Met Arg Gln Gln Cys Cys Gln Gln Leu Ala Arg Ile Pro Gln Gln
225                 230                 235                 240

Leu Gln Cys Ala Ala Ile His Gly Ile Val His Ser Ile Ile Met Gln
            245                 250                 255
```

```
Gln Glu Gln Gln Gln Gln Gln Gln Gln Gln Gln Gln Gly
            260                 265                 270

Ile Gln Ile Met Arg Pro Leu Phe Gln Leu Val Gln Gln Gly Ile
            275                 280                 285

Ile Gln Pro Gln Pro Ala Gln Leu Glu Val Ile Arg Ser Leu Val
290                 295                 300

Leu Gly Thr Leu Pro Thr Met Cys Asn Val Phe Val Pro Pro Glu Cys
305                 310                 315                 320

Ser Thr Thr Lys Ala Pro Phe Ala Ser Ile Val Ala Asp Ile Gly Gly
                325                 330                 335

Gln

<210> SEQ ID NO 121
<211> LENGTH: 327
<212> TYPE: PRT
<213> ORGANISM: Triticum aestivum

<400> SEQUENCE: 121

Met Lys Thr Leu Leu Ile Leu Thr Ile Leu Ala Met Ala Ile Thr Ile
1               5                   10                  15

Gly Thr Ala Asn Ile Gln Val Asp Pro Ser Gly Gln Val Gln Trp Leu
                20                  25                  30

Gln Gln Gln Leu Val Pro Gln Leu Gln Gln Pro Leu Ser Gln Gln Pro
            35                  40                  45

Gln Gln Thr Phe Pro Gln Pro Gln Gln Thr Phe Pro His Gln Pro Gln
        50                  55                  60

Gln Gln Val Pro Gln Pro Gln Gln Pro Gln Gln Pro Phe Leu Gln Pro
65                  70                  75                  80

Gln Gln Pro Phe Pro Gln Gln Pro Gln Gln Pro Phe Pro Gln Thr Gln
                85                  90                  95

Gln Pro Gln Gln Pro Phe Pro Gln Gln Pro Gln Gln Pro Phe Pro Gln
            100                 105                 110

Thr Gln Gln Pro Gln Gln Pro Phe Pro Gln Gln Pro Gln Gln Pro Phe
        115                 120                 125

Pro Gln Thr Gln Gln Pro Gln Gln Pro Phe Pro Leu Gln Gln Pro
130                 135                 140

Gln Gln Pro Phe Pro Gln Pro Gln Gln Leu Pro Gln Pro Gln Gln
145                 150                 155                 160

Pro Gln Gln Ser Phe Pro Gln Gln Arg Pro Phe Ile Gln Pro Ser
                165                 170                 175

Leu Gln Gln Gln Leu Asn Pro Cys Lys Asn Ile Leu Leu Gln Gln Ser
            180                 185                 190

Lys Pro Ala Ser Leu Val Ser Ser Leu Trp Ser Ile Ile Trp Pro Gln
        195                 200                 205

Ser Asp Cys Gln Val Met Arg Gln Gln Cys Cys Gln Gln Leu Ala Gln
210                 215                 220

Ile Pro Gln Gln Leu Gln Cys Ala Ala Ile His Ser Val Val His Ser
225                 230                 235                 240

Ile Ile Met Gln Gln Gln Gln Gln Gln Gln Gln Gln Gly Ile Asp
                245                 250                 255

Ile Phe Leu Pro Leu Ser Gln His Glu Gln Val Gly Gln Gly Ser Leu
            260                 265                 270

Val Gln Gly Gln Gly Ile Ile Gln Pro Gln Gln Pro Ala Gln Leu Glu
        275                 280                 285

Ala Ile Arg Ser Leu Val Leu Gln Thr Leu Pro Ser Met Cys Asn Val
```

```
                  290                 295                 300
Tyr Val Pro Pro Glu Cys Ser Ile Met Arg Ala Pro Phe Ala Ser Ile
305                 310                 315                 320

Val Ala Gly Ile Gly Gly Gln
                325

<210> SEQ ID NO 122
<211> LENGTH: 314
<212> TYPE: PRT
<213> ORGANISM: Triticum aestivum

<400> SEQUENCE: 122

Met Lys Thr Leu Leu Ile Leu Thr Ile Leu Ala Met Ala Thr Thr Ile
1               5                   10                  15

Ala Thr Ala Asn Met Gln Val Asp Pro Ser Gly Gln Val Gln Trp Pro
                20                  25                  30

Gln Gln Gln Pro Phe Pro Gln Pro Gln Gln Pro Phe Cys Glu Gln Pro
            35                  40                  45

Gln Arg Thr Ile Pro Gln Pro His Gln Thr Phe His His Gln Pro Gln
        50                  55                  60

Gln Thr Phe Pro Gln Pro Glu Gln Thr Tyr Pro His Gln Pro Gln Gln
65                  70                  75                  80

Gln Phe Pro Gln Thr Gln Gln Pro Gln Gln Pro Phe Pro Gln Pro Gln
                85                  90                  95

Gln Thr Phe Pro Gln Gln Pro Gln Leu Pro Phe Pro Gln Gln Pro Gln
            100                 105                 110

Gln Pro Phe Pro Gln Pro Gln Gln Pro Gln Pro Phe Pro Gln Pro Ser
        115                 120                 125

Gln Gln Pro Gln Gln Pro Phe Pro Gln Pro Gln Gln Gln Phe Pro Gln
    130                 135                 140

Pro Gln Gln Pro Gln Gln Ser Phe Pro Gln Gln Gln Pro Leu Ile
145                 150                 155                 160

Gln Pro Tyr Leu Gln Gln Gln Met Asn Pro Cys Lys Asn Tyr Leu Leu
                165                 170                 175

Gln Gln Cys Asn Pro Val Ser Leu Val Ser Ser Leu Val Ser Met Ile
            180                 185                 190

Leu Pro Arg Ser Asp Cys Lys Val Met Arg Gln Cys Cys Gln Gln
        195                 200                 205

Leu Ala Gln Ile Pro Gln Gln Leu Gln Cys Ala Ala Ile His Gly Ile
    210                 215                 220

Val His Ser Ile Ile Met Gln Glu Gln Gln Gln Gln Gln Gln Gln Gln
225                 230                 235                 240

Gln Gln Gln Gln Gln Gln Gln Gly Ile Gln Ile Met Arg Pro Leu
                245                 250                 255

Phe Gln Leu Val Gln Gly Gln Gly Ile Ile Gln Pro Gln Gln Pro Ala
            260                 265                 270

Gln Leu Glu Val Ile Arg Ser Leu Val Leu Gly Thr Leu Pro Thr Met
        275                 280                 285

Cys Asn Val Phe Val Pro Pro Glu Cys Ser Thr Thr Lys Ala Pro Phe
    290                 295                 300

Ala Ser Ile Val Ala Asp Ile Gly Gly Gln
305                 310

<210> SEQ ID NO 123
<211> LENGTH: 308
<212> TYPE: PRT
```

<213> ORGANISM: Triticum aestivum

<400> SEQUENCE: 123

Met Lys Thr Leu Leu Ile Gln Thr Ile Leu Val Met Ala Ile Thr Ile
1               5                   10                  15

Ala Thr Ala Asn Met Gln Val Asp Pro Ser Gly Gln Val Pro Arg Pro
            20                  25                  30

Gln Gln Gln Pro Phe Pro Gln Pro His Gln Pro Phe Ser Gln Gln Pro
        35                  40                  45

Gln Gln Thr Phe Pro Gln Pro Gln Gln Thr Phe Pro His Gln Pro Gln
    50                  55                  60

Gln Gln Phe Ser Gln Pro Gln Pro Gln Gln Gln Phe Ile Gln Pro
65                  70                  75                  80

Gln Gln Pro Phe Pro Gln Pro Gln Gln Thr Tyr Pro Gln Arg Pro
                85                  90                  95

Gln Gln Pro Phe Pro Gln Thr Gln Gln Pro Gln Gln Pro Phe Pro Gln
            100                 105                 110

Ser Gln Gln Pro Gln Gln Pro Phe Pro Gln Ser Gln Gln Pro Gln Gln
        115                 120                 125

Pro Phe Pro Gln Pro Gln Gln Phe Pro Gln Pro Gln Gln
    130                 135                 140

Gln Ser Phe Pro Gln Gln Pro Ser Leu Ile Gln Ser Leu Gln
145                 150                 155                 160

Gln Gln Leu Asn Pro Cys Lys Asn Phe Leu Leu Gln Gln Cys Lys Pro
                165                 170                 175

Val Ser Leu Val Ser Ser Leu Trp Ser Met Ile Leu Pro Arg Ser Asp
            180                 185                 190

Cys Gln Val Met Arg Gln Cys Cys Gln Gln Leu Ala Gln Ile Pro
        195                 200                 205

Gln Gln Leu Gln Cys Ala Ala Ile His Ser Ile Val His Ser Ile Ile
    210                 215                 220

Met Gln Gln Glu Gln Gln Glu Gln Arg Gln Gly Val Gln Ile Leu Val
225                 230                 235                 240

Pro Leu Ser Gln Gln Gln Val Gly Gln Gly Thr Leu Val Gln Gly
                245                 250                 255

Gln Gly Ile Ile Gln Pro Gln Pro Ala Gln Leu Glu Val Ile Arg
            260                 265                 270

Ser Leu Val Leu Gln Thr Leu Ala Thr Met Cys Asn Val Tyr Val Pro
        275                 280                 285

Pro Tyr Cys Ser Thr Ile Arg Ala Pro Phe Ala Ser Ile Val Ala Gly
    290                 295                 300

Ile Gly Gly Gln
305

<210> SEQ ID NO 124
<211> LENGTH: 302
<212> TYPE: PRT
<213> ORGANISM: Triticum aestivum

<400> SEQUENCE: 124

Met Lys Thr Leu Leu Ile Leu Thr Ile Leu Ala Met Ala Thr Thr Ile
1               5                   10                  15

Ala Thr Ala Asn Met Gln Val Asp Pro Ser Gly Gln Val Gln Trp Pro
            20                  25                  30

Gln Gln Gln Pro Phe Pro Gln Pro Gln Gln Pro Phe Cys Glu Gln Pro
        35                  40                  45

```
Gln Arg Thr Ile Pro Gln Pro His Gln Thr Phe His His Gln Pro Gln
     50                  55                  60

Gln Thr Phe Pro Gln Pro Glu Gln Thr Tyr Pro His Gln Pro Gln Gln
 65                  70                  75                  80

Gln Phe Pro Gln Thr Gln Gln Pro Gln Gln Pro Phe Pro Gln Pro Gln
             85                  90                  95

Gln Thr Phe Pro Gln Gln Pro Gln Leu Pro Phe Pro Gln Gln Pro Gln
            100                 105                 110

Gln Pro Phe Pro Gln Pro Gln Gln Pro Gln Gln Pro Phe Pro Gln Ser
            115                 120                 125

Gln Gln Pro Gln Gln Pro Phe Pro Gln Pro Gln Gln Phe Pro Gln
            130                 135                 140

Pro Gln Gln Pro Gln Gln Ser Phe Pro Gln Gln Gln Pro Ala Ile
145                 150                 155                 160

Gln Ser Phe Leu Gln Gln Gln Met Asn Pro Cys Lys Asn Phe Leu Leu
            165                 170                 175

Gln Gln Cys Asn His Val Ser Leu Val Ser Ser Leu Val Ser Ile Ile
            180                 185                 190

Leu Pro Arg Ser Asp Cys Gln Val Met Gln Gln Cys Cys Gln Gln
            195                 200                 205

Leu Ala Gln Ile Pro Gln Gln Leu Gln Cys Ala Ala Ile His Ser Val
210                 215                 220

Ala His Ser Ile Ile Met Gln Glu Gln Gln Gln Gly Val Pro Ile
225                 230                 235                 240

Leu Arg Pro Leu Phe Gln Leu Ala Gln Gly Leu Gly Ile Ile Gln Pro
            245                 250                 255

Gln Gln Pro Ala Gln Leu Glu Gly Ile Arg Ser Leu Val Leu Lys Thr
            260                 265                 270

Leu Pro Thr Met Cys Asn Val Tyr Val Pro Pro Asp Cys Ser Thr Ile
            275                 280                 285

Asn Val Pro Tyr Ala Asn Ile Asp Ala Gly Ile Gly Gly Gln
            290                 295                 300

<210> SEQ ID NO 125
<211> LENGTH: 298
<212> TYPE: PRT
<213> ORGANISM: Triticum aestivum

<400> SEQUENCE: 125

Met Lys Thr Leu Leu Ile Leu Thr Ile Leu Ala Met Ala Val Thr Ile
 1                5                  10                  15

Gly Thr Ala Asn Met Gln Val Gly Pro Ser Gly Gln Val Gln Trp Pro
             20                  25                  30

Gln Gln Gln Pro Val Leu Leu Pro Gln Gln Pro Phe Ser Gln Gln Pro
             35                  40                  45

Gln Gln Thr Phe Pro Gln Pro Gln Gln Thr Phe Pro His Gln Pro Gln
     50                  55                  60

Gln Gln Phe Ser Gln Pro Gln Gln Gln Gln Phe Ile Gln Pro
 65                  70                  75                  80

Gln Gln Pro Phe Pro Gln Gln Pro Gln Gln Thr Tyr Pro Gln Arg Pro
             85                  90                  95

Gln Gln Pro Phe Pro Gln Thr Gln Gln Pro Gln Gln Pro Phe Pro Gln
            100                 105                 110

Ser Gln Gln Pro Gln Gln Pro Phe Pro Gln Pro Gln Gln Gln Phe Pro
            115                 120                 125
```

```
Gln Pro Gln Gln Pro Gln Gln Ser Phe Pro Gln Gln Pro Ser Leu
    130                 135                 140
Ile Gln Gln Ser Leu Gln Gln Leu Asn Pro Cys Lys Asn Phe Leu
145                 150                 155                 160
Leu Gln Gln Cys Lys Pro Val Ser Leu Val Ser Ser Leu Trp Ser Met
                165                 170                 175
Ile Leu Pro Arg Ser Asp Cys Gln Val Met Arg Gln Cys Cys Gln
            180                 185                 190
Gln Leu Ala Gln Ile Pro Gln Gln Leu Gln Cys Ala Ala Ile His Ser
        195                 200                 205
Ile Val His Ser Ile Ile Met Gln Gln Glu Gln Gln Glu Gln Arg Gln
    210                 215                 220
Gly Val Gln Ile Leu Val Pro Leu Ser Gln Gln Gln Val Gly Gln
225                 230                 235                 240
Gly Thr Leu Val Gln Gly Gln Gly Ile Ile Gln Pro Gln Gln Pro Ala
                245                 250                 255
Gln Leu Glu Val Ile Arg Ser Ser Val Leu Gln Thr Leu Ala Thr Met
            260                 265                 270
Cys Asn Val Tyr Val Pro Pro Tyr Cys Ser Thr Ile Arg Ala Pro Phe
                275                 280                 285
Ala Ser Ile Val Ala Gly Ile Gly Gly Gln
    290                 295

<210> SEQ ID NO 126
<211> LENGTH: 295
<212> TYPE: PRT
<213> ORGANISM: Triticum aestivum

<400> SEQUENCE: 126

Met Lys Thr Leu Leu Ile Val Thr Ile Leu Ala Met Ala Thr Thr Ile
1               5                   10                  15
Ala Thr Ala Asn Met Gln Val Asp Pro Gly Tyr Gln Val Gln Trp Pro
            20                  25                  30
Gln Gln Gln Pro Ser Pro Gln Pro Gln Gln Pro Phe Cys Gln Pro
        35                  40                  45
Gln Gln Thr Ile Pro Gln Pro His Gln Thr Phe His His Gln Pro Gln
    50                  55                  60
Gln Thr Tyr Pro His Gln Pro Gln Gln Phe Pro Gln Thr Gln Gln
65                  70                  75                  80
Pro Gln Gln Pro Phe Pro Gln Pro Gln Gln Thr Phe Pro Gln Gln Pro
                85                  90                  95
Gln Leu Pro Phe Pro Gln Gln Pro Gln Gln Pro Phe Pro Gln Pro Gln
            100                 105                 110
Gln Pro Gln Gln Gln Phe Pro Gln Ser Gln Gln Pro Gln Gln Pro Leu
        115                 120                 125
Pro Gln Pro Gln Gln Phe Leu Gln Pro Gln Gln Pro Gln Gln Ser
    130                 135                 140
Phe Pro Gln Gln Gln Pro Leu Ile Gln Leu Ser Leu Gln Gln Gln
145                 150                 155                 160
Met Asn Pro Cys Lys Asn Phe Leu Leu Gln Gln Cys Asn Pro Val Ser
                165                 170                 175
Leu Val Ser Ser Leu Ile Ser Met Ile Leu Pro Arg Ser Asp Cys Gln
            180                 185                 190
Val Met Gln Gln Gln Cys Cys Gln Gln Leu Ala Gln Ile Pro Gln Gln
        195                 200                 205
```

```
Leu Gln Cys Ala Ala Ile His Ser Val Val His Ser Ile Ile Met Gln
    210                 215                 220

Gln Glu Gln Arg Gln Gly Val Gln Ile Arg Arg Pro Leu Phe Gln Leu
225                 230                 235                 240

Val Gln Gly Gln Gly Ile Ile Gln Pro Gln Pro Ala Gln Leu Glu
                245                 250                 255

Val Ile Arg Ser Leu Val Leu Arg Thr Leu Pro Thr Met Cys Asn Val
            260                 265                 270

Tyr Val Ser Pro Asp Cys Ser Thr Ile Asn Ala Pro Phe Ala Asn Ile
        275                 280                 285

Val Val Gly Ile Gly Gly Gln
        290                 295

<210> SEQ ID NO 127
<211> LENGTH: 282
<212> TYPE: PRT
<213> ORGANISM: Triticum aestivum

<400> SEQUENCE: 127

Met Asn Ile Gln Val Asp Pro Ser Ser Gln Val Pro Trp Pro Gln Gln
1               5                   10                  15

Gln Pro Phe Pro Gln Pro His Gln Pro Phe Ser Gln Gln Pro Gln Gln
            20                  25                  30

Thr Phe Pro Gln Pro Gln Gln Thr Phe Pro His Gln Pro Gln Gln Gln
        35                  40                  45

Phe Ser Gln Pro Gln Gln Pro Gln Gln Phe Ile Gln Pro Gln Gln
    50                  55                  60

Pro Phe Pro Gln Gln Pro Gln Gln Thr Tyr Pro Gln Arg Pro Gln Gln
65                  70                  75                  80

Pro Phe Pro Gln Thr Gln Gln Pro Gln Gln Pro Phe Pro Gln Ser Gln
                85                  90                  95

Gln Pro Gln Gln Pro Phe Pro Gln Pro Gln Gln Gln Phe Pro Gln Pro
            100                 105                 110

Gln Gln Pro Gln Gln Ser Phe Pro Gln Gln Gln Pro Ser Leu Ile Gln
        115                 120                 125

Gln Ser Leu Gln Gln Gln Leu Asn Pro Cys Lys Asn Phe Leu Leu Gln
    130                 135                 140

Gln Cys Lys Pro Val Ser Leu Val Ser Ser Leu Trp Ser Met Ile Leu
145                 150                 155                 160

Pro Arg Ser Asp Cys Gln Val Met Arg Gln Gln Cys Cys Gln Gln Leu
                165                 170                 175

Ala Gln Ile Pro Gln Gln Leu Gln Cys Ala Ala Ile His Ser Ile Val
            180                 185                 190

His Ser Ile Ile Met Gln Gln Glu Gln Gln Glu Gln Arg Gln Gly Val
        195                 200                 205

Gln Ile Leu Val Pro Leu Ser Gln Gln Gln Gln Val Gly Gln Gly Thr
    210                 215                 220

Leu Val Gln Gly Gln Gly Ile Ile Gln Pro Gln Gln Pro Ala Gln Leu
225                 230                 235                 240

Glu Val Ile Arg Ser Leu Val Leu Gln Thr Leu Ala Thr Met Cys Asn
                245                 250                 255

Val Tyr Val Pro Pro Tyr Cys Ser Thr Ile Arg Ala Pro Phe Ala Ser
            260                 265                 270

Ile Val Ala Gly Ile Gly Gly Gln Tyr Arg
        275                 280
```

<210> SEQ ID NO 128
<211> LENGTH: 279
<212> TYPE: PRT
<213> ORGANISM: Triticum aestivum

<400> SEQUENCE: 128

```
Met Asn Ile Gln Val Asp Pro Ser Ser Gln Val Gln Trp Pro Gln Gln
1               5                   10                  15

Gln Pro Val Pro Gln Pro His Gln Pro Phe Ser Gln Gln Pro Gln Gln
            20                  25                  30

Thr Phe Pro Gln Pro Gln Gln Thr Phe Pro His Gln Pro Gln Gln Gln
        35                  40                  45

Phe Pro Gln Pro Gln Gln Pro Gln Gln Gln Phe Leu Gln Pro Gln Gln
    50                  55                  60

Pro Phe Pro Gln Gln Pro Gln Gln Pro Tyr Pro Gln Gln Pro Gln Gln
65                  70                  75                  80

Pro Phe Pro Gln Thr Gln Gln Pro Gln Gln Leu Phe Pro Gln Ser Gln
                85                  90                  95

Gln Pro Gln Gln Gln Phe Ser Gln Pro Gln Gln Gln Phe Pro Gln Pro
            100                 105                 110

Gln Gln Pro Gln Gln Ser Phe Pro Gln Gln Gln Pro Pro Phe Ile Gln
        115                 120                 125

Pro Ser Leu Gln Gln Gln Val Asn Pro Cys Lys Asn Phe Leu Leu Gln
130                 135                 140

Gln Cys Lys Pro Val Ser Leu Val Ser Ser Leu Trp Ser Met Ile Trp
145                 150                 155                 160

Pro Gln Ser Asp Cys Gln Val Met Arg Gln Gln Ser Cys Gln Gln Leu
                165                 170                 175

Ala Gln Ile Pro Gln Gln Leu Gln Cys Ala Ala Ile His Thr Val Ile
            180                 185                 190

His Ser Ile Ile Met Gln Gln Glu Gln Gln Gln Gly Met His Ile Leu
        195                 200                 205

Leu Pro Leu Tyr Gln Gln Gln Val Gly Gln Gly Thr Leu Val Gln
    210                 215                 220

Gly Gln Gly Ile Ile Gln Pro Gln Gln Pro Ala Gln Leu Glu Ala Ile
225                 230                 235                 240

Arg Ser Leu Val Leu Gln Thr Leu Pro Thr Met Cys Asn Val Tyr Val
                245                 250                 255

Pro Pro Glu Cys Ser Ile Ile Lys Ala Pro Phe Ser Val Val Ala
            260                 265                 270

Gly Ile Gly Gly Gln Tyr Arg
        275
```

<210> SEQ ID NO 129
<211> LENGTH: 277
<212> TYPE: PRT
<213> ORGANISM: Triticum aestivum

<400> SEQUENCE: 129

```
Met Asn Ile Gln Val Asp Pro Ser Gly Gln Val Pro Trp Pro Gln Gln
1               5                   10                  15

Gln Pro Phe Pro Gln Pro His Gln Pro Phe Ser Gln Gln Pro Gln Gln
            20                  25                  30

Thr Phe Pro Gln Pro Gln Gln Thr Phe Pro His Gln Pro Gln Gln Gln
        35                  40                  45
```

```
Phe Ser Gln Pro Gln Gln Pro Gln Gln Gln Phe Ile Gln Pro Gln Gln
 50                  55                  60

Pro Gln Gln Thr Tyr Pro Gln Arg Pro Gln Gln Pro Phe Pro Gln Thr
 65                  70                  75                  80

Gln Gln Pro Gln Gln Pro Phe Pro Gln Ser Gln Gln Pro Gln Gln Pro
                 85                  90                  95

Phe Pro Gln Pro Gln Gln Gln Phe Pro Gln Pro Gln Gln Pro Gln Gln
                100                 105                 110

Ser Phe Pro Gln Gln Gln Pro Ser Leu Ile Gln Gln Ser Leu Gln Gln
                115                 120                 125

Gln Leu Asn Pro Cys Lys Asn Phe Leu Leu Gln Gln Cys Lys Pro Val
        130                 135                 140

Ser Leu Val Ser Ser Leu Trp Ser Met Ile Leu Pro Arg Ser Asp Cys
145                 150                 155                 160

Gln Val Met Arg Gln Gln Cys Cys Gln Gln Leu Ala Gln Ile Pro Gln
                165                 170                 175

Gln Leu Gln Cys Ala Ala Ile His Ser Ile Val His Ser Ile Ile Met
                180                 185                 190

Gln Gln Glu Gln Gln Glu Gln Arg Gln Gly Val Gln Ile Leu Val Pro
            195                 200                 205

Leu Ser Gln Gln Gln Val Gly Gln Gly Thr Leu Val Gln Gly Gln
210                 215                 220

Gly Ile Ile Gln Pro Gln Gln Pro Ala Gln Leu Glu Val Ile Arg Ser
225                 230                 235                 240

Leu Val Leu Gln Thr Leu Ala Thr Met Cys Asn Val Tyr Val Pro Pro
                245                 250                 255

Tyr Cys Ser Thr Ile Arg Ala Pro Phe Ala Ser Ile Val Ala Gly Ile
                260                 265                 270

Gly Gly Gln Tyr Arg
            275

<210> SEQ ID NO 130
<211> LENGTH: 275
<212> TYPE: PRT
<213> ORGANISM: Triticum aestivum

<400> SEQUENCE: 130

Met Asn Ile Gln Val Asp Pro Ser Ser Gln Val Gln Trp Pro Gln Gln
1               5                  10                  15

Gln Pro Phe Leu Gln Pro His Gln Pro Phe Ser Gln Gln Pro Gln Gln
            20                  25                  30

Ile Phe Pro Gln Pro Gln Gln Thr Phe Pro His Gln Pro Gln Gln Gln
        35                  40                  45

Phe Pro Gln Pro Gln Gln Pro Gln Gln Phe Leu Gln Pro Arg Gln
 50                  55                  60

Pro Phe Pro Gln Gln Pro Gln Gln Pro Tyr Pro Gln Gln Pro Gln Gln
 65                  70                  75                  80

Pro Phe Pro Gln Thr Gln Gln Pro Gln Gln Pro Phe Pro Gln Ser Lys
                 85                  90                  95

Gln Pro Gln Gln Pro Phe Pro Gln Pro Gln Gln Pro Gln Gln Ser Phe
                100                 105                 110

Pro Gln Gln Gln Pro Ser Leu Ile Gln Gln Ser Leu Gln Gln Gln Leu
            115                 120                 125

Asn Pro Cys Lys Asn Phe Leu Leu Gln Gln Cys Lys Pro Val Ser Leu
        130                 135                 140
```

```
Val Ser Ser Leu Trp Ser Ile Ile Leu Pro Pro Ser Asp Cys Gln Val
145                 150                 155                 160

Met Arg Gln Gln Cys Cys Gln Gln Leu Ala Gln Ile Pro Gln Gln Leu
                165                 170                 175

Gln Cys Ala Ala Ile His Ser Val Val His Ser Ile Ile Met Gln Gln
            180                 185                 190

Glu Gln Gln Glu Gln Leu Gln Gly Val Gln Ile Leu Val Pro Leu Ser
        195                 200                 205

Gln Gln Gln Gln Val Gly Gln Gly Ile Leu Val Gln Gly Gln Gly Ile
    210                 215                 220

Ile Gln Pro Gln Gln Pro Thr Gln Leu Glu Val Ile Arg Ser Leu Val
225                 230                 235                 240

Leu Gln Thr Leu Pro Thr Met Cys Asn Val Tyr Val Pro Pro Tyr Cys
                245                 250                 255

Ser Thr Phe Arg Ala Pro Phe Ala Ser Ile Val Ala Gly Ile Gly Gly
                260                 265                 270

Gln Tyr Arg
        275

<210> SEQ ID NO 131
<211> LENGTH: 274
<212> TYPE: PRT
<213> ORGANISM: Triticum aestivum

<400> SEQUENCE: 131

Met Asn Ile Gln Val Asp Pro Ser Ser Gln Val Gln Trp Pro Gln Gln
1               5                   10                  15

Gln Pro Phe Leu Gln Pro His Gln Pro Phe Ser Gln Gln Pro Gln Gln
                20                  25                  30

Ile Phe Pro Gln Pro Gln Gln Thr Phe Pro His Gln Pro Gln Gln Gln
            35                  40                  45

Phe Ser Gln Pro Gln Gln Pro Gln Gln Phe Ile Gln Pro Gln Gln
    50                  55                  60

Pro Phe Pro Gln Gln Pro Gln Gln Pro Phe Pro Gln Thr Gln Gln Pro
65                  70                  75                  80

Gln Gln Pro Phe Pro Gln Ser Gln Gln Pro Gln Gln Pro Phe Pro Gln
                85                  90                  95

Pro Gln Gln Gln Phe Pro Gln Pro Gln Gln Pro Gln Gln Ser Phe Pro
                100                 105                 110

Gln Gln Gln Pro Ser Leu Ile Gln Gln Ser Leu Gln Gln Gln Leu Asn
            115                 120                 125

Pro Cys Lys Asn Phe Leu Leu Gln Gln Cys Lys Pro Val Ser Leu Val
        130                 135                 140

Ser Ser Leu Trp Ser Met Ile Leu Pro Arg Ser Asp Cys Gln Val Met
145                 150                 155                 160

Arg Gln Gln Cys Cys Gln Gln Leu Ala Gln Ile Pro Gln Gln Leu Gln
                165                 170                 175

Cys Ala Ala Ile His Ser Ile Val His Ser Ile Ile Met Gln Gln Glu
            180                 185                 190

Gln Gln Glu Gln Arg Gln Gly Val Gln Ile Leu Val Pro Leu Ser Gln
        195                 200                 205

Gln Gln Gln Val Gly Gln Gly Ile Leu Val Gln Gly Gln Gly Ile Ile
    210                 215                 220

Gln Pro Gln Gln Pro Thr Gln Leu Glu Val Ile Arg Ser Leu Val Leu
225                 230                 235                 240
```

```
Gln Thr Leu Pro Thr Met Cys Asn Val Tyr Val Pro Lys Cys Ser
            245                 250                 255

Ile Met Arg Ala Pro Phe Ala Ser Ile Val Ala Gly Ile Gly Gly Gln
            260                 265                 270

Tyr Arg

<210> SEQ ID NO 132
<211> LENGTH: 258
<212> TYPE: PRT
<213> ORGANISM: Triticum aestivum

<400> SEQUENCE: 132

Met Lys Thr Leu Leu Ile Leu Thr Ile Leu Ala Met Ala Ile Thr Ile
1               5                   10                  15

Gly Thr Ala Asn Ile Gln Val Asp Pro Ser Gly Gln Val Gln Trp Leu
            20                  25                  30

Gln Gln Gln Leu Val Pro Gln Leu Gln Gln Pro Leu Ser Gln Pro
            35                  40                  45

Gln Gln Thr Phe Pro Gln Pro Gln Gln Thr Phe Pro Gln Thr Gln Gln
    50                  55                  60

Pro Gln Gln Pro Phe Pro Gln Leu Gln Gln Pro Gln Gln Pro Phe Pro
65                  70                  75                  80

Gln Pro Gln Gln Gln Leu Pro Gln Pro Gln Gln Pro Gln Gln Ser Phe
            85                  90                  95

Pro Gln Gln Gln Arg Ser Phe Ile Gln Pro Ser Leu Gln Gln Gln Leu
            100                 105                 110

Asn Pro Cys Lys Asn Ile Leu Leu Gln Gln Cys Lys Pro Ala Ser Leu
            115                 120                 125

Val Ser Ser Leu Trp Ser Ile Ile Trp Pro Gln Ser Asp Cys Gln Val
    130                 135                 140

Met Arg Gln Gln Cys Cys Gln Gln Leu Ala Gln Ile Pro Gln Gln Leu
145                 150                 155                 160

Gln Cys Ala Ala Ile His Ser Val Val His Ser Ile Ile Met Gln Gln
            165                 170                 175

Gln Gln Gln Gln Gln Gln Gln Gly Met His Ile Phe Leu Pro Leu
            180                 185                 190

Ser Gln Gln Gln Val Gly Gln Gly Ser Leu Val Gln Gly Gln Gly
    195                 200                 205

Ile Ile Gln Pro Gln Gln Pro Ala Gln Leu Glu Ala Ile Arg Ser Leu
    210                 215                 220

Val Leu Gln Thr Leu Pro Ser Met Cys Asn Val Tyr Val Pro Pro Glu
225                 230                 235                 240

Cys Ser Ile Met Arg Ala Pro Phe Ala Ser Ile Val Ala Gly Ile Gly
            245                 250                 255

Gly Gln

<210> SEQ ID NO 133
<211> LENGTH: 257
<212> TYPE: PRT
<213> ORGANISM: Triticum aestivum

<400> SEQUENCE: 133

Met Asn Ile Gln Val Asp Pro Ser Ser Val Gln Trp Pro Gln Gln
1               5                   10                  15

Gln Pro Val Pro Gln Pro His Gln Pro Phe Ser Gln Pro Gln Gln
            20                  25                  30
```

Gln Phe Leu Gln Pro Gln Gln Pro Phe Pro Gln Gln Pro Gln Gln Pro
            35                  40                  45

Tyr Pro Gln Gln Pro Gln Gln Pro Phe Pro Gln Thr Gln Gln Pro Gln
50                  55                  60

Gln Leu Phe Pro Gln Ser Gln Gln Pro Gln Gln Gln Phe Ser Gln Pro
65                  70                  75                  80

Gln Gln Gln Phe Pro Gln Pro Gln Gln Pro Gln Gln Ser Phe Pro Gln
                85                  90                  95

Gln Gln Pro Pro Phe Ile Gln Pro Ser Leu Gln Gln Gln Val Asn Pro
            100                 105                 110

Cys Lys Asn Phe Leu Leu Gln Gln Cys Lys Pro Val Ser Leu Val Ser
            115                 120                 125

Ser Leu Trp Ser Met Ile Trp Pro Gln Ser Asp Cys Gln Val Met Arg
            130                 135                 140

Gln Gln Cys Cys Gln Gln Leu Ala Gln Ile Pro Gln Gln Leu Gln Cys
145                 150                 155                 160

Ala Ala Ile His Thr Ile Ile His Ser Ile Met Gln Gln Glu Gln
                165                 170                 175

Gln Glu Gln Gln Gln Gly Met His Ile Leu Pro Leu Tyr Gln Gln
            180                 185                 190

Gln Gln Val Gly Gln Gly Thr Leu Val Gln Gly Gln Gly Ile Ile Gln
            195                 200                 205

Pro Gln Gln Pro Ala Gln Leu Glu Ala Ile Arg Ser Leu Val Leu Gln
210                 215                 220

Thr Leu Pro Thr Met Cys Asn Val Tyr Val Pro Pro Glu Cys Ser Ile
225                 230                 235                 240

Ile Lys Ala Pro Phe Ser Ser Val Val Ala Gly Ile Gly Gly Gln Tyr
            245                 250                 255

Arg

<210> SEQ ID NO 134
<211> LENGTH: 256
<212> TYPE: PRT
<213> ORGANISM: Triticum aestivum

<400> SEQUENCE: 134

Met Lys Thr Leu Leu Ile Leu Thr Ile Ile Ala Val Ala Leu Thr Thr
1               5                   10                  15

Thr Thr Ala Asn Ile Gln Val Asp Pro Ser Gly Gln Val Gln Trp Pro
            20                  25                  30

Gln Gln Gln Gln Pro Phe Pro Gln Pro Gln Gln Pro Gln Gln Pro Phe
            35                  40                  45

Pro Gln Pro Gln Gln Pro Gln Leu Pro Phe Pro Gln Gln Pro Gln Gln
        50                  55                  60

Pro Phe Pro Gln Pro Gln Gln Pro Gln Gln Pro Phe Pro Gln Leu Gln
65                  70                  75                  80

Gln Pro Gln Gln Pro Leu Pro Gln Pro Gln Gln Pro Gln Gln Pro Phe
                85                  90                  95

Pro Gln Gln Gln Gln Pro Leu Ile Gln Pro Tyr Leu Gln Gln Gln Met
            100                 105                 110

Asn Pro Cys Lys Asn Tyr Leu Leu Gln Gln Cys Asn Pro Val Ser Leu
            115                 120                 125

Val Ser Ser Leu Val Ser Met Ile Leu Pro Arg Ser Asp Cys Lys Val
            130                 135                 140

Met Arg Gln Gln Cys Cys Gln Gln Leu Ala Arg Ile Pro Gln Gln Leu

-continued

```
                145                 150                 155                 160
        Gln Cys Ala Ala Ile His Gly Ile Val His Ser Ile Ile Met Gln Gln
                        165                 170                 175
        Glu Gln Gln Gln Gln Gln Gln Gln Gln Gln Gln Gln Gln Gly Ile
                    180                 185                 190
        Gln Ile Met Arg Pro Leu Phe Gln Leu Val Gln Gly Gln Gly Ile Ile
                        195                 200                 205
        Gln Pro Gln Gln Pro Ala Gln Leu Glu Val Ile Arg Ser Leu Val Leu
                    210                 215                 220
        Gly Thr Leu Pro Thr Met Cys Asn Val Phe Val Pro Pro Glu Cys Ser
        225                 230                 235                 240
        Thr Thr Lys Ala Pro Phe Ala Ser Ile Val Ala Asp Ile Gly Gly Gln
                        245                 250                 255

<210> SEQ ID NO 135
<211> LENGTH: 251
<212> TYPE: PRT
<213> ORGANISM: Triticum aestivum

<400> SEQUENCE: 135

Met Lys Thr Leu Leu Ile Leu Thr Ile Leu Ala Met Ala Ile Thr Ile
        1               5                   10                  15
        Gly Thr Ala Asn Met Gln Val Asp Pro Ser Ser Gln Val Gln Trp Pro
                    20                  25                  30
        Gln Gln Gln Pro Val Pro Gln Pro His Gln Pro Phe Ser Gln Pro
                    35                  40                  45
        Gln Gln Thr Phe Pro Gln Pro Gln Gln Thr Phe Pro His Gln Pro Gln
                50                  55                  60
        Gln Gln Phe Pro Gln Pro Gln Gln Pro Gln Gln Phe Leu Gln Pro
        65                  70                  75                  80
        Gln Gln Pro Phe Pro Gln Gln Pro Gln Gln Pro Tyr Pro Gln Gln Pro
                        85                  90                  95
        Gln Gln Pro Phe Pro Gln Thr Gln Gln Pro Gln Gln Leu Phe Pro Gln
                    100                 105                 110
        Ser Gln Gln Pro Gln Gln Phe Ser Gln Pro Gln Gln Gln Phe Pro
                    115                 120                 125
        Gln Pro Gln Gln Pro Gln Gln Ser Phe Pro Gln Gln Pro Pro Phe
                130                 135                 140
        Ile Gln Pro Ser Leu Gln Gln Gln Val Asn Pro Cys Lys Asn Phe Leu
        145                 150                 155                 160
        Leu Gln Gln Cys Lys Pro Val Ser Leu Val Ser Ser Leu Trp Ser Met
                        165                 170                 175
        Ile Trp Pro Gln Ser Asp Cys Gln Val Met Arg Gln Gln Cys Cys Gln
                    180                 185                 190
        Gln Leu Ala Gln Ile Pro Gln Gln Leu Gln Cys Ala Ala Ile His Thr
                    195                 200                 205
        Ile Ile His Ser Ile Ile Met Gln Gln Glu Gln Glu Gln Gln
                210                 215                 220
        Gly Met His Ile Leu Leu Pro Leu Tyr Gln Gln Gln Val Gly Gln
        225                 230                 235                 240
        Gly Thr Leu Val Gln Gly Gln Gly Ile Ile Gln
                        245                 250

<210> SEQ ID NO 136
<211> LENGTH: 241
<212> TYPE: PRT
```

<213> ORGANISM: Triticum aestivum

<400> SEQUENCE: 136

| | | | | | | | | | | | | | | | |
|---|---|---|---|---|---|---|---|---|---|---|---|---|---|---|---|
| Met | Lys | Thr | Leu | Leu | Ile | Leu | Thr | Ile | Ile | Ala | Val | Ala | Leu | Thr | Thr |
| 1 | | | | 5 | | | | | 10 | | | | | 15 | |
| Thr | Thr | Ala | Asn | Ile | Gln | Val | Asp | Pro | Ser | Gly | Gln | Val | Gln | Trp | Pro |
| | | | 20 | | | | | 25 | | | | | 30 | | |
| Gln | Gln | Gln | Gln | Pro | Phe | Pro | Gln | Pro | Gln | Gln | Pro | Phe | Ser | Gln | Gln |
| | | | 35 | | | | | 40 | | | | | 45 | | |
| Pro | Gln | Gln | Ile | Phe | Pro | Gln | Pro | Gln | Gln | Thr | Phe | Pro | His | Gln | Pro |
| | 50 | | | | | 55 | | | | | 60 | | | | |
| Gln | Gln | Ala | Phe | Pro | Gln | Pro | Gln | Gln | Thr | Phe | Pro | His | Gln | Pro | Gln |
| 65 | | | | | 70 | | | | | 75 | | | | | 80 |
| Gln | Gln | Phe | Pro | Gln | Pro | Gln | Pro | Gln | Gln | Pro | Phe | Pro | Gln | Gln | |
| | | | | 85 | | | | | 90 | | | | | 95 | |
| Pro | Gln | Gln | Gln | Phe | Pro | Gln | Pro | Gln | Gln | Pro | Gln | Gln | Pro | Phe | Pro |
| | | | 100 | | | | | 105 | | | | | 110 | | |
| Gln | Gln | Pro | Gln | Gln | Gln | Phe | Pro | Gln | Pro | Gln | Gln | Pro | Gln | Gln | Pro |
| | | | 115 | | | | | 120 | | | | | 125 | | |
| Phe | Pro | Gln | Pro | Gln | Gln | Pro | Gln | Leu | Pro | Phe | Pro | Gln | Gln | Pro | Gln |
| | 130 | | | | | 135 | | | | | 140 | | | | |
| Gln | Pro | Phe | Pro | Gln | Pro | Gln | Gln | Pro | Gln | Gln | Pro | Phe | Pro | Gln | Leu |
| 145 | | | | | 150 | | | | | 155 | | | | | 160 |
| Gln | Gln | Pro | Gln | Gln | Pro | Leu | Pro | Gln | Pro | Gln | Gln | Pro | Gln | Gln | Pro |
| | | | | 165 | | | | | 170 | | | | | 175 | |
| Phe | Pro | Gln | Gln | Gln | Pro | Leu | Ile | Gln | Pro | Tyr | Leu | Gln | Gln | Gln | |
| | | | 180 | | | | | 185 | | | | | 190 | | |
| Met | Asn | Pro | Cys | Lys | Asn | Tyr | Leu | Leu | Gln | Gln | Cys | Asn | Pro | Val | Ser |
| | | | 195 | | | | | 200 | | | | | 205 | | |
| Leu | Val | Ser | Ser | Leu | Val | Ser | Met | Ile | Leu | Pro | Arg | Ser | Asp | Cys | Lys |
| | | | 210 | | | | | 215 | | | | | 220 | | |
| Val | Met | Arg | Gln | Gln | Cys | Cys | Gln | Gln | Leu | Ala | Arg | Ile | Pro | Gln | Gln |
| 225 | | | | | 230 | | | | | 235 | | | | | 240 |
| Leu | | | | | | | | | | | | | | | |

<210> SEQ ID NO 137
<211> LENGTH: 381
<212> TYPE: PRT
<213> ORGANISM: Triticum aestivum

<400> SEQUENCE: 137

| | | | | | | | | | | | | | | | |
|---|---|---|---|---|---|---|---|---|---|---|---|---|---|---|---|
| Ala | Arg | Glu | Leu | Asn | Pro | Ser | Glu | Gln | Glu | Leu | Gln | Gln | Gln | Pro | |
| 1 | | | | 5 | | | | | 10 | | | | | 15 | |
| Arg | Phe | Gln | Lys | Gly | Gln | Gln | Pro | Phe | Pro | Gln | Gln | Ser | Tyr | Pro | Gln |
| | | | 20 | | | | | 25 | | | | | 30 | | |
| Gln | Pro | Tyr | Pro | Ser | His | Gln | Pro | Phe | Pro | Thr | Pro | Gln | Gln | Tyr | Ser |
| | | | 35 | | | | | 40 | | | | | 45 | | |
| Pro | Tyr | Gln | Pro | Gln | Gln | Pro | Phe | Pro | Gln | Pro | Gln | Gln | Pro | Thr | Leu |
| | 50 | | | | | 55 | | | | | 60 | | | | |
| Ile | Gln | Pro | Gln | Gln | Pro | Phe | Pro | Gln | Gln | Pro | Gln | Gln | Pro | Gln | Gln |
| 65 | | | | | 70 | | | | | 75 | | | | | 80 |
| Pro | Phe | Pro | Gln | Pro | Gln | Gln | Leu | Pro | Leu | Gln | Pro | Gln | Gln | Pro | |
| | | | | 85 | | | | | 90 | | | | | 95 | |
| Phe | Pro | Gln | Pro | Gln | Gln | Pro | Ile | Pro | Gln | Gln | Pro | Gln | Ser | Phe | |
| | | | 100 | | | | | 105 | | | | | 110 | | |

Pro Gln Gln Pro Gln Arg Pro Glu Gln Gln Phe Pro Gln Pro Gln
            115                 120                 125

Gln Ile Ile Pro Gln Gln Thr Gln Gln Pro Phe Pro Leu Gln Pro Gln
130                 135                 140

Gln Pro Phe Pro Gln Gln Pro Gln Arg Pro Phe Ala Gln Gln Pro Glu
145                 150                 155                 160

Gln Ile Ile Ser Gln Gln Pro Phe Pro Leu Glu Pro Gln Gln Pro Ser
            165                 170                 175

Tyr Gln Pro Gln Gln Pro Phe Pro Gln Gln Pro Gly Gln Ile Ile Pro
            180                 185                 190

Gln Gln Pro Gln Gln Pro Ser Pro Leu Gln Pro Gln Gln Pro Phe Ser
            195                 200                 205

Gln Gln Pro Gln Arg Pro Gln Gln Pro Phe Pro Gln Gln Pro Gln Gln
            210                 215                 220

Ile Ile Pro Gln Gln Pro Gln Gln Pro Phe Pro Leu Gln Pro Gln Gln
225                 230                 235                 240

Pro Val Pro Gln Gln Pro Gln Arg Pro Phe Gly Gln Gln Pro Glu Gln
            245                 250                 255

Ile Ile Ser Gln Arg Pro Gln Gln Pro Phe Pro Leu Gln Pro Gln Gln
            260                 265                 270

Pro Phe Ser Gln Pro Gln Gln Pro Phe Pro Gln Gln Pro Gly Gln Ile
            275                 280                 285

Ile Pro Gln Gln Pro Gln Gln Pro Phe Pro Leu Gln Pro Gln Gln Pro
            290                 295                 300

Phe Pro Gln Gln Pro Glu Gln Ile Ile Pro Gln Gln Pro Gln Gln Pro
305                 310                 315                 320

Phe Pro Leu Gln Pro Gln Gln Pro Phe Pro Gln Gln Pro Glu Gln Ile
            325                 330                 335

Ile Pro Gln Gln Pro Gln Gln Pro Phe Pro Leu Gln Pro Gln Gln Pro
            340                 345                 350

Ser Pro Gln Gln Pro Pro His Gln Gln Leu Pro Phe Pro Gln Pro Gln
            355                 360                 365

Gln Pro Phe Val Ser Ser Gly Thr Ser Ile Gly Gly Gln
            370                 375                 380

<210> SEQ ID NO 138
<211> LENGTH: 354
<212> TYPE: PRT
<213> ORGANISM: Triticum aestivum

<400> SEQUENCE: 138

Met Lys Pro His His Asp Gly Tyr Lys Tyr Thr Cys Ser Ile Ile Val
1               5                   10                  15

Thr Phe His Tyr Pro Asn Phe Lys His Gln Asp Gln Lys His Gln Phe
            20                  25                  30

Gln Glu Ser Ile Lys His Lys Ser Lys Met Lys Thr Phe Ile Ile Phe
            35                  40                  45

Val Leu Leu Ser Met Pro Met Ser Ile Val Ile Ala Ala Arg His Leu
50                  55                  60

Asn Pro Ser Asp Gln Glu Leu Gln Ser Pro Gln Gln Phe Leu Glu
65                  70                  75                  80

Lys Thr Ile Ile Ser Ala Ala Thr Ile Ser Thr Ser Ile Phe Thr
            85                  90                  95

Thr Thr Thr Ile Ser His Thr Pro Thr Ile Phe Pro Pro Ser Thr Thr
            100                 105                 110

```
Thr Thr Ile Ser Pro Thr Pro Thr Asn Pro Pro Thr Thr Thr Met
        115                 120                 125
Thr Ile Pro Leu Ala Thr Pro Thr Thr Thr Thr Phe Ser Pro Ala
130                 135                 140
Pro Thr Thr Ile Ser Leu Ala Thr Thr Thr Ile Ser Leu Ala Pro
145                 150                 155                 160
Thr Thr Asn Ser Pro Ile Thr Thr Thr Ile Pro Ala Ala Thr Pro
            165                 170                 175
Glu Thr Thr Thr Thr Ile Pro Pro Ala Thr Arg Thr Asn Asn Tyr Ala
                180                 185                 190
Ser Thr Ala Thr Thr Ile Ser Leu Leu Thr Ala Thr Thr Thr Pro Pro
        195                 200                 205
Ala Thr Pro Thr Thr Ile Leu Ser Ala Thr Thr Thr Ile Ser Pro
    210                 215                 220
Ala Pro Thr Ile Ile Ser Pro Ala Thr Arg Thr Asn Asn Ser Leu Ala
225                 230                 235                 240
Thr Pro Thr Thr Ile Pro Ala Thr Ala Thr Ile Pro Pro Ala
                245                 250                 255
Thr Arg Thr Asn Asn Ser Pro Ala Thr Ala Thr Thr Ile Pro Pro Ala
            260                 265                 270
Pro Gln Gln Arg Phe Pro His Thr Arg Gln Lys Phe Pro Arg Asn Pro
        275                 280                 285
Asn Asn His Ser Leu Cys Ser Thr His His Phe Pro Ala Gln Gln Pro
    290                 295                 300
Phe Pro Gln Gln Pro Gly Gln Ile Ile Pro Gln Gln Pro Gln Gln Pro
305                 310                 315                 320
Leu Pro Leu Gln Pro Gln Gln Pro Phe Pro Trp Gln Pro Glu Gln Arg
                325                 330                 335
Ser Ser Gln Gln Pro Gln Gln Pro Phe Ser Leu Gln Pro Gln Gln Pro
        340                 345                 350
Phe Ser

<210> SEQ ID NO 139
<211> LENGTH: 345
<212> TYPE: PRT
<213> ORGANISM: Triticum aestivum

<400> SEQUENCE: 139

Ala Arg Gln Leu Asn Pro Ser Glu Gln Glu Leu Gln Ser Pro Gln Gln
1               5                   10                  15
Ala Val Pro Lys Glu Gln Ser Tyr Pro Gln Gln Pro Tyr Pro Ser His
                20                  25                  30
Gln Pro Phe Pro Thr Pro Gln Gln Tyr Ser Pro Tyr Gln Pro Gln Gln
            35                  40                  45
Pro Phe Pro Gln Pro Gln Gln Pro Thr Pro Ile Gln Pro Gln Gln Pro
        50                  55                  60
Phe Pro Gln Gln Pro Gln Gln Pro Phe Pro Gln Pro Gln Gln Leu
65                  70                  75                  80
Pro Leu Gln Pro Gln Gln Pro Phe Pro Gln Pro Gln Leu Pro Val Ser
                85                  90                  95
Gln Gln Pro Gln Gln Pro Phe Pro Gln Gln Pro Gln Arg Pro Gln Gln
            100                 105                 110
Gln Phe Pro Gln Gln Pro Gln Ile Ile Pro Gln Gln Thr Gln Gln
        115                 120                 125
Pro Phe Pro Leu Gln Pro Gln Gln Pro Phe Pro Gln Gln Pro Gln Arg
```

-continued

```
                130                 135                 140
Pro Phe Ala Gln Gln Pro Glu Gln Leu Ile Ser Gln Gln Pro Phe Pro
145                 150                 155                 160

Leu Gln Pro His Gln Pro Phe Phe Gln Pro Gln Gln Pro Phe Pro Gln
                165                 170                 175

Gln Pro Gly Gln Ile Ile Pro Lys Gln Pro Gln Gln Pro Ser Thr Leu
                180                 185                 190

Gln Pro Gln Gln Pro Phe Ser Gln Gln Pro Gln Arg Pro Gln Gln Pro
                195                 200                 205

Phe Pro Gln Gln Pro Gln Gln Ile Ile Pro Gln Gln Pro Gln Gln Pro
210                 215                 220

Phe Pro Leu Gln Pro Gln Gln Pro Val Pro Gln Gln Pro Gln Arg Pro
225                 230                 235                 240

Phe Gly Gln Gln Pro Glu Gln Ile Ile Ser Gln Arg Pro Gln Gln Pro
                245                 250                 255

Phe Pro Leu Gln Pro Gln Gln Pro Phe Ser Gln Pro Gln Gln Pro Leu
                260                 265                 270

Pro Gln Gln Pro Gly Gln Ile Ile Pro Gln Gln Pro Gln Gln Pro Phe
                275                 280                 285

Pro Leu Gln Pro Gln Gln Pro Phe Pro Gln Gln Ser Lys Gln Ile Ile
                290                 295                 300

Pro Gln Gln Pro Gln Gln Pro Phe Pro Leu Gln Pro Gln Gln Pro Ser
305                 310                 315                 320

Pro Gln Gln Pro Gln Leu Pro Phe Pro Gln Pro Gln Gln Pro Phe Val
                325                 330                 335

Ser Ser Gly Thr Gly Ile Gly Gly Gln
                340                 345

<210> SEQ ID NO 140
<211> LENGTH: 321
<212> TYPE: PRT
<213> ORGANISM: Triticum aestivum

<400> SEQUENCE: 140

Ala Arg Gln Leu Asn Pro Ser Glu Gln Glu Leu Gln Ser Pro Gln Gln
1               5                   10                  15

Ala Val Pro Lys Glu Gln Ser Tyr Pro Gln Gln Pro Gln Gln Pro Phe
                20                  25                  30

Pro Gln Pro Gln Gln Pro Thr Pro Ile Gln Pro Gln Gln Ser Phe Pro
                35                  40                  45

Gln Gln Pro Gln Gln Pro Phe Pro Gln Pro Gln Gln Leu Pro Leu
50                  55                  60

Gln Pro Gln Gln Pro Phe Pro Gln Pro Gln Pro Ile Pro Gln Gln
65                  70                  75                  80

Pro Gln Gln Ser Tyr Pro Gln Gln Pro Gln Arg Pro Gln Gln Gln Phe
                85                  90                  95

Leu Gln Gln Pro Gln Gln Ile Ile Pro Gln Gln Thr Gln Gln Pro Phe
                100                 105                 110

Pro Leu Gln Pro Gln Gln Pro Phe Pro Gln Pro Gln Arg Pro Phe
                115                 120                 125

Ala Gln Gln Pro Glu Gln Ile Ile Ser Gln Gln Pro Phe Pro Leu Gln
                130                 135                 140

Pro Gln Gln Leu Phe Ser Gln Pro Gln Gln Pro Phe Pro Gln Gln Pro
145                 150                 155                 160

Gly Gln Ile Ile Asn Gln Gln Pro Gln Gln Pro Ser Pro Leu Gln Pro
```

```
                    165                 170                 175
Gln Gln Pro Phe Ser Gln Gln Pro Gln Arg Pro Gln Gln Pro Phe Pro
                180                 185                 190

Gln Gln Pro Gln Gln Ile Ile Pro Pro Gln Pro Gln Gln Pro Phe Ser
            195                 200                 205

Leu Gln Pro Gln Gln Pro Val Pro Gln Gln Pro Gln Arg Pro Phe Gly
        210                 215                 220

Gln Gln Pro Glu Gln Ile Ile Ser Gln Arg Pro Gln Gln Pro Phe Pro
225                 230                 235                 240

Leu Gln Pro Lys Gln Pro Phe Ser Gln Pro Gln Gln Pro Phe Pro Gln
                245                 250                 255

Gln Pro Gly Gln Ile Ile Pro Gln Gln Pro Gln Gln Pro Phe Pro Leu
            260                 265                 270

Gln Pro Gln Gln Pro Phe Pro Gln Pro Glu Gln Ile Ile Ser Gln
        275                 280                 285

Gln Pro Gln Gln Pro Phe Pro Leu Gln Pro Gln Gln Pro Ser His Gln
            290                 295                 300

Gln Pro Gln Leu Pro Phe Pro Gln Pro Gln Gln Pro Phe Val Val Val
305                 310                 315                 320

Glu

<210> SEQ ID NO 141
<211> LENGTH: 6
<212> TYPE: PRT
<213> ORGANISM: Artificial Sequence
<220> FEATURE:
<223> OTHER INFORMATION: Glutenin-like polypeptide

<400> SEQUENCE: 141

Pro Gly Gln Gly Gln Gln
1               5

<210> SEQ ID NO 142
<211> LENGTH: 9
<212> TYPE: PRT
<213> ORGANISM: Artificial Sequence
<220> FEATURE:
<223> OTHER INFORMATION: Glutenin-like polypeptide

<400> SEQUENCE: 142

Gly Tyr Tyr Pro Thr Ser Pro Gln Gln
1               5

<210> SEQ ID NO 143
<211> LENGTH: 838
<212> TYPE: PRT
<213> ORGANISM: Triticum aestivum

<400> SEQUENCE: 143

Met Ala Lys Arg Leu Val Leu Phe Val Ala Val Val Ala Leu Val
1               5                   10                  15

Ala Leu Thr Val Ala Glu Gly Glu Ala Ser Glu Gln Leu Gln Cys Glu
                20                  25                  30

Arg Glu Leu Gln Glu Leu Gln Glu Arg Glu Leu Lys Ala Cys Gln Gln
            35                  40                  45

Val Met Asp Gln Gln Leu Arg Asp Ile Ser Pro Glu Cys His Pro Val
        50                  55                  60

Val Val Ser Pro Val Ala Gly Gln Tyr Glu Gln Gln Ile Val Val Pro
65                  70                  75                  80
```

-continued

```
Lys Gly Gly Ser Phe Tyr Pro Gly Glu Thr Thr Pro Gln Gln Leu
                85                  90                  95
Gln Gln Arg Ile Phe Trp Gly Ile Pro Ala Leu Leu Lys Arg Tyr Tyr
            100                 105                 110
Pro Ser Val Thr Ser Pro Gln Gln Val Ser Tyr Tyr Pro Gly Gln Ala
        115                 120                 125
Ser Pro Gln Arg Pro Gly Gln Gln Pro Gly Gln Gly Gln
    130                 135                 140
Ser Gly Gln Gly Gln Gln Gly Tyr Tyr Pro Thr Ser Pro Gln Gln Pro
145                 150                 155                 160
Gly Gln Trp Gln Gln Pro Glu Gly Gln Pro Gly Tyr Tyr Pro Thr
                165                 170                 175
Ser Pro Gln Gln Pro Gly Gln Leu Gln Gln Pro Ala Gln Gly Gln Gln
            180                 185                 190
Pro Gly Gln Gly Gln Gly Arg Gln Pro Gly Gln Gly Pro Gly
        195                 200                 205
Tyr Tyr Pro Thr Ser Ser Gln Leu Gln Pro Gly Gln Leu Gln Gln Pro
    210                 215                 220
Ala Gln Gly Gln Gly Gln Gln Pro Gly Gln Gly Gln Gly Gln
225                 230                 235                 240
Gln Pro Gly Gln Gly Gln Pro Gly Gln Gly Gln Gly Gln Gln
                245                 250                 255
Pro Gly Gln Gly Gln Pro Gly Gln Gly Gln Gly Gln Gln Leu
            260                 265                 270
Gly Gln Gly Gln Gly Tyr Tyr Pro Thr Ser Leu Gln Gln Ser Gly
        275                 280                 285
Gln Gly Gln Pro Gly Tyr Tyr Pro Thr Ser Leu Gln Gln Leu Gly Gln
    290                 295                 300
Gly Gln Ser Gly Tyr Tyr Pro Thr Ser Pro Gln Gln Pro Gly Gln Gly
305                 310                 315                 320
Gln Gln Pro Gly Gln Leu Gln Gln Pro Ala Gln Gly Gln Gln Pro Glu
                325                 330                 335
Gln Gly Gln Gln Gly Gln Gln Pro Gly Gln Gly Gln Gly Gln Gln
            340                 345                 350
Pro Gly Gln Gly Gln Gln Pro Gly Gln Gly Gln Pro Gly Tyr Tyr Pro
        355                 360                 365
Thr Ser Pro Gln Gln Ser Gly Gln Gly Gln Pro Gly Tyr Tyr Pro Thr
    370                 375                 380
Ser Ser Gln Gln Pro Thr Gln Ser Gln Gln Pro Gly Gln Gly Gln Gln
385                 390                 395                 400
Gly Gln Gln Val Gly Gln Gly Gln Ala Gln Gln Pro Gly Gln Gly
                405                 410                 415
Gln Gln Pro Gly Gln Gly Gln Pro Gly Tyr Tyr Pro Thr Ser Pro Leu
            420                 425                 430
Gln Ser Gly Gln Gly Gln Pro Gly Tyr Tyr Leu Thr Ser Pro Gln Gln
        435                 440                 445
Ser Gly Gln Gly Gln Pro Gly Gln Leu Gln Ser Ala Gln Gly
    450                 455                 460
Gln Lys Gly Gln Gln Pro Gly Gln Gly Gln Pro Gly Gln Gly Gln
465                 470                 475                 480
Gln Gly Gln Gln Pro Gly Gln Gly Gln Gly Gln Pro Gly Gln
                485                 490                 495
Gly Gln Pro Gly Tyr Tyr Pro Thr Ser Pro Gln Gln Ser Gly Gln Gly
            500                 505                 510
```

Gln Gln Pro Gly Gln Trp Gln Gln Pro Gly Gln Gly Gln Pro Gly Tyr
            515                 520                 525
Tyr Pro Thr Ser Pro Leu Gln Pro Gly Gln Gly Gln Pro Gly Tyr Asp
        530                 535                 540
Pro Thr Ser Pro Gln Gln Pro Gly Gln Gly Gln Pro Gly Gln Leu
545                 550                 555                 560
Gln Gln Pro Ala Gln Gly Gln Gly Gln Leu Ala Gln Gly Gln
            565                 570                 575
Gln Gly Gln Gln Pro Ala Gln Val Gln Gly Gln Gln Pro Ala Gln
            580                 585                 590
Gly Gln Gln Gly Gln Leu Gly Gln Gly Gln Gly Gln Gln Pro
            595                 600                 605
Gly Gln Gly Gln Gln Pro Ala Gln Gly Gln Gly Gln Gln Pro Gly
            610                 615                 620
Gln Gly Gln Gln Gly Gln Pro Gly Gln Gly Gln Pro Gly Gln
625                 630                 635                 640
Gly Gln Pro Trp Tyr Tyr Pro Thr Ser Pro Gln Glu Ser Gly Gln Gly
            645                 650                 655
Gln Gln Pro Gly Gln Trp Gln Gln Pro Gly Gln Trp Gln Pro Gly
            660                 665                 670
Gln Gly Gln Pro Gly Tyr Tyr Leu Thr Ser Pro Leu Gln Leu Gly Gln
            675                 680                 685
Gly Gln Gln Gly Tyr Tyr Pro Thr Ser Leu Gln Gln Pro Gly Gln Gly
            690                 695                 700
Gln Gln Pro Gly Gln Trp Gln Gln Ser Gly Gln Gly Gln His Gly Tyr
705                 710                 715                 720
Tyr Pro Thr Ser Pro Gln Leu Ser Gly Gln Gly Gln Arg Pro Gly Gln
            725                 730                 735
Trp Leu Gln Pro Gly Gln Gly Gln Gly Tyr Tyr Pro Thr Ser Pro
            740                 745                 750
Gln Gln Ser Gly Gln Gly Gln Gln Leu Gly Gln Trp Leu Gln Pro Gly
            755                 760                 765
Gln Gly Gln Gln Gly Tyr Tyr Pro Thr Ser Leu Gln Gln Thr Gly Gln
            770                 775                 780
Gly Gln Gln Ser Gly Gln Gly Gln Gly Tyr Tyr Ser Ser Tyr His
785                 790                 795                 800
Val Ser Val Glu His Gln Ala Ala Ser Leu Lys Val Ala Lys Ala Gln
            805                 810                 815
Gln Leu Ala Ala Gln Leu Pro Ala Met Cys Arg Leu Glu Gly Gly Asp
            820                 825                 830
Ala Leu Ser Ala Ser Gln
            835

<210> SEQ ID NO 144
<211> LENGTH: 5
<212> TYPE: PRT
<213> ORGANISM: Artificial Sequence
<220> FEATURE:
<223> OTHER INFORMATION: Byssus-like polypeptide

<400> SEQUENCE: 144

Gly Pro Gly Gly Gly
1               5